United States Patent
Yokohama et al.

[11] Patent Number: 5,919,824
[45] Date of Patent: Jul. 6, 1999

[54] AMINOPHENOL DERIVATIVES

[75] Inventors: Shuichi Yokohama; Keiichi Kawagoe; Yasuyuki Takeda; Yoshihiro Yokomizo; Aki Yokomizo, all of Tokyo, Japan

[73] Assignee: Daiichi Pharmaceutical Co., Ltd., Tokyo, Japan

[21] Appl. No.: 08/894,799

[22] PCT Filed: Mar. 12, 1996

[86] PCT No.: PCT/JP96/00611

§ 371 Date: Sep. 12, 1997

§ 102(e) Date: Sep. 12, 1997

[87] PCT Pub. No.: WO96/28416

PCT Pub. Date: Sep. 19, 1996

[30] Foreign Application Priority Data

Mar. 14, 1995 [JP] Japan .................................. 7-054752
Feb. 2, 1996 [JP] Japan .................................. 8-017634

[51] Int. Cl.$^6$ .......................... A61K 37/44; C07C 59/235
[52] U.S. Cl. ..................... 514/563; 514/522; 514/535; 514/539; 514/540; 514/541; 514/542; 514/562; 514/564; 514/595; 514/596; 514/597; 514/598; 514/925; 514/927; 558/417; 560/17; 560/29; 560/34; 562/431; 562/439; 564/48; 564/49; 564/50
[58] Field of Search ..................... 514/595, 596, 514/597, 522, 535, 539, 540, 541, 542, 562, 563, 564, 598, 925, 927; 564/47, 56, 48, 49, 50; 558/417; 560/17, 29, 34; 562/431, 439

[56] References Cited

U.S. PATENT DOCUMENTS 4,645,678   2/1987   Nofre et al. ............................ 426/548
5,382,590   1/1995   Bourzat et al. ......................... 514/396
5,663,204   9/1997   Dubroeucq et al. ..................... 514/596

*Primary Examiner*—Shailendra Kumar
*Attorney, Agent, or Firm*—Oblon, Spivak, McClelland, Maier & Neustadt, P.C.

[57] ABSTRACT

Aminophenol derivatives represented by the following formula (1):

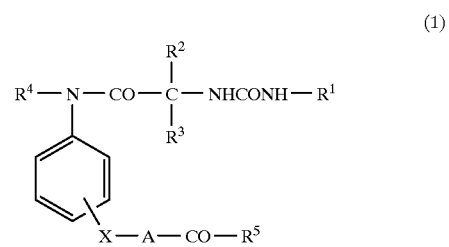

wherein X is O or S; A is alkylene, $R^1$ is phenyl, etc., $R^2$ and $R^3$ are H or alkyl; $R^4$ is substituted carbamoylalkyl, etc.; $R^5$ is substituted amino, etc.; their salts, and optical isomers of the derivatives and salts. Also disclosed are gastrin receptor antagonists, cholecystokinin receptor antagonists, and medicines for digestive diseases. The compounds have strong binding inhibition against gastrin receptor or CCK-A receptor and also they have higher selectivity to either group of CCK-A receptor or gastrin receptor, and therefore, the compounds are useful for preventing and treating gastrointestinal diseases including peptic ulcers as well as central nervous system diseases.

28 Claims, No Drawings

AMINOPHENOL DERIVATIVES

This application is a 371 of PCT/JP96/00611, filed Mar. 12, 1996.

TECHNICAL FIELD

The present invention relates to aminophenol derivatives having binding inhibition against cholecystokinin receptors including gastrin receptor and useful as therapeutic agents for digestive diseases and central nervous system diseases.

BACKGROUND ART

Cholecystokinin (CCK) is a brain/gastrointestinal tract hormone and has a close connection with the central nervous system and the gastrointestinal tract. CCK receptors are categorized into two groups: CCK-A receptor which is found primarily within components of the digestive tract such as the pancreas or the biliary system and CCK-B receptor which is found in the brain. CCK-A receptor is considered to significantly participate in control of gastrointestinal motility and pancreatic juice system. CCK-B receptor is considered to significantly participate in appetite regulation and psychic activities.

On the other hand, Gastrin, known as a hormone stimulating gastric acid secretion and CCK have in common five C-terminal amino acid residues. Therefore, both are called members of the gastrin/CCK family. Gastrin receptor, which may be found in the gastrointestinal tract, pancreas, and the biliary system, are primarily found in gastric mucosal cells (parietal cells) and participate in the control of gastric acid and pepsin secretion. The gene encoding CCK-B receptor and gastrin receptor were cloned, and as a result, it was found that the amino acid sequences of the two receptors are identical (Y-M. Lee, et al., J. Biological Chem. 268 (11) 8164–8169, 1993).

As described hereinbefore, there are two groups of CCK receptors, and the CCK-B receptor is considered to be identical to the gastrin receptor. Various diseases are considered to manifest themselves through these receptors.

Accordingly, development of compounds having strong binding inhibition against one of CCK-A or gastrin (CCK-B) group of receptors is desired.

Accordingly, a general object of the present invention is to provide a compound exhibiting strong binding inhibition against members of either the gastrin (CCK-B) receptor or the CCK-A receptor.

DISCLOSURE OF THE INVENTION

The present inventors synthesized a vast number of aminophenol derivatives and investigated each derivative's action on CCK-A receptor and gastrin receptor. As a result, they found that the compounds represented by the following formula (1) have stronger gastrin receptor binding inhibition or CCK-A receptor binding inhibition than previously known compounds and thus are useful as medicines. The present invention was accomplished based on this finding.

Accordingly, the present invention provides a compound represented by the following formula (1):

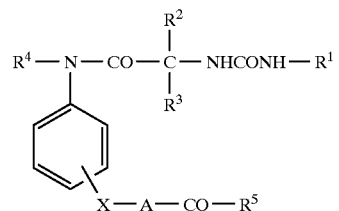

wherein X represents an oxygen atom or a sulfur atom,
A represents a linear or branched alkylene group,
$R^1$ represents a phenyl group which may have a substituent,
$R^2$ and $R^3$, which may be identical to or different from each other, each independently represent a hydrogen atom or an alkyl group,
$R^4$ represents an alkyl or alkenyl group which may have a substituent,
$R^5$ represents a hydroxyl group, an alkoxyl group, an aralkyl group, an aryl group, a cycloalkyl group which may have a substituent, or a group —N($R^6$)$R^7$ wherein R6 and $R^7$ are identical to or different from each other, each independently representing a hydrogen atom, an alkyl group which may have a substituent, an alkoxyl group, a phenyl group which may have a substituent, an aralkyl group which may have a substituent, a pyridyl group which may have a substituent, a thiazolyl group which may have a substituent, or $R^6$ and $R^7$, together with the adjacent nitrogen atom, form a saturated or unsaturated heterocyclic ring which may have a substituent; a salt thereof; or an optical isomer of the compound or the salt.

The present invention also provides a medicine which contains as an active component a compound of formula (1), a salt thereof, or an optical isomer of the compound or the salt.

The present invention also provides an anti-cholecystokinin agent and an anti-gastrin agent containing, as an active component, a compound of formula (1), a salt thereof, or an optical isomer of the compound or the salt.

The present invention also provides a preventive and therapeutic agent for peptic ulcers, gastritis, rectal/colonic cancer, Zollinger-Ellison syndrome, and anxiety syndrome, which contains as an active component a compound of formula (1), a salt thereof, or an optical isomer of the compound or the salt.

The present invention further provides use of a compound of formula (1), a salt thereof, or an optical isomer of the compound or the salt in medicines.

The present invention further provides a pharmaceutical composition which contains a compound of formula (1), a salt thereof, or an optical isomer of the compound or the salt and a pharmaceutically acceptable carrier.

The present invention further provides a method for treating diseases caused by cholecyctokinin or gastrin, which includes administering an effective amount of a compound of formula (1), a salt thereof, or an optical isomer of the compound or the salt to the subject in need thereof.

DETAILED DESCRIPTION OF PREFERRED EMBODIMENT

In the present invention, the term "alkyl group" is used to encompass linear alkyl, branched alkyl, cyclic alkyl, and linear or branched alkyl which has cyclic alkyl as a portion thereof. Generally, the alkyl group has 1–15 carbon atoms. Examples of the alkyl group include methyl, ethyl, n-propyl, isopropyl, n-butyl, isobutyl, secondary butyl, tertiary butyl, n-pentyl, n-hexyl, n-heptyl, n-octyl, cyclopropyl, cyclobutyl, cyclopentyl, cyclohexyl, cycloheptyl, adamantyl, cyclobutylmethyl, cyclobutylethyl, cyclobutylpropyl, cyclopentylmethyl, cyclopentylethyl, cyclopentylpropyl, cyclohexylmethyl, cyclohexylethyl, cyclohexylpropyl, cycloheptylmethyl, cycloheptylethyl, and cycloheptylpropyl. They preferably have 1–10 carbon atoms.

The term "alkenyl group" encompasses linear alkenyl, branched alkenyl, cyclic alkenyl, and linear or branched alkenyl which has cyclic alkenyl as a portion thereof. Generally, the alkenyl group has 3–8 carbon atoms. Examples of the alkenyl group include allyl, cyclopentenyl, and cyclohexenyl. They preferably have 3–6 carbon atoms.

The term "alkoxyl group" encompasses linear or branched alkoxyl, and its carbon number is 1–8 in general. Examples of the alkoxyl group include methoxy, ethoxy, n-propoxy, isopropoxy, n-butoxy, n-pentyloxy, and n-hexyloxy. They preferably have 1–6 carbon atoms.

The term "aryl group" encompasses C6–C14 aromatic hydrocarbon groups such as phenyl, naphthyl, and alkyl-substituted phenyl. Examples of the aryl group include phenyl, tolyl, xylyl, and naphthyl.

The term "aralkyl group" encompasses C7–C20 aromatic hydrocarbon—$C_{1-8}$ alkyl groups such as phenyl $C_{1-8}$ alkyl, naphthyl $C_{1-8}$ alkyl, biphenylmethyl, and trityl. Examples of the aralkyl group include benzyl, phenethyl, phenylpropyl, naphthylmethyl, biphenylmethyl, and trityl.

In formula (1), X represents an oxygen atom or a sulfur atom. Preferably, X is an oxygen atom. The position at which X is bound may assume ortho, meta, or para with respect to the position of the nitrogen atom in the benzene ring. Ortho and meta are preferred.

The linear or branched alkylene group represented by A may be a C1–C18 linear or branched alkylene group.

Preferably, A is a C1–C8 linear alkylene group. Specific examples of A include methylene, ethylene, trimethylene, tetramethylene, and pentamethylene, with methylene being particularly preferred.

$R^1$ represents a phenyl group which may have a substituent. Substituents or atoms which may be bound to the phenyl group are, but not limited to, one or more substituents or atoms selected from the group consisting of a halogen atom, an alkyl group, an alkoxyl group, an alkylthio group, a hydroxyl group, a carboxyl group, a hydroxyalkyl group, a nitro group, an acyl group, a cyano group, an amino group, a carbamoyl group, a sulfamoyl group, a trifluoromethanesulfonylamino group, an alkoxycarbonyl group, an alkoxyaminocarbonyl group, a sulfo group, an acyloxyalkyl group, an alkoxyalkyl group, a carboxyalkyl group, an alkoxycarbonylalkyl group, a carboxyalkyloxy group, an alkoxycarbonylalkyloxy group, a sulfoalkyl group, an alkoxyaminoalkyl group, a hydroxyiminoalkyl group, a 2-oxo-1,3,4-triazolyl group which may have an alkyl substituent on nitrogen, a 5-oxo-1,2,4-oxadiazolyl group which may have an alkyl substituent on nitrogen, a hydroxyimino group, an alkoxyimino group, a 1-azacycloalkyl group, and a 5-tetrazolyl group. Preferably, the substituents which may be bound to these phenyl groups are $C_{1-8}$ alkyl, hydroxy $C_{1-8}$ alkyl, $C_{1-8}$ acyl, carboxy $C_{1-8}$ alkyl, $C_{1-8}$ alkoxycarbonyl $C_{1-8}$ alkyl, sulfo $C_{1-8}$ alkyl, hydroxyimino $C_{1-8}$ alkyl, 5-tetrazolyl, N-$C_{1-8}$ alkyl-N-$C_{1-8}$ alkoxyl, $C_{1-8}$ alkylamino, di-$C_{1-8}$ alkylamino (whose alkyl groups are identical to or different from each other), $C_{1-8}$ alkoxyimino $C_{1-8}$ alkyl, or aryl $C_{1-8}$ alkoxyimino $C_{1-8}$ alkyl.

Examples of particularly preferred species of $R^1$ include carboxy $C_{1-8}$ alkylphenyl and $C_{1-8}$ alkoxycarbonyl $C_{1-8}$ alkylphenyl. Specifically, carboxymethylphenyl, 1-carboxyethylphenyl, alkoxycarbonylmethylphenyl, and 1-alkoxycarbonylethyl are even more preferred.

$R^2$ and $R^3$ are identical to or different from each other, each independently representing a hydrogen atom or an alkyl group. The alkyl group may be any one of the aforementioned C1–C8 alkyl groups. Preferably, $R^2$ and $R^3$ are both hydrogen atoms.

$R^4$ represents an alkyl or alkenyl group which may have a substituent. Examples of the substituent include aryl, carboxyl, alkoxylcarbonyl, aryloxycarbonyl, aralkyloxycarbonyl, hydroxyl, alkoxyl, amino, alkylamino, dialkylamino, and a group —$CON(R^8)R^9$ wherein $R^8$ and $R^9$ are identical to or different from each other, each independently representing a hydrogen atom, an alkyl group which may have a substituent, an alkoxyl group, an aralkyl group, or a phenyl group which may have a substituent, or $R^8$ and $R^9$ together with the adjacent nitrogen atom, form a saturated or unsaturated heterocyclic ring which may have a substituent. The substituent may include one or more species of these groups. Examples of the group —$N(R^8)R^9$ include amino, alkylamino, dialkylamino, alkoxyamino, aralkylamino, phenylamino, N-alkyl-N-phenylamino (whose phenyl group may be substituted by one or more members selected from the group consisting of a halogen atom, an alkyl group, an alkoxyl group, a hydroxyl group, a cyano group, a nitro group, a benzyloxy group, an alkylthio group, a trifluoromethyl group and an acetyl group), and a saturated or unsaturated heterocyclic ring which is formed by $R^8$ and $R^9$ together with the adjacent nitrogen atom and which may have a substituent (for example, 1-pyrrolidinyl, 1-piperidinyl, 1-homopiperidinyl, 1-(3,3-dialkylpiperidinyl), 8-azaspiro-[4.5]decane-8-yl, 1-indolyl, and 1-(1,2,3,4-tetrahydroquinolyl).

Preferred examples of $R^4$ are a linear alkyl, a branched alkyl, a linear alkyl having partially a cycloalkyl, an alkoxycarbonylmethyl, and N-alkyl-N-substituted phenyl-carbomoylalkyl. Of these, n-butyl, 3-methylbutyl, 4-methylpentyl, 3-methylpentyl, 3-ethylpentyl, 4-ethylhexyl, cyclopentylmethyl, cyclopentylethyl, cyclohexylmethyl, cyclohexylethyl, tert-butoxycarbonylmethyl, N-methyl-N-phenylcarbomoylmethyl are particularly preferred.

Examples of the cycloalkyl group which may have a substituent represented by $R^5$ include cyclopropyl, cyclobutyl, cyclopentyl, cyclohexyl, cycloheptyl, and adamantyl. $R^5$ is preferably —$N(R^6)R^7$. Examples of the alkyl groups which may have substituents represented by $R^6$ and $R^7$ include alkyl groups which may be substituted by one or more members selected from the group consisting of a halogen atom, a hydroxyl group, an alkoxyl group, an acetyl group, and a trifluoromethyl group. Preferably, $R^6$ and $R^7$ in this category are C1–C10 alkyl and particularly C1–C6 alkyl. Examples of the phenyl, aralkyl, pyridyl, and thiazolyl groups which may have substituents represented by $R^6$ and $R^7$ include phenyl, aralkyl, pyridyl, and thiazolyl groups which may be substituted by one or more members selected from the group consisting of a hydroxyl group, a halogen atom, an alkyl group, an alkoxyl group, an acetyl group, a trifluoromethyl group, a nitro group, a cyano group, an alkylthio group, and a benzyloxy group.

Preferably, $R^6$ and $R^7$ in this category are phenyl groups which have been substituted by one or more members selected from the group consisting of a halogen atom, an alkyl group, and an alkoxyl group.

Examples of the saturated or unsaturated heterocyclic ring formed by —N($R^6$)$R^7$ include 1-pyrrolidinyl, 1-piperidinyl, 1-homopiperidinyl, 1-morpholinyl, 1-thiomorpholinyl, 1-indolyl, and 1-(1,2,3,4-tetrahydroquinolinyl). Any of these heterocyclic rings may be substituted by an alkyl group, a halogen atom, a hydroxyl group, a trifluoromethyl group or an alkoxyl group. An example of alkyl-substituted 1-piperidinyl is 1-(3,3-dialkylpiperidinyl), and an example of alkyl-substituted 1-piperazinyl is 4-alkyl-1-piperazinyl.

$R^5$ is preferably —N($R^6$)$R^7$, and more preferably, —N($R^6$)$R^7$ in which $R^6$ is an alkyl group which may have a substituent and $R^7$ is a phenyl group which may have a substituent. Particularly preferably, $R^5$ is —N($R^6$)$R^7$ in which $R^6$ is a methyl group and $R^7$ is a phenyl group which may have a substituent.

Among the above-described substituents, particularly preferred combinations may be such that $R^1$ is 1-alkoxycarbonylmethylphenyl, 2-alkoxycarbonylethylphenyl, carboxymethylphenyl, or 1-carboxyethylphenyl; $R^2$ and $R^3$ are hydrogen; $R^4$ is n-butyl, 3-methylbutyl, 4-methylpentyl, 3-methylpentyl, 3-ethylpentyl, 4-ethylhexyl, cyclopentylmethyl, cyclopentylethyl, cyclohexylmethyl, cyclohexylethyl, tert-butoxycarbonylmethyl, or N-methyl-N-phenylcarbamoylmethyl; X is oxygen bound to an ortho- or meta-position; A is methylene; $R^5$ is —N($R^6$)$R^7$ (wherein either one of $R^6$ or $R^7$ is a methyl or ethyl group, and the other is a phenyl group substituted by one or more members selected from a methyl group, a methoxy group, a fluorine atom, a bromine atom, and a chlorine atom).

No particular limitation is imposed on the salts of compound (1) of the present invention so long as they are pharmacologically acceptable. They are preferably alkali metal salts such as sodium salts and potassium salts.

The compound (1) of the present invention may have one or more asymmetric carbons, and thus, compound (1) may have a variety of stereoisomers. The compound (1) of the invention encompasses both racemic modifications and optical isomers. Moreover, the compound (1) may be present as a solvate such as a hydrate.

The following are typical compounds of the present invention.

(1) 2-[3-[3-[N-[2-[N-Methyl-N-(3-methylphenyl)-carbamoylmethyloxy]phenyl]-N-(N-methyl-N-phenylcarbamoylmethyl)carbamoylmethyl]ureido]phenyl]acetic acid (1–73)

(2) (±)-2-[3-[3-[N-[3-[N-Methyl-N-(2-methylphenyl)-carbamoylmethyloxy]phenyl]-N-(N-methyl-N-phenylcarbamoylmethyl)carbamoylmethyl]ureido]phenyl]-propionic acid (1–79)

(3) (±)-2-[3-[3-[N-[2-[N-(3-Methoxyphenyl)-N-methylcarbamoylmethyloxy]phenyl]-N-,(N-methyl-N-phenylcarbamoylmethyl)carbamoylmethyl]ureido]phenyl]-propionic acid (1–86)

(4) 2-[3-[3-[N-[2-[N-(3-Methoxyphenyl)-N-methylcarbamoylmethyloxy]phenyl]-N-(N-methyl-N-phenylcarbamoylmethyl)carbamoylmethyl]ureido]phenyl]acetic acid (1–87)

(5) Sodium (±)-2-[3-[3-[N-[2-[N-methyl-N-(3,5-dimethylphenyl)carbamoylmethyloxy]phenyl]-N-(N-methyl-N-phenylcarbamoylmethyl)carbamoylmethyl]ureido]phenyl]-propionate (1–92)

(6) 2-[3-[3-[N-[2-[N-(3,5-Dimethoxyphenyl)-N-methylcarbamoylmethyloxy]phenyl]-N-(N-methyl-N-phenylcarbamoylmethyl)carbamoylmethyl]ureido]phenyl]acetic acid (1–85)

(7) Methyl (±)-2-[3-[3-[N-[3-[N-methyl-N-(3,5-dimethylphenyl)carbamoylmethyloxy]phenyl]-N-(N-methyl-N-phenylcarbamoylmethyl)carbamoylmethyl]ureido]phenyl]-propionate (1–20)

(8) 2-[3-[3-[N-(N-Methyl-N-phenylcarbamoylmethyl)-N-[2-(N-methyl-N-phenylcarbamoylmethyloxy)phenyl]-carbamoylmethyl]ureido]phenyl]acetic acid (1–90)

(9) 2-[2-Methoxy-3-[3-[N-N-methyl-N-phenylcarbamoylmethyl)-N-[2-(N-methyl-N-phenylcarbamoylmethyloxy)phenyl]carbamoylmethyl]ureido]-phenyl]acetic acid (1–157)

(10) (±)-2-[3-[3-[N-[2-[N-Methyl-N-(2,5-dimethylphenyl)carbamoylmethyloxy]phenyl]-N-(N-methyl-N-phenylcarbamoylmethyl)carbamoylmethyl]ureido]phenyl]-propionic acid (1–174)

(11) (±)-2-[3-[3-[N-[3-[N-Methyl-N-(2,5-dimethylphenyl)carbamoylmethyloxy]phenyl]-N-(N-methyl-N-phenylcarbamoylmethyl)carbamoylmethyl ureido]phenyl]-propionic acid (1–176)

(12) (+)-2-[3-[3-[N-[2-[N-Methyl-N-(2,6-dimethylphenyl)carbamoylmethyloxy]phenyl]-N-(N-methyl-N-phenylcarbamoylmethyl)carbamoylmethyl]ureido]phenyl]-propionic acid (1–178)

(13) 2-[3-[3-[N-[3-[N-Methyl-N-(2,6-dimethylphenyl)carbamoylmethyloxy]phenyl]-N-(N-methyl-N-phenylcarbamoylmethyl)carbamoylmethyl]ureido]phenyl]acetic acid (1–179)

(14) (+)-2-[3-[3-[N-[3-[N-Methyl-N-(2,6-dimethylphenyl)carbamoylmethyloxy]phenyl]-N-(N-methyl-N-phenylcarbamoylmethyl)carbamoylmethyl]ureido]phenyl]propionic acid (1–180)

(15) 2-[3-[3-[N-[2-[N-Methyl-N-(3,5-dimethylphenyl)carbamoylmethyloxy]phenyl]-N-(3-methylbutyl)carbamoylmethyl]ureido]phenyl]acetic acid (1–181)

(16) (±)-2-[3-[3-[N-[2-[N-Methyl-N-(3,5-dimethylphenyl)carbamoylmethyloxy]phenyl]-N-(3-methylbutyl)carbamoylmethyl]ureido]phenyl]propionic acid (1–182)

(17) 2-[3-[3-[N-[2-(N-Methyl-N-phenylcarbamoylmethyloxy)phenyl]-N-(3-methylbutyl)-carbamoylmethyl]ureido]phenyl]acetic acid (1–183)

(18) 2-[3-[3-[N-[2-[N-Methyl-N-(2-methylphenyl)-carbamoylmethyloxylphenyl]-N-(3-methylbutyl)-carbamoylmethyl]ureido]phenyl]acetic acid (1–184)

(19) 2-[3-[3-[N-[2-[N-Methyl-N-(3-methylphenyl)carbamoylmethyloxy]phenyl]-N-(3-methylbutyl)carbamoylmethyl]ureido]phenyl]acetic acid (1–185)

(20) 2-[3-[3-[N-[2-[N-Methyl-N-(2,6-dimethylphenyl)-carbamoylmethyloxy]phenyl]-N-(3-methylbutyl)-carbamoylmethyl]ureido]phenyl]acetic acid (1–186)

(21) 2-[3-[3-[N-[2-[N-(3-Chlorophenyl)-N-methylcarbamoylmethyloxy]phenyl]-N-(3-methylbutyl)-carbamoylmethyl]ureido]phenyl]acetic acid (1–187)

(22) (±)-2-[3-[3-[N-[2-[N-(3-Chrolophenyl)-N-methylcarbamoylmethyloxy]phenyl]-N-(3-methylbutyl)-carbamoylmethyl]ureido]phenyl]propionic acid (1–188)

(23) 2-[3-[3-[N-[2-[N-(3-Bromophenyl)-N-methylcarbamoylmethyloxy]phenyl]-N-(3-methylbutyl)-carbamoylmethyl]ureido]phenyl]acetic acid (1–189)

(24) (±)-2-[3-[3-[N-[2-[N-(3-Bromophenyl)-N-methylcarbamoylmethyloxy]phenyl]-N-(3-methylbutyl)-carbamoylmethyl]ureido]phenyl] propionic acid (1–190)

(25) 2-[3-[3-[N-[3-[N-Methyl-N-(2-methylphenyl)carbamoylmethyloxy]phenyl]-N-(3-methylbutyl)carbamoylmethyl]ureido]phenyl]acetic acid (1–194)

(26) 2-[3-[3-[N-[3-[N-Methyl-N-( 3,5-dimethylphenyl)-carbamoylmethyloxy]phenyl]-N-(3-methylbutyl)-carbamoylmethy]ureido]phenyl]acetic acid (1–195)

(27) 2-[3-[3-[N-(1-Adamantylmethyl)-N-[3-(N-methyl-N-phenylcarbamoylmethyloxy)phenyl]carbamoylmethyl]ureido]-phenyl]acetic acid (1–203)

(28) 2-[3-[3-[N-Benzyl-N-[3-(N-methyl-N-phenylcarbamoylmethyloxy)phenyl]carbamoylmethyl]ureido]-phenyl]acetic acid (1–206)

(29) (±)-2-[3-[3-[N-[3-(N-Methyl-N-phenylcarbamoylmethyloxy)phenyl]-N-(3-phenylbutyl)-carbamoylmethylureido]phenyl]acetic acid (1–210)

(30) 2-[3-[3-[N-[2-(N-Methyl-N-phenylcarbamoylmethyloxy)phenyl]-N-(2-methylpropyl)-carbamoylmethyl]ureido]phenyl]acetic acid (1–213)

(31) 2-[3-[3-[N-Cyclohexylmethyl-N-[2-(N-methyl-N-phenylcarbamoylmethyloxy)phenyl]carbamoylmethyl]ureido]-phenyl]acetic acid (1–214)

(32) 2-[3-[3-[N-Benzyl-N-[2-(N-methyl-N-phenylcarbamoylmethyloxy)phenyl]carbamoylmethyl]ureido]-phenyl]acetic acid (1–215)

(33) (±)-2-[3-[3-[N-[2-(N-Methyl-N-phenylcarbamoylmethyloxy)phenyl]-N-(3-methylpentyl)-carbamoylmethyl]ureido]phenyl]acetic acid (1–218)

(34) (±)-2-[3-[3-[N-[2-(N-Methyl-N-phenylcarbamoylmethyloxy)phenyl]-N-(3-phenylbutyl)-carbamoylmethyllureidolphenyl]acetic acid (1–219)

(35) 2-[3-[3-[N-[2-(N-Methyl-N-phenylcarbamoylmethyloxy)phenyl]-N-(4-methyl-3-pentenyl)-carbamoylmethyllureido]phenyl]acetic acid (1–220)

(36) 2-[3-[3-[N-[2-(N-Methyl-N-phenylcarbamoylmethyloxy)phenyl]-N-(4-methylpentyl)-carbamoylmethyl]ureido]phenyl]acetic acid (1–221)

(37) (±)-2-[3-[3-[N-[2-(N-Methyl-N-phenylcarbamoylmethyloxy)phenyl]-N-(3,4-dimethylpentyl)-carbamoylmethyl]ureido]phenyl]acetic acid (1–222)

(38) (±)-2-[3-[3-[N-(3-Cyclohexylbutyl)-N-[2-(N-methyl-N-phenylcarbamoylmethyloxy)phenyl]carbamoylmethyl]ureido]-phenyl]acetic acid (1–223)

(39) 2-[3-[3-[N-(3-Ethylpentyl)-N-[2-(N-methyl-N-phenylcarbamoylmethyloxy)phenyl]carbamoylmethyl]ureido]-phenyl]acetic acid (1–224)

(40) (±)-2-[3-[3-[N-[2-(N-Methyl-N-phenylcarbamoylmethyloxy)phenyl]-N-(3-methylhexyl)-carbamoylmethyl]ureido]phenyl]acetic acid (1–225)

(41) 2-[3-[3-[N-Cyclohexylmethyl-N-[2-[N-methyl-N-(3,5-dimethylphenyl)carbamoylmethyloxy]phenyl]carbamoylmethyl]-ureido]phenyl]acetic acid (1–226)

(42) (+)-2-[3-[3-[N-Cyclohexylmethyl-N-[2-[N-methyl-N-(3,5-dimethylphenyl)carbamoylmethyloxy]phenyl]-carbamoylmethyl]ureido]phenyl]propionic acid (1–227)

(43) 2-[3-[3-[N-(2-Ethylbutyl)-N-[2-(N-methyl-N-phenylcarbamoylmethyloxy)phenyl]carbamoylmethyl]ureido]-phenyl]acetic acid (1–228)

(44) 2-[3-[3-[N-Cyclohexylmethyl-N-[2-[N-methyl-N-(3-methylphenyl)carbamoylmethyloxy]phenyl]carbamoylmethyl]-ureido]phenyl]acetic acid (1–230)

(45) (±)-2-[3-[3-[N-Cyclohexylmethyl-N-[2-[N-methyl-N-(3-methylphenyl)carbamoylmethyloxy]phenyl]carbamoylmethyl-ureido]phenyl]propionic acid (1–231)

(46) 2-[3-[3-[N-[2-(N-Methyl-N-phenylcarbamoylmethyloxy)phenyl]-N-[(1-methylcyclohexyl)-methyl]carbamoylmethyl]ureido]phenyl]acetic acid (1–232)

(47) 2-[3-[3-[N-[2-(1-Adamantyl)ethyl]-N-[2-(N-methyl-N-phenylcarbamoylmethyloxy)phenyl]carbamoylmethyl]-ureido]phenyl]acetic acid (1–234)

(48) 2-[3-[3-[N-(1-Adamantylmethyl)-N-[2-(N-methyl-N-phenylcarbamoylmethyloxy)phenyl]carbamoylmethyl]-ureido]phenyl]acetic acid (1–235)

(49) N-Methyl-N-(3,5-dimethylphenyl)-2-[2-[N-cyclohexylmethyl-N-[2-(3-[3-(N,N-dimethylamino)-phenyl]ureidolacetyl]amino]phenoxy]acetamide (1–236)

(50) (±)-2-[3-[3-[N-[2-[N-Methyl-N-(3,5-dimethylphenyl)carbamoylmethyloxy]phenyl]-N-(3-methylpentyl)carbamoylmethyl]ureido]phenyl]acetic acid (1–237)

(51) (±)-2-[3-[3-[N-[2-[N-(3-Chlorophenyl)-N-methylcarbamoylmethyloxy]phenyl]-N-(3-methylpentyl)carbamoylmethyl]ureido]phenyl]acetic acid (1–238)

(52) Methyl 2-[3-[3-[N-[2-[N-methyl-N-(3,5-dimethylphenyl)carbamoylmethyloxy]phenyl]-N-(3-methylbutyl)carbamoylmethyl]ureido]phenyl]acetate (1–239)

(53) Methyl 2-[3-[3-[N-[2-[N-methyl-N-(3,5-dimethylphenyl)carbamoylmethyloxy]phenyl]-N-(3-methyl- 2-butenyl)carbamoylmethyl]ureido]phenyl] acetate (1–240)

(54) Methyl 2-[3-[3-[N-[2-(N-methyl-N-phenylcarbamoylmethyloxy)phenyl]-N-(3-methylbutyl)-carbamoylmethyl]ureido]phenyl]acetate (1–242)

(55) Methyl 2-[3-[3-[N-[2-[N-(3-chlorophenyl)-N-methylcarbamoylmethyloxy]phenyl]-N-(3-methylbutyl)carbamoylmethyl]ureido]phenyl]acetate (1–246)

(56) Methyl (±)-2-[3-[3-[N-[2-[N-(3-chlorophenyl)-N-methylcarbamoylmethyloxy]phenyl]-N-(3-methylbutyl)-carbamoylmethyl]ureido]phenyl] propionate (1–247)

(57) 2-[3-[3-[N-[3-[N-(3,5-Difluorophenyl)-N-methylcarbamoylmethyloxy]phenyl]-N-(3-methylbutyl)-carbamoylmethyl]ureido]phenyl]acetic acid (1–268)

(58) (±)-2-[3-[3-[N-[3-[N-(3,5-Difluorophenyl)-N-methylcarbamoylmethyloxy]phenyl]-N-(3-

(59) 2-[3-[3-[N-[2-[N-(3,5-Difluorophenyl)-N-methylcarbamoylmethyloxy]phenyl]-N-(3-methylbutyl)-carbamoylmethyl]ureido]phenyl]acetic acid (1–272)

(60) (±)-2-[3-[3-[N-[2-[N-(3,5-Difluorophenyl)-N-methylcarbamoylmethyloxy]phenyl]-N-(3-methylbutyl)-carbamoylmethyl]ureido]phenyl] propionic acid (1–273)

(61) Potassium [3-[3-[N-[2-[N-(3,5-difluorophenyl)-N-methylcarbamoylmethyloxy]phenyl]-N-(3-methylbutyl)-carbamoylmethyl]ureido]phenyl] methanesulfonate (1–274)

(62) Potassium (±)-1-[3-[3-[N-[2-[N-(3,5-difluorophenyl)-N-methylcarbamoylmethyloxy] phenyl]-N-( 3-methylbutyl)carbamoylmethyl]ureido] phenyl]ethanesulfonate (1–275)

(63) 2-[3-[3-[N-[2-[N-(2,5-Difluorophenyl)-N-methylcarbamoylmethyloxy]phenyl]-N-(3-methylbutyl)-carbamoylmethyl]ureido]phenyl]acetic acid (1–277)

(64) (±)-2-[3-[3-[N-[3-[N-(3,5-Difluorophenyl)-N-methylcarbamoylmethyloxy]phenyl]-N-(N-methyl-N-phenylcarbamoylmethyl)carbamoylmethyl]ureido] phenyl]-propionic acid (1–279)

(65) 2-[3-[3-[N-[3-[N-Methyl-N-(3,5-dimethylphenyl) carbamoylmethyloxy]phenyl]-N-(3-methyl-2-butenyl) carbamoylmethyl]ureido]phenyl]acetic acid (1–280)

(66) 2-[3-[3-[N-(2-Cyclopentylethyl)-N-[2-[N-methyl-N-(3,5-dimethylphenyl)carbamoylmethyloxy]phenyl]-carbamoylmethyl]ureido]phenyl]acetic acid (1–284)

(67) 2-[3-[3-[N-(2-Cyclohexylethyl)-N-[2-(N-methyl-N-phenylcarbamoylmethyloxy)phenyl]carbamoylmethyl] ureido]-phenyl]acetic acid (1–285)

(68) 2-[3-[3-[N-(3-Cyclohexylpropyl)-N-[2-(N-methyl-N-phenylcarbamoylmethyloxy)phenyl] carbamoylmethyl]ureido]-phenyl]acetic acid (1–286)

(69) 2-[3-[3-[N-Cyclopentylmethyl-N-[2-[N-methyl-N-(3,5-dimethyl)phenylcarbamoylmethyloxy]phenyl]-carbamoylmethyl]ureido]phenyl]acetic acid (1–287)

(70) 2-[3-[3-[N-Cyclopentylmethyl-N-[2-(N-methyl-N-phenylcarbamoylmethyloxy)phenyl]carbamoylmethyl] ureido]-phenyl]acetic acid (1–288)

(71) 2-[3-[3-[N-[2-[N-(3-Chlorophenyl)-N-methylcarbamoylmethyloxy]phenyl]-N-cyclopentylmethyl]-carbamoylmethyl]ureido]phenyl] acetic acid (1–289)

(72) 2-[3-[3-[N-Cyclobutylmethyl-N-[2-(N-methyl-N-phenylcarbamoylmethyloxy)phenyl]carbamoylmethyl] ureido]-phenyl]acetic acid (1–290)

(73) 2-[3-[3-[N-Cyclobutylmethyl-N-[2-[N-methyl-N-(3,5-dimethylphenyl)carbamoylmethyloxy]phenyl] carbamoylmethyl]-ureido]phenyl]acetic acid (1–291)

(74) 2-[3-[3-[N-[2-[N-(3-Chlorophenyl)-N-methylcarbamoylmethyloxylphenyl]-N-cyclobutylmethylcarbamoylmethyl]ureido]phenyl] acetic acid (1–292)

(75) 2-[3-[3-[N-Cycloheptylmethyl-N-[2-(N-methyl-N-phenylcarbamoylmethyloxy)phenyl]carbamoylmethyl] ureido]-phenyl]acetic acid (1–293)

(76) 2-[3-[3-[N-[2-[N-(3-Chlorophenyl)-N-methylcarbamoylmethyloxy]phenyl]-N-cycloheptylmethylcarbamoylmethyl]ureido]phenyl] acetic acid (1–294)

(77) 2-[3-[3-[N-Butyl-N-[2-(N-methyl-N-phenylcarbamoylmethyloxy)phenyl]carbamoylmethyl] ureido]-phenyl]acetic acid (1–295)

(78) 2-[3-[3-[N-Butyl-N-[2-[N-methyl-N-(3,5-dimethylphenyl)carbamoylmethyloxy]phenyl] carbamoylmethyl]-ureido]phenyl]acetic acid (1–296)

(79) 2-[3-[3-[N-Butyl-N-[2-[N-( 3-Chlorophenyl)-methylcarbamoylmethyloxy]phenyl]carbamoylmethyl] ureido]-phenyl]acetic acid (1–297)

(80) 2-[3-[3-[N-[2-[N-(2-Methoxyphenyl)-N-methylcarbamoylmethyloxy]phenyl]-N-(3-methylbutyl)-carbamoylmethyl]ureido]phenyl]acetic acid (1–310)

(81) 2-[3-[3-[N-[2-[N-(3-Methoxyphenyl)-N-methylcarbamoylmethyloxy]phenyl]-N-(3-methylbutyl)-carbamoylmethyl]ureido]phenyl]acetic acid (1–311)

(82) 2-[3-[3-[N-[2-[N-(3,5-Dichlorophenyl)-N-methylcarbamoylmethyloxy]phenyl]-N-(3-methylbutyl)-carbamoylmethyllureido]phenyl]acetic acid (1–313)

(83) 2-[3-[3-[N-[2-[N-(3,5-Dimethoxyphenyl)-N-methylcarbamoylmethyloxy]phenyl]-N-(3-methylbutyl)-carbamoylmethyl]ureido]phenyl]acetic acid (1–314)

(84) 2-[3-[3-[N-[2-[N-(3-Fluorophenyl)-N-methylcarbamoylmethyloxy]phenyl]-N-(3-methylbutyl)-carbamoylmethyl]ureido]phenyl]acetic acid (1–316)

(85) (±)-2-[3-[3-[N-[2-[N-(3-Methoxyphenyl)-N-methylcarbamoylmethyloxy]phenyl]-N-(3-methylbutyl)-carbamoylmethyl]ureido]phenyl] propionic acid (1–317)

(86) (+)-2-[3-[3-[N-[2-[N-(3,5-Dimethoxyphenyl)-N-methylcarbamoylmethyloxy]phenyl]-N-(N-methyl-N-phenylcarbamoylmethyl)carbamoylmethyl]ureido] phenyl]-propionic acid (1–329)

(87) 2-[3-[3-[N-[2-[N-(3,5-Dimethoxyphenyl)-N-methylcarbamoylmethyloxy]phenyl]-N-(N-methyl-N-phenylcarbamoylmethyl)carbamoylmethyl]ureido] phenyl]acetic acid (1–330)

(88) (±)-2-[3-[3-[N-[2-[N-(2,5-Dimethoxyphenyl)-N-methylcarbamoylmethyloxy]phenyl]-N-(N-methyl-N-phenylcarbamoylmethyl)carbamoylmethyl]ureido] phenyl]-propionic acid (1–331)

(89) (±)-2-[3-[3-[N-[3-[N-(3-Methoxyphenyl)-N-methylcarbamoylmethyloxy]phenyl]-N-(N-methyl-N-phenylcarbamoylmethyl)carbamoylmethyl]ureido] phenyl]-propionic acid (1–335)

(90) 2-[3-[3-[N-[3-[N-(3-Methoxyphenyl)-N-methylcarbamoylmethyloxy]phenyl]-N-(N-methyl-N-phenylcarbamoylmethyl)carbamoylmethyl]ureido] phenyl]acetic acid (1–336)

(91) 3-[3-[N-(N-Methyl-N-phenylcarbamoylmethyl)-N-[3-(N-methyl-N-phenylcarbamoylmethyloxy)phenyl] carbamoylmethyl]ureido]benzoic acid (1–346)

(92) N-Methyl-N-phenyl-2-[2-[N-(N-methyl-N-phenyl-carbamoylmethyl)-N-[2-[3-(3-methylphenyl)ureido] acetyl]-amino]phenoxy]acetamide (1–347)

(93) 2-[3-[3-[N-(4-Ethylhexyl)-N-[2-(N-methyl-N-phenylcarbamoylmethyloxy)phenyl]carbamoylmethyl] ureido]-phenyl]acetic acid (1–369)

(94) (±)-2-[3-[3-[N-[2-[N-Methyl-N-(3,5-dimethylphenyl)carbamoylmethyloxylphenyl]-N-(3-methylpentyl)carbamoylmethyl]ureido]phenyl]acetic acid (1–371)

(95) (±)-2-[3-[3-[N-[2-[N-(3-Chlorophenyl)-N-methylcarbamoylmethyloxy]phenyl]-N-(3-methylpentyl)-carbamoylmethyl]ureido]phenyl]acetic acid (1–373)

(96) 2-[3-[3-[N-(3,3-Dimethyl-2-oxobutyl)-N-[2-(N-methyl-N-phenylcarbamoylmethyloxy)phenyl]carbamoylmethyl]-ureido]phenyl]acetic acid (1–377)

(97) 2-[3-[3-[N-[2-[N-(3-Chlorophenyl)-N-methylcarbamoylmethyloxy]phenyl]-N-(4-methylpentyl)-carbamoylmethyl]ureido]phenyl]acetic acid (1–379)

(98) (±)-2-[3-[3-[N-[2-(N-Methyl-N-phenylcarbamoylmethyloxy)phenyl]-N-(3-methylbutyl)-carbamoylmethyl]ureido]phenyl] propionic acid (1–381)

(99) (±)-2-[3-[3-[N-[2-[N-(3-Chlorophenyl)-N-methylcarbamoylmethyloxy]phenyl]-N-(4-methylpentyl)-carbamoylmethyl]ureido]phenyl] propionic acid (1–383)

(100) 2-[3-[3-[N-[2-(N-Methyl-N-phenylcarbamoylmethyloxy)phenyl]-N-(3,3-dimethylbutyl)-carbamoylmethyl]ureido]phenyl]acetic acid (1–389)

(101) (±)-2-[3-[3-[N-[2-[N-(3,5-Difluorophenyl)-N-methylcarbamoylmethyloxy]phenyl]-N-(3-methylpentyl)-carbamoylmethyl]ureido]phenyl]acetic acid (1–391)

(102) Calcium (±)-2-[3-[3-[N-[2-[N-(3-chlorophenyl)-N-methylcarbamoylmethyloxy]phenyl]-N-(3-methylbutyl)-carbamoylmethyl]ureido]phenyl] propionate (1–392)

(103) 3-[3-[N-[2-(N-Methyl-N-phenylcarbamoylmethyloxy)phenyl]-N-(3-methylbutyl)carbamoylmethyl]ureido]benzoic acid (1–400)

(104) (±)-2-[3-[3-[N-[2-[N-(3-Chlorophenyl)-N-methylcarbamoylmethyloxy]phenyl]-N-(N-methyl-N-phenylcarbamoylmethyl)carbamoylmethyl]ureido] phenyl]-propionic acid (1–403)

(105) (+)-2-Methoxy-2-[3-[3-[N-[3-[N-methyl-N-(3,5-dimethylphenyl)carbamoylmethyloxy]phenyl]-N-(N-methyl-N-phenylcarbamoylmethyl)carbamoylmethyl]ureido]phenyl]acetic acid (1–425)

(106) 3-[3-[N-[2-[N-(3,5-Difluorophenyl)-N-methylcarbamoylmethyloxy]phenyl]-N-(3-methylbutyl)-carbamoylmethyl]ureido]benzoic acid (1–433)

(107) Methyl (S)-(+)-2-[3-[3-[N-[2-(N-methyl-N-phenylcarbamoylmethyloxy)phenyl]-N-(3-methylpentyl)-carbamoylmethyl]ureido]phenyl]acetate (1–434)

(108) (S)-(+)-2-[3-[3-[N-[2-(N-Methyl-N-phenylcarbamoylmethyloxy)phenyl]-N-(3-methylpentyl)-carbamoylmethyl]ureido]phenyl]acetic acid (1–435)

Methods for preparing the compounds of the present invention will next be described.

Among the compounds of the present invention, those having an asymmetric carbon in the molecule may be prepared by ultimately performing optical resolution using known techniques or by performing optical resolution of intermediates using known techniques, thereby obtaining optically active compounds. When optically active starting materials are used, optically active final compounds can be obtained.

The compounds of the present invention may be prepared, for example, by any of the following methods A through N.

Method A:

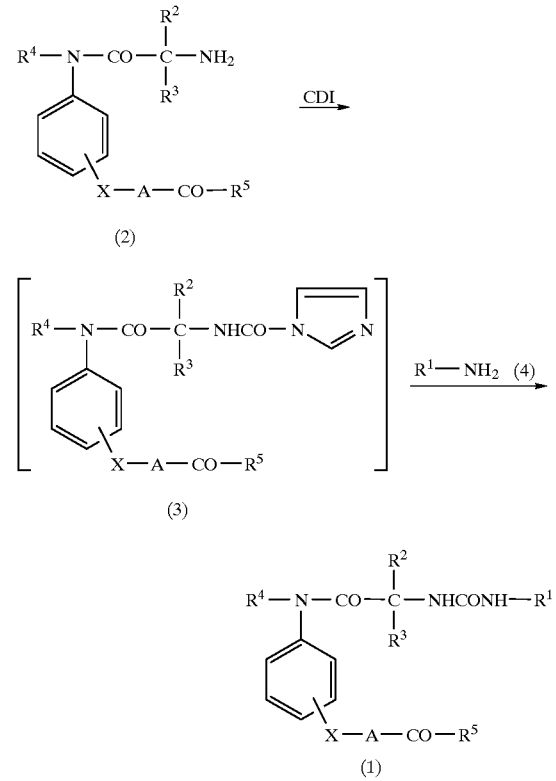

wherein $R^1$, $R^2$, $R^3$, $R^4$, $R^5$, X, and A have the same meanings as defined above, and CDI stands for N,N'-carbonyl diimidazole. If any of the compounds involved in the above reaction has one or more substituents which may affect the reaction, they must be protected using suitable protective groups commonly used in the synthetic chemistry which remain unaffected by the reaction prior to the reaction.

Briefly, compound (1) of the present invention can be prepared by reacting a compound (2) with N,N'-carbonyl diimidazole (CDI) to yield a compound (3), and subsequently, reacting the compound (3), being separated or unseparated, with an amine derivative (4).

The reaction may be carried out by reacting compound (2) with CDI in, for example, an inert solvent such as tetrahydrofuran or N,N-dimethylformamide at 0–60° C., preferably at room temperature, to yield an intermediate, imidazolide (3), and subsequently by refluxing the imidazolide (3), without being separated, together with amine derivative (4) with heat in toluene.

Method B:

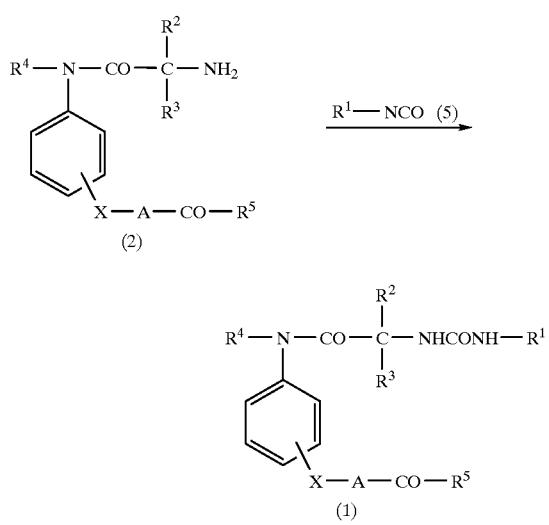

wherein $R^1$, $R^2$, $R^3$, $R^4$, $R^5$, X, and A have the same meanings as defined above. If any of the compounds involved in the above reaction has one or more substituents which may affect the reaction, they must be protected using suitable protective groups commonly used in the synthetic chemistry which remain unaffected by the reaction prior to the reaction.

Briefly, compound (1) of the present invention can be prepared by reacting a compound (2) with an isocyanate derivative (5).

If $R^1$ has a protective carboxyl group like alkoxycarbonylalkylphenyl, or if $R^1$ has no reactive group, the above reaction scheme may be directly carried out. On the other hand, if $R^1$ has a free carboxy group, the carboxy group is preferably protected by, for example, an ester residue in advance.

This reaction may be carried out by condensing a compound (2) and an isocyanate derivative (5) in an inert solvent such as tetrahydrofuran at $-10°$ C.–$60°$ C., preferably at room temperature.

Method C:

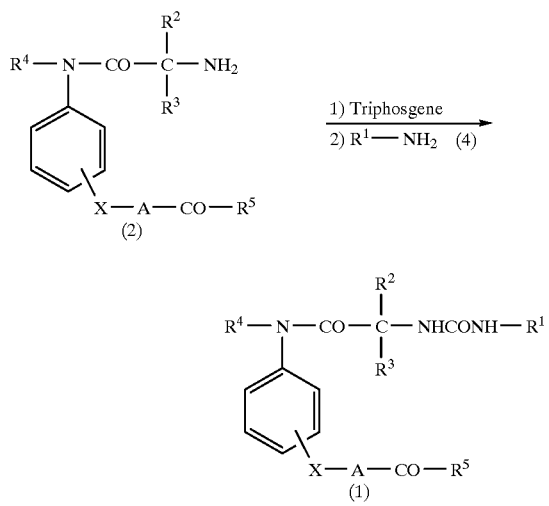

wherein $R^1$, $R^2$, $R^3$, $R^4$, $R^5$, X, and A have the same meanings as defined above. If any of the compounds involved in the above reaction has one or more substituents which may affect the reaction, they must be protected using suitable protective groups commonly used in the synthetic chemistry which remain unaffected by the reaction prior to the reaction.

Briefly, compound (1) of the present invention can be prepared by reacting a compound (2) with triphosgene and subsequently with an amine derivative (4).

This reaction may be carried out by first reacting a compound (2) with triphosgene in an inert solvent such as chloroform in the presence of a base such as triethylamine or pyridine at $-78°$ C.–$-50°$ C., preferably at $-20°$ C. to room temperature, and subsequently, adding an amine derivative (4) to the resulting mixture to cause a reaction.

Method D:

Compound (1) in which $R^4$ is a phenylalkyl group which may have a substituent on the alkyl group or benzene ring may also be prepared by the following method.

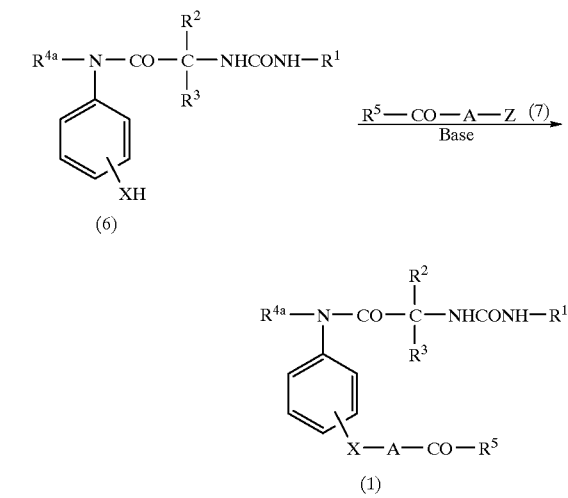

wherein $R^{4a}$ represents a phenylalkyl group which may have a substituent on the alkyl group or benzene ring, $R^1$, $R^2$, $R^3$, $R^5$, A, X, and Z have the same meanings as defined above. If any of the compounds involved in the above reaction has one or more substituents which may affect the reaction, they must be protected using suitable protective groups commonly used in the synthetic chemistry which remain unaffected by the reaction prior to the reaction.

Briefly, compound (1) of the present invention can be prepared by reacting a compound (6) with a compound (7). This reaction may be carried out by reacting compound (6) with compound (7) in a solvent such as N,N-dimethylformamide in the presence of a base such as potassium carbonate or sodium carbonate at 50–90° C., preferably at 60–70° C.

Method E:

Compound (1) in which $R^5$ is a group $—N(R^6)(R^7)$, at least one of $R^6$ and $R^7$ is a phenyl group having a substituent and the substituent is a hydroxyl group may also be prepared by reductively removing the benzyl group of a compound in which the substituent on phenyl is benzyloxy on the benzene ring. This may be done by catalytic hydrogenation. Under normal circumstances, the reaction may be carried out in a hydrogen gas atmosphere of 1 atm at room temperature in the presence of a palladium-on-carbon catalyst. However, it is also possible to perform the reaction with the application of heat and pressure. The solvents generally used are methanol, ethanol, ethyl acetate, or their mixtures. Other solvents may also be used so far as they do not affect the reaction.

Method F:

Compound (1) in which $R^1$ is phenyl having a substituent and the substituent is tetrazolyl may also be prepared by treating a compound in which the substituent on phenyl is cyano with a reaction mixture of aluminum chloride and sodium azide in N,N-dimethylformamide at 70–110° C., preferably 90–100° C.

Method G:

Compound (1) in which $R^1$ is phenyl having a substituent and the substituent is hydroxyalkyl may also be prepared by reducing a compound in which the substituent on phenyl is acyl using sodium borohydride in a solvent such as methanol, ethanol, chloroform, or dichloromethane. As reducing agents used in this reaction, other reducing agents which affect ketones or aldehydes only may also be useful.

Method H:

Compound (1) in which $R^1$ is phenyl having a substituent and the substituent is hydroxyimino, hydroxyiminoalkyl, alkoxyimino, or alkoxyiminoalkyl may also be prepared by reacting a compound in which the substituent on phenyl is acyl with hydroxylamine hydrochloride or alkoxyamine hydrochloride in a solvent such as methanol or ethanol in the presence of an excessive amount of a base such as pyridine at 10–50° C., preferably at room temperature.

Method I:

Compound (1) in which $R^5$ is hydroxy may also be prepared by reacting a compound (1) in which $R^5$ is alkoxyl with an acid or an alkali. Briefly, compound (1) in which $R^5$ is hydroxy may be prepared by hydrolyzing a compound (1) in which $R^5$ is methoxy or ethoxy using an aqueous alkali hydroxide solution such as an aqueous sodium hydroxide solution in a solvent such as methanol, ethanol, or tetrahydrofuran. Also, compound (1) in which $R^5$ is hydroxy may be prepared by treating a compound (1) in which $R^5$ is tertiary butoxy with an acid, preferably trifluoroacetic acid, without a solvent or in a solvent such as chloroform at a temperature between 0° C. and room temperature.

Method J:

Compound (1) in which $R^5$ is a group $—N(R^6)(R^7)$ may also -be prepared by reacting a compound (1) in which $R^5$ is hydroxy with primary or secondary amine corresponding to the group $—N(R^6)(R^7)$ in an inert solvent such as dichloromethane, chloroform, tetrahydrofuran, or ethyl acetate in the presence of a condensing agent such as N,N'-dicyclohexylcarbodiimide or 1-ethyl-3-(3-dimethylaminopropyl)carbodiimide hydrochloride at 0–40° C. In the present reaction, when 1-ethyl-3-(3-dimethylaminopropyl)carbodiimide hydrochloride is used as a condensing agent, a base in an amount that suffices for neutralizing hydrochloric acid is needed. To this end, under normal circumstances, an excessive amount of 4-dimethylaminopyridine may be added. As condensing agents, other condensing agents that are routinely used for forming an amide bond can also be used.

Method K:

Compound (1) in which $R^5$ is a group $—N(R^6)(R^7)$, either one of $R^6$ or $R^7$ is a hydrogen atom, and the other is a hydrogen atom, a methyl group, or an ethyl group may be prepared by reacting a compound (1) in which $R^5$ is methoxy or ethoxy with concentrated ammonia water, an aqueous solution of monomethylamine, or an aqueous solution of monoethylamine without use of a solvent or in a solvent such as methanol, ethanol, or tetrahydrofuran at room temperature.

Method L:

Compound (1) in which $R^1$ is phenyl having a substituent and the substituent is alkoxycarbonylalkyl group may be prepared by reacting a compound (1) in which $R^1$ is phenyl which has been substituted by carboxyalkyl with dialkylpyrocarbonate in tetrahydrofuran in the presence of 4-dimethylaminopyridine at 10–50° C., preferably at room temperature. In the present invention, the amount of alkoxyl group in the resulting alkoxycarbonyl alkyl group differs depending on the species of the alkyl group in the dialkylpyrocarbonate used in the reaction. Namely, if dimethylpyrocarbonate is used, compound (1) in which $R^1$ is a methoxycarbonylalkyl-substituted phenyl group can be obtained.

Method M:

By refluxing with heat a compound (1) in which $R^1$ is a phenyl group which may have a substituent and the substituent is an alkoxycarbonylalkyl group in alcohol in the presence of titanium (IV) isopropoxide, it is possible to convert the compound (1) into a compound (1) in which $R^1$ is a phenyl group substituted by an alkoxycarbonylalkyl group, which group corresponds to the alcohol (with the case where methanol is used as the alcohol being excluded). For example, by refluxing, with heat, a compound in which $R^1$ is a phenyl group substituted by a methoxycarbonylalkyl group in isopropanol in the presence of titanium (IV) isopropoxide, a compound (1) in which $R^1$ has been substituted by an isopropoxycarbonylalkyl group can be prepared.

Method N:

When a compound (1) in which $R^1$ is a phenyl group which has been substituted by an alkoxycarbonyl group, alkoxyalkyl group, or an alkoxyalkyloxy group is processed using an acid or an alkali, it is possible to obtain a compound (1) in which $R^1$ is a phenyl group which may have a substituent and the substituent is a carboxyl group, carboxyalkyl group, or a carboxyalkyloxy group. In order to obtain a compound (1) in which the alkoxyl group is a tertiary butyl group, an acid, preferably trifluoroacetic acid, may be used in the presence of a solvent such as dichloromethane or in the absence of a solvent. In order to obtain a compound (1) in which the alkoxyl group is another alkyl group, an aqueous alkali hydroxide solution such as an aqueous NaOH solution may be used. Compound (1) having a carboxyl group can be converted into a corresponding carboxylic acid salt by processing with an equimolar amount of an alkali hydroxide.

Compound (2) used in Methods A, B, and C above may be prepared, for example, in accordance with the following reaction scheme.

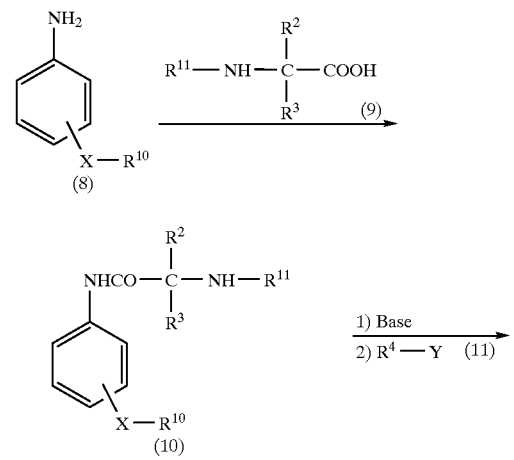

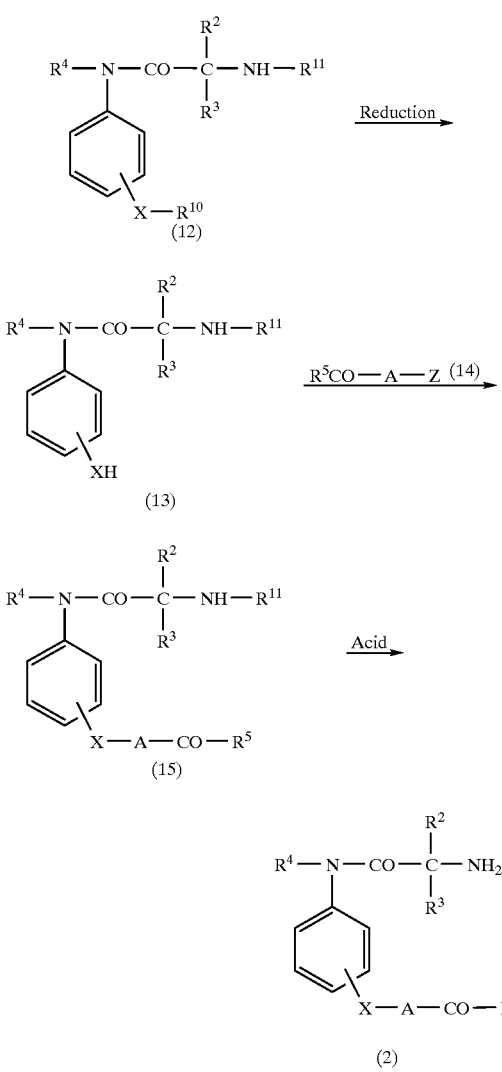

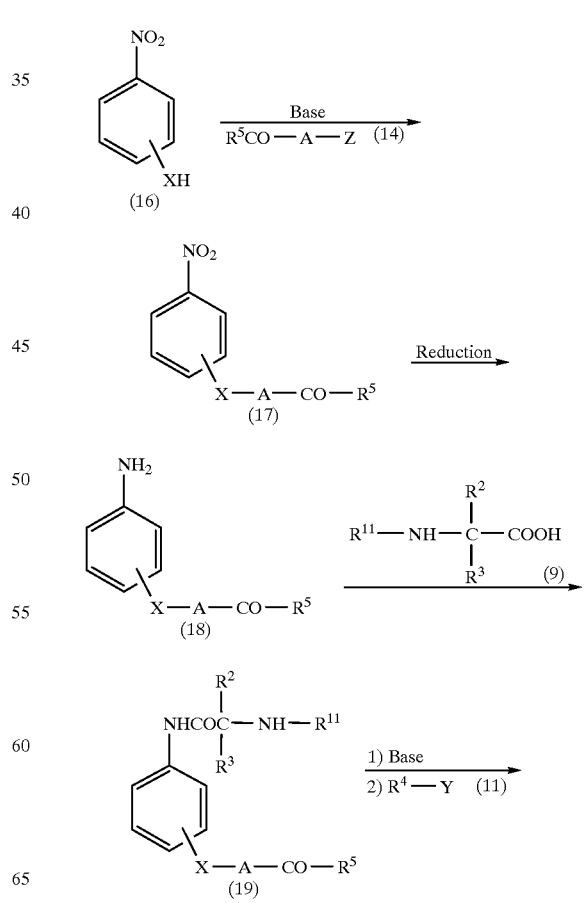

wherein $R^{10}$ represents a protective group for oxygen or sulfur which may be removed by a reduction reaction, $R^{11}$ represents an amino protective group which can be removed by an acid, Y and Z each independently represent a halogen atom, and $R^2$, $R^3$, $R^4$, $R^5$, X, and A have the same meanings as defined above. If any of the compounds involved in the above reaction has one or more substituents which may affect the reaction, they must be protected using suitable protective groups commonly used in the synthetic chemistry which remain unaffected by the reaction prior to the reaction.

As protective groups for oxygen and sulfur in the starting compound (8), benzyl and benzhydryl are preferred. As amino protective groups represented by $R^{11}$, tertiary butoxycarbonyl is preferred among others. As halogen atoms represented by Y and Z, bromine, chlorine, and iodine are preferred.

The reaction of compounds (8) and (9) may be carried out, for example, in an inert solvent such as dichloromethane, chloroform, tetrahydrofuran, or ethyl acetate in the presence of a condensing agent such as N,N'-dicyclohexylcarbodiimide or 1-ethyl-3-(3-dimethylaminopropyl)carbodiimide hydrochloride at a temperature between 0° C. and 40° C. In the present invention, when 1-ethyl-3-(3-dimethylaminopropyl)carbodiimide hydrochloride is used as a condensing agent, a base in an amount that suffices for neutralizing hydrochloric acid is needed. To this end, under normal circumstances, an excessive amount of 4-dimethylaminopyridine may be added.

In order to prepare a compound (12) from a compound (10), compound (10) is first reacted with a base such as sodium hydride or potassium hydride in an inert solvent such as tetrahydrofuran at 30–60° C., preferably 50–60° C., and subsequently, compound (11) is allowed to react while cooling.

Compound (13) may be prepared by removing a protective group for $R^{10}$ in compound (10) by a routine catalytic hydrogenation method. Solvents which are generally used for this purpose are ethanol, methanol, tetrahydrofuran, ethyl acetate, or a mixture thereof. As catalysts, palladium-on-carbon is generally employed. The reaction is generally allowed to proceed at room temperature under 1 atm. However, it may also be carried out with heating and pressurizing.

Compound (15) may be prepared by reacting a compound (14) with a compound (13) in N,N-dimethylformamide in the presence of a base such as potassium carbonate or sodium carbonate at a temperature between room temperature and 70° C., preferably between 50° C. and 70° C.

Compound (2) may be prepared by treating a compound (15) with an acid, preferably trifluoroacetic acid, in a solvent such as dichloromethane between 0° C. and room temperature.

The intermediate compound (15) may also be prepared according to the following reaction scheme.

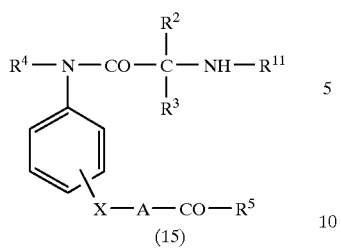

(15)

wherein $R^2$, $R^3$, $R^4$, $R^5$, $R^{11}$, A, X, Y, and Z have the same meanings as defined above. If any of the compounds involved in the above reaction has one or more substituents group which may affect the reaction, they must be protected using suitable protective groups commonly used in the synthetic chemistry which remain unaffected by the reaction prior to the reaction.

Compound (17) may be prepared by reacting a compound (16) with a compound (14) in N,N-dimethylformamide in the presence of a base such as potassium carbonate or sodium carbonate at a temperature between room temperature and 70° C., preferably between 50° C. and 70° C.

Compound (18) may be prepared by catalytically hydrogenating compound (17) using ethanol, methanol, tetrahydrofuran, or a mixture thereof as a solvent and in the presence of a catalyst such as palladium-on-carbon or Raney nickel. If X in compound (17) is S, the catalyst is preferably palladium-on-carbon. Under normal circumstances, the reaction is allowed to proceed at room temperature. It is also possible to perform the reaction with the application of heat. The pressure of a hydrogen gas under which the reaction is carried out is normally 1 atm. However, pressure may be applied. In this nitro-reducing reaction, other known methods for reducing a nitro group may also be used.

Compound (19) may be obtained by reacting compounds (18) and (9) in an inert solvent such as dichloromethane, chloroform, tetrahydrofuran, or ethyl acetate in the presence of a condensing agent such as N,N'-dicyclohexylcarbodiimide or 1-ethyl-3-(3-dimethylaminopropyl)carbodiimide hydrochloride at a temperature between 0° C. and 40° C. In the present invention, when 1-ethyl-3-(3-dimethylaminopropyl)carbodiimide hydrochloride is used as a condensing agent, a base in an amount that suffices for neutralizing hydrochloric acid is needed. To this end, under normal circumstances, an excessive amount of 4-dimethylaminopyridine may be added.

In order to prepare a compound (15) from a compound (19), compound (19) is first reacted with a base such as sodium hydride or potassium hydride in an inert solvent such as tetrahydrofuran at 30–60° C., preferably 50–60° C., and subsequently, compound (11) is allowed to react at a temperature between −30° C. and room temperature, preferably with cooling on ice.

A starting material (6) for preparing a compound (1) in which $R^4$ is a phenylalkyl group which may have a substituent on the alkyl group or benzene ring may be prepared, for example, in accordance with the following reaction scheme.

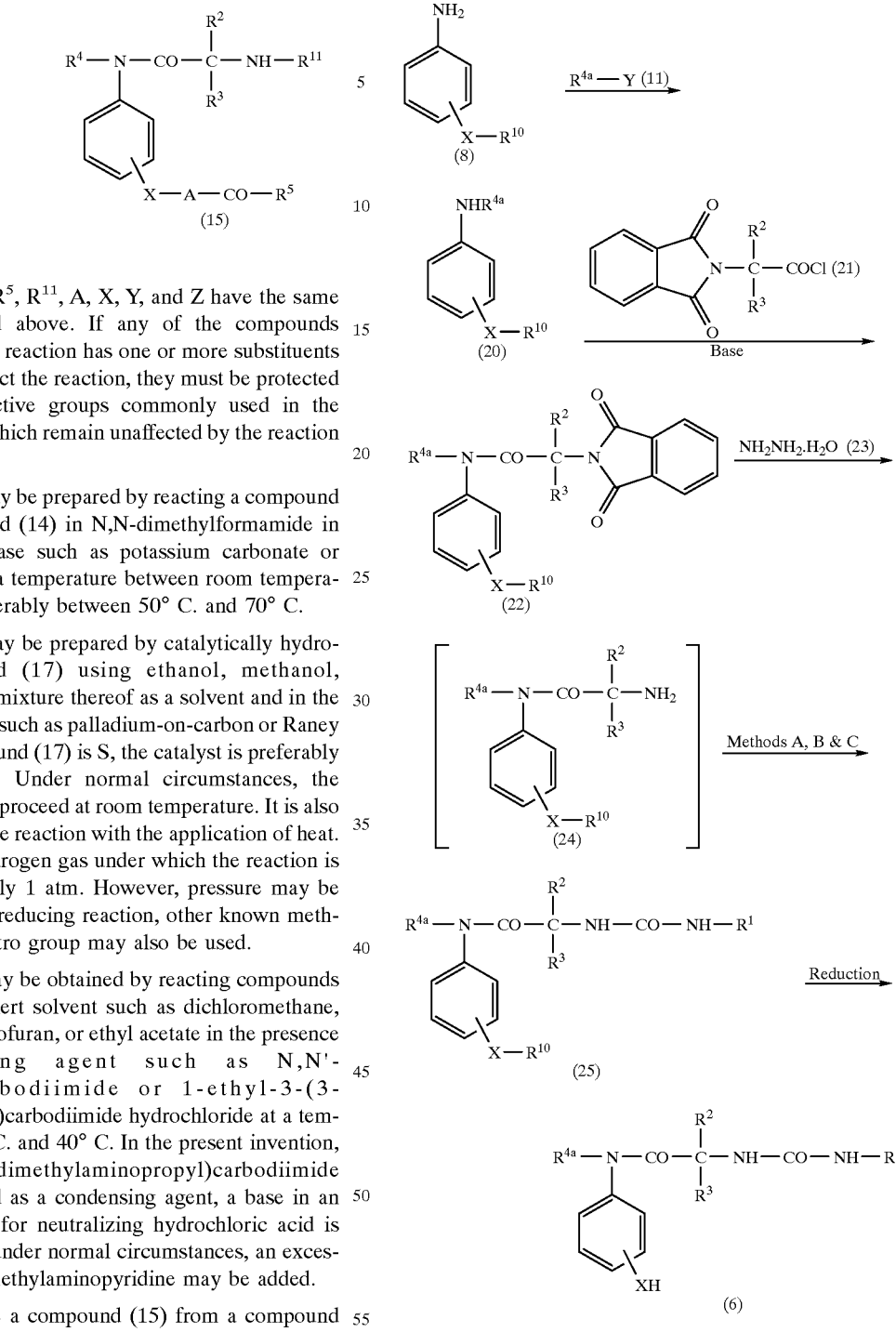

wherein $R^{4a}$ is a phenylalkyl group which may have a substituent on the alkyl group or benzene ring, and $R^1$, $R^2$, $R^3$, X, and $R^{10}$ have the same meanings as defined above. If any of the compounds involved in the above reaction has one or more substituents which may affect the reaction, they must be protected using suitable protective groups commonly used in the synthetic chemistry which remain unaffected by the reaction prior to the reaction.

Compound (20) may be prepared by reacting compound (8) and compound (11) in a solvent such as N,N-dimethylformamide in the presence of a base such as potassium carbonate or sodium carbonate at a temperature between room temperature and 80° C.

Compound (22) may be prepared by an acylation method which is routinely used for acylating amines. Briefly, compound (22) may be prepared by reacting compounds (20) and (21) in an inert solvent such as dichloromethane or chloroform in the presence of a base such as triethylamine at a temperature between 0° C. and 50° C., preferably at room temperature.

Compound (25) may be prepared by first reacting a compound (22) and a hydrazine monohydrate (23) in a solvent mixture of methanol and chloroform at a temperature between 10° C. and 60° C., preferably at room temperature, to yield a compound (24) then subjecting the compound (24) to the above-described methods A, B, or C after it is separated or not separated.

Compound (6) may be prepared by subjecting a compound (25) to a routine catalytic hydrogenation. Solvents which are generally used in the reduction reaction are ethanol, methanol, tetrahydrofuran, ethyl acetate, or a mixture thereof. Other solvents may also be used. As catalysts, palladium-on-carbon such as 5% palladium-on-carbon is ordinarily used. The reaction is usually carried out at room temperature and under 1 atm. However, it may also be performed with the application of heat and pressure.

Compound (20) may also be prepared in accordance with the following reaction scheme.

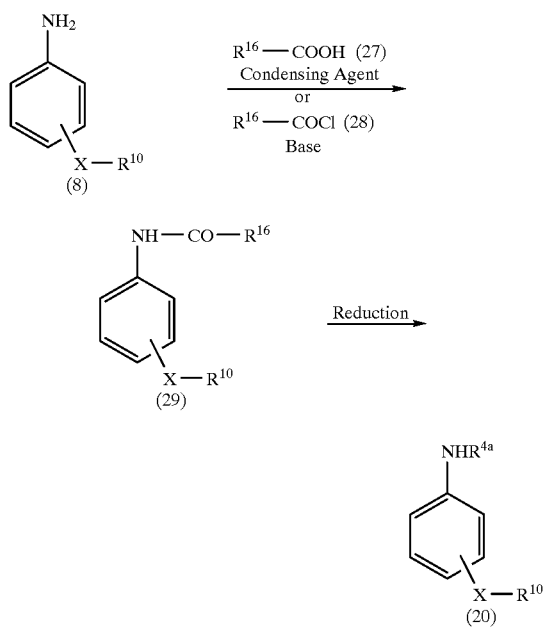

wherein $R^{4a}$ represents a phenylalkyl group which may have a substituent on the alkyl group or benzene ring, $R^{16}$ represents a group which is obtained by removing a methylene group from $R^{4a}$, and $R^{10}$ and X have the same meanings as defined above.

Compound (29) may be prepared by carrying out a routine reaction for forming an amide bond using a compound (8) as a starting material. Briefly, compound (29) may be prepared by reacting compounds (8) and (27) in an inert solvent such as chloroform in the presence of a condensing agent such as N,N'-dicyclohexylcarbodiimide or 1-ethyl-3-(3-dimethylaminopropyl)carbodiimide hydrochloride at a temperature between 0° C. and 40° C. In the present invention, when 1-ethyl-3-(3-dimethylaminopropyl)carbodiimide hydrochloride is used as a condensing agent, a base in an amount that suffices for neutralizing hydrochloric acid is needed. To this end, under normal circumstances, an excessive amount of 4-dimethylaminopyridine may be added. As condensing agents, other agents generally used for forming an amide bond may also be used.

Compound (29) may also be prepared by reacting a compound (8) and an acid chloride (28). That is, compound (8) and acid chloride (28) are allowed to react in an inert solvent such as chloroform or dichloromethane in the presence of a base such as pyridine or triethylamine at a temperature between O.C and room temperature.

Compound (20) may be prepared by reducing a compound (29) in a solvent such as tetrahydrofuran using a reducing agent such as a borane-tetrahydrofuran complex at room temperature. In the present reaction, other reducing agents (such as aluminum lithium hydride) which reduce an amide to an amine. Moreover, heat may be applied during reaction.

Among a variety of starting compounds (15), those in which $R^5$ is alkoxy may also be prepared, for example, in accordance with the following reaction scheme.

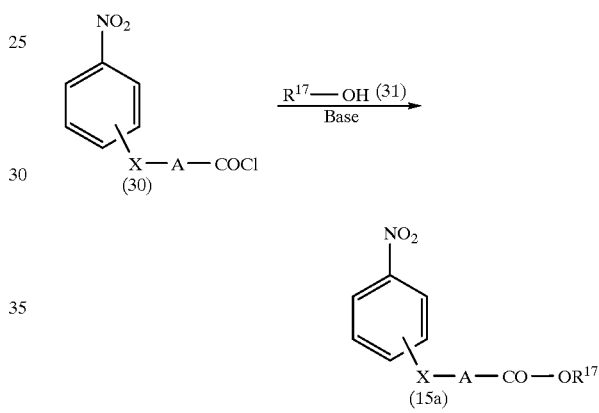

wherein $R^{17}$ represents an alkyl group, and X and A have the same meanings as described above.

In detail, the compound (15a) may be prepared by reacting compounds (30) and (31) in an inert solvent such as chloroform or dichloromethane in the presence of a base such as triethylamine or pyridine at a temperature between 0C and 40° C., preferably at room temperature. Synthesis of compound (30) which is an acid chloride may be carried out using a corresponding carboxylic acid as a starting material and in accordance with a routine method for preparing an acid chloride.

Compound (7) ($R^5CO$—A—Z) in which $R^5$ is a group —N($R^6$)($R^7$), either one of $R^6$ or $R^7$ is an alkyl group, and the other is a heterocyclic aromatic ring or a phenyl group which may have a substituent may also be prepared in accordance with the following reaction scheme:

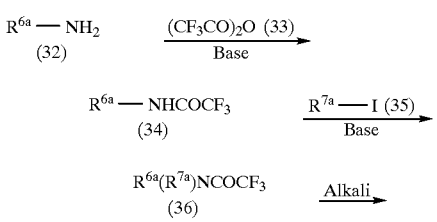

-continued

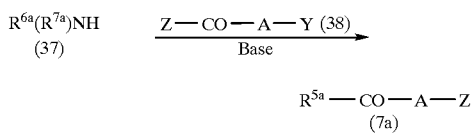

wherein $R^{5a}$ represents a group —$N(R^{6a})(R^{7a})$, $R^{6a}$ represents a phenyl group which may have a substituent or a heterocyclic aromatic ring, $R^{7a}$ represents an alkyl group, Y and Z are halogen atoms and preferably chlorine or bromine and are usually of the identical species, A has the same meanings as defined above, and the substituent in a phenyl group or in a heterocyclic aromatic ring having a substituent is one or more substituents selected from the group consisting of a halogen atom, an alkyl group, an alkoxy group, an alkylthio group, a benzyloxy group, a cyano group, a trifluoromethyl group, and a nitro group.

Compound (34) may be prepared by reacting a compound (32) and trifluoroacetic anhydride (33) in the presence of a base such as pyridine at a temperature between 0° C. and 40° C., preferably at room temperature. Although this reaction is normally carried out without using a solvent, an inert solvent such as chloroform may be used.

Compound (36) may be prepared by reacting compounds (34) and (35) in a solvent such as N,N'-dimethylformamide in the presence of a base such as potassium carbonate or sodium carbonate at a temperature between 10° C. and 60° C., and preferably between 20° C. and 50° C.

Compound (37) may be prepared by removing a trifluoroacetyl group of compound (36) using a routine hydrolizing method. Briefly, compound (37) may be prepared by treating a compound (36) with an aqueous alkali hydroxide solution such as an aqueous 1N sodium hydroxide solution in a solvent such as tetrahydrofuran at room temperature. Other solvents such as methanol and ethanol are also advantageously used in this reaction.

Compound (7a) may be prepared by applying a routine acylating method for amines to a starting material, compound (37). Briefly, compound (7a) may be prepared by reacting compounds (37) and (38) in an inert solvent such as chloroform in the presence of a base at a temperature between 0° C. and 40° C. As the base, an organic base such as triethylamine or pyridine is commonly used, with pyridine being more preferred in the present reaction.

If any of the compounds used in the above reaction has a terminal ester, it may be converted into a corresponding carboxylic acid or a salt thereof by a method described hereinabove.

After the above-described reactions are completed, target compounds can be separated from the reaction mixtures and purified by routine methods such as recrystallization, any of a variety of chromatography procedures, or any suitable combination of these. Salts of the compound (1) of the present invention can be obtained by treating a free acid with an alkali hydroxide, etc., by routine methods, or by treating a free base with hydrochloric acid, etc., by routine methods.

The thus-obtained compounds (1) of the present invention and their salts and optical isomers of the compounds (1) and the salts have potent gastrin receptor binding inhibition or CCK-A receptor binding inhibition. Some of the compounds (1) exhibit selectivity toward the gastrin receptor and some other compounds (1) exhibit selectivity toward the CCK-A receptor.

As described hereinbefore, two types of CCK receptors are known: those which are found primarily within components of the digestive tract such as the pancreas or the biliary system (CCK-A receptor) and those which are found in the brain (CCK-B receptor). The CCK-A receptor is considered to significantly participate in motility of gastrointestinal tract and secretion of pancreatic juice, and the CCK-B receptor is considered to participate in psychic activities and appetite regulation in the cerebrum. Gastrin receptor which is primarily found in gastric mucosal cells (parietal cells) and is considered to be identical to CCK-B receptor participates in the control of gastric acid and pepsin secretion. Accordingly, binding inhibitors of these receptors are considered to be useful in the prevention and treatment of digestive tract diseases and central nervous system diseases which are closely connected to their respective peptide hormones.

Among the compounds (1) of the present invention, salts of compounds (1), and optical isomers of compounds (1) or salts of compounds (1), particularly preferred ones are those having potent gastrin receptor binding inhibition and exhibiting markedly higher affinity to gastrin receptors than to CCK-A receptors. Such compounds are useful as preventive and therapeutic agents for peptic ulcers, gastritis, rectal/colonic cancer, Zollinger-Ellison syndrome, and anxiety syndrome.

Medicines containing the compounds of the present invention may be prepared into injection preparations for intravenous injection, intramuscular injection, or for subcutaneous injection, and administered to subjects in need thereof by injection. Alternatively, they may be administered orally or transdermally. Intravenous administration and oral administration are preferred.

When the compounds of the present invention are used as medicines, the compounds of the invention are preferably formulated into pharmaceutical compositions containing the compounds and pharmaceutically acceptable carriers. As pharmaceutical compositions, there are compositions for oral administration and injection compositions. Compositions for oral administration include tablets, powders, granules, capsules, solutions, syrups, elixirs, and oil-base or water-base suspensions. When injection compositions are formulated, the compositions may include stabilizers, preservatives, solution adjuvants, etc.

The dose of the compounds of the present invention to a human subject varies depending on his disease, conditions, body weight, etc. In general, a dose of 1–1,000 mg/day, which is administered at a time or in several divided times, is preferred in cases of oral administration.

EXAMPLES

The present invention will next be described by way of referential examples and examples, which should not be construed as limiting the invention.

Referential Example 1

N-(2-Benzyloxyphenyl)-2-(N-tertiary butoxycarbonylamino)acetamide (S2)

2-Benzyloxyaniline (S1) (16.4 g), 4-dimethylaminopyridine (11.0 g), and N-tertiarybutoxycarbonylglycine (14.4 g) were dissolved in dichloromethane. To the resulting solution, 1-ethyl-3-(3-dimethylaminopropyl)carbodiimide hydrochloride (16.3 g) was added and stirred for 12 hours at room temperature. The reaction mixture was washed -successively with 1N HCl, saturated aqueous sodium hydrogencarbonate solution and brine, then dried over anhydrous magnesium sulfate. The solvent was distilled off under reduced pressure, obtaining 11.5 g of the compound S2 as white powder.

mp 80–82° C. $^1$H-NMR (CDCl$_3$)δ: 1.41 (9H, s), 3.91 (2H, d), 5.12 (2H, s), 5.18 (1H, brs), 6.93–7.03 (3H, m), 7.35–7.41 (5H, m), 8.37–8.38 (2H, m)

Referential Example 2

N-Methyl-N-phenyl-2-[N-(2-benzyloxyphenyl)-N-[2-(N-tertiarybutoxycarbonylamino)acetyl]amino]acetamide (S3)

Sodium hydride (60% in oil) (0.18 g) was suspended in tetrahydrofuran (20 ml). To the resulting suspension, compound S2 (1.1 g) in tetrahydrofuran (20 ml) was added with stirring under ice cooling. The mixture was stirred for 1.5 hours at 55–60° C. The reaction mixture was cooled and N-methyl-N-phenyl-2-bromoacetamide (1.8 g) in tetrahydrofuran (10 ml) was added. The resulting mixture was stirred for further 2 hours at room temperature. Insoluble matter was filtered off, and the filtrate was concentrated. The residue was partitioned between chloroform and 1N HCl. The organic layer was washed with brine and dried over anhydrous magnesium sulfate. The solvent was distilled off under reduced pressure, obtaining 1.1 g of the compound S3 as powder.

mp 168–170° C. $^1$H-NMR (CDCl$_3$)δ: 1.38 (9H, s), 3.27 (3H, s), 3.37 (1H, d), 3.56 (1H, dd) 3.80 (1H, dd), 4.78 (1H, d), 4.95 (1H, d), 5.00 (1H, d) 5.38 (1H, brs), 6.94–7.00 (2H, m), 7.12 (2H, m), 7.21–7.35 (6H, m), 7.37–7.43 (3H, m), 7.66–7.68 (1H, m)

Referential Example 3

N-Methyl-N-phenyl-2-[N-[2-(N-tertiary butoxycarbonylamino)acetyl]-N-(2-hydroxyphenyl)amino]acetamide (S4)

Compound S3 (41 g) and 5% palladium-on-carbon (50% wet) (8.15 g) were suspended in a mixture of tetrahydrofuranethanol (900 ml: 300 ml) and the resulting suspension was stirred for 2 hours in a hydrogen atmosphere of 1 atm. The catalyst was removed by filtration, and the filtrate was concentrated under reduced pressure. The residue was dissolved in chloroform, and the resulting solution was dried over anhydrous magnesium sulfate. The solvent was distilled off under reduced pressure, obtaining 32 g of the compound S4.

mp 185–188° C. $^1$H-NMR (CDCl$_3$)δ: 1.39 (9H, s), 3.30 (1H, d), 3.34 (3H, s), 3.56 (1H, dd) 3.80 (1H, dd), 4.74 (1H, d), 5.19 (1H, brs), 6.81 (1H, m) 6.91 (1H, m), 7.03 (1H, m), 7.23–7.33 (3H, m), 7.42–7.49 (3H, m), 10.6 (1H, s)

Referential Example 4

N-Methyl-N-phenyl-2-[2-[N-[2-(N-tertiary butoxycarbonylamino)acetyl]-N-(N-methyl-N-phenylcarbamoylmethyl)amino]phenoxy]acetamide (S5)

Compound S4 (50 g), N-methyl-N-phenyl-2-bromoacetamide (33 g), and anhydrous potassium carbonate (21 g) were dissolved in N,N-dimethylformamide (500 ml). The resulting solution was stirred at 65–70° C. for 2 days. The reaction mixture was poured into ice-water and extracted with ethyl acetate. The extract was washed with brine and dried over anhydrous magnesium sulfate. The solvent was distilled off, obtaining 56 g of the compound S5 as powder.

$^1$H-NMR (CDCl$_3$)δ: 1.37 (9H, s), 3.24 (3H, s), 3.27 (3H, s), 3.49–3.57 (2H, m) 3.76 (1H, dd), 4.35 (2H, s), 4.73 (1H, d), 5.38 (1H, s) 6.64 (1H, d), 6.96 (1H, t), 7.17–7.42 (11H, m), 7.70 (1H, d)

Referential Example 5

N-Methyl-N-phenyl-2-[2-[N-(2-aminoacetyl)-N-(N-methyl-N-phenylcarbamoylmethyl)amino]phenoxy]acetamide (S6)

Trifluoroacetic acid (20 ml) was added to compound S5 (2.0 g) in dichloromethane (30 ml) under ice cooling. The resulting mixture was stirred for 1 hour at the same temperature. The reaction mixture was concentrated under reduced pressure. Subsequently, the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 1.6 g of the compound S6 as powder.

$^1$H-NMR (CDCl$_3$)δ: 1.71 (2H, brs), 3.16 (2H, s), 3.24 (3H, s), 3.28 (3H, s), 3.44 (1H, d), 4.34 (2H, s), 4.78 (1H, d), 6.64 (1H, d), 6.97 (1H, t), 7.19–7.42 (11H, m), 7.68 (1H, d)

Referential Example 6

N-Methyl-N-phenyl-2-(2-nitrophenoxy)acetamide (S8)

2-Nitrophenol S7 (2.8 g), anhydrous potassium carbonate (4.1 g), and N-methyl-N-phenyl-2-bromoacetamide (4.5 g) were suspended in N,N-dimethylformamide (50 ml), and the resulting suspension was stirred at 65–70° C. for 3 hours. The reaction mixture was poured into ice-water and extracted with ethyl acetate. The extract was washed with water and brine, then dried over anhydrous magnesium sulfate. The solvent was distilled off, obtaining 5.4 g of the compound S8.

$^1$H-NMR (CDCl$_3$)δ: 3.31 (3H, s), 4.59 (2H, s), 6.97 (1H, d), 7.03 (1H, t), 7.24 (2H, d), 7.37–7.49 (4H, m), 7.81 (1H, d)

Referential Example 7

N-Methyl-N-phenyl-2-(2-aminophenoxy)acetamide (S9)

Compound S8 (5.0 g) was dissolved in a mixture of methanol (100 ml) and ethyl acetate (100 ml), and 5% palladium carbon (50% wt) (1.0 g) was added to the resulting solution. The solution was stirred for 30 minutes in a hydrogen atmosphere of 1 atm. The reaction mixture was filtered, and the solvent was distilled off under reduced pressure. The residue was dissolved in chloroform and dried over anhydrous magnesium sulfate. The solvent was distilled off under reduced pressure, obtaining 5.0 g of the compound S9 as an oily substance.

$^1$H-NMR (CDCl$_3$)δ: 3.31 (3H, s), 3.91 (2H, brs), 4.43 (2H, s), 6.59–6.63 (2H, m), 6.68(1H, d), 6.79 (1H, d), 7.21 (2H, dd), 7.36–7.46 (3H, m)

Referential Example 8

N-Methyl-N-phenyl-2-[2-[N-[2-(N-tertiary butoxycarbonylamino)acetyl]amino]phenoxy]acetamide (S10).

Compound S9 (5.0 g) and N-tertiarybutoxycarbonyl glycine (3.1 g) were dissolved in dichloromethane (100 ml). Subsequently, 1-ethyl-3-(3-dimethylaminopropyl)carbodiimide hydrochloride (4.0 g) and 4-dimethylaminopyridine (2.6 g) were added to the resulting solution, and the solution was stirred for 7 hours at room temperature. The solvent was distilled off under reduced pressure and the residue was partitioned between ethyl acetate and 1N HCl. The two layers were separated. The organic layer was washed sucessively with water, saturated aqueous sodium bicarbonate solution, water and brine, then dried over anhydrous magnesium sulfate. The solvent was distilled off under reduced pressure, obtaining 6.6 g of the compound S10 as powder.

$^1$H-NMR (CDCl$_3$)δ: 1.48 (9H, s), 3.30 (3H, s), 4.08 (2H, d), 4.43 (2H, s), 5.41 (1H, brs), 6.73 (1H, d), 6.95 (1H, t), 7.03 (1H, t), 7.18 (2H, d), 7.42–7.48 (3H, m), 8.29 (1H, d), 9.64 (1H, s)

Referential Example 9

N-Methyl-N-phenyl-2-[2-[N-[2-(N-tertiary butoxycarbonylamino)acetyl]-N-(N-methyl-N-phenylcarbamoylmethyl)amino]phenoxy]acetamide (S5)

Sodium hydride (60% in oil) (0.7 g) was added to a solution of compound S10 (6.0 g) in tetrahydrofuran (30 ml) under ice cooling, and the resulting mixture was stirred at 55–60° C. for 10 minutes. N-Methyl-N-phenyl-2-bromoacetamide (4.0 g) in tetrahydrofuran (20 ml) was added to the reaction mixture under ice cooling. The resulting mixture was stirred for 1 hour at room temperature. The reaction mixture was poured into ice-water and extracted with ethyl acetate. The extract was washed with water and brine, then dried over anhydrous magnesium sulfate. The solvent was distilled off under reduced pressure. Subsequently, the residue was washed with n-hexane/diethyl ether, obtaining 6.8 g of the compound S5 as powder.

Referential Example 10

N-(2,3-Dimethylphenyl)-2-(2-nitrophenoxy) acetamide (S12)

2-(2-Nitrophenoxy)acetic acid S11 (5.28 g) and 2,3-dimethylaniline (3.25 g) were dissolved in dichloromethane (100 ml). 1-Ethyl-3-(3-dimethylaminopropyl)carbodiimide hydrochloride (6.17g) and 4-dimethylaminopyridine (3.93 g) were added to the solution, and the solution was stirred overnight at room temperature. The reaction mixture was concentrated under reduced pressure, and the residue was dissolved in dichloromethane. The resulting solution was washed successively with 1N HCl saturated aqueous sodium hydrogencarbonate solution and brine, then dried over anhydrous magnesium sulfate. The solvent was distilled off under reduced pressure, obtaining 7.7 g of the compound S12.

$^1$H-NMR (CDCl$_3$)δ: 2.26 (3H, s), 2.33 (3H, s), 4.80 (2H, s), 7.04–8.09 (7H, m), 8.71 (1H, brs)

Referential Example 11

N-Methyl-N-(2,3-dimethylphenyl)-2-(2-nitrophenoxy)acetamide (S13)

Sodium hydride (60% in oil) (1.36 g) was suspended in tetrahydrofuran (100 ml). Compound S12 (7.71 g) in tetrahydrofuran (300 ml) was added to the suspension in a dropwise manner under ice cooling. The mixture was stirred at 55–60° C. for 1.5 hour. Methyl iodide (2.1 ml) was added to the reaction mixture, and the resulting mixture was stirred overnight at room temperature. The reaction mixture was poured into ice-water and extracted with chloroform. The extract was washed with water and brine then dried over anhydrous magnesium sulfate. The solvent was distilled off under reduced pressure, obtaining 8.07 g of the compound S13 as an oily substance.

$^1$H-NMR (CDCl$_3$)δ: 2.15 (3H, s), 2.33 (3H, s), 3.22 (3H, s), 4.38–4.56 (2H, dd), 6.96–7.83 (7H, m)

Referential Example 12

N-Methyl-N-(2,3-dimethylphenyl)-2-bromoacetamide (S15)

N-Methyl-2,3-dimethylaniline S14 (4.6 g) and triethylamine (5.0 ml) were dissolved in dichloromethane (50 ml). 2-Bromoacetyl bromide (3.0 ml) in dichloromethane (30 ml) was added to the resulting solution under ice cooling and the solution was stirred for 2 hours at room temperature. The reaction mixture was washed successively with 1N HCl, water and brine, then dried over anhydrous magnesium sulfate. The solvent was distilled off under reduced pressure, obtaining 8.4 g of the title compound as an oily substance.

$^1$H-NMR (CDCl$_3$)δ: 2.16(3H, s), 2.33 (3H, s), 3.22 (3H, s), 3.59 (2H, q), 7.05 (1H, d), 7.15 (1H, d), 7.20 (1H, t)

Referential Example 13

N-(3,5-Dichlorophenyl)-N-methyl-2-[3-[N-(2-aminoacetyl)-N-(N-methyl-N-phenylcarbamoylmethyl)amino]phenoxy]acetamide (S18):

In a manner similar to those described in Referential Examples 1 through 12, N-(3,5-dichlorophenyl)-N-methyl-2-[3-[N-(2-(N-tertiarybutoxycarbonylamino)acetyl]-N-(N-methyl-N-phenylcarbamoylmethyl)amino]phenoxy] acetamide (S40) (6.7 g) was obtained, and this compound was dissolved in dichloromethane (200 ml). Trifluoroacetic acid (100 ml) was added thereto under ice cooling and the resulting solution was stirred for 1 hour at the same temperature. The reaction mixture was concentrated under reduced pressure and the residue was dissolved in chloroform. The resulting solution was washed successively with saturated aqueous sodium hydrogencarbonate soltuion, water and brine, then dried over anhydrous magnesium sulfate. The solvent was distilled off under reduced pressure, obtaining 5.2 g of the compound 18 as powder.

$^1$H-NMR (CDCl$_3$)δ: 1.98 (2H, brs), 3.21 (2H, s), 3.29 (3H, s), 3.31 (3H, s), 4.06 (2H, s), 4.50 (2H, brs), 6.82 (1H, brs), 6.92 (1H, d), 7.17–7.42 (10H, m)

Referential Example 14

N-Methyl-N-(3,5-dimethylphenyl)-2-[3-[N-(2-aminoacetyl)-N-(N-methyl-N-phenylcarbamoylmethyl)amino]phenoxy]acetamide (S19)

In a manner similar to those described in Referential Examples 1 through 12, N-methyl-N-(3,5-dimethylphenyl)-2-[3-[N-[2-(N-tertiarybutoxycarbonylamino)acetyl]-N-(N-methyl-N-phenylcarbamoylmethyl)amino]phenoxy] acetamide (S41) (11.5 g) was obtained, and this compound was dissolved in dichloromethane (200 ml). Trifluoroacetic acid (100 ml) was added to the solution under ice cooling and the resulting solution was stirred for 1.5 hour at the same temperature. The reaction mixture was concentrated under reduced pressure and the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 9.6 g of the compound S19 as powder.

$^1$H-NMR (CDCl$_3$)δ: 2.03 (2H, brs), 2.35 (6H, s), 3.23 (2H, s), 3.28 (6H, s), 4.06 (2H, s), 4.41 (2H, s), 6.79 (1H, d), 6.86 (1H, s), 6.91 (2H, s), 7.02 (1H, s), 7.21–7.42 (7H, m)

Referential Example 15

N-Methyl-N-(3-methylphenyl)-2-[2-[N-(2-aminoacetyl)-N-(N-methyl-N-phenylcarbamoylmethyl)amino]phenoxy]acetamide (S20)

In a manner similar to those described in Referential Examples 1 through 12, N-methyl-N-(3-methylphenyl)-2-

[2-[N-[2-(N-tertiarybutoxycarbonylamino)acetyl]-N-(N-methyl-N-phenylcarbamoylmethyl)amino]phenoxy]acetamide (S42) (5.0 g) was obtained. This compound was dissolved in dichloromethane (50 ml). Trifluoroacetic acid (30 ml) was added to the solution under ice cooling and the resulting solution was stirred for 1 hour at the same temperature. The reaction mixture was concentrated under reduced pressure. The residue was dissolved in chloroform, and washed successively with saturated aqueous sodium hydrogencarbonate solution, water and brine, then dried over anhydrous magnesium sulfate. The solvent was distilled off under reduced pressure, obtaining 4.1 g of the compound S20 as powder.

$^1$H-NMR (CDCl$_3$)$\delta$: 1.97 (2H, brs), 2.38 (3H, s), 3.20 (2H, s), 3.22 (3H, s), 3.28 (3H, s), 3.46 (1H, d), 4.35 (2H, s), 4.74 (1H, d), 6.64 (1H, d), 6.95–7.02 and 7.18–7.42 (11H, m), 7.68 (1H, d)

Referential Example 16

N-Methyl-N-(2,3-dimethylphenyl)-2-[3-[N-(2-aminoacetyl)-N-(N-methyl-N-phenylcarbamoylmethyl)amino]phenoxy]acetamide (S21)

In a manner similar to those described in Referential Examples 1 through 12, N-methyl-N-(2,3-dimethylphenyl)-2-[3-[N-[2-(N-tertiarybutoxycarbonylamino)acetyl-N-(N-methyl-N-phenylcarbamoylmethyl)amino]phenoxy] acetamide (S43) (5.0 g) was obtained. This compound was dissolved in dichloromethane (50 ml). Trifluoroacetic acid (50 ml) was added to the solution under ice cooling, and the resulting solution was stirred for 30 minutes at the same temperature. The reaction mixture was concentrated under reduced pressure. Subsequently, the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 4.0 g of the title compound as powder.

$^1$H-NMR (CDCl$_3$)$\delta$: 2.17 (2H, brs), 2.18 (3H, s), 2.33 (3H, s), 3.23 (3H, s), 3.28 (3H, s), 3.25 (2H, s), 4.05 (2H, q), 4.17 (1H, d), 4.38 (1H, d), 6.76 (1H, dd), 6.84 (1H, s), 6.93 (1H, d), 7.11–7.44 (9H, m)

Referential Example 17

N-Methyl-N-(2-methylphenyl)-2-[3-[N-(2-aminoacetyl)-N-(N-methyl-N-phenylcarbamoylmethyl)amino] phenoxy]acetamide (S22):

In a manner similar to those described in Referential Examples 1 through 12, N-methyl-N-(2-methylphenyl)-2-[3-[N-[2-(N-tertiarybutoxycarbonylamino)cetyl]-N-(N-methyl-N-phenylcarbamoylmethyl)amino]phenoxy] acetamide (S44) (2.2 g) was obtained. This compound was dissolved in dichloromethane (50 ml). Trifluoroacetic acid (20 ml) was added to the solution under ice cooling and stirred for 1 hour at the same temperature. The reaction mixture was concentrated under reduced pressure. Subsequently, the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 1.8 g of the compound S22 as powder.

$^1$H-NMR (CDCl$_3$)$\delta$: 1.66 (2H, brs), 2.29 (3H, s), 3.17 (2H, s), 3.25 (3H, s), 3.29 (3H, s), 4.05 (2H, q), 4.18 (1H, d), 4.37 (1H, d), 6.76 (1H, dd), 6.83 (1H, s), 6.93 (1H, d), 7.20–7.44 (10H, m)

Referential Example 18

N-Methyl-N-(3-methylphenyl)-2-[3-[N-(2-aminoacetyl)-N-(N-methyl-N-phenylcarbamoylmethyl)amino]phenoxy]acetamide (S23)

In a manner similar to those described in Referential Examples 1 through 12, N-methyl-N-(3-methylphenyl)-2-[3-[N-[2-(N-tertiarybutoxycarbonylamino)cetyl]-N-(N-methyl-N-phenylcarbamoylmethyl)amino]phenoxy] acetamide (4.5 g) (S45). This compound was dissolved in dichloromethane (50 ml). Trifluoroacetic acid (30 ml) was added to the solution under ice cooling and the solution was stirred for 1 hour at the same temperature. The reaction mixture was concentrated under reduced pressure. Subsequently, the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 3.7 g of the title compound as an oily substance.

$^1$H-NMR (CDCl$_3$)$\delta$: 1.75 (2H, brs), 2.39 (3H, s), 3.18 (2H, s), 3.29 (3H, s), 3.31 (3H, s), 4.05 (2H, s), 4.40 (2H, s), 6.79 (1H, d), 6.84 (1H, s), 6.91 (1H, d), 7.12–7.44 (10H, m)

Referential Example 19

N-(3,5-Dimethoxyphenyl)-N-methyl-2-[2-[N-(2-aminoacetyl)-N-(N-methyl-N-phenylcarbamoylmethyl)amino]phenoxy]acetamide (S24)

In a manner similar to those described in Referential Examples 1 through 12, N-(3,5-dimethoxyphenyl)-N-methyl-2-[2-[N-[2-(N-tertiarybutoxycarbonylamino) acetyl]-N-(N-methyl-N-phenylcarbamoylmethyl)amino] phenoxy]acetamide (S46) (4.7 g) was obtained. This compound was dissolved in dichloromethane (12 ml). Trifluoroacetic acid (12 ml) was added to the solution and the resulting solution was stirred for 20 minutes at room temperature. The reaction mixture was partitioned between chloroform and saturated aqueous sodium hydrogencarbonate solution. The organic layer was washed with brine and dried over anhydrous magnesium sulfate. The solvent was distilled off under reduced pressure, obtaining 4.0 g of the compound S24 as powder.

$^1$H-NMR (CDCl$_3$)$\delta$: 1.78 (2H, brs), 3.20 (3H, m), 3.21 (3H, s), 3.27 (2H, m), 3.47 (1H, d),3.83 (6H, s), 4.43 (2H, brs), 4.75 (1H, d), 6.34 (2H, m), 6.46 (1H, m), 6.64 (1H, m), 6.95–7.41 (7H, m), 7.68 (1H, d)

Referential Example 20

N-(3-Methoxyphenyl)-N-methyl-2-[2-[N-( 2-aminoacetyl)-N-(N-methyl-N-phenylcarbamoylmethyl)amino]phenoxy]acetamide (S25)

In a manner similar to those described in Referential Examples 1 through 12, N-(3-methoxyphenyl)-N-methyl-2-[2-[N-[2-(N-tertiarybutoxycarbonylamino)acetyl]-N-(N-methyl-N-phenylcarbamoylmethyl)amino]phenoxy] acetamide (S47) (2.5 g) was obtained. This compound was dissolved in dichloromethane (6 ml). Trifluoroacetic acid (6 ml) was added to the solution and the resulting solution was stirred for 20 minutes at room temperature. The reaction mixture was partitioned between chloroform and saturated aqueous sodium hydrogencarbonate solution. The organic layer was washed with brine and dried over anhydrous magnesium sulfate. The solvent was distilled off under reduced pressure, obtaining 2.0 g of the compound S25 as powder.

$^1$H-NMR (CDCl$_3$)δ: 1.74 (2H, brs), 3.18 (2H, m), 3.23 (3H, s), 3.28 (3H, s), 3.45 (1H, d), 3.83 (3H, s), 4.38 (2H, brs), 4.75 (1H, d), 6.63–6.65 (1H, m), 6.74–6.80 (2H, m), 6.90–6.99 (2H, m), 7.22–7.41 (7H, m), 7.68–7.70 (1H, m)

Referential Example 21

N-(2-Methoxyphenyl)-N-methyl-2-[2-[N-(2-aminoacetyl)-N-(N-methyl-N-phenylcarbamoylmethyl)amino]-phenoxy]acetamide (S26)

In a manner similar to those described in Referential Examples 1 through 12, N-(2-methoxyphenyl)-N-methyl-2-[2-[N-[2-(N-tertiarybutoxycarbonylamino)acetyl]-N-(N-methyl-N-phenylcarbamoylmethyl)amino]phenoxy] acetamide (S48) (2.7 g) was obtained. This compound was dissolved in dichloromethane (10 ml). Trifluoroacetic acid (10 ml) was added to the solution and the resulting solution was stirred for 20 minutes at room temperature. The reaction mixture was partitioned between chloroform and saturated aqueous sodium hydrogencarbonate solution. The organic layer was washed with brine and dried over anhydrous magnesium sulfate. The solvent was distilled off under reduced pressure, obtaining 2.5 g of the compound S26 as powder.

$^1$H-NMR (CDCl$_3$)δ: 1.87 (2H, brs), 3.16 (3H, s), 3.14–3.23 (2H, m), 3.27 (3H, s), 3.39–3.49 (1H, m), 3.89 (3H, s), 4.21–4.35 (2H, m), 4.74 (1H, d), 6.69–7.69 (13H, m)

Referential Example 22

N-(2-Methoxyphenyl)-N-methyl-2-[3-[N-(2-aminoacetyl)-N-(N-methyl-N-phenylcarbamoylmethyl)amino]phenoxy]acetamide (S27)

In a manner similar to those described in Referential Examples 1 through 12, N-(2-methoxyphenyl)-N-methyl-2-[3-[N-[2-(N-tertiarybutoxycarbonylamino)acetyl]-N-(N-methyl-N-phenylcarbamoylmethyl)amino]phenoxy] acetamide (S49) (0.60 g) was obtained. This compound was dissolved in dichloromethane (2 ml). Trifluoroacetic acid (2 ml) was added to the solution and the resulting solution was stirred for 2 hours at room temperature. The reaction mixture was partitioned between chloroform and saturated aqueous sodium hydrogencarbonate solution. The organic layer was washed with brine and dried over anhydrous magnesium sulfate. The solvent was distilled off under reduced pressure, obtaining 0.49 g of the compound S27 as an oily substance.

$^1$H-NMR (CDCl$_3$)δ: 1.61 (2H, brs), 3.18 (2H, s), 3.22 (3H, s), 3.28 (3H, s), 3.87 (3H, s), 4.02 (1H, d), 4.10 (1H, d), 4.30 (1H, d), 4.39 (1H, d), 6.75–7.44 (13H, m)

Referential Example 23

N-Methyl-N-(3,5-dimethylphenyl)-2-[2-[N-(2-aminoacetyl)-N-(N-methyl-N-phenylcarbamoylmethyl)amino]phenoxyacetamide (S28)

In a manner similar to those described in Referential Examples 1 through 12, N-methyl-N-(3,5-dimethylphenyl)-2-[N-[2-(N-tertiarybutoxycarbonylamino)acetyl]-N-(N-methyl-N-phenylcarbamoylmethyl)amino]phenoxy] acetamide (S50) (7.0 g) was obtained. This compound was dissolved in dichloromethane (100 ml). Trifluoroacetic acid (50 ml) was added thereto under ice cooling and the resulting solution was stirred for 1 hour at the same temperature. The reaction mixture was concentrated under reduced pressure and the residue was dissolved in chloroform. The resulting solution was successively washed with saturated aqueous sodium hydrogencarbonate solution, water and brine, then dried over anhydrous magnesium sulfate. The solvent was distilled off under reduced pressure, obtaining 5.6 g of the compound S28 as powder.

$^1$H-NMR (CDCl$_3$)δ: 1.98 (2H, brs), 2.34 (6H, s), 3.20 (3H, s), 3.27 (3H, s), 3.24 (2H, s), 3.49 (1H, d), 4.36 (2H, s), 4.73 (1H, d), 6.64 (1H, d), 6.81 (2H, s), 6.96–7.01 and 7.23–7.42 (8H, m), 7.66 (1H, d)

Referential Example 24

N-Ethyl-N-(3,5-dimethylphenyl)-2-[3-[N-(2-aminoacetyl)-N-(N-methyl-N-phenylcarbamoylmethyl)amino]phenoxy]acetamide (S29)

In a manner similar to those described in Referential Examples 1 through 12, N-ethyl-N-(3,5-dimethylphenyl)-2-[3-[N-[2-(N-tertiarybutoxycarbonylamino)acetyl]-N-(N-methyl-N-phenylcarbamoylmethyl)amino]phenoxy] acetamide (S51) (5.5 g) was obtained. This compound was dissolved in dichloromethane (50 ml). Trifluoroacetic acid (50 ml) was added thereto under ice cooling and the solution was stirred for 1 hour at the same temperature. The reaction mixture was concentrated under reduced pressure and the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 4.2 g of the compound S29 as powder.

$^1$H-NMR (CDCl$_3$)δ: 1.14 (3H, t), 1.74 (2H, brs), 2.35 (6H, s), 3.19 (2H, s), 3.28 (3H, s), 3.75 (2H, q), 4.06 (2H, s), 4.35 (2H, s), 6.77–6.93 (5H, m), 7.03 (1H, s), 7.21–7.42 (6H, m)

Referential Example 25

N-(3-Bromophenyl)-N-methyl-2-[3-N-(2-aminoacetyl)-N-(N-methyl-N-phenylcarbamoylmethyl)amino]phenoxy]acetamide (S30)

In a manner similar to those described in Referential Examples 1 through 12, N-(3-bromophenyl)-N-methyl-2-[3-[N-[2-(N-tertiarybutoxycarbonylamino)acetyl]-N-(N-methyl-N-phenylcarbamoylmethyl)amino]phenoxy] acetamide (S52) (10.0 g) was obtained. This compound was dissolved in dichloromethane (100 ml). Trifluoroacetic acid (100 ml) was added thereto under ice cooling and the resulting solution was stirred for 1 hour at the same temperature. The reaction mixture was concentrated under reduced pressure and the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 6.2 g of the compound S30 as an oily substance.

$^1$H-NMR (CDCl$_3$)δ: 1.80 (2H, brs), 3.18 (2H, s), 3.29(3H, s), 3.31 (3H, s), 4.06 (2H, s), 4.43 (2H, s), 6.78–6.93 (3H, m), 7.21–7.53 (10H, m)

Referential Example 26

N-(3-Bromophenyl)-N-methyl-2-[2-N-(2-aminoacetyl)-N-(N-methyl-N-phenylcarbamoylmethyl)amino]phenoxy]acetamide (S31)

In a manner similar to those described in Referential Examples 1 through 12, N-(3-bromophenyl)-N-methyl-2-[2-[N-[2-(N-tertiarybutoxycarbonylamino)acetyl]-N-(N-methyl-N-phenylcarbamoylmethyl)amino]phenoxy]acetamide (S53) (10.0 g) was obtained. This compound was dissolved in dichloromethane (100 ml). Trifluoroacetic acid (100 ml) was added thereto under ice cooling and the resulting solution was stirred for 1 hour at the same temperature. The reaction mixture was concentrated under reduced pressure and the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 7.8 g of the compound S31 as powder.

$^1$H-NMR (CDCl$_3$)δ: 2.45 (2H, brs), 3.22 (2H, s), 3.27 (6H, s), 3.49 (1H, d), 4.38 (2H, s), 4.71 (1H, d), 6.66 (1H, d), 6.99 (1H, t), 7.17–7.52 (10H, m), 7.66 (1H, dd)

Referential Example 27

N-Methyl-N-(2-methylphenyl)-2-[2-N-(2-aminoacetyl)-N-(N-methyl-N-phenylcarbamoylmethyl)amino]phenoxy]acetamide (S32)

In a manner similar to those described in Referential Examples 1 through 12, N-methyl-N-(2-methylphenyl)-2-[2-[N-[2-(N-tertiarybutoxycarbonylamino)acetyl]-N-(N-methyl-N-phenylcarbamoylmethyl)amino]phenoxy]acetamide (S54) (6.5 g) was obtained. This compound was dissolved in dichloromethane (100 ml). Trifluoroacetic acid (50 ml) was added thereto under ice cooling and the resulting solution was stirred for 1 hour at the same temperature. The reaction mixture was concentrated under reduced pressure and the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 5.7 g of the title compound as an oily substance.

$^1$H-NMR (CDCl$_3$)δ: 1.74 (2H, brs), 2.26 (3H, s), 3.19 (2H, s), 3.17(3H, s), 3.27 (3H, s), 3.44 (1H, d), 4.09 (1H, d), 4.32 (1H, d), 4.74 (1H, d), 6.63 (1H, m), 6.97 (1H, d), 7.15–7.42 (1OH, m), 7.68 (1H, d)

Referential Example 28

N-(3-Cyanophenyl)-N-methyl-2-[3-[N-( 2-aminoacetyl)-N-(N-methyl-N-phenylcarbamoylmethyl)amino]phenoxy]acetamide (S33)

In a manner similar to those described in Referential Examples 1 through 12, N-(3-cyanophenyl)-N-methyl-2-[3-[N-[2-(N-tertiarybutoxycarbonylamino)acetyl]-N-(N-methyl-N-phenylcarbamoylmethyl)amino]phenoxy]acetamide (S55) (3.0 g) was obtained. This compound was dissolved in dichloromethane (10 ml). Trifluoroacetic acid (10 ml) was added to the solution and the resulting solution was stirred for 1 hour at room temperature. The reaction mixture was partitioned between chloroform and saturated aqueous sodium hydrogencarbonate solution. The organic layer was washed with water and brine, then dried over anhydrous magnesium sulfate. The solvent was distilled off under reduced pressure, obtaining 2.3 g of the title compound as white powder.

$^1$H-NMR (CDCl$_3$)δ: 1.67 (2H, brs), 3.17 (2H, s), 3.31 (3H, s), 3.35 (3H, s), 4.05 (2H, s), 4.45 (2H, brs), 6.81 (1H, s), 6.89 (2H, d), 7.22 (3H, m), 7.34–7.45 (3H, m), 7.53–7.67 (4H, m)

Referential Example 29

N-Methyl-N-(2,3-dimethylphenyl)-2-[2-N-(2-aminoacetyl)-N-(N-methyl-N-phenylcarbamoylmethyl)amino]phenoxy]acetamide (S34)

In a manner similar to those described in Referential Examples 1 through 12, N-methyl-N-(2,3-dimethylphenyl)-2-[2-[N-[2-(N-tertiarybutoxycarbonylamino)acetyl]-N-(N-methyl-N-phenylcarbamoylmethyl)amino]phenoxy]acetamide (S56) (1.27 g) was obtained. This compound was dissolved in dichloromethane (100 ml). Trifluoroacetic acid (25 ml) was added thereto under ice cooling and the resulting solution was stirred for 3 hours at room temperature. The reaction mixture was concentrated under reduced pressure and the residue was dissolved in chloroform. The resulting solution was washed with water and brine, then dried over anhydrous magnesium sulfate. The solvent was distilled off under reduced pressure, obtaining 0.92 g of the title compound as powder.

$^1$H-NMR (CDCl$_3$)δ: 2.16 (3H, s), 2.32 (3H, s), 3.16 (3H, s), 3.27 (3H, s), 3.43–4.76 (6H, m), 6.62–7.69 (12H, m)

Referential Example 30

N-(3-Chlorophenyl)-N-methyl-2-[3-[N-(2-aminoacetyl)-N-(N-methyl-N-phenylcarbamoylmethyl)amino]phenoxy]acetamide (S35)

In a manner similar to those described in Referential Examples 1 through 12, N-(3-chlorophenyl)-N-methyl-2-[3-[N-[2-(N-tertiarybutoxycarbonylamino)acetyl]-N-(N-methyl-N-phenylcarbamoylmethyl)amino]phenoxy]acetamide (S57) (18.7 g) was obtained. This compound was dissolved in dichloromethane (200 ml). Trifluoroacetic acid (40 ml) was added thereto under ice cooling and the resulting solution was stirred for 2 hours at room temperature. The reaction mixture was concentrated under reduced pressure and the residue was dissolved in chloroform. The resulting solution was washed successively with saturated aqueous sodium hydrogencarbonate solution, water and brine, then dried over anhydrous magnesium sulfate. The solvent was distilled off under reduced pressure, obtaining 15.0 g of the title compound as powder.

$^1$H-NMR (CDCl$_3$)δ: 3.19 (2H, s), 3.30 (3H, s), 3.32 (3H, s), 4.06 (2H, s), 4.43 (2H, s), 6.79–7.45 (13H, m)

Referential Example 31

N-(2-Methoxyphenyl)-N-methyl-2-[2-[N-(1-imidazolyl)carbonylamino]acetyl-N-(N-methyl-N-phenylcarbamoylmethyl)amino]phenoxy]acetamide (S36)

Compound S26 (2.3 g) was dissolved in tetrahydrofuran (50 ml). N,N'-Carbonyldiimidazole (1.1 g) was added to the solution and the solution was stirred for 2 hours at room temperature. The reaction mixture was concentrated under reduced pressure. The reaction mixture was partitioned between ethyl acetate and water. The organic layer was washed with brine and dried over anhydrous magnesium sulfate. The solvent was distilled off under reduced pressure, obtaining 2.7 g of the title compound as powder.

$^1$H-NMR (CDCl$_3$)δ: 3.19 (3H, m), 3.27 (3H, s), 3.62 (1H, m), 3.91 (3H, m), 4.07 (2H, m), 4.35 (2H, m), 4.63 (1H, m), 6.67–8.11 (17H, m)

Referential Example 32

N-(2-Methoxyphenyl)-N-methyl-2-[3-[N-(2-[N-(1-imidazolyl)carbonylamino]acetyl-N-(N-methyl-N-phenylcarbamoylmethyl)amino]phenoxy]acetamide (S37)

Compound S27 (2.7 g) was dissolved in tetrahydrofuran (50 ml). N,N'-Carbonyldiimidazole (1.3 g) was added to the solution and the resulting solution was stirred for 2 hours at room temperature. The reaction mixture was concentrated under reduced pressure. The reaction mixture was partitioned between ethyl acetate and water. The organic layer was washed with brine and dried over anhydrous magnesium sulfate. The solvent was distilled off under reduced pressure, obtaining 3.1 g of the title compound as powder.

$^1$H-NMR (CDCl$_3$)δ: 3.23 (3H, s), 3.29 (3H, s), 3.90 (3H, s), 3.98 (2H, d), 4.11 (2H, m), 4.36 (1H, d), 4.44 (1H, d), 6.72–8.08 (17H, m)

Referential Example 33

N-(2-Methoxyphenyl)-N-methyl-2-[2-[N-(2-[N-(1-imidazolyl)carbonylamino]acetyl-N-(N-methyl-N-phenylcarbamoylmethyl)amino]phenoxy]acetamide (S38)

Compound S25 (2.0 g) was dissolved in tetrahydrofuran (50 ml). N,N'-Carbonyldiimidazole (1.0 g) was added to the solution and the resulting solution was stirred for 2 hours at room temperature. The reaction mixture was concentrated under reduced pressure. The reaction mixture was partitioned between ethyl acetate and water. The organic layer was washed with brine and dried over anhydrous magnesium sulfate. The solvent was distilled off under reduced pressure, obtaining 2.4 g of the title compound as powder.

$^1$H-NMR (CDCl$_3$)δ: 3.27 (6H, m), 3.63 (1H, m), 3.84 (3H, s), 3.95 (1H, m), 4.09 (1H, m), 4.44 (2H, m), 4.65 (1H, m), 6.59–8.16 (17H, m)

Referential Example 34

N-(3,5-Dimethoxyphenyl)-N-methyl-2-[2-[N-[2-[N-(1-imidazolyl)carbonylamino]acetyl-N-(N-methyl-N-phenylcarbamoylmethyl)amino]phenoxy] acetamide (S34)

Compound S24 (4.0 g) was dissolved in tetrahydrofuran (50 ml). N,N'-Carbonyldiimidazole (1.9 g) was added to the solution and the resulting solution was stirred for 2 hours at room temperature. The reaction mixture was concentrated under reduced pressure. The reaction mixture was partitioned between ethyl acetate and water. The organic layer was washed with brine and dried over anhydrous magnesium sulfate. The solvent was distilled off under reduced pressure, obtaining 4.7 g of the title compound as powder.

$^1$H-NMR (CDCl$_3$)δ: 3.23 (3H, s), 3.26 (3H, s), 3.62 (1H, m), 3.81 (6H, s), 3.96 (1H, m), 4.08 (1H, m), 4.49 (2H, m), 4.65 (1H, m), 6.36–8.16 (16H, m)

Referential Example 35 tert-Butyl 2-(3-nitrophenyl)acetate (S59)

3-Nitrophenylacetic acid (10.0 g) was dissolved in a mixture (70 ml) of tertiarybutanol and tetrahydrofuran. Di(tertiarybutyl) dicarbonate (18.1 g) and 4-dimethylaminopyridine (1.4 g) were added to the mixture with stirring at room temperature and the solution was stirred for 1 hour at the same temperature. The reaction mixture was added into ice-water and extracted with diethyl ether. The extract was successively washed with 1N HCl, water saturated aqueous sodium hydrogencarbonate solution, and brine, then dried over anhydrous magnesium sulfate. The solvent was distilled off under reduced pressure and the residue was purified by silica gel column chromatography (eluted with n-hexane/ethyl acetate=20:1), obtaining 13.3 g of the title compound.

$^1$H-NMR (CDCl$_3$)δ: 1.46 (9H, s), 3.65 (2H, s), 7.50 (1H, m), 7.62 (1H, d), 8.13 (1H, d), 8.16 (1H, s)

Referential Example 36 tert-Butyl 2-(3-aminophenyl)acetate (S60)

Compound S59 (5.2 g) was dissolved in methanol (80 ml). 5% Palladium-carbon (1.0 g, 50% wet) was added to the solution. The resulting solution was catalytically hydrogenated for 3 hours at room temperature in a hydrogen atmosphere of 1 atm. The reaction mixture was filtered. The solvent was distilled off under reduced pressure, obtaining 4.3 g of the compound S60.

$^1$H-NMR (CDCl$_3$)δ: 1.44 (9H, s), 3.42(2H, s), 3.63 (2H. brs), 6.56–6.60 (2H, m) 6.65 (1H, d), 7.09 (1H, t)

Referential Example 37 tert-Butyl (±)-2-(3-nitrophenyl)propionate (S62)

2-(3-Nitrophenyl)propionic acid (18.2 g) and 4-dimethylaminopyridine (1.2 g) were dissolved in tertiary butanol (100 ml). To the solution was added a solution of di(tertiarybutyl) dicarbonate (30.5 g) in tertiarybutanol (100 ml) with stirring at room temperature. The resultant solution was stirred for 20 minutes at 35–40° C. The solvent was distilled off under reduced pressure and the residue was dissolved in ethyl acetate. The resulting solution was washed successively with 1N HCl, water, saturated aqueous sodium hydrogencarbonate solution and brine, then dried over anhydrous magnesium sulfate. The solvent was distilled off under reduced pressure, obtaining 23.4 g of the title compound.

$^1$H-NMR (CDCl$_3$)δ: 1.41 (9H, s), 1.51 (3H, d), 3.73 (1H, q), 7.50 (1H, t), 7.64 (1H, d), 8.12 (1H, dd), 8.19 (1H, d)

Referential Example 38 tert-Butyl (±)-2-(3-aminophenyl)propionate (S63)

Compound S62 (5.0 g) was dissolved in methanol (100 ml). 5% Palladium-carbon (1.0 g, 50% wet) was added to the solution. The mixture was catalytically hydrogenated for 4 hours at room temperature in a hydrogen atmosphere of 1 atm. The reaction mixture was filtered. The solvent was distilled off under reduced pressure. The residue was dissolved in chloroform and dried over anhydrous magnesium sulfate. The solvent was distilled off under reduced pressure, obtaining 4.2 g of the title compound.

$^1$H-NMR (CDCl$_3$)δ: 1.40 (9H, s), 1.41 (3H, d), 3.50 (1H, q), 3.63 (2H, brs), 6.56 (1H, d), 6.63 (1H, s), 6.69 (1H, d), 7.10 (1H, t)

Example 1

Methyl (±)-2-[3-[3-[N-[3-[N-(2-methoxyphenyl)-N-methylcarbamoylmethyloxy]phenyl]-N-(N-methyl-N-phenylcarbamoylmethyl)carbamoylmethyl]ureido]phenyl]propionate (1-1)

Compound S37 (0.58 g) was dissolved in toluene (50 ml). Methyl (±)-2-(3-aminophenyl)propionate (0.36 g) was added to the solution. The mixture was refluxed for 2 hours. The reaction mixture was cooled, and partitioned between ethyl acetate and water. The two layers were separated and the aqueous layer was extracted with ethyl acetate. The combined organic layer was washed successively with 1N HCl, water and brine, then dried over anhydrous magnesium sulfate. The solvent was distilled off under reduced pressure and the residue was purified by silica gel column chromatography (eluted with chloroform/methanol=98:2–97:3), obtaining 0.47 g of the compound (1-1).

$^1$H-NMR (CDCl$_3$)δ: 1.45 (3H, d), 3.22 (3H, s), 3.24 (3H, s), 3.62 (3H, s), 3.65 (1H, q), 3.86 (2H, d), 3.88 (3H, s), 4.05 (1H, d), 4.13 (1H, d), 4.32 (1H, d), 4.42 (1H, d), 5.83 (1H, brs), 6.86–7.03 (6H, m), 7.15–7.38 (12H, m)

Example 2

Methyl 2-[3-[3-[N-[3-[N-(2-methoxyphenyl)-N-methylcarbamoylmethyloxy]phenyl]-N-(N-methyl-N-phenylcarbamoylmethyl)carbamoylmethyl]ureido]phenyl]acetate (1-2)

Compound S37 (0.58 g) was dissolved in toluene (50 ml). Methyl 2-(3-aminophenyl)acetate (0.33 g) was added to the solution. The mixture was refluxed for 3 hours. The reaction mixture was cooled. Ethyl acetate and water were added to the liquid to separate the organic layer. The aqueous layer was extracted with ethyl acetate. The combined organic layer was washed successively with 1N HCl, water and brine, then dried over anhydrous magnesium sulfate. The solvent was distilled off under reduced pressure. The residue was purified by silica gel column chromatography (eluted with chloroform/methanol=98:2–97:3), obtaining 0.39 g of the compound (1-2) as powder.

$^1$H-NMR (CDCl$_3$)δ: 3.22 (3H, m), 3.24 (3H, s), 3.55 (2H, s), 3.65 (3H, s), 3.86 (2H, d), 3.88 (3H, s), 4.05 (1H, d), 4.12 (1H, d), 4.32 (1H, d), 4.42 (1H, d), 5.85 (1H, brs), 6.80–7.03 (6H, m), 7.15–7.38 (12H, m)

Example 3

Methyl 2-[3-[3-[N-[2-[N-(2-methoxyphenyl)-N-methylcarbamoylmethyloxy]phenyl]-N-(N-methyl-N-phenylcarbamoylmethyl)carbamoylmethyl]ureido]phenyl]acetate (1-3)

Compound S36 (0.77 g) was dissolved in toluene (50 ml). Methyl 2-(3-aminophenyl)acetate hydrochloride (0.53 g) and 4-dimethylaminopyridine (0.32 g) were added to the solution. The mixture was refluxed for 2 hours. The reaction mixture was cooled. Chloroform and water were added to the mixture to separate the organic layer. The aqueous layer was extracted with chloroform. The combined organic layer was washed successively with 1N HCl, water and brine, then dried over anhydrous magnesium sulfate. The solvent was distilled off under reduced pressure. The residue was purified by silica gel column chromatography (eluted with chloroform/methanol=98:2–97:3), obtaining 0.28 g of the title compound as powder.

$^1$H-NMR (CDCl$_3$)δ: 3.21 (3H, m), 3.24 (3H, s), 3.36–3.47 (1H, m), 3.55 (2H, s), 3.66 (3H, s), 3.89 (2H, s), 3.95 (3H, s), 4.28–4.43 (2H, m), 4.69 (1H, m), 5.95 (1H, brs), 6.63–7.06 (5H, m), 7.16–7.43 (12H, m), 7.70 (1H, d)

Example 4

Methyl (±)-2-[3-[3-[N-[2-[N-(2-methoxyphenyl)-N-methylcarbamoylmethyloxy]phenyl]-N-(N-methyl-N-phenylcarbamoylmethyl)carbamoylmethyl]ureido]phenyl]propionate (1-4)

Compound S36 (0.77 g) was dissolved in toluene (50 ml). Methyl (±)-2-(3-aminophenyl)propionate (0.47 g) was added to the solution. The mixture was refluxed for 12 hours. The reaction mixture was cooled. Chloroform and water were added to the mixture to separate the organic layer. The aqueous layer was extracted with chloroform. The combined organic layer was washed successively with 1N HCl, water and brine, then dried over anhydrous magnesium sulfate. The solvent was distilled off under reduced pressure. The residue was purified by silica gel column chromatography (eluted with chloroform/methanol=98:2–97:3), obtaining 0.45 g of the compound (1-4) as powder.

$^1$H-NMR (CDCl$_3$)δ: 1.45 (3H, d), 3.24 (3H, s), 3.25 (3H, s), 3.34–3.45 (1H, m), 3.63 (3H, s), 3.66 (1H, m), 3.89 (2H, s), 3.96 (3H, s), 4.28–4.43 (2H, m), 4.66–4.74 (1H, m), 5.94 (1H, brs), 6.63–7.06 (5H, m), 7.17–7.43 (12H, m), 7.70 (1H, d)

Example 5

Methyl 2-[3-[3-[N-[2-[N-(3-methoxyphenyl)-N-methylcarbamoylmethyloxy]phenyl]-N-(N-methyl-N-phenylcarbamoylmethyl)carbamoylmethyl]ureido]phenyl]acetate (1-5)

Compound S38 (1.0 g) was dissolved in toluene (50 ml). Methyl 2-(3-aminophenyl)acetate (0.56 g) was added to the solution. The mixture was refluxed for 2 hours. The reaction mixture was cooled. Chloroform and water were added to the mixture to separate the organic layer. The aqueous layer was extracted with chloroform. The combined organic layer was washed successively with 1N HCl, water and brine, then dried over anhydrous magnesium sulfate. The solvent was distilled off under reduced pressure. The residue was purified by silica gel column chromatography (eluted with chloroform/methanol=99:1–98:2) and crystallized from ethyl acetate-ether, obtaining 0.48 g of the compound (1-5) as crystalline powder.

mp 124–126° C. $^1$H-NMR (CDCl$_3$)δ: 3.23 (3H, s), 3.27 (3H, s), 3.52 (1H, m), 3.55 (2H, s), 3.65 (3H, s), 3.83 (3H, s), 3.95 (2H, d), 4.45 (2H, brs), 4.68 (1H, d), 5.98 (1H, brs), 6.61 (1H, d), 6.78–7.00 (5H, m), 7.14–7.36 (11H, m), 7.69 (1H, d)

Example 6

Methyl (±)-2-[3-[3-[N-[2-[N-(3-methoxyphenyl)-N-methylcarbamoylmethyloxy]phenyl]-N-(N-methyl-N-phenylcarbamoylmethyl)carbamoylmethyl]ureido]phenyl]propionate (1-6)

Compound S38 (1.0 g) was dissolved in toluene (50 ml). Methyl (±)-2-(3-aminophenyl)propionate (0.61 g) was added to the solution. The mixture was refluxed for 2 hours. The reaction mixture was cooled. Chloroform and water were added to the mixture to separate the organic layer. The aqueous layer was extracted with chloroform. The combined organic layer was washed successively with 1N HCl, water and brine, then dried over anhydrous magnesium sulfate.

The solvent was distilled off under reduced pressure. The residue was purified by silica gel column chromatography (eluted with chloroform/methanol=99:1–98:2) and crystallized from ethyl acetate-diethyl ether, obtaining 0.71 g of the compound (1–6) as crystalline powder.

mp 144–145° C. $^1$H-NMR (CDCl$_3$)δ: 1.45 (3H, d), 3.24 (3H, s), 3.29 (3H, s), 3.42 (1H, d), 3.62–3.68 (4H, m), 3.84 (3H, s), 3.96 (2H, brs), 4.46 (2H, brs), 4.68 (1H, d), 5.96 (1H, brs), 6.60 (1H, d), 6.83–6.98 (5H, m), 7.15–7.38 (llH, m), 7.69 (1H, d)

Example 7

Methyl 2-[3-[3-[N-[2-[N-(3,5-dimethoxyphenyl)-N-methylcarbamoylmethyloxy]phenyl]-N-(N-methyl-N-phenylcarbamoylmethyl)carbamoylmethyl]ureido]phenyl]acetate (1–7)

Compound S39 (1.0 g) was dissolved in toluene (50 ml). Methyl 2-(3-aminophenyl)acetate (0.54 g) was added to the solution. The mixture was refluxed for 2 hours. The reaction mixture was cooled. Chloroform and water were added to the mixture to separate the organic layer. The aqueous layer was extracted with chloroform. The combined organic layer was washed successively with 1N HCl, water and brine, then dried over anhydrous magnesium sulfate. The solvent was distilled off under reduced pressure. The residue was purified by silica gel column chromatography (eluted with chloroform/methanol=99:1–98:2) and crystallized from ethyl acetate-diethyl ether, obtaining 0.58 g of the compound (1–7) as crystalline powder.

mp 164–166° C. $^1$H-NMR (CDCl$_3$)δ: 3.25 (3H, s), 3.27 (3H, m), 3.47 (1H, d), 3.55 (2H, s), 3.66 (3H, s), 3.81 (6H, s), 3.96 (2H, m), 4.51 (2H, brs), 4.68 (1H, d), 5.93 (1H, brs), 6.38–6.62 (4H, m), 6.88–7.00 (2H, m), 7.15–7.39 (10H, m), 7.70 (1H, d)

Example 8

Methyl (±)-2-[3-[3-[N-[2-[N-(3,5-dimethoxyphenyl)-N-methylcarbamoylmethyloxy]phenyl]-N-(N-methyl-N-phenylcarbamoylmethyl)carbamoylmethyl]ureido]phenyl]propionate (1–8)

Compound S39 (1.0 g) was dissolved in toluene (50 ml). Methyl (±)-2-(3-aminophenyl)propionate (0.58 g) was added to the solution. The mixture was refluxed for 2 hours. The reaction mixture was cooled. Chloroform and water were added to the mixture to separate the organic layer. The aqueous layer was extracted with chloroform. The combined organic layer was washed successively with 1N HCl, water and brine, then dried over anhydrous magnesium sulfate. The solvent was distilled off under reduced pressure. The residue was purified by silica gel column chromatography (eluted with chloroform/methanol=99:1–98:2) and crystallized by adding ethyl acetate, obtaining 0.63 g of the compound (1–8) as powder.

mp 188–189° C. $^1$H-NMR (CDCl$_3$)δ: 1.45 (3H, m), 3.28 (6H, m), 3.48 (1H, d), 3.62–3.68 (4H, m), 3.81 (6H, s), 3.96 (2H, d), 4.51 (2H, brs), 4.68 (1H, d), 5.95 (1H, brs), 6.40–6.62 (4H, m), 6.88–7.00 (2H, m), 7.15–7.40 (10H, m), 7.69–7.71 (1H, d)

Example 9

Methyl (±)-2-[3-[3-[N-[3-[N-ethyl-N-(3,5-dimethylphenyl)carbamoylmethyloxy]phenyl]-N-(N-methyl-N-phenylcarbamoylmethyl)carbamoylmethyl]ureido]phenyl]propionate (1–9)

Compound S29 (1.0 g) was dissolved in tetrahydrofuran (20 ml). N,N'-Carbonyldiimidazole (0.36 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). Methyl (±)-2-(3-aminophenyl)propionate (0.72 g) was added to the solution. The mixture was refluxed for 1 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from ethyl acetate/diethyl ether, obtaining 0.7 g of the compound (1–9) as crystalline powder.

mp 121–123° C. $^1$H-NMR (CDCl$_3$)δ: 1.14 (3H, t), 1.44 (3H, d), 2.35 (6H, s), 3.24 (3H, s), 3.62 (3H, s), 3.64 (1H, q), 3.75 (2H, q), 3.86 (2H, d), 4.08 (2H, s), 4.38 (2H, s), 5.84 (1H, br s), 6.79 (1H, d), 6.89 (2H, s), 6.91 (1H, d), 6.99 (1H, d), 7.03 (1H, s), 7.15–7.38 (llH, m) MS (m/z): 708 (M+1)$^+$

Example 10

Methyl (±)-2-[3-[3-[N-[3-[N-(3-bromophenyl)-N-methylcarbamoylmethyloxy]phenyl]-N-(N-methyl-N-phenylcarbamoylmethyl)carbamoylmethyl]ureido]phenyl]propionate (1–10)

Compound S30 (1.5 g) described in Referential Example 25 was dissolved in tetrahydrofuran (20 ml). N,N'-Carbonyldiimidazole (0.5 g) was added to the solution. The resultant mixture was stirred for 15 minutes at room temperature. The reaction mixture was concentrated under reduced pressure. The residue was dissolved in toluene (30 ml). Methyl (±)-2-(3-aminophenyl)propionate (1.0 g) was added to the solution. The mixture was refluxed for 1 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from ethyl acetate/diethyl ether, obtaining 1.3 g of the compound (1–10) as crystalline powder.

mp 142–144° C. $^1$H-NMR (CDCl$_3$)δ: 1.42 (3H, d), 3.21 (3H, s), 3.31 (3H, s), 3.61 (3H, s), 3.62 (1H, q), 3.88 (2H, s), 4.09 (2H, s), 4.47 (2H, s), 6.09 (1H, brs), 6.86–6.93 (3H, m), 7.01 (1H, d), 7.11–7.50 (13H, m), 7.94 (1H, s)

Elementary analysis (for $C_{37}H_{38}BrN_5O_7$) Calculated: C, 59.68; H, 5.14; N, 9.40 Found: C, 59.23; H, 5.14; N, 9.29

Example 11

Methyl 2-[3-[3-[N-[3-[N-(3-bromophenyl)-N-methylcarbamoylmethyloxy]phenyl]-N-(N-methyl-N-phenylcarbamoylmethyl)carbamoylmethyl]ureido]phenyl]acetate (1–11)

Compound S30 (1.2 g) was dissolved in tetrahydrofuran (20 ml). N,N'-Carbonyldiimidazole (0.4 g) was added to the solution. The mixture was stirred for 15 minutes at room temperature. The reaction mixture was concentrated under reduced pressure and the residue was dissolved in toluene (30 ml). Methyl 2-(3-aminophenyl)acetate (0.73 g) was added to the resultant solution. The mixture was refluxed for 1 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from ethyl acetate/diethyl ether, obtaining 0.8 g of the compound (1–11) as crystalline powder.

mp 141–143° C. $^1$H-NMR (CDCl$_3$)δ: 3.23(3H, s), 3.30 (3H, s), 3.53 (2H, s), 3.64 (3H, s), 3.85 (2H, d), 4.09 (2H, s), 4.46 (2H, s), 6.08 (1H, brs), 6.82–6.91 (3H, m), 7.02 (1H, d), 7.11–7.48 (13H, m), 7.93 (1H, brs)

Elementary analysis (for C$_{37}$H$_{36}$BrN$_5$O$_7$) Calculated: C, 59.18; H, 4.97; N, 9.59 Found: C, 58.94; H, 4.96; N, 9.46

Example 12

Methyl 2-[3-[3-[N-[3-[N-ethyl-N-(3,5-dimethylphenyl)carbamoylmethyloxy]phenyl]-N-(N-methyl-N-phenylcarbamoylmethyl)carbamoylmethyl]ureido]phenyl]acetate (1–12):

Compound S29 (1.0 g) was dissolved in tetrahydrofuran (20 ml). N,N'-Carbonyldiimidazole (0.36 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). Methyl 2-(3-aminophenyl) acetate (0.70 g) was added to the resulting solution. The mixture was refluxed for 3 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from ethyl acetate/diethyl ether, obtaining 0.4 g of the compound (1–12) as crystalline powder.

mp 104–106° C. $^1$H-NMR (CDCl$_3$)δ: 1.14 (3H, t), 2.35 (6H, s), 3.24 (3H, s), 3.54 (2H, s), 3.65 (3H, s), 3.75 (2H, q), 3.86 (2H, s), 4.08 (2H, s), 4.38 (2H, s), 5.84 (1H, brs), 6.79 (1H, d), 6.89 (2H, s), 6.91 (1H, d), 6.99 (1H, d), 7.03 (1H, s), 7.14–7.37 (11H, m) MS (m/z): 694 (M+1)$^+$ Example 13

Methyl 2-[3-[3-[N-[3-[N-(3-cyanophenyl)-N-methylcarbamoylmethyloxy]phenyl]-N-(N-methyl-N-phenylcarbamoylmethyl)carbamoylmethyl]ureido] phenyl]acetate (1–13)

Compound S33 (1.0 g) was dissolved in tetrahydrofuran (30 ml). N,N'-Carbonyldiimidazole (0.5 g) was added to the solution. The mixture was stirred for 2 hours at room temperature. The reaction mixture was concentrated under reduced pressure and the residue was dissolved in ethyl acetate (200 ml). The resulting solution was washed with water and brine, then dried over anhydrous magnesium sulfate. The solvent was distilled off under reduced pressure. Toluene (40 ml) and methyl 2-(3-aminophenyl)acetate (0.7 g) were added to the residue. The resulting mixture was refluxed for 1 hour. Ethyl acetate (150 ml) was added to the reaction mixture. The resulting solution was washed successively with 1N HCl, water and brine, then dried over anhydrous magnesium sulfate. The solvent was distilled off under reduced pressure. The residue was purified by silica gel column chromatography (eluted with chloroform/methanol=20:1), obtaining 0.7 g of the compound (1–13) as white powder.

mp 86–90° C. $^1$H-NMR (CDCl$_3$)δ: 3.24 (3H, m), 3.33 (3H, s), 3.52 (2H, s), 3.64 (3H, s), 3.84 (2H, d), 4.09 (2H, s), 4.47 (2H, brs), 6.06 (1H, brs), 6.84–7.01 (4H, m), 7.11–7.36 (9H, m), 7.60–7.65 (4H, m), 7.89 (1H, s)

Example 14

Methyl (±)-2-[3-[3-[N-[3-[N-(3-chlorophenyl)-N-methylcarbamoylmethyloxy]phenyl]-N-(N-methyl-N-phenylcarbamoylmethyl)carbamoylmethyl]ureido] phenyl]propionate (1–14)

Compound S35 (5.0 g) was dissolved in tetrahydrofuran (300 ml). N,N'-Carbonyldiimidazole (2.12 g) was added to the solution under ice cooling. The mixture was stirred for 4 hours at room temperature. The reaction mixture was concentrated under reduced pressure. 2.37 g of the residue was dissolved in toluene (150 ml). Methyl (±)-2-(3-aminophenyl)propionate (0.91 g) was added to the solution and the solution was refluxed for 7 hours. The reaction mixture was concentrated under reduced pressure and the residue was dissolved in chloroform. The resulting solution was washed successively with 1N HCl, water and brine, then dried over anhydrous magnesium sulfate. The solution was concentrated under reduced pressure. The residue was purified by silica gel column chromatography (chloroform/methanol=30:1) and crystallized from dichloromethane/diethyl ether, obtaining 0.74 g of the compound (1–14) as crystalline powder.

$^1$H-NMR (CDCl$_3$)δ: 1.45 (3H, d), 3.26 (3H, s), 3.32 (3H, s), 3.58–3.68 (4H, m), 3.85 (2H, d), 4.08 (2H, s), 4.11 (2H, s), 5.77 (1H, brs), 6.81–7.39 (18H, m)

Example 15

Methyl 2-[3-[3-[N-[3-[N-methyl-N-(3-methylphenyl)carbamoylmethyloxy]phenyl]-N-(N-methyl-N-phenylcarbamoylmethyl)carbamoylmethyl]ureido]phenyl]acetate (1–15)

Compound S23 (3.0 g) was dissolved in tetrahydrofuran (300 ml). N,N'-Carbonyldiimidazole (1.23 g) was added to the solution under ice cooling. The mixture was stirred for 4 hours at room temperature. The reaction mixture was concentrated under reduced pressure. 2 g of the residue was dissolved in toluene (150 ml). Methyl 2-(3-aminophenyl) acetate (1.16 g) was added to the solution and the solution was refluxed for 5 hours. The reaction mixture was concentrated under reduced pressure and the residue was dissolved in chloroform. The resulting solution was washed successively with 1N HCl, water and brine, then dried over anhydrous magnesium sulfate. The solution was concentrated under reduced pressure. The residue was purified by silica gel column chromatography (chloroform/methanol= 30:1) and crystallized from ethyl acetate/diethyl ether, obtaining 0.57 g of the compound (1–15) as crystalline powder.

¹H-NMR (CDCl₃)δ: 2.38 (3H, s), 3.25 (3H, s), 3.31 (3H, s), 3.55 (2H, s), 3.66 (3H, s), 3.85 (2H, d), 4.08 (2H, s), 4.43 (2H, s), 5.80 (1H, brs), 6.79–6.99 and 7.13–7.40 (18H, m)

Example 16

Methyl (±)-2-[3-[3-[N-[3-[N-methyl-N-(3-methylphenyl)carbamoylmethyloxy]phenyl]-N-(N-methyl-N-phenylcarbamoylmethyl)carbamoylmethyl]ureido]phenyl] propionate (1–16):

Compound S23 (3.0 g) was dissolved in tetrahydrofuran (300 ml). N,N'-Carbonyldiimidazole (1.23 g) was added to the solution under ice cooling. The mixture was stirred for 5 hours at room temperature. The reaction mixture was concentrated under reduced pressure. 1.8 g of the residue was dissolved in toluene (150 ml). Methyl (±)-2-(3-aminophenyl)propionate (1.14 g) was added to the solution and the solution was refluxed for 5 hours. The reaction mixture was concentrated under reduced pressure and the residue was dissolved in chloroform. The solution was washed successively with 1N HCl, water and brine, then dried over anhydrous magnesium sulfate. The solution was concentrated under reduced pressure. The residue was purified by silica gel column chromatography (chloroform/methanol=30:1) and crystallized from ethyl acetate/diethyl ether, obtaining 0.56 g of the compound (1–16) as crystalline powder.

¹H-NMR (CDCl₃)δ: 1.48 (3H, d), 2.39 (3H, s), 3.26 (3H, s), 3.31 (3H, s), 3.63 (3H, s), 3.85 (2H, d), 4.08 (2H, s), 4.43 (2H, s), 5.69 (1H, brs), 6.80–7.41 (17H, m)

Example 17

Methyl (±)-2-[3-[3-[N-[2-[N-methyl-N-(2,3-dimethylphenyl)carbamoylmethyloxy]phenyl]-N-(N-methyl-N-phenylcarbamoylmethyl)carbamoylmethyl]ureido]phenyl] propionate (1–17)

Compound S34 (2.43 g) was dissolved in tetrahydrofuran (300 ml). N,N'-Carbonyldiimidazole (1.07 g) was added to the solution under ice cooling. The mixture was stirred for 4 hours at room temperature. The reaction mixture was concentrated under reduced pressure. 1.5 g of the residue was dissolved in toluene (150 ml). Methyl (+)-2-(3-aminophenyl)propionate (0.93 g) was added to the solution and the solution was refluxed with heat for 7 hours. The reaction mixture was concentrated under reduced pressure and the residue was dissolved in chloroform. The solution was washed successively with 1N HCl, water and brine, then dried over anhydrous magnesium sulfate. The solution was concentrated under reduced pressure. The residue was purified by silica gel column chromatography (chloroform/methanol=30:1), obtaining 0.37 g of the compound (1–17) as powder.

¹H-NMR (CDCl₃)δ: 1.45 (3H, d), 2.16–2.34 (6H, m), 3.23 (3H, s), 3.24 (3H, s), 3.62–3.68 (5H, m), 3.96–4.70 (5H, m), 5.97 (1H, brs), 6.59–7.70 (17H, m)

Example 18

Methyl 2-[3-[3-[N-[2-[N-methyl-N-(2,3-dimethylphenyl)carbamoylmethyloxy]phenyl]-N-(N-methyl-N-phenylcarbamoylmethyl)carbamoylmethyl]ureido]phenyl] acetate (1–18)

Compound S34 (2.37 g) was dissolved in tetrahydrofuran (300 ml). N,N'-Carbonyldiimidazole (2.12 g) was added to the solution under ice cooling. The mixture was stirred for 4 hours at room temperature. The reaction mixture was concentrated under reduced pressure. 2.37 g of the residue was dissolved in toluene (150 ml). Methyl 2-(3-aminophenyl)acetate (1.53 g) was added to the solution and the solution was refluxed for 7 hours. The reaction mixture was concentrated under reduced pressure and the residue was dissolved in chloroform. The solution was washed successively with 1N HCl, water and brine, then dried over anhydrous magnesium sulfate. The solution was concentrated under reduced pressure. The residue was purified by silica gel column chromatography (chloroform/methanol=30:1), obtaining 0.38 g of the compound (1–18) as powder.

¹H-NMR (CDCl₃)δ: 2.16–2.34 (6H, m), 3.14–3.23 (6H, m), 3.65 (3H, s), 3.47–4.69 (8H, m), 6.00 (1H, brs), 6.59–7.69 (17H, m)

Example 19

Methyl 2-[3-[3-[N-[3-[N-methyl-N-(3,5-dimethylphenyl)carbamoylmethyloxy]phenyl]-N-(N-methyl-N-phenylcarbamoylmethyl)carbamoylmethyl]ureido]phenyl] acetate (1–19)

Compound S19 (3.15 g) was dissolved in tetrahydrofuran (150 ml). N,N'-Carbonyldiimidazole (1.26 g) was added to the solution under ice cooling. The mixture was stirred for 4 hours at room temperature. The reaction mixture was concentrated under reduced pressure. 2.03 g of the residue was dissolved in toluene (100 ml). Methyl 2-(3-aminophenyl)acetate (1.15 g) was added to the solution and the solution was refluxed for 6 hours. The reaction mixture was concentrated under reduced pressure and the residue was dissolved in chloroform. The solution was washed successively with 1N HCl, water and brine, then dried over anhydrous magnesium sulfate. The solution was concentrated under reduced pressure. The residue was purified by silica gel column chromatography (chloroform/methanol=50:1), obtaining 0.86 g of the compound (1–19) as crystals.

¹H-NMR (CDCl₃)δ: 2.34 (6H, s), 3.26–3.66 (6H, m), 3.56 (2H, s), 3.66 (3H, s), 3.85 (2H, s), 4.08 (2H, s), 4.43 (2H, s), 5.69 (1H, brs), 6.79–7.41 (17H, m)

Example 20

Methyl (±)-2-[3-[3-[N-[3-[N-methyl-N-(3,5-dimethylphenyl)carbamoylmethyloxy]phenyl]-N-(N-methyl-N-phenylcarbamoylmethyl)carbamoylmethyl]ureido]phenyl] propionate (1–20)

Compound S19 (3.15 g) was dissolved in tetrahydrofuran (150 ml). N,N'-Carbonyldiimidazole (1.26 g) was added to the solution under ice cooling. The mixture was stirred for 4 hours at room temperature. The reaction mixture was concentrated under reduced pressure. 1.50 g of the residue was dissolved in toluene (100 ml). Methyl (±)-2-(3-aminophenyl)propionate (0.92 g) was added to the solution and the solution was refluxed for 6 hours. The reaction mixture was concentrated under reduced pressure and the residue was dissolved in chloroform. The solution was washed successively with 1N HCl, water and brine, then dried over anhydrous magnesium sulfate. The solution was concentrated under reduced pressure. The residue was purified by silica gel column chromatography (chloroform/methanol=50:1) and recrystallized from ethyl acetate-n-hexane, obtaining 0.67 g of the compound (1–20) as crystals.

¹H-NMR (CDCl₃)δ: 1.48 (3H, d), 2.34 (6H, s), 3.26 (3H, s), 3.29 (3H, s), 3.63–3.68 (4H, m), 3.84 (2H, s), 4.08 (2H, s), 4.43 (2H, s), 5.70 (1H, brs), 6.79–7.41 (17H, m)

Example 21

Methyl 2-[3-[N-[2-[N-methyl-N-(3,5-dimethylphenyl)carbamoylmethyloxy]phenyl]-N-(N-methyl-N-phenylcarbamoylmethyl)carbamoylmethyl] ureido]phenyl]acetate (1–21)

Compound S28 (1.0 g) was dissolved in tetrahydrofuran (20 ml). N,N'-Carbonyldiimidazole (0.37 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). Methyl 2-(3-aminophenyl) acetate (0.68 g) was added to the solution. The mixture was refluxed for 3 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was crystallized from ethyl acetate/diethyl ether, obtaining 0.85 g of the compound (1–21) as crystalline powder.

mp 191–192° C. $^1$H-NMR (CDCl$_3$)δ: 2.35 (6H, s), 3.22 (3H, s), 3.24 (3H, s), 3.52 (1H, d), 3.54 (2H, s), 3.65 (3H, s), 3.95 (2H, s), 4.43 (2H, s), 4.68 (1H, d), 6.61 (1H, d), 6.85–6.87 (3H, m), 6.98 (1H, t), 7.03 (1H, s), 7.12–7.36 (9H, m), 7.53 (1H, brs), 7.69 (1H, d) MS (m/z): 680 (M+1)$^+$

Example 22

Methyl (±)-2-[3-[3-[N-[2-[N-methyl-N-(3,5-dimethylphenyl)carbamoylmethyloxy]phenyl]-N-(N-methyl-N-phenylcarbamoylmethyl)carbamoylmethyl] ureido]phenyl]propionate (1–22)

Compound S28 (1.0 g) was dissolved in tetrahydrofuran (20 ml). N,N'-Carbonyldiimidazole (0.37 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). Methyl (+)-2-(3-aminophenyl)propionate (0.68 g) was added to the solution. The mixture was refluxed for 3 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was crystallized from ethyl acetate/diethyl ether, obtaining 0.9 g of the title compound as crystalline powder.

mp 186–188° C. $^1$H-NMR (CDCl$_3$)δ: 1.44 (3H, d), 2.35 (6H, s), 3.22 (3H, s), 3.25 (3H, s), 3.52 (1H, d), 3.61 (3H, s), 3.62 (1H, q), 3.95 (2H, s), 4.44 (2H, s), 4.68 (1H, d), 6.61 (1H, d), 6.82–7.20 and 7.23–7.36 (14H, m), 7.52 (1H, brs), 7.69 (1H, d) MS (m/z): 694 (M+1)$^+$

Example 23

Methyl 2-[3-[3-[N-[2-[N-(3-bromophenyl)-N-methylcarbamoylmethyloxy]phenyl]-N-(N-methyl-N-phenylcarbamoylmethyl)carbamoylmethyl]ureido] phenyl] acetate (1–23)

Compound S31 (1.5 g) was dissolved in tetrahydrofuran (20 ml). N,N'-Carbonyldiimidazole (0.5 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). Methyl 2-(3-aminophenyl) acetate (0.92 g) was added to the solution. The mixture was refluxed for 0.5 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from ethyl acetate/diethyl ether, obtaining 1.2 g of the compound (1–23) as crystalline powder.

mp 99–102° C. $^1$H-NMR (CDCl$_3$)δ: 3.21(3H, s), 3.23 (3H, s), 3.53 (2H, s), 3.60 (1H, d), 3.64 (3H, s), 3.91 (2H, s), 4.44 (2H, s), 4.66 (1H, d), 6.66 (1H, brs), 6.85 (1H, d), 6.99 (1H, t), 7.11–7.60 (14H, m), 7.67 (1H, d)

Example 24

Methyl (±)-2-[3-[3-[N-[2-[N-(3-bromophenyl)-N-methylcarbamoylmethyloxy]phenyl]-N-(N-methyl-N-phenylcarbamoylmethyl)carbamoylmethyl]ureido] phenyl] propionate (1–24)

Compound S31 (1.5 g) was dissolved in tetrahydrofuran (20 ml). N,N'-Carbonyldiimidazole (0.5 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). Methyl (±)-2-(3-aminophenyl) propionate (1.0 g) was added to the solution. The mixture was refluxed for 30 minutes and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from ethyl acetate/diethyl ether, obtaining 1.2 g of the compound (1–24) as crystalline powder.

mp 130–132° C. $^1$H-NMR (CDCl$_3$)δ: 1.43 (3H, d), 3.22 (3H, s), 3.25 (3H, s), 3.56–3.65 (2H, m), 3.62 (3H, s), 3.92 (2H, s), 4.45 (2H, s), 4.66 (1H, d), 6.07 (1H, brs), 6.65 (1H, brs), 6.87 (1H, d), 6.99 (1H, brs), 7.12–7.52 (14H, m), 7.67 (1H, d)

Elementary analysis (for $C_{37}H_{38}BrN_5O_7$) Calculated: C, 59.68; H, 5.14; N, 9.40 Found: C, 59.31; H, 5.13; N, 9.31

Example 25

Methyl 2-[3-[3-[N-[2-[N-methyl-N-(2-methylphenyl) carbamoylmethyloxy]phenyl]-N-(N-methyl-N-phenylcarbamoylmethyl)carbamoylmethyl]ureido]phenyl] acetate (1–25)

Compound S32 (1.0 g) was dissolved in tetrahydrofuran (20 ml). N,N'-Carbonyldiimidazole (0.38 g) was added to the solution. The mixture was stirred for 15 minutes at room temperature. The reaction mixture was concentrated under reduced pressure and the residue was dissolved in toluene (30 ml). Methyl 2-(3-aminophenyl)acetate (0.69 g) was added to the solution. The mixture was refluxed for 30 minutes and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from n-hexane/ethyl acetate/diethyl ether, obtaining 0.8 g of the compound (1–25) as crystalline powder.

mp 124–126° C. $^1$H-NMR (CDCl$_3$)δ: 2.27 (3/2H, s), 2.29 (3/2H, s), 3.21(3H, s), 3.22 (3H, s), 3.51 (1H, d), 3.55 (2H, s), 3.65 (3H, s), 3.94 (2H, d), 4.18 (1H, d), 4.41 (1H, d), 4.67 (1H, d), 6.02 (1H, brs), 6.62 (1H, m), 6.87 (1H, d), 6.98 (1H, t), 7.13–7.41 (14H, m), 7.69 (1H, d) MS (m/z): 666 (M+1)$^+$ Example 26

Methyl (±)-2-[3-[3-[N-[2-[N-methyl-N-(2-methylphenyl)carbamoylmethyloxy]phenyl]-N-(N-methyl-N-phenylcarbamoylmethyl)carbamoylmethyl]ureido]phenyl] propionate (1–26)

Compound S32 (1.0 g) was dissolved in tetrahydrofuran (20 ml). N,N'-Carbonyldiimidazole (0.38 g) was added to the solution. The mixture was stirred for 15 minutes at room temperature. The reaction mixture was concentrated under reduced pressure and the residue was dissolved in toluene (30 ml). Methyl (±)-2-(3-aminophenyl)propionate (0.75 g) was added to the solution. The mixture was refluxed for 30 minutes and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated under reduced pressure. The residue was crystallized from n-hexane/ethyl acetate/diethyl ether, obtaining 0.7 g of the compound (1–26) as crystalline powder.

mp 137–139° C. $^1$H-NMR (CDCl$_3$)δ: 1.45 (3H, d), 2.27 (3/2H, s), 2.30 (3/2H, s), 3.23 (6H, s), 3.50 (1H, d), 3.62 (3H, s), 3.65 (1H, q), 3.94 (2H, d), 4.17 (1H, d), 4.41 (1H, d), 4.67 (1H, d), 5.99 (1H, brs), 6.63 (1H, d), 6.88 (1H, d), 6.98 (1H, t), 7.14–7.37 (14H, m), 7.69 (1H, d) MS (m/z): 680 (M+1)$^+$ Example 27

Methyl 2-[3-[3-[N-[2-[N-methyl-N-(3-methylphenyl)carbamoylmethyloxy]phenyl]-N-(N-methyl-N-phenylcarbamoylmethyl)carbamoylmethyl]ureido]phenyl] acetate (1–27)

Compound S20 (1.0 g) was dissolved in tetrahydrofuran (20 ml). N,N'-Carbonyldiimidazole (0.38 g) was added to the solution. The mixture was stirred for 15 minutes at room temperature. The reaction mixture was concentrated under reduced pressure and the residue was dissolved in chloroform. The organic layer was washed with water and brine, then dried over anhydrous magnesium sulfate. The solvent was distilled off under reduced pressure and the residue was dissolved in toluene (30 ml). Methyl 2-(3-aminophenyl)acetate (0.69 g) was added to the solution. The mixture was refluxed for 1 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol= 50:1). The eluate was concentrated and the residue was crystallized from n-hexane/ethyl acetate/diethyl ether, obtaining 0.8 g of the compound (1–27) as crystalline powder.

mp 133–135° C. $^1$H-NMR (CDCl$_3$)δ: 2.40 (3H, s), 3.23 (3H, s), 3.27 (3H, s), 3.49 (1H, d), 3.55 (2H, s), 3.66 (3H, s), 3.95 (2H, s), 4.42 (2H, s), 4.68 (1H, d), 6.60 (1H, d), 6.87 (1H, d), 6.98 (1H, t), 7.03–7.06 and 7.14–7.38 (14H, m), 7.69 (1H, d) MS (m/z): 666 (M+1)+

Example 28

Methyl (±)-2-[3-[3-[N-[2-[N-methyl-N-(3-methylphenyl)carbamoylmethyloxy]phenyl]-N-(N-methyl-N-phenylcarbamoylmethyl)carbamoylmethyl]ureido]phenyl] propionate (1–28):

Compound S20 (1.0 g) was dissolved in tetrahydrofuran (20 ml). N,N'-Carbonyldiimidazole (0.38 g) was added to the solution. The mixture was stirred for 15 minutes at room temperature. The reaction mixture was concentrated under reduced pressure and the residue was dissolved in chloroform. The organic layer was washed with water and brine, then dried over anhydrous magnesium sulfate. The solvent was distilled off under reduced pressure and the residue was dissolved in toluene (30 ml). Methyl (+)-2-(3-aminophenyl) propionate (0.75 g) was added to the solution. The mixture was refluxed for 3 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated and the residue was crystallized from n-hexane/ethyl acetate/diethyl ether, obtaining 0.6 g of the title compound as crystalline powder.

mp 142–145° C. $^1$H-NMR (CDCl$_3$)δ: 1.45 (3H, d), 2.40 (3H, s), 3.24 (3H, s), 3.27 (3H, s), 3.47 (1H, d), 3.63 (3H, s), 3.65 (1H, q), 3.95 (2H, s), 4.42 (2H, s), 4.68 (1H, d), 6.60 (1H, d), 6.89 (1H, d), 6.96–7.38 (15H, m), 7.70 (1H, d) MS (m/z): 688 (M+1)$^+$

Example 29

Methyl 2-[3-[3-[N-[3-[N-methyl-N-(2,3-dimethylphenyl)carbamoylmethyloxy]phenyl]-N-(N-methyl-N-phenylcarbamoylmethyl)carbamoylmethyl]ureido]phenyl] acetate (1–29)

Compound S21 (1.0 g) was dissolved in tetrahydrofuran (20 ml). N,N'-Carbonyldiimidazole (0.37 g) was added to the solution. The mixture was stirred for 15 minutes at room temperature. The reaction mixture was concentrated under reduced pressure and the residue was dissolved in chloroform. The organic layer was washed with water and brine, then dried over anhydrous magnesium sulfate. The solvent was distilled off under reduced pressure and the residue was dissolved in toluene (30 ml). Methyl 2-(3-aminophenyl) propionate (0.68 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated and the residue was crystallized from ethyl acetate/diethyl ether, obtaining 0.85 g of the compound (1–29) as crystalline powder.

mp 169–171° C. $^1$H-NMR (CDCl$_3$)δ: 2.19 (3H, s), 2.33 (3H, s), 3.22 (3H, s), 3.23 (3H, s), 3.53 (2H, s), 3.64 (3H, s), 3.85 (2H, d), 4.08 (2H, s), 4.40 (2H, s), 6.00 (1H, brs), 6.78 (1H, d), 6.86 (1H, d), 6.91 (1H, s), 7.03 (1H, d), 7.12–7.36 (12H, m), 7.72 (1H, s) MS (m/z): 680 (M+1)$^+$ Elementary analysis (for C$_{38}$H$_{41}$N$_5$O$_7$) Calculated: C, 67.14; H, 6.08; N, 10.30 Found: C, 67.05; H, 6.08; N, 10.22

Example 30

Methyl (±)-2-[3-[3-[N-[3-[N-methyl-N-(2,3-dimethylphenyl)carbamoylmethyloxy]phenyl]-N-(N-methyl-N-phenylcarbamoylmethyl) carbamoylmethyl]ureido]phenyl] propionate (1–30)

Compound S21 (1.0 g) was dissolved in tetrahydrofuran (20 ml). N,N'-Carbonyldiimidazole (0.37 g) was added to the solution. The mixture was stirred for 15 minutes at room temperature. The reaction mixture was concentrated under reduced pressure and the residue was dissolved in chloroform. The organic layer was washed with water and brine, then dried over anhydrous magnesium sulfate. The solvent was distilled off under reduced pressure and the residue was dissolved in toluene (30 ml). Methyl (±)-2-(3-aminophenyl) propionate (0.73 g) was added to the solution. The mixture was refluxed for 3.5 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated and the residue was crystallized from ethyl acetate/diethyl ether, obtaining 0.83 g of the compound (1–30) as crystalline powder.

mp 181–182° C. $^1$H-NMR (CDCl$_3$)δ: 1.44 (3H, d), 2.19 (3H, s), 2.33 (3H, s), 3.23 (6H, s), 3.62 (3H, s), 3.65 (1H, q), 3.85 (2H, d), 4.08 (2H, s), 4.19 (1H, d), 4.40 (1H, d), 5.90 (1H, brs), 6.78 (1H, d), 6.89 (2H, m), 7.00 (1H, d), 7.12–7.37 (12H, m), 7.44 (1H, s) MS (m/z): 694 (M+1)$^+$ Elementary analysis (for C$_{39}$H$_{43}$N$_5$O$_7$) Calculated: C, 67.52; H, 6.25; N, 10.09 Found: C, 67.14; H, 6.25; N, 10.02

Example 31

Methyl 2-[3-[3-[N-[3-[N-methyl-N-(2-methylphenyl) carbamoylmethyloxy]phenyl]-N-(N-methyl-N-phenylcarbamoylmethyl) carbamoylmethyl]ureido]phenyl] acetate (1–31)

Compound S22 (1.5 g) was dissolved in tetrahydrofuran (20 ml). N,N'-Carbonyldiimidazole (0.56 g) was added to the solution. The mixture was stirred for 15 minutes at room temperature. The reaction mixture was concentrated under reduced pressure and the residue was dissolved in chloroform. The organic layer was washed with water and brine, then dried over anhydrous magnesium sulfate. The solvent was distilled off under reduced pressure and the residue was dissolved in toluene (30 ml). Methyl 2-(3-aminophenyl) acetate (1.1 g) was added to the solution. The mixture was refluxed for 30 minutes and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated, obtaining 1.1 g of the compound (1–31) as powder.

$^1$H-NMR (CDCl$_3$)δ: 2.30 (3H, s), 3.21 (3H, s), 3.25 (3H, s), 3.52 (2H, s), 3.63 (3H, s), 3.85 (2H, d), 4.08 (2H, s), 4.21 (1H, d), 4.41 (1H, d), 6.15 (1H, brs), 6.77 (1H, d), 6.83 (1H, d), 6.91 (1H, s), 7.02–7.38 (14H, m), 8.11 (1H, brs)

Example 32

Methyl (±)-2-[3-[3-[N-[3-[N-methyl-N-(2-methylphenyl)carbamoylmethyloxy]phenyl]-N-(N-methyl-N-phenylcarbamoylmethyl) carbamoylmethyl]ureido]phenyl] propionate (1–32)

Compound S22 (1.5 g) was dissolved in tetrahydrofuran (20 ml). N,N'-Carbonyldiimidazole (0.56 g) was added to the solution. The mixture was stirred for 15 minutes at room temperature. The reaction mixture was concentrated under reduced pressure and the residue was dissolved in chloroform. The organic layer was washed with water and brine, then dried over anhydrous magnesium sulfate. The solvent was distilled off under reduced pressure and the residue was dissolved in toluene (30 ml). Methyl (+)-2-(3aminophenyl) propionate (1.1 g) was added to the solution. The mixture was refluxed for 30 minutes and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated, obtaining 1.2 g of the compound (1–32) as powder.

$^1$H-NMR (CDCl$_3$)δ: 1.42 (3H, d), 2.30 (3H, s), 3.21 (3H, s), 3.25 (3H, s), 3.59 (3H, s), 3.63 (1H, q), 3.86 (2H, d), 4.09 (2H, s), 4.21 (1H, d), 4.41 (1H, d), 6.14 (1H, brs), 6.77 (1H, d), 6.86 (1H, d), 6.91 (1H, s), 7.03 (1H, d), 7.10–7.42 (13H, m), 8.05 (1H, brs)

Example 33

Methyl 2-[3-[3-[N-(N-methyl-N-phenylcarbamoylmethyl)-N-[2-(N-methyl-N-phenylcarbamoylmethyloxy)phenyl] carbamoylmethyl]ureido] phenyl]acetate (1–33)

Compound S6 (3.9 g) was dissolved in tetrahydrofuran (150 ml). N,N'-Carbonyldiimidazole (1.6 g) was added to the solution and stirred for 15 minutes at room temperature. The reaction mixture was concentrated under reduced pressure and the residue was dissolved in chloroform. The solution was washed successively with 1N HCl, water and brine, then dried over anhydrous magnesium sulfate. The solvent was distilled off under reduced pressure and the residue was dissolved in toluene (150 ml). Methyl 2-(3-aminophenyl) acetate (2.9 g) was added to the solution. The mixture was refluxed for 20 hours. The reaction mixture was concentrated under reduced pressure and the residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=39:1), obtaining 3.6 g of the compound (1–32) as crystalline powder.

mp 147–149° C. $^1$H-NMR (CDCl$_3$)δ: 3.22(3H, s), 3.27 (3H, s), 3.54 (2H, s), 3.55 (1H, d), 3.64 (3H, s), 3.92 (2H, d), 4.40 (2H, s), 4.68 (1H, d), 6.06 (1H, brs), 6.62 (1H, d), 6.86 (1H, d), 6.98 (1H, t), 7.12–7.52 (15H, m), 7.68 (1H, d) MS (m/z): 652 (M+1)$^+$ Elementary analysis (for C$_{36}$H$_{37}$N$_5$O$_7$) Calculated: C, 66.35; H, 5.72; N, 10.75 Found: C, 66.41; H, 5.67; N, 10.71

Example 34 tert-Butyl 2-[3-[3-[N-[3-[N-ethyl-N-(3,5-dimethylphenyl)carbamoylmethyloxy]phenyl]-N-(N-methyl-N-phenylcarbamoylmethyl)carbamoylmethyl]ureido]phenyl] acetate (1–34)

Compound S29 (1.0 g) was dissolved in tetrahydrofuran (20 ml). N,N'-Carbonyldiimidazole (0.36 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl 2-(3-aminophenyl) acetate (0.83 g) was added to the solution. The mixture was refluxed for 2.5 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 0.9 g of the compound (1–34) as powder.

$^1$H-NMR (CDCl$_3$)δ: 1.14 (3H, t), 1.42 (9H, s), 2.35 (6H, s), 3.25 (3H, s), 3.46 (2H, s), 3.75 (2H, q), 3.85 (2H, d), 4.08 (2H, s), 4.38 (2H, s), 5.73 (1H, brs), 6.78–7.11 and 7.18–7.38 (17H, m)

Example 35 tert-Butyl 2-[3-[3-[N-[3-[N-(3-bromophenyl)-N-methylcarbamoylmethyloxy]phenyl]-N-(N-methyl-N-phenylcarbamoylmethyl)carbamoylmethyl]ureido]phenyl] acetate (1–34)

Compound S30 (1.2 g) was dissolved in tetrahydrofuran (20 ml). N,N'-Carbonyldiimidazole (0.4 g) was added to the solution. The mixture was stirred for 15 minutes at room temperature. The reaction mixture was concentrated under reduced pressure and the residue was dissolved in toluene (30 ml). tert-Butyl 2-(3-aminophenyl) acetate (0.91 g) was added to the solution. The mixture was refluxed for 1.5 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 1.2 g of the compound (1–35) as powder.

$^1$H-NMR (CDCl$_3$)δ: 1.42 (9H, s), 3.26(3H, s), 3.31 (3H, s), 3.46 (2H, s), 3.84 (2H, d), 4.08 (2H, s), 4.45 (2H, s), 5.79 (1H, brs), 6.81–7.00 and 7.16–7.49 (18H, m)

Example 36 tert-Butyl (±)-2-[3-[3-[N-[3-[N-(3-bromophenyl)-N-methylcarbamoylmethyloxy]phenyl]-N-(N-methyl-N-phenylcarbamoylmethyl)carbamoylmethyl]ureido]phenyl]propionate (1–36)

Compound S30 (1.2 g) was dissolved in tetrahydrofuran (20 ml). N,N'-Carbonyldiimidazole (0.4 g) was added to the solution. The mixture was stirred for 15 minutes at room temperature. The reaction mixture was concentrated under reduced pressure and the residue was dissolved in toluene (30 ml). tert-Butyl (±)-2-(3-aminophenyl) propionate (0.97 g) was added to the solution. The mixture was refluxed for 1 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 1.1 g of the compound (1–36) as powder.

$^1$H-NMR (CDCl$_3$)δ: 1.38 (9H, s), 1.39 (3H, d), 3.26(3H, s), 3.31 (3H, s), 3.54 (1H, q), 3.85 (2H, d), 4.08 (2H, s), 4.46 (2H, s), 5.78 (1H, brs), 6.80–7.00 and 7.16–7.50 (18H, m)

Example 37 tert-Butyl (±)-2-[3-[3-[N-[3-[N-ethyl-N-(3,5-dimethylphenyl)carbamoylmethyloxy]phenyl]-N-(N-methyl-N-phenylcarbamoylmethyl)carbamoylmethyl]ureido]phenyl] acetate (1–37)

Compound S29 (1.0 g) was dissolved in tetrahydrofuran (20 ml). N,N'-Carbonyldiimidazole (0.36 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). tert-Butyl (±)-2-(3-aminophenyl) propionate (0.89 g) was added to the solution. The mixture was refluxed for 2.5 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 1.0 g of the compound (1–37) as powder.

$^1$H-NMR (CDCl$_3$)δ: 1.14 (3H, t), 1.37–1.39 (12H, m), 2.35 (6H, s), 3.24 (3H, s), 3.55 (1H, q), 3.74 (2H, q), 3.87 (2H, s), 4.09 (2H, s), 4.39 (2H, s), 5.78 (1H, brs), 6.80–7.04 and 7.19–7.38 (17H, m)

Example 38 tert-Butyl (±)-2-[3-[3-[N-[3-[N-(2-methoxyphenyl)-Nmethylcarbamoylmethyloxy]phenyl]-N-(N-methyl-N-phenylcarbamoylmethyl)carbamoylmethyl]ureido]phenyl]propionate (1–38)

Compound S37 (0.58 g) was dissolved in toluene. tert-Butyl (±)-2-(3-aminophenyl)propionate (0.44 g) was added to the solution and the solution was refluxed for 3 hours. The reaction mixture was cooled, and then ethyl acetate and water was added thereto to separate the organic layer. The aqueous layer was extracted with ethyl acetate. The combined organic layer was washed successively with 1N HCl, water, and brine, then dried over anhydrous magnesium sulfate. The solvent was distilled under reduced pressure. The residue was purified by silica gel column chromatography (eluted with chloroform/methanol=98:2), obtaining 0.44 g of the compound (1–38) as an oily substance.

$^1$H-NMR (CDCl$_3$)δ: 1.38 (9H, s), 1.39 (3H, d), 3.22 (3H, s), 3.24 (3H, s), 3.54 (1H, q), 3.87 (2H, s), 3.88 (3H, s), 4.05 (1H, d), 4.13 (1H, d), 4.32 (1H, d), 4.42 (1H, d), 5.77 (1H, brs), 6.80–7.40 (18H, m)

Example 39 tert-Butyl 2-[3-[3-[N-[3-[N-(2-methoxyphenyl)-N-methylcarbamoylmethyloxy]phenyl]-N-(N-methyl-N-phenylcarbamoylmethyl)carbamoylmethyl]ureido]phenyl] acetate (1–39)

Compound S37 (0.58 g) was dissolved in toluene. tert-Butyl 2-(3-aminophenyl)acetate (0.41 g) was added to the solution and refluxed for 3 hours. The reaction mixture was cooled, and then ethyl acetate and water was added thereto to separate the organic layer. The aqueous layer was extracted with ethyl acetate. The combined organic layer was washed successively with 1N HCl, water, and brine, then dried over anhydrous magnesium sulfate. The solvent was distilled under reduced pressure. The residue was purified by silica gel column chromatography (eluted with chloroform/methanol=98:2), obtaining 0.35 g of the compound (1–39) as an oily substance.

$^1$H-NMR (CDCl$_3$)δ: 1.42 (9H, s), 3.22 (3H, s), 3.26 (3H, s), 3.46 (2H, s), 3.85 (2H, d), 3.88 (3H, s), 4.04 (1H, d), 4.12 (1H, d), 4.32 (1H, d), 4.42 (1H, d), 5.63 (1H, brs), 6.80–7.42 (18H, m)

Example 40 tert-Butyl 2-[3-[3-[N-[2-[N-methyl-N-( 2,3-dimethylphenyl)carbamoylmethyloxy]phenyl]-N-(N-methyl-N-phenylcarbamoylmethyl)carbamoylmethyl]ureido]phenyl] acetate (1–40)

Compound S34 (1.74 g) was dissolved in tetrahydrofuran (100 ml). N,N'-Carbonyldiimidazole (1.23 g) was added to the solution under ice cooling. The mixture was stirred for 4 hours at room temperature. The reaction mixture was concentrated under reduced pressure. The residue was dissolved in toluene (100 ml). tert-Butyl 2-(3-aminophenyl) acetate (1.64 g) was added to the solution and the solution was refluxed for 6 hours. The reaction mixture was concentrated under reduced pressure and the residue was dissolved in chloroform. The solution was washed successively with 1N HCl, water and brine, then dried over anhydrous magnesium sulfate. The solution was concentrated under reduced pressure. The residue was purified by silica gel column chromatography (chloroform/methanol=40:1), obtaining 1.48 g of the compound (1–40) as powder.

$^1$H-NMR (CDCl$_3$)δ: 1.42 (9H, s), 2.18 (3H, d), 2.33 (3H, s), 3.21 (3H, s), 3.23 (3H, s), 3.45–4.70 (8H, m), 5.98 (1H, brs), 6.59–7.68 (17H, m)

Example 41 tert-Butyl (±)-2-[3-[3-[N-[2-[N-methyl-N-(2,3-dimethylphenyl)carbamoylmethyloxy]phenyl]-N-(N-methyl-N-phenylcarbamoylmethyl)carbamoylmethyl]ureido]phenyl] propionate (1–41)

Compound S34 (3.31 g) was dissolved in tetrahydrofuran (150 ml). N,N'-Carbonyldiimidazole (1.32 g) was added to the solution under ice cooling. The mixture was stirred for 2 hours at room temperature. The reaction mixture was concentrated under reduced pressure. The residue was dissolved in toluene (100 ml). tert-Butyl (±)-2-(3-aminophenyl) propionate (2.66 g) was added to the solution and refluxed for 6 hours. The reaction mixture was concentrated under reduced pressure and the residue was dissolved in chloroform. The solution was washed successively with 1N HCl, water and brine, then dried over anhydrous magnesium sulfate. The solution was concentrated under reduced pressure. The residue was purified by silica gel column chromatography (chloroform/methanol=20:1), obtaining 1.46 g of the compound (1–41) as powder.

$^1$H-NMR (CDCl$_3$)δ: 1.37–1.45 (12H, m), 2.16–2.34 (6H, m), 3.23–3.24 (6H, m), 3.44–4.70 (7H, m), 5.91 (1H, brs), 6.61–7.70 (17H, m)

Example 42 tert-Butyl 2-[3-[3-[N-[2-[N-methyl-N-(3,5-dimethylphenyl)carbamoylmethyloxy]phenyl]-N-(N-methyl-N-phenylcarbamoylmethyl)carbamoylmethyl]ureido]phenyl] acetate (1–42)

Compound S28 (1.5 g) was dissolved in tetrahydrofuran (20 ml). N,N'-Carbonyldiimidazole (0.55 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl 2-(3-aminophenyl) acetate (1.3 g) was added to the solution. The mixture was refluxed for 6 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was crystallized from ethyl acetate/diethyl ether, obtaining 1.1 g of the compound (1–42) as crystalline powder.

mp 183–185° C. $^1$H-NMR (CDCl$_3$)δ: 1.41 (9H, s), 2.35 (6H, s), 3.22 (3H, s), 3.24 (3H, s), 3.43 (2H, s), 3.47 (1H, d), 3.95 (2H, s), 4.43 (2H, s), 4.68 (1H, d), 6.04 (1H, brs), 6.61 (1H, d), 6.82–7.20, 7.25–7.44 (15H, m), 7.69 (1H, d) MS (m/z): 722 (M+1)$^+$ Example 43 tert-Butyl (±)-2-[3-[3-[N-[2-[N-methyl-N-(3,5-dimethylphenyl)carbamoylmethyloxy]phenyl]-N-(N-methyl-N-phenylcarbamoylmethyl)carbamoylmethyl]ureido]phenyl] propionate (1–43):

Compound S28 (1.5 g) was dissolved in tetrahydrofuran (20 ml). N,N'-Carbonyldiimidazole (0.55 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl (±)-2-(3-aminophenyl)propionate (1.4 g) was added to the solution. The mixture was refluxed for 6 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was crystallized from ethyl acetate/diethyl ether, obtaining 0.95 g of the compound (1–43) as crystalline powder.

mp 146–149° C. $^1$H-NMR (CDCl$_3$)δ: 1.36–1.39 (12H, m), 2.35 (6H, s), 3.22 (3H, s), 3.25 (3H, s), 3.52–3.55 (2H, m), 3.95 (2H, s); 4.44 (2H, s), 4.69 (1H, d), 6.07 (1H, brs), 6.61 (1H, d), 6.86–7.34 (14H, m), 7.49 (1H, brs), 7.69 (1H, d) MS (m/z): 736 (M+1)$^+$ Example 44 tert-Butyl 2-[3-[3-[N-[2-[N-(3-bromophenyl)-N-methylcarbamoylmethyloxy]phenyl]-N-(N-methyl-N-phenylcarbamoylmethyl)carbamoylmethyl]ureido]phenyl] acetate (1–44)

Compound S31 (1.5 g) was dissolved in tetrahydrofuran (20 ml). N,N'-Carbonyldiimidazole (0.5 g) was added to the solution. The mixture was stirred for 15 minutes at room temperature. The reaction mixture was concentrated under reduced pressure and the residue was dissolved in chloroform. The solution was washed successively with 1N HCl, water and brine, then dried over anhydrous magnesium sulfate. The solvent was distilled off under reduced pressure and the residue was dissolved in toluene (30 ml). tert-Butyl 2-(3-aminophenyl)acetate (1.2 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 1.3 g of the compound (1–44) as powder.

$^1$H-NMR (CDCl$_3$)δ: 1.41 (9H, s), 3.23(3H, s), 3.25 (3H, s), 3.44 (2H, s), 3.58 (1H, d), 3.92 (2H, s), 4.43 (2H, s), 4.66 (1H, d), 5.97 (1H, brs), 6.64 (1H, brs), 6.88 (1H, d), 6.99 (1H, t), 7.19–7.52 (14H, m), 7.68 (1H, d)

Example 45 tert-Butyl (±)-2-[3-[3-[N-[2-[N-(3-bromophenyl)-N-methylcarbamoylmethyloxy]phenyl]-N-(N-methyl-N-phenylcarbamoylmethyl)-carbamoylmethyl]ureido]phenyl] propionate (1–45)

Compound S31 (1.5 g) was dissolved in tetrahydrofuran (20 ml). N,N'-Carbonyldiimidazole (0.5 g) was added to the solution. The mixture was stirred for 15 minutes at room temperature. The reaction mixture was concentrated under reduced pressure and the residue was dissolved in chloroform. The solution was washed successively with 1N HCl, water and brine, then dried over anhydrous magnesium sulfate. The solvent was distilled off under reduced pressure and the residue was dissolved in toluene (30 ml). tert-Butyl (±)-2-(3-aminophenyl)propionate (1.2 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 1.3 g of the compound (1–45) as powder.

$^1$H-NMR (CDCl$_3$)δ: 1.38 (9H, s), 1.40 (3H, d), 3.24(3H, s), 3.27 (3H, s), 3.51–3.54 (2H, m), 3.93 (2H, s), 4.44 (2H, s), 4.66 (1H, d), 5.93 (1H, brs), 6.63 (1H, brs), 6.90 (1H, d), 6.99 (1H, brs), 7.08–7.53 (14H, m), 7.68 (1H, d)

Example 46 tert-Butyl 2-[3-[3-[N-[2-[N-methyl-N-(2-methylphenyl)carbamoylmethyloxy]phenyl]-N-(N-methyl-N-phenylcarbamoylmethyl)carbamoylmethyl]ureido]phenyl]acetate (1–46)

Compound S32 (1.5 g) was dissolved in tetrahydrofuran (20 ml). N,N'-Carbonyldiimidazole (0.56 g) was added to the solution. The mixture was stirred for 15 minutes at room temperature. The reaction mixture was concentrated under reduced pressure and the residue was dissolved in toluene (30 ml). tert-Butyl 2-(3-aminophenyl)acetate (1.3 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 1.4 g of the compound (1–46) as powder.

$^1$H-NMR (CDCl$_3$)δ: 1.41 (9H, s), 2.27 (3H, s), 3.21 (6H, s), 3.44 (2H, s), 3.52 (1H, d), 3.93 (2H, s), 4.17 (1H, d), 4.41 (1H, d), 4.67 (1H, d), 6.01 (1H, brs), 6.62 (1H, m), 6.87 (1H, d), 6.97 (1H, t), 7.15–7.33 (14H, m), 7.69 (1H, d)

Example 47 tert-Butyl (+)-2-[3-[3-[N-[2-[N-methyl-N-(2-methylphenyl)carbamoylmethyloxy]phenyl]-N-(N-methyl-N-phenylcarbamoylmethyl)carbamoylmethyl]ureido]phenyl] propionate (1–47)

Compound S32 (1.5 g) was dissolved in tetrahydrofuran (20 ml). N,N'-Carbonyldiimidazole (0.56 g) was added to the solution. The mixture was stirred for 15 minutes at room temperature. The reaction mixture was concentrated under reduced pressure and the residue was dissolved in toluene (30 ml). tert-Butyl (±)-2-(3-aminophenyl)propionate (1.4 g) was added to the solution. The mixture was refluxed for 0.5 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 1.4 g of the compound (1–47) as powder.

$^1$H-NMR (CDCl$_3$)δ: 1.37 (9H, s), 1.39 (3H, d), 2.27 (3/2H, s), 2.31 (3/2H, s), 3.23 (6H, s), 3.48 (1H, d), 3.53 (1H, q), 3.95 (2H, d), 4.15 (1H, d), 4.41 (1H, d), 4.67 (1H, d), 5.94 (1H, brs), 6.61 (1H, d), 6.90 (1H, d), 6.97 (1H, t), 7.14–7.38 (14H, m), 7.69 (1H, d)

Example 48 tert-Butyl 2-[3-[3-[N-[3-[N-(3,5-dichlorophenyl)-N-methylcarbamoylmethyloxy]phenyl]-N-(N-methyl-N-phenylcarbamoylmethyl)carbamoylmethyl]ureido]phenyl]acetate (1–48):

Compound S18 (2.5 g) was dissolved in tetrahydrofuran (20 ml). N,N'-Carbonyldiimidazole (0.92 g) was added to the solution. The mixture was stirred for 30 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl 2-(3-aminophenyl)acetate (1.9 g) was added to the solution. The mixture was refluxed for 3 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol= 50:1). The eluate was concentrated and the residue was crystallized from dichloromethane/diethyl ether, obtaining 1.2 g of the compound (1–48) as crystalline powder.

mp 132–135° C. $^1$H-NMR (CDCl$_3$)δ: 1.41 (9H, s), 3.24 (3H, s), 3.30 (3H, s), 3.44 (2H, s), 3.86 (2H, d), 4.09 (2H, s), 4.52 (2H, brs), 5.93 (1H, brs), 6.84–7.03 and 7.13–7.37 (16H, m), 7.53 (1H, s)

Elementary analysis (for C$_{39}$H$_{41}$Cl$_2$N$_5$O$_7$) Calculated: C, 61.42; H, 5.42; N, 9.18 Found: C, 61.32; H, 5.48; N, 9.44

Example 49 tert-Butyl (±)-2-[3-[3-[N-[3-[N-(3,5-dichlorophenyl)-N-methylcarbamoylmethyloxy]phenyl]-N-(N-methyl-N-phenylcarbamoylmethyl)carbamoylmethyl]ureido] phenyl]propionate (1–49)

Compound S18 (2.5 g) was dissolved in tetrahydrofuran (50 ml). N,N'-Carbonyldiimidazole (0.92 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl (±)-2-(3-aminophenyl)propionate (2.1 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated and the residue was crystallized from dichloromethane/diethyl ether, obtaining 1.2 g of the compound (1–49) as crystalline powder.

mp 149–152° C. $^1$H-NMR (CDCl$_3$)δ: 1.38 (9H, s), 1.40 (3H, d), 3.26 (3H, s), 3.31 (3H, s), 3.54 (1H, q), 3.85 (2H, d), 4.08 (2H, s), 4.52 (2H, brs), 5.78 (1H, brs), 6.84 (1H, brs), 6.93 (1H, d), 7.00 (1H, d), 7.16–7.40 (13H, m)

Elementary analysis (for C$_{40}$H$_{43}$Cl$_2$N$_5$O$_7$) Calculated: C, 61.86; H, 5.58; N, 9.02 Found: C, 61.66; H, 5.57; N, 9.27

Example 50 tert-Butyl (±)-2-[3-[3-[N-[3-[N-methyl-N-( 3,5-dimethylphenyl)carbamoylmethyloxy]phenyl]-N-(N-methyl-N-phenylcarbamoylmethyl)carbamoylmethyl]ureido]phenyl] propionate (1–50)

Compound S19 (2.5 g) was dissolved in tetrahydrofuran (50 ml). N,N'-Carbonyldiimidazole (1.0 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl (+)-2-(3-aminophenyl)propionate (2.3 g) was added to the solution. The mixture was refluxed for 5 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated and the residue was crystallized from n-hexane/dichloromethane/diethyl ether, obtaining 1.8 g of the compound (1–50) as crystalline powder.

mp 193–194° C. $^1$H-NMR (CDCl$_3$)δ: 1.37 (9H, s), 1.39 (3H, d), 2.34 (6H, s), 3.24 (3H, s), 3.29 (3H, s), 3.53 (1H, q), 3.86 (2H, d), 4.08 (2H, s), 4.43 (2H, s), 5.85 (1H, brs), 6.80 (1H, d), 6.92 (3H, brs), 6.99–7.01 (2H, brs), 7.14–7.37 (11H, m) MS (m/z): 736 (M+1)$^+$ Elementary analysis (for C$_{42}$H$_{49}$N$_5$O$_7$) Calculated: C, 68.55; H, 6.71; N, 9.52 Found: C, 68.72; H, 6.76; N, 9.62

Example 51 tert-Butyl 2-[3-[3-[N-[2-[N-methyl-N-(3-methylphenyl)carbamoylmethyloxy]phenyl]-N-(N-methyl-N-phenylcarbamoylmethyl)carbamoylmethyl]ureido]phenyl]acetate (1–51)

Compound S10 (3.0 g) was dissolved in tetrahydrofuran (50 ml). N,N'-Carbonyldiimidazole (1.12 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl 2-(3-aminophenyl)acetate (2.6 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated and the residue was crystallized from dichloromethane/diethyl ether, obtaining 2.7 g of the compound (1–51) as crystalline powder.

mp 128–130° C. $^1$H-NMR (CDCl$_3$)δ: 1.41 (9H, s), 2.39 (3H, s), 3.23 (3H, s), 3.27 (3H, s), 3.44 (2H, s), 3.50 (1H, d), 3.94 (2H, d), 4.42 (2H, s), 4.68 (1H, d), 5.98 (1H, brs), 6.60 (1H, d), 6.87 (1H, d), 6.95–7.37 (15H, m), 7.69 (1H, d) MS (m/z): 708 (M+1)+

Example 52 tert-Butyl (±)-2-[3-[3-[N-[2-[N-methyl-N-(3-methylphenyl)carbamoylmethyloxy]phenyl]-N-(N-methyl-N-phenylcarbamoylmethyl)carbamoylmethyl]ureido]phenyl] propionate (1–52)

Compound S20 (3.0 g) was dissolved in tetrahydrofuran (50 ml). N,N'-Carbonyldiimidazole (1.12 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl (±)-2-(3-aminophenyl)propionate (2.8 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated and the residue was crystallized from dichloromethane/diethyl ether, obtaining 2.7 g of the compound (1–52) as crystalline powder.

mp 140–142° C. $^1$H-NMR (CDCl$_3$)δ: 1.38 (9H, s), 1.39 (3H, d), 2.40 (3H, s), 3.24 (3H, s), 3.29 (3H, s), 3.48 (1H, d), 3.53 (1H, q), 3.96 (2H, s), 4.42 (2H, s), 4.68 (1H, d), 6.60 (1H, brs), 6.90 (1H, d), 6.97–7.38 (15H, m), 7.70 (1H, d) MS (m/z): 722 (M+1)$^+$ Elementary analysis (for C$_{41}$H$_{47}$N$_5$O$_7$) Calculated: C, 68.22; H, 6.56; N, 9.70 Found: C, 67.95; H, 6.36; N, 9.57

Example 53 tert-Butyl 2-[3-[3-[N-[3-[N-methyl-N-( 2,3-dimethylphenyl)carbamoylmethyloxy]phenyl]-N-(N-methyl-N-phenylcarbamoylmethyl) carbamoylmethyl]ureido]phenyl]acetate (1–53)

Compound S21 (1.7 g) was dissolved in tetrahydrofuran (30 ml). N,N'-Carbonyldiimidazole (1.12 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl 2-(3-aminophenyl) acetate (1.4 g) was added to the solution. The mixture was refluxed for 2 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol= 50:1). The eluate was concentrated, obtaining 1.7 g of the compound (1–53) as powder.

$^1$H-NMR (CDCl$_3$)δ: 1.42 (9H, s), 2.19 (3H, s), 2.33 (3H, s), 3.23 (3H, s), 3.25 (3H, s), 3.46 (2H, s), 3.84 (2H, s), 4.08 (2H, s), 4.19 (1H, d), 4.40 (1H, d), 6.78 (1H, d), 6.89–7.39 (16H, m)

Example 54 tert-Butyl (±)-2-[3-[3-[N-[3-[N-methyl-N-(2,3-dimethylphenyl)carbamoylmethyloxy]phenyl]-N-(N-methyl-N-phenylcarbamoylmethyl) carbamoylmethyl]ureido]phenyl] propionate (1–54)

Compound S21 (1.7 g) was dissolved in tetrahydrofuran (50 ml). N,N'-Carbonyldiimidazole (0.68 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl (±)-2-(3-aminophenyl)propionate (1.5 g) was added to the solution. The mixture was refluxed for 1.5 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated, obtaining 1.3 g of the compound (1–54) as powder.

$^1$H-NMR (CDCl$_3$)δ: 1.37 (9H, s), 1.39 (3H, d), 2.19 (3H, s), 2.33 (3H, s), 3.23 (3H, s), 3.24 (3H, s), 3.54 (1H, q), 3.84 (2H, d), 4.07 (2H, s), 4.19 (1H, d), 4.40 (1H, d), 6.78 (1H, d), 6.89–7.38 (16H, m)

Example 55 tert-Butyl 2-[3-[3-[N-[3-[N-methyl-N-(2-methylphenyl)carbamoylmethyloxy]phenyl]-N-(N-methyl-N-phenylcarbamoylmethyl) carbamoylmethyl]ureido]phenyl]acetate (1–55)

Compound S22 (1.5 g) was dissolved in tetrahydrofuran (50 ml). N,N'-Carbonyldiimidazole (0.56 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). tert-Butyl 2-(3-aminophenyl) acetate (1.3 g) was added to the solution. The mixture was refluxed for 0.5 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol= 50:1). The eluate was concentrated, obtaining 1.5 g of the compound (1–55) as powder.

$^1$H-NMR (CDCl$_3$)δ: 1.42 (9H, s), 2.30 (3H, s), 3.24 (3H, s), 3.25 (3H, s), 3.46 (2H, s), 3.84 (2H, s), 4.07 (2H, s), 4.20 (1H, d), 4.40 (1H, d), 6.77 (1H, d), 6.89 (1H, s), 6.93 (1H, d), 6.98 (1H, d), 7.10–7.41 (14H, m)

Example 56 tert-Butyl (±)-2-[3-[3-[N-[3-[N-methyl-N-(2-methylphenyl)carbamoylmethyloxy]phenyl]-N-(N-methyl-N-phenylcarbamoylmethyl) carbamoylmethyl]ureido]phenyl] propionate (1–56)

Compound S22 (1.5 g) was dissolved in tetrahydrofuran (50 ml). N,N'-Carbonyldiimidazole (0.56 g) was added to the solution. The mixture was stirred for 15 minutes at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (30 ml). tert-Butyl (±)-2-(3-aminophenyl)propionate (1.4 g) was added to the solution. The mixture was refluxed for 0.5 hour and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1). The eluate was concentrated, obtaining 1.5 g of the compound (1–56) as powder.

$^1$H-NMR (CDCl$_3$)δ: 1.38 (9H, s), 1.40 (3H, d), 2.30 (3H, s), 3.24 (6H, s), 3.54 (1H, q), 3.85 (2H, s), 4.08 (2H, s), 4.20 (1H, d), 4.40 (1H, d), 6.78 (1H, d), 6.89 (1H, s), 6.95 (1H, d), 6.98 (1H, d), 7.19–7.39 (14H, m)

Example 57 tert-Butyl (±)-2-[3-[3-[N-[3-[N-methyl-N-(3-methylphenyl)carbamoylmethyloxy]phenyl]-N-(N-methyl-N-phenylcarbamoylmethyl)carbamoylmethyl]ureido]phenyl] propionate (1–57)

Compound S23 (2.0 g) was dissolved in tetrahydrofuran (50 ml). N,N'-Carbonyldiimidazole (0.75 g) was added to the solution. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl (±)-2-(3-aminophenyl)propionate (1.9 g) was added to the solution. The mixture was refluxed for 4 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=50:1), obtaining 2.1 g of the compound (1–57) as powder.

$^1$H-NMR (CDCl$_3$)δ: 1.37 (9H, s), 1.42 (3H, d), 2.38 (3H, s), 3.23 (3H, s), 3.31 (3H, s), 3.53 (1H, q), 3.85 (2H, d), 4.09 (2H, s), 4.43 (2H, s), 5.98 (1H, brs), 6.80 (1H, d), 6.89–6.91 (2H, m), 7.01 (1H, d), 7.12–7.36 (13H, m), 7.65 (1H, brs)

Example 58 tert-Butyl 2-[3-[3-[N-[3-[N-methyl-N-(3-methylphenyl)carbamoylmethyloxy]phenyl]-N-(N-methyl-N-phenylcarbamoylmethyl)carbamoylmethyl]ureido]phenyl]acetate (1–58)

Compound S23 (1.5 g) was dissolved in tetrahydrofuran (50 ml). N,N'-Carbonyldiimidazole (0.56 g) was added to the solution. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure and the residue was dissolved in toluene (50 ml). tert-Butyl 2-(3-aminophenyl)acetate (1.3 g) was added to the solution. The mixture was refluxed for 3.5 hours and concentrated under reduced pressure. The residue was partitioned between chloroform and 1N HCl. The two layers were separated. The organic layer was washed with water and brine, then dried over anhydrous magnesium sulfate. The solvent was distilled off under reduced pressure. The residue was purified by silica gel column chromatography (eluted with chloroform/methanol=24:1), obtaining 1.1 g of the compound (1–58) as powder.

$^1$H-NMR (CDCl$_3$)δ: 1.41 (9H, s), 2.38 (3H, s), 3.23 (3H, s), 3.31 (3H, s), 3.44 (2H, s), 3.85 (2H, d), 4.08 (2H, s), 4.43 (2H, s), 5.96 (1H, brs), 6.80 (1H, d), 6.87–6.91 (2H, m), 7.01 (1H, d), 7.12–7.36 (13H, m), 7.64 (1H, brs)

Example 59

2-[3-[3-[N-[3-[N-Ethyl-N-(3,5-dimethylphenyl)carbamoylmethyloxy]phenyl]-N-(N-methyl-N-phenylcarbamoylmethyl)carbamoylmethyl]ureido]phenyl]acetic acid (1–59)

Compound (1–34) (0.9 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solvent was washed with water and brine, then dried over anhydrous magnesium sulfate. The solvent was distilled off under reduced pressure, obtaining 0.7 g of the compound (1–59) as powder.

$^1$H-NMR (CDCl$_3$)δ: 1.13 (3H, t), 2.33 (6H, s), 3.21 (3H, s), 3.48 (2H, s), 3.74–3.78 (4H, m), 4.04 (2H, s), 4.37 (2H, s), 6.25 (1H, brs), 6.74 (1H, d), 6.79 (1H, d), 6.88 (2H, s), 6.95–7.36 (12H, m), 8.06 (1H, s)

Example 60

2-[3-[3-[N-[3-[N-(3-Bromophenyl)-N-methylcarbamoylmethyloxy]phenyl]-N-(N-methyl-N-phenylcarbamoylmethyl)carbamoylmethyl]ureido]phenyl]acetic acid (1–60)

Compound (1–35) (1.2 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 0.9 g of the compound (1–60) as powder.

$^1$H-NMR (CDCl$_3$)δ: 3.21(3H, s), 3.28 (3H, s), 3.46 (2H, s), 3.78 (2H, s), 4.05 (2H, s), 4.44 (2H, s), 6.27 (1H, brs), 6.77–7.47 (17H, m), 8.10 (1H, s)

Example 61

(±)-2-[3-[3-[N-[3-[N-(3-Bromophenyl)-N-methylcarbamoylmethyloxy]phenyl]-N-(N-methyl-N-phenylcarbamoylmethyl)carbamoylmethyl]ureido]phenyl]propionic acid (1–61)

Compound (1–36) (1.1 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The organic layer was washed with water and brine, then dried over anhydrous magnesium sulfate. The solvent was distilled off under reduced pressure, obtaining 0.83 g of the compound (1–61) as powder.

$^1$H-NMR (CDCl$_3$)δ: 1.39 (3H, d), 3.21(3H, s), 3.29 (3H, s), 3.59 (1H, q), 3.78 (2H, s), 4.04 (2H, s), 4.45 (2H, s), 6.28 (1H, brs), 6.74–7.48 (17H, m), 8.13 (1H, s)

Example 62

(±)-2-[3-[3-[N-[3-[N-Ethyl-N-(3,5-dimethylphenyl) carbamoylmethyloxy]phenyl]-N-(N-methyl-N-phenylcarbamoylmethyl)carbamoylmethyl]ureido] phenyl]propionic acid (1–62)

Compound (1–37) (1.0 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 0.72 g of the compound (1–62) as powder.

$^1$H-NMR (CDCl$_3$+DMSO-d$_6$)δ: 1.13 (3H, t), 1.40 (3H, d), 2.33 (6H, s), 3.21 (3H, s), 3.60 (1H, q), 3.73–3.78 (4H, m), 4.04 (2H, s), 4.37 (2H, s), 6.27 (1H, brs), 6.72 (1H, d), 6.84 (1H, d), 6.88 (2H, s), 6.93–7.39 (12H, m), 8.08 (1H, s)

Example 63

(±)-2-[3-[3-[N-[3-[N-(2-Methoxyphenyl)-Nmethylcarbamoylmethyloxy]phenyl]-N-(N-methyl-N-phenylcarbamoylmethyl)carbamoylmethyl]ureido] phenyl]propionic acid (1–63)

Compound (1–38) (0.44 g) was dissolved in dichloromethane (1 ml). Trifluoroacetic acid (1 ml) was added to the solution and stirred for 2 hours at room temperature. The reaction mixture was partitioned between chloroform and water. The aqueous layer was extracted with chloroform. The combined organic layer was washed with brine, and dried over anhydrous magnesium sulfate. The solvent was distilled off under reduced pressure. The residue was crystallized from diethyl ether, obtaining 0.35 g of the compound (1–63) as crystalline powder.

mp 115–118° C. $^1$H-NMR(DMSO-d$_6$)δ: 1.30 (3H, d), 3.08 (3H, s), 3.19 (3H, s), 3.56 (1H, q), 3.61 (2H, brs), 3.85 (3H, s), 4.04 (2H, m), 4.26 (1H, d), 4.45 (1H, d), 6.27 (1H, brs), 6.79–7.46 (17H, m), 8.84 (1H, s), 12.18 (1H, brs)

Example 64

2-[3-[3-[N-[3-[N-(2-Methoxyphenyl)-N-methylcarbamoylmethyloxy]phenyl]-N-(N-methyl-N-phenylcarbamoylmethyl)carbamoylmethyl]ureido] phenyl]acetic acid (1–64)

Compound (1–39) (0.35 g) was dissolved in -dichloromethane (1 ml). Trifluoroacetic acid (1 ml) was added to the solution and stirred for 2 hours at room temperature. The reaction mixture was partitioned between chloroform and water. The aqueous layer was extracted with chloroform. The combined organic layer was washed with brine and dried over anhydrous magnesium sulfate. The solvent was distilled off under reduced pressure. The residue was crystallized from diethyl ether, obtaining 0.28 g of the compound (1–64) as crystalline powder.

mp 110–113° C. $^1$H-NMR(DMSO-d$_6$)δ: 3.08 (3H, s), 3.18 (3H, s), 3.46 (2H, s), 3.60 (2H, brs), 3.85 (3H, s),4.03 (2H, m), 4.26 (1H, d), 4.45 (1H, d), 6.29 (1H, brs), 6.76–7.46 (17H, m), 8.80 (1H, s)

Example 65

2-[3-[3-[N-[2-[N-Methyl-N-(2,3-dimethylphenyl) carbamoylmethyloxy]phenyl]-N-(N-methyl-N-phenylcarbamoylmethyl)carbamoylmethyl]ureido] phenyl]acetic acid (1–65)

Compound (1–40) (1.48 g) was dissolved in methylene chloride (50 ml). Trifluoroacetic acid (25 ml) was added to the solution while stirring on ice. The mixture was stirred for 30 minutes at room temperature. The reaction mixture was concentrated under reduced pressure. The residue was dissolved in chloroform. The solution was washed with water and brine, then dried over anhydrous magnesium sulfate. The solution was concentrated under reduced pressure, obtaining 0.51 g of the compound (1–65).

$^1$H-NMR (CDCl$_3$)δ: 2.13 (3H, d), 2.30 (3H, d), 3.14–3.17 (6H, m), 3.41–4.70 (8H, m), 6.32–7.99 (18H, m)

Example 66

2-[3-[3-[N-[2-[N-Methyl-N-(3,5-dimethylphenyl) carbamoylmethyloxy]phenyl]-N-(N-methyl-N-phenylcarbamoylmethyl)carbamoylmethyl]ureido] phenyl]acetic acid (1–66)

Compound (1–42) (0.6 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was crystallized from dichloromethane/diethyl ether, obtaining 0.4 g of the compound (1–66) as crystalline powder.

mp 227–228° C. $^1$H-NMR (CDCl$_3$+DMSO-d$_6$)δ: 2.35 (6H, s), 3.21(3H, s), 3.25 (3H, s), 3.48 (2H, s), 3.57 (1H, d), 3.67 (1H, d), 3.88 (1H, d), 4.40 (2H, s), 4.74 (1H, d), 6.67 (1H, d), 6.81–6.85 (3H, m), 6.97 (1H, t), 7.02 (1H, s), 7.12 (1H, t), 7.24–7.42 (8H, m), 7.66 (1H, d), 8.38 (1H, s) MS (m/z): 666 (M+1)$^+$

Example 67

(±)-2-[3-[3-[N-[2-[N-Methyl-N-(3,5-dimethylphenyl) carbamoylmethyloxy]phenyl]-N-(N-methyl-N-phenylcarbamoylmethyl) carbamoylmethyl]ureido]phenyl]propionic acid (1–67)

Compound (1–43) (0.6 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was crystallized from dichloromethane/diethyl ether, obtaining 0.38 g of the compound (1–67) as crystalline powder.

mp 221–222° C. $^1$H-NMR (CDCl$_3$+DMSO-d$_6$)δ: 1.42 (3H, d), 2.35 (6H, s), 3.22(3H, s), 3.25 (3H, s), 3.54–3.62 (2H, m), 3.70 (1H, d), 3.89 (1H, d), 4.40 (2H, s), 4.74 (1H, d), 6.65 (1H, d), 6.85–6.88 (3H, m), 6.97 (1H, t), 7.03 (1H, s), 7.13 (1H, t), 7.23–7.42 (8H, m), 7.66 (1H, d), 8.29 (1H, s) MS (m/z): 680 (M+1)$^+$

Example 68

(±)-2-[3-[3-[N-[2-[N-Methyl-N-(2,5-dimethylphenyl) carbamoylmethyloxy]phenyl]-N-(N-methyl-N-phenylcarbamoylmethyl) carbamoylmethyl]ureido]phenyl]propionic acid (1–68)

Compound (1–41) (1.46 g) was dissolved in dichloromethane (100 ml). Trifluoroacetic acid (20 ml) was added to the solution under ice cooling. The mixture was stirred for 4 hours at room temperature. The reaction mixture was concentrated under reduced pressure and the residue was dissolved in chloroform. The solution was washed with water and brine, then dried over anhydrous magnesium sulfate. The solution was concentrated under reduced pressure, obtaining 0.31 g of the compound (1–68) as powder.

$^1$H-NMR (CDCl$_3$)δ: 1.45 (3H, d), 2.17–2.32 (6H, m), 3.16–3.23 (6H, m), 3.52–4.69 (7H, m), 6.28–7.68 (18H, m)

Example 69

2-[3-[3-[N-[2-[N-(3-Bromophenyl)-N-methylcarbamoylmethyloxy]phenyl]-N-(N-methyl-N-phenylcarbamoylmethyl)carbamoylmethyl]ureido]phenyl]acetic acid (1–69)

Compound (1–44) (1.0 g) was dissolved in dichloromethane (20 ml). Trifluoroacetic acid (20 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 0.8 g of the compound (1–70) as powder.

$^1$H-NMR (CDCl$_3$)δ: 3.17(3H, s), 3.20 (3H, s), 3.47 (2H, s), 3.59 (1H, d), 3.83 (2H, s), 4.39 (2H, s), 4.68 (1H, d), 6.33 (1H, brs), 6.65 (1H, brs), 6.80 (1H, d), 6.94–7.46 (14H, m), 7.65 (1H, d), 7.88 (1H, s)

Example 70

(±)-2-[3-[3-[N-[2-[N-(3-Bromophenyl)-N-methylcarbamoylmethyloxy]phenyl]-N-(N-methyl-N-phenylcarbamoylmethyl)carbamoylmethyl]ureido]phenyl]propionic acid (1–70)

Compound (1–45) (1.3 g) was dissolved in dichloromethane (20 ml). Trifluoroacetic acid (20 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 1.0 g of the compound (1–70) as powder.

$^1$H-NMR (CDCl$_3$)δ: 1.40 (3H, d), 3.18(3H, s), 3.19 (3H, s), 3.60–3.62 (2H, m), 3.82 (2H, s), 4.39 (2H, s), 4.68 (1H, d), 6.35 (1H, brs), 6.65 (1H, brs), 6.86 (1H, d), 6.96 (1H, t), 7.09–7.47 (13H, m), 7.64 (1H, d), 7.91 (1H, s)

Example 71

2-[3-[3-[N-[2-[N-Methyl-N-(2-methylphenyl)carbamoylmethyloxy]phenyl]-N-(N-methyl-N-phenylcarbamoylmethyl)carbamoylmethyl]ureido]phenyl]acetic acid (1–71)

Compound (1–46) (1.3 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 0.9 g of the compound (1–71) as powder.

$^1$H-NMR (CDCl$_3$)δ: 2.19 (3/2H, s), 2.27 (3/2H, s), 3.15 (3H, s), 3.21 (3H, s), 3.48 (2H, s), 3.58 (1H, d), 3.81–3.88 (2H, m), 4.14 (1H, d), 4.38 (1H, d), 4.70 (1H, d), 6.34 (1H, brs), 6.63 (1H, t), 6.81 (1H, d), 6.94–7.40 (14H, m), 7.67 (1H, d), 7.82 (1H, s) MS (m/z): 652 (M+1)$^+$ Example 72

(±)-2-[3-[3-[N-[2-[N-Methyl-N-(2-methylphenyl)carbamoylmethyloxy]phenyl]-N-(N-methyl-N-phenylcarbamoylmethyl)carbamoylmethyl]ureido]phenyl]propionic acid (1–72)

Compound (1–47) (1.3 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 1.0 g of the compound (1–72) as powder.

$^1$H-NMR (CDCl$_3$)δ: 1.44 (3H, m), 2.18(3/4H, s), 2.20 (3/4H, s), .2.27 (3/2H, s), 3.15(3H, s), 3.20 (3H, s), 3.57 (1H, d), 3.63 (1H, q), 3.80–3.88 (2H, m), 4.13 (1H, d), 4.36 (1H, d), 4.67 (1H, d), 6.36 (1H, brs), 6.63 (1H, t), 6.88 (1H, d), 6.95(1H, t), 7.05–7.45(13H, m), 7.66 (1H, d), 7.85 (1H, s) MS (m/z): 666 (M+1)$^+$ Example 73

2-[3-[3-[N-[2-[N-Methyl-N-(3-methylphenyl)carbamoylmethyloxy]phenyl]-N-(N-methyl-N-phenylcarbamoylmethyl)carbamoylmethyl]ureido]phenyl]acetic acid (1–73)

Compound (1–51) (1.5 g) was dissolved in dichloromethane (20 ml). Trifluoroacetic acid (20 ml) was added to the solution under ice cooling. The mixture was stirred for 2.5 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was purified by silica gel column chromatography (eluted with chloroform/methanol=15:1), obtaining 0.87 g of the compound (1–73) as powder.

mp 195–199° C. $^1$H-NMR (DMSO-d$_6$)δ: 2.40 (3H, s), 3.21 (3H, s), 3.24 (3H, s), 3.52 (2H, s), 3.56–3.60 (2H, m), 3.84 (1H, dd), 4.56 (3H, brs), 6.34 (1H, brs), 6.85 (1H, d), 6.93 (1H, brs), 7.09–7.51 (14H, m), 7.67 (1H, d), 8.86 (1H, s) MS (m/z): 652 (M+1)$^+$ Example 74

(±)-2-[3-[3-[N-[2-[N-Methyl-N-(3-methylphenyl)carbamoylmethyloxy]phenyl]-N-(N-methyl-N-phenylcarbamoylmethyl)carbamoylmethyl]ureido]phenyl]propionic acid (1–74)

Compound (1–52) (1.5 g) was dissolved in dichloromethane (20 ml). Trifluoroacetic acid (20 ml) was added to the solution under ice cooling. The mixture was stirred for 1.5 hour at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was purified by silica gel column chromatography (eluted with chloroform/methanol=15:1), obtaining 0.87 g of the compound (1–74) as powder.

mp 174–177° C. $^1$H-NMR (DMSO-d$_6$)δ: 1.30 (3H, d), 2.33 (3H, s), 3.13 (3H, s), 3.16 (3H, s), 3.35–3.55 (3H, m), 3.75 (1H, dd), 4.49 (3H, brs), 6.24 (1H, brs), 6.80 (1H, d), 6.83 (1H, brs), 7.02–7.44 (14H, m), 7.59 (1H, d), 8.82 (1H, s) MS (m/z): 666 (M+1)$^+$

Example 75

2-[3-[3-[N-[3-[N-(3,5-Dichlorophenyl)-N-methylcarbamoylmethyloxy]phenyl]-N-(N-methyl-N-phenylcarbamoylmethyl)carbamoylmethyl]ureido]phenyl]acetic acid (1–75)

Compound (1–43) (0.76 g) was dissolved in dichloromethane (20 ml). Trifluoroacetic acid (20 ml) was added to the solution under ice cooling. The mixture was stirred for 2 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was purified by silica gel column chromatography (eluted with chloroform/methanol=9:1), obtaining 0.6 g of the compound (1–75) as powder.

$^1$H-NMR (CDCl$_3$)δ: 3.21 (3H, s), 3.28 (3H, s), 3.47 (2H, s), 3.80 (2H, s), 4.05 (2H, s), 4.51 (2H, brs), 6.25 (1H, brs), 6.78 (2H, d), 6.95–7.43 (14H, m), 8.04 (1H, s)

Example 76

(±)-2-[3-[3-[N-[3-[N-(3,5-dichlorophenyl)-N-methylcarbamoylmethyloxy]phenyl]-N-(N-methyl-N-phenylcarbamoylmethyl)carbamoylmethyl]ureido]phenyl]propionic acid (1–76)

Compound (1–49) (0.78 g) was dissolved in dichloromethane (20 ml). Trifluoroacetic acid (20 ml) was added to the solution under ice cooling. The mixture was stirred for 2 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was purified by silica gel column chromatography (eluted with chloroform/methanol=9:1), obtaining 0.62 g of the compound (1–76) as powder.

$^1$H-NMR (CDCl$_3$)δ: 1.42 (3H, d), 3.23 (3H, s), 3.29 (3H, s), 3.62 (1H, d), 3.80 (2H, s), 4.03 (2H, q), 4.52 (2H, brs), 6.28 (1H, brs), 6.79–6.97 and 7.10–7.40 (16H, m), 7.97 (1H, s)

Example 77

(±)-2-[3-[3-[N-[3-[N-Methyl-N-(3,5-dimethylphenyl) carbamoylmethyloxy]phenyl]-N-(N-methyl-N-phenylcarbamoylmethyl)carbamoylmethyl]ureido]phenyl]propionic acid (1–77)

Compound (1–50) (1.0 g) was dissolved in dichloromethane (20 ml). Trifluoroacetic acid (20 ml) was added to the solution under ice cooling. The mixture was stirred for 2 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was purified by silica gel column chromatography (eluted with chloroform/methanol=9:1), obtaining 0.8 g of the compound (1–77) as powder.

$^1$H-NMR (CDCl$_3$)δ: 1.39 (3H, d), 2.32 (6H, s), 3.21 (3H, s), 3.28 (3H, s), 3.58 (1H, q), 3.78 (2H, s), 4.04 (2H, s), 4.43 (2H, s), 6.27 (1H, s), 6.73 (1H, d), 6.84–7.33 (15H, m), 8.12 (1H, brs) MS (m/z): 680 (M+1)$^+$

Example 78

2-[3-[3-[N-[3-[N-Methyl-N-(2-methylphenyl) carbamoylmethyloxy]phenyl]-N-(N-methyl-N-phenylcarbamoylmethyl)carbamoylmethyl]ureido]phenyl]acetic acid (1–78)

Compound (1–55) (1.5 g) was dissolved in dichloromethane (20 ml). Trifluoroacetic acid (10 ml) was added to the solution under ice cooling. The mixture was stirred for 1.5 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 1.0 g of the compound (1–78) as powder.

$^1$H-NMR (CDCl$_3$)δ: 2.28 (3H, s), 3.22 (3H, s), 3.24 (3H, s), 3.50 (2H, s), 3.78 (2H, s), 4.03 (2H, q), 4.19 (1H, d), 4.39 (1H, d), 6.28 (1H, brs), 6.72 (1H, d), 6.81 (1H, d), 6.87 (1H, s), 6.96 (1H, d), 7.05–7.38 (13H, m), 8.05 (1H, s)

Example 79

(±)-2-[3-[3-[N-[3-[N-Methyl-N-(2-methylphenyl) carbamoylmethyloxy]phenyl]-N-(N-methyl-N-phenylcarbamoylmethyl)carbamoylmethyl]ureido]phenyl]propionic acid (1–79)

Compound (1–56) (1.5 g) was dissolved in dichloromethane (20 ml). Trifluoroacetic acid (10 ml) was added to the solution under ice cooling. The mixture was stirred for 1 hour at room temperature. The reaction mixture was concentrated under reduced pressure and the residue was dissolved in chloroform. The solution was washed with water and brine, then dried over anhydrous magnesium sulfate. The solvent was distilled off under reduced pressure, obtaining 1.2 g of the compound (1–79) as powder.

$^1$H-NMR (CDCl$_3$)δ: 1.42 (3H, d), 2.28 (3H, s), 3.22 (3H, s), 3.24 (3H, s), 3.61 (1H, q), 3.77 (2H, s), 4.01–4.06 (2H, m), 4.19 (1H, d), 4.39 (1H, d), 6.29 (1H, brs), 6.72 (1H, d), 6.85 (2H, brs), 6.95 (1H, d), 7.07–7.42 (13H, m), 8.06 (1H, s)

Example 80

2-[3-[3-[N-[3-[N-Methyl-N-(2,3-dimethylphenyl) carbamoylmethyloxy]phenyl]-N-(N-methyl-N-phenylcarbamoylmethyl)carbamoylmethyl]ureido]phenyl]acetic acid (1–80)

Compound (1–53) (1.3 g) was dissolved in dichloromethane (20 ml). Trifluoroacetic acid (20 ml) was added to the solution under ice cooling. The mixture was stirred for 2 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was purified by silica gel column chromatography (eluted with chloroform/methanol=9:1), obtaining 0.96 g of the compound (1–80) as powder.

mp 142–163° C. $^1$H-NMR (DMSO-d$_6$)δ: 2.13 (3H, s), 2.28 (3H, s), 3.09 (3H, s), 3.18 (3H, s), 3.36 (2H, s), 3.60 (2H, s), 4.03 (2H, s), 4.23 (1H, d), 4.39 (2H, s), 6.37 (1H, s), 6.78 (1H, d), 6.90 (1H, s), 6.99 (1H, d), 7.07–7.46 (12H, m), 8.85 (1H, s) MS (m/z): 666 (M+1)$^+$

Example 81

(±)-2-[3-[3-[N-[3-[N-Methyl-N-(2,3-dimethylphenyl) carbamoylmethyloxy]phenyl]-N-(N-methyl-N-phenylcarbamoylmethyl) carbamoylmethyl]ureido]phenyl]propionic acid (1–81)

Compound (1–54) (1.3 g) was dissolved in dichloromethane (20 ml). Trifluoroacetic acid (20 ml) was added to the solution under ice cooling. The mixture was stirred for 2 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was purified by silica gel column chromatography (eluted with chloroform/methanol=9:1), obtaining 0.8 g of the compound (1–81) as powder.

mp 135–147° C. $^1$H-NMR (DMSO-d$_6$)δ: 1.29 (3H, d), 2.13 (3H, s), 2.28 (3H, s), 3.09 (3H, s), 3.19 (3H, s), 3.49 (1H, q), 3.60 (2H, s), 4.03 (2H, s), 4.24 (1H, d), 4.40 (1H, d), 6.32 (1H, s), 6.77–6.82 (3H, m), 6.90 (1H, s), 7.00 (1H, d), 7.09–7.46 (11H, m), 8.87 (1H, s) MS (m/z): 680 (M+1)$^+$

Example 82

2-[3-[3-[N-[3-[N-Methyl-N-(3-methylphenyl) carbamoylmethyloxy]phenyl]-N-(N-methyl-N-phenylcarbamoylmethyl)carbamoylmethyl]ureido] phenyl]acetic acid (1–82)

Compound (1–58) (1.1 g) was dissolved in dichloromethane (50 ml). Trifluoroacetic acid (20 ml) was added to the solution under ice cooling. The mixture was stirred for 7 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was dissolved in diethyl ether and n-hexane was added to give 0.8 g of the compound (1–82) as powder.

mp 114–120° C. $^1$H-NMR (CDCl$_3$)δ: 2.37 (3H, s), 3.22 (3H, s), 3.29 (3H, s), 3.50 (2H, s), 3.80 (2H,, s), 4.05 (2H, s), 4.42 (2H, s), 6.21 (1H, brs), 6.75 (1H, d), 6.82 (1H, d), 6.89 (1H, s), 6.95 (1H, d), 7.08–7.38 (13H, m), 7.90 (1H, brs) MS (m/z): 652 (M+1)$^+$ Example 83

(±)-2-[3-[3-[N-[3-[N-Methyl-N-(3-methylphenyl) carbamoylmethyloxy]phenyl]-N-(N-methyl-N-phenylcarbamoylmethyl)carbamoylmethyl]ureido] phenyl]propionic acid (1–83)

Compound (1–57) (2.1 g) was dissolved in dichloromethane (50 ml). Trifluoroacetic acid (20 ml) was added to the solution under ice cooling. The mixture was stirred for 7 hours at room temperature. The reaction mixture was concentrated under reduced pressure and the residue was dissolved in chloroform. The solution was washed with water and brine, then dried over anhydrous magnesium sulfate. The solvent was distilled off under reduced pressure. The residue was dissolved in diethyl ether and n-hexane was added to give 1.7 g of the compound (1–83) as powder.

mp 120–127° C. $^1$H-NMR (CDCl$_3$)δ: 1.42 (3H, d), 2.37 (3H, s), 3.22 (3H, s), 3.29 (3H, s), 3.61 (1H, q), 3.78 (2H, s), 4.04 (2H, s), 4.42 (2H, s), 6.27 (1H, brs), 6.74 (1H, d), 6.85 (1H, d), 6.87 (1H, s), 6.94 (1H, d), 7.07–7.42 (13H, m), 8.00 (1H, brs) MS (m/z): 666 (M+1)$^+$ Example 84

(±)-2-[3-[3-[N-[2-[N-(3,5-Dimethoxyphenyl)-N-methylcarbamoylmethyloxy]phenyl]-N-(N-methyl-N-phenylcarbamoylmethyl)carbamoylmethyl]ureido] phenyl]propionic acid (1–84)

Compound (1–8) (0.44 g) was dissolved in a mixture of tetrahydrofuran (30 ml) and methanol (10 ml). 0.25N Sodium hydroxide (5 ml) was added to the solution and the mixture was stirred for 12 hours at room temperature. The reaction mixture was concentrated under reduced pressure. The residue was partitioned between chloroform and 2N HCl. The aqueous layer was extracted with chloroform. The combined organic layer was washed with brine and dried over anhydrous magnesium sulfate. The solvent was distilled off under reduced pressure. The residue was crystallized from dichloromethane/diethyl ether, obtaining 0.26 g of the compound (1–84) as crystalline powder.

mp 209–210° C. $^1$H-NMR (CDCl$_3$)δ: 1.48 (3H, m), 3.22 (6H, s), 3.58 (1H, d), 3.66 (1H, m), 3.76–3.86 (8H, m), 4.46 (2H, brs), 4.69 (1H, dd), 6.34–6.63 (5H, m), 6.89–7.02 (3H, m), 7.14–7.37 (7H, m), 7.51–7.76 (3H, m)

Example 85

2-[3-[3-[N-[2-[N-(3,5-Dimethoxyphenyl)-N-methylcarbamoylmethyloxy]phenyl]-N-(N-methyl-N-phenylcarbamoylmethyl)carbamoylmethyl]ureido] phenyl]acetic acid (1–85)

Compound (1–7) (0.38 g) was dissolved in tetrahydrofuran (30 ml). 0.25N Sodium hydroxide (3 ml) was added to the solution and the mixture was stirred for 12 hours at room temperature. The reaction mixture was concentrated under reduced pressure. The residue was partitioned between chloroform and 2N HCl. The aqueous layer was extracted with chloroform. The combined organic layer was washed with brine and dried over anhydrous magnesium sulfate. The solvent was distilled off under reduced pressure. The residue was crystallized from dichloromethane/diethyl ether, obtaining 0.24 g of the compound (1–85) as crystalline powder.

mp 202–203° C. $^1$H-NMR (CDCl$_3$)δ: 3.22 (3H, s), 3.25 (3H, s), 3.54 (2H, s), 3.56 (1H, m), 3.79 (6H, s), 3.87 (2H, d), 4.48 (2H, brs), 4.71 (1H, d), 6.31–6.63 (5H, m), 6.84–7.00 (3H, m), 7.14–7.36 (7H, m), 7.48–7.71 (3H, m)

Example 86

(±)-2-[3-[3-[N-[2-[N-(3-Methoxyphenyl)-N-methylcarbamoylmethyloxy]phenyl]-N-(N-methyl-N-phenylcarbamoylmethyl)carbamoylmethyl]ureido] phenyl]propionic acid (1–86)

Compound (1–6) (0.31 g) was dissolved in tetrahydrofuran (4 ml). 0.25N Sodium hydroxide (4 ml) was added to the solution and the mixture was stirred for 3 hours at room temperature. The reaction mixture was concentrated under reduced pressure. The residue was partitioned between chloroform and 2N HCl. The aqueous layer was extracted with chloroform. The combined organic layer was washed with brine and dried over anhydrous magnesium sulfate. The solvent was distilled off under reduced pressure. The residue was crystallized from dichloromethane/ether, obtaining 0.08 g of the compound (1–86) as crystalline powder.

mp 127–128° C. $^1$H-NMR (CDCl$_3$)δ: 1.49 (3H, m), 3.23 (6H, m), 3.55 (1H, d), 3.68 (1H, m), 3.80–3.90 (5H, m), 4.41 (2H, brs), 4.68 (1H, dd), 6.31–7.68 (19H, m)

Example 87

2-[3-[3-[N-[2-[N-(3-Methoxyphenyl)-N-methylcarbamoylmethyloxy]phenyl]-N-(N-methyl-N-phenylcarbamoylmethyl)carbamoylmethyl]ureido]phenyl]acetic acid (1–87)

Compound (1–5) (0.34 g) was dissolved in tetrahydrofuran (3 ml). 0.25N Sodium hydroxide (3 ml) was added to the solution and the mixture was stirred for 3 hours at room temperature. The reaction mixture was concentrated under reduced pressure. The residue was partitioned between chloroform and 2N HCl. The aqueous layer was extracted with chloroform. The combined organic layer was washed with brine and dried over anhydrous magnesium sulfate. The solvent was distilled off under reduced pressure. The residue was crystallized from dichloromethane/diethyl ether, obtaining 0.15 g of the compound (1–87) as crystalline powder.

mp 184–186° C. $^1$H-NMR (CDCl$_3$)δ: 3.23 (3H, s), 3.24 (3H, s), 3.53 (2H, s), 3.58 (1H, m), 3.81 (3H, s), 3.85 (2H, m), 4.42 (2H, brs), 4.70 (1H, d), 6.34–7.70 (19H, m)

Example 88

(±)-2-[3-[3-[N-[2-[N-(2-Methoxyphenyl)-N-methylcarbamoylmethyloxy]phenyl]-N-(N-methyl-N-phenylcarbamoylmethyl)carbamoylmethyl]ureido]phenyl]propionic acid (1–88)

Compound (1–4) (0.14 g) was dissolved in tetrahydrofuran (3 ml). 0.25N Sodium hydroxide (1.1 ml) was added to the solution and stirred for 24 hours at room temperature. The reaction mixture was concentrated under reduced pressure. The residue was partitioned between chloroform and 1N HCl. The aqueous layer was extracted with chloroform. The combined organic layer was washed with brine and dried over anhydrous magnesium sulfate. The solvent was distilled off under reduced pressure, obtaining 0.08 g of the compound (1–88) as powder.

$^1$H-NMR (CDCl$_3$)δ: 1.47 (3H, m), 3.16–3.24 (6H, m), 3.52–3.84 (4H, m), 3.88 (3H, m), 4.28 (1H, d), 4.36 (1H, d), 4.64–4.70 (1H, m), 6.22–7.48 (17H, m), 7.66 (2H, m)

Example 89

2-[3-[3-[N-[2-[N-(2-Methoxyphenyl)-N-methylcarbamoylmethyloxy]phenyl]-N-(N-methyl-N-phenylcarbamoylmethyl)carbamoylmethyl]ureido]phenyl]acetic acid (1–89)

Compound (1–3) (0.35 g) was dissolved in tetrahydrofuran (3 ml). 0.25N Sodium hydroxide (1 ml) was added to the solution and the mixture was stirred for 4 hours at room temperature. The reaction mixture was concentrated under reduced pressure. The residue was partitioned between chloroform 2N HCl. The aqueous layer was extracted with chloroform. The combined organic layer was washed with brine and dried over anhydrous magnesium sulfate. The solvent was distilled off under reduced pressure, obtaining 0.11 g of the compound (1–89) as powder.

$^1$H-NMR (CDCl$_3$)δ: 3.17 (3H, s), 3.23 (3H, s), 3.45–3.58 (3H, m), 3.86–3.90 (2H, m), 3.92 (3H, s), 4.25 (2H, m), 4.66–4.74 (1H, m), 6.27–7.48 (17H, m), 7.69 (2H, m)

Example 90

2-[3-[3-[N-(N-Methyl-N-phenylcarbamoylmethyl)-N-[2-(N-methyl-N-phenylcarbamoylmethyloxy)phenyl]carbamoylmethyl]ureido]phenyl]acetic acid (1–90)

Compound (1–33) (0.11 g) was dissolved in tetrahydrofuran (20 ml). 1N Sodium hydroxide (20 ml) was added to the solution and stirred for 1 hour at room temperature. The reaction mixture was washed with ethyl acetate, acidified with 1N HCl, and then extracted with chloroform. The extract was washed with water and brine, then dried over anhydrous magnesium sulfate. The solvent was distilled off under reduced pressure. The residue was purified by silica gel column chromatography (eluted with chloroform/methanol=19:1). The eluate was concentrated, obtaining 0.06 g of the compound (1–90) as powder.

mp 168–170° C. $^1$H-NMR (DMSO-d$_6$)δ: 3.16 (6H, s), 3.33 (2H, s), 3.49 (1H, d), 3.75 (1H, dd), 4.47–4.53 (4H, m), 6.33 (1H, s), 6.77–7.60 (18H, m), 8.84 (1H, s) MS (m/z): 638 (M+1)$^+$

Example 91

2-[3-[3-[N-[3-[N-Methyl-N-(3,5-dimethylphenyl)carbamoylmethyloxy]phenyl]-N-(N-methyl-N-phenylcarbamoylmethyl)carbamoylmethyl]ureido]phenyl]acetic acid (1–91)

Compound (1–19) (0.10 g) was dissolved in tetrahydrofuran (20 ml). 0.25N Sodium hydroxide (20 ml) was added to the solution and the mixture was stirred for 1 hour at room temperature. The reaction mixture was acidified with 1N HCl and extracted with chloroform. The extract was washed with brine, then dried over anhydrous magnesium sulfate. The solvent was distilled off, obtaining 0.07 g of the compound (1–91) as powder.

$^1$H-NMR (CDCl$_3$)δ: 2.33 (6H, s), 3.20 (3H, s), 3.28 (3H, s), 3.45–4.48 (8H, m), 6.27–7.99 (18H, m)

Example 92

Sodium (±)-2-[3-[3-[N-[2-[N-methyl-N-(3,5-dimethylphenyl)carbamoylmethyloxy]phenyl]-N-(N-methyl-N-phenylcarbamoylmethyl)carbamoylmethyl]ureido]phenyl]sodium propionate (1–92)

Compound (1–67) (0.07 g) was suspended in ethanol (10 ml). 1N sodium hydroxide (0.1 m) was added to the suspension and the mixture was stirred for 10 minutes at room temperature. The reaction mixture was concentrated under reduced pressure. Water was added to the residue, and insoluble matter was filtered off. The filtrate was concentrated and lyophilized, obtaining 0.07 g of the compound (1–92) as powder.

$^1$H-NMR (DMSO-d$_6$)δ: 1.22 (3H, d), 2.28 (6H, s), 3.12 (3H, s), 3.16 (3H, s), 3.35–3.60 (4H, m), 3.70 (1H, m), 4.50 (2H, brs), 6.73 (1H, d), 6.84 (1H, brs), 6.95–7.04 (6H, m), 7.18 (1H, s), 7.31–7.44 (7H, m), 7.58 (1H, d), 9.40 (1H, brs)

Example 93

N-Phenyl-2-[3-[N-(N-methyl-N-phenylcarbamoylmethyl)-N-[2-[3-(3-methylphenyl)ureido]acetyl]amino]phenoxy]-acetamide (1–93)

mp 215–217° C. $^1$H-NMR (DMSO-d$_6$)δ: 2.22 (3H, s), 3.16 (3H, s), 3.67 (2H, s), 4.06 (2H, s), 4.74 (2H, s), 6.30

(1H, brs), 6.70 (1H, d). 7.04–7.65 (17H, m) 8.72 (1H, s), 10.14 (1H, s) MS (m/z): 580 (M+1)$^+$ Elementary Analysis (for $C_{33}H_{33}N_5O_5$) Calculated: C, 68.38; H, 5.74; N, 12.08 Found: C, 68.15; H, 5.89; N 11.78

Example 94

N-Methyl-N-phenyl-2-[3-[N-(N-methyl-N-phenylcarbamoylmethyl)-N-[2-[3-(3-methylphenyl)ureido]acetyl]amino]phenoxy]acetamide (1–94)

mp 145–146° C. $^1$H-NMR (CDCl$_3$)δ: 2.25 (3H, s), 3.22 (3H, s), 3.32 (3H, s), 3.85 (2H, d), 4.08 (2H, s), 4.42 (2H, s), 6.03 (1H, brs), 6.76–7.47 (18H, m), 7–66 (1H, s) MS (m/z): 594 (M+1)$^+$

Example 95

N-Ethyl-N-phenyl-2-[3-[N-(N-methyl-N-phenylcarbamoylmethyl)-N-[2-[3-(3-methylphenyl)ureido]acetyl]amino]phenoxy]acetamide (1–95)

mp 135–137° C. $^1$H-NMR (CDCl$_3$)δ: 1.14 (3H, t), 2.25 (3H, s), 3.22 (3H, s), 3.79 (2H, q), 3.86 (2H, d), 4.07 (2H, s), 4.36 (2H, s), 6. 05 (1H, brs), 6.76–7.48 (18H, m), 7.72 (1H, s) MS (m/z): 608 (M+1)$^+$

Example 96

N-Phenyl-N-propyl-2-[3-[N-(N-methyl-N-phenylcarbamoylmethyl)-N-[2-[3-(3-methylphenyl)ureido]acetyl]amino]phenoxy]acetamide (1–96)

mp 149–150° C. $^1$H-NMR (CDCl$_3$)δ: 0.89 (3H, t), 1.55 (2H, m), 2.25 (3H, s), 3.22 (3H, s), 3.69 (2H, t), 3.86 (2H, d). 4. 07 (2H, s), 4.37 (2H, s), 6.08 (1H, brs), 6.75–7.47 (18H, m), 7.78 (1H, s) MS (m/z): 622 (M+1)$^+$

Example 97

N-Benzyl-N-methyl-2-[3-[N-(N-methyl-N-phenylcarbamoylmethyl)-N-[2-[3-(3-methylphenyl)ureido]acetyl]amino]phenoxy]acetamide (1–97)

mp 98–100° C. $^1$H-NMR (CDCl$_3$)δ: 2.25 (3H, s), 2.93 (3H, s), 3.21 (3H, s), 3.90 (2H, d), 4.10 (2H, s), 4.59 (2H, s), 4.76 (2H, s), 6.08 (1H, brs), 6.76 (1H, d), 6.98–7.35 (17H, m), 7.79 (1H, s) MS (m/z): 630 (M+1)$^+$

Example 98

1-[2-[3-[N-(N-Methyl-N-phenylcarbamoylmethyl)-N-[2-[3-(3-methylphenyl)ureido]acetyl]amino]phenoxy]acetyl]indoline (1–98)

mp 110–120° C. $^1$H-NMR (CDCl$_3$)δ: 2.24 (3H, s), 3.14 (5H, m), 3.91 (2H, d), 4.09 (4H, m), 4.77 (2H, s), 6.04 (1H, m), 6.76 (1H, d), 7.01–7.34 (15H, m), 7.59 (1H, s), 8.21 (1H, d)

Example 99

1-[2-[3-[N-(N-Methyl-N-phenylcarbamoylmethyl)-N-[2-[3-(3-methylphenyl)ureido]acetyl]amino]phenoxy]acetyl]-1,2,3,4-tetrahydroquinone (1–99)

mp 101–104° C. $^1$H-NMR (CDCl$_3$)δ: 1.96 (2H, m), 2.26 (3H, s), 2.69 (2H, m), 3.21 (3H, s), 3.80 (2H, m), 3.88 (2H, d), 4.07 (2H, s), 4.82 (2H, s), 5.96 (1H, m), 6.77–7.44 (18H, m)

Example 100

N-Diphenylmethyl-2-[3-[N-(N-methyl-N-phenylcarbamoylmethyl)-N-[2-[3-(3-methylphenyl)ureido]acetyl]amino]phenoxy]acetamide (1–100)

mp 175–177° C. $^1$H-NMR (CDCl$_3$)δ: 2.26 (3H, s), 3.21 (3H, S), 3.87 (2H, d), 4. 06 (2H, s), 4.57 (2H, s), 5.96 (1H, m), 6.36 (1H, d), 6.79 (1H, d), 6.92 (1H, m). 7.08–7.36 (23H, m)

Example 101

N-Methyl-N-(3-methylphenyl)-2-[3-[N-(N-methyl-N-phenylcarbamoylmethyl)-N-[2-[3-(3-methylphenyl)ureido]acetyl]amino]phenoxy] acetamide (1–101)

mp 133–135° C. $^1$H-NMR (CDCl$_3$)δ: 2.25 (3H, s), 2.38 (3H, s), 3.21 (3H, s), 3.31 (3H, s), 3.86 (2H, d), 4.08 (2H, s), 4.42 (2H, s), 6.09 (1H, brs), 6.74–7.35 (17H, m), 7.79 (1H, s) MS (m/z): 608 (M+1)$^+$ Elementary Analysis (for $C_{35}H_{37}N_5O_5$) Calculated: C, 69.18; H, 6.14; N, 11.52 Found: C, 68.96; H, 6.27; N, 11.41

Example 102

N,N-Diethyl-2-[3-[N-(N-methyl-N-phenylcarbamoylmethyl)-N-[2-[3-(3-methylphenyl)ureido]acetyl]amino]phenoxy]acetamide (1–102)

mp 138–140° C. $^1$H-NMR (CDCl$_3$)δ: 1.14 (3H, t), 1.22 (3H, t), 2.27 (3H, s), 3.22 (3H, s), 3.35 (2H, q), 3.40 (2H, q), 3.90 (2H, d), 4.09 (2H, s), 4.68 (2H, s), 6.01 (1H, brs), 6.79 (1H, d), 6.97–7.37 (12H, m), 7.58 (1H, s)

MS (m/z): 560 (M+1)$^+$

Elementary Analysis (for $C_{31}H_{37}N_5O_5$) Calculated: C, 66.53; H, 6.66; N, 12.51 Found: C, 66.13; H, 6.98; N, 12.16

Example 103

N-Methoxy-N-methyl-2-[3-[N-(N-methyl-N-phenylcarbamoylmethyl)-N-[2-[3-(3-methylphenyl)ureido]acetyl]amino]phenoxy]acetamide (1–103)

$^1$H-NMR (CDCl$_3$)δ: 2.25 (3H, s), 3.21 (3H, s), 3.22 (3H, s), 3.75 (3H, s), 3.90 (2H, d), 4.09 (2H, s), 4.84 (2H, s), 6.10 (1H, m), 6.75 (1H, d), 6.94 (1H, d), 7.05–7.35 (11H, m), 7.84 (1H, s)

Example 104

N-(3-Methoxypropyl)-N-(n-pentyl)-2-[3-[N-(N-methyl-N-phenylcarbamoylmethyl)-N-[2-[3-(3-methylphenyl)ureido]acetyl]amino]phenoxy] acetamide (1–104)

$^1$H-NMR (CDCl$_3$)δ: 0.88 (3H, m), 1.23–1.86 (8H, m), 2.26 (3H, s), 3.21 (3H, s), 3.25–3.44 (6H, m), 3.30 (3H, s), 3.90 (2H, d), 4.09 (2H, s), 4.69 (2H, s), 6.06 (1H, brs), 6.76 (1H, d), 6.92–7.35 (12H, m), 7.72 (1H, s) MS (m/z): 646 (M+1)$^+$

Example 105

1-[2-[3-[N-(N-Methyl-N-phenylcarbamoylmethyl)-N-[2-[3-(3-methylphenyl)ureido]acetyl]amino] phenoxy]acetyl]pyrrolidine (1–105)

mp 100–102° C. $^1$H-NMR (DMSO-d$_6$)δ: 1.75–1.90 (4H, n), 2.22 (3H, s), 3.18 (3H, s), 3.30–3.34 (4H, m), 3.64 (2H, brs), 4.05 (2H, brs), 4.74 (2H, brs), 6.29 (1H, brs), 6.69 (1H, d), 6.94–7.17 and 7.36–7.46 (12H, m), 8.72 (1H, s) MS (m/z): 558 (M+1)$^+$

Example 106

1-[2-[3-[N-(N-Methyl-N-phenylcarbamoylmethyl)-N-[2-[3-(3-methylphenyl)ureido]acetyl]amino] phenoxy]acetyl]piperidine (1–106)

mp 106–108 C. $^1$H-NMR (CDCl$_3$)δ: 1.56–1.65 (6H, m), 2.26 (3H, s), 3.22 (3H, s), 3.44 (2H, brs), 3.56,(2H, brs), 3.90

(2H, d), 4.10 (2H, s), 4.68 (2H, s), 6.06 (1H, brs), 6.77 (1H, d), 6.95–7.36 (12H, m), 7.71 (1H, s) MS (m/z): 572 (M+1)$^+$

Example 107

1-[2-[3-[N-(N-Methyl-N-phenylcarbamoylmethyl)-N-[2-[3-(3-methylphenyl)ureido]acetyl]amino]phenoxy]acetyl]hexamethyleneimine (1–107)

mp 147–148° C. $^1$H-NMR (CDCl$_3$)δ: 1.56 and 1.72–1.80 (8H, m), 2.27 (3H, s), 3.23 (3H, s), 3.46 (2H, m), 3.54 (2H, m), 3. 90 (2H, d), 4.10 (2H, s), 4.70 (2H, s), 6.00 (1H, brs), 6.78 (1H, d), 6.96–7.36 (12H, m), 7.58 (1H, s) MS (m/z): 586 (M+1)$^+$

Example 108

N-Cyclohexyl-N-methyl-2-[3-[N-(N-methyl-N-phenylcarbamoylmethyl)-N-[2-[3-( 3-methylphenyl)ureido]acetyl]amino]phenoxy]acetamide (1–108)

mp 99–104° C. $^1$H-NMR (CDCl$_3$)δ: 1.26–1.86 (10H, m), 2.27 (3H, s), 2.85 (3/2H s), 2.87 (3/2H, s), 3.22 (3H, s), 3.57 (1/2H, m), 3.90 (2H, d), 4.09 (2H, s), 4.37 (1/2H, m), 4.67 (1H, s), 4.72 (1H, s), 6.01 (1H, m), 6.78 (1H, m), 6.93–7.57 (13H, m)

Example 109

N-(1-Adamantyl)-2-[3-[N-(N-methyl-N-phenylcarbamoylmethyl)-N-[2-[3-(3-methylphenyl)ureido]acetyl]amino]phenoxy]acetamide (1–109)

mp 130–132° C. $^1$H-NMR (DMSO-d$_6$)δ: 1.61 (6H, brs), 1.95 (6H, brs), 1.99 (3H, brs), 2.22 (3H, s), 3.19 (3H, s), 3.65 (2H, s), 4.05 (2H, s), 4.43 (2H, s), 6.29 (1H, brs), 6.69 (1H, d), 6.96–7.18 and 7.35–7.46 (13H, 8.70 (1H, s) MS (m/z): 638 (M+1)$^+$

Example 110

8-[2-[3-[N-(N-Methyl-N-phenylcarbamoylmethyl)-N-[2-[3-(3-methylphenyl)ureido]acetyl]amino]phenoxy]acetyl]-8-azaspiro[4,5]decane (1–110)

mp 187–188° C. $^1$H-NMR (CDCl$_3$)δ: 1.45 (8H, brs), 1.63 (4H, brs), 2.27 (3H, s), 3.23 (3H, s), 3.41 (2H, brs), 3.57 (2H, brs), 3.91 (2H, d), 4.10 (2H, s), 4.68 (2H, s), 6.01 (1H, brs), 6.78 (1H, d), 6.95–7.36 (12H, m), 7.57 (1H, s) MS (m/z): 626 (M+1)$^+$

Example 111

N-Cyclohexyl-N-methyl-2-[2-[N-(N-methyl-N-phenylcarbamoylmethyl)-N-[2-[3-(3-methylphenyl)ureido]acetyl]amino]phenoxy]acetamide (1–111)

mp 153–155° C. $^1$H-NMR (CDCl$_3$)δ: 1.06–1.78 (10H, m), 2.25 (3H, s), 2.75 & 2.80 (3H, s), 3.21 (3H, s), 3.57 (1H, d), 3.92–3.98 (2H, m), 4.14 (1H, brs), 4.67–4.77 (3H, m), 6.17 (1H, brs), 6.74–6.83, 6.97–7.34 and 7.59–7.73 (14H, m) MS (m/z): 600 (M+1)$^+$

Example 112

N-Methyl-N-(4-methylphenyl)-2-[2-[N-(N-methyl-N-phenylcarbamoylmethyl)-N-[2-[3-(3-methylphenyl)ureido]acetyl]amino]phenoxy]acetamide (1–112)

mp 122–125° C. $^1$H-NMR (CDCl$_3$)δ: 2.26 (6H, s), 3.21 (3H, s), 3.23 (3H, s), 3.55 (1H, d), 3.89–3.92 (2H, m), 4.59 (2H. s). 4.76 (1H, d), 6.03 (1H, brs), 6.75–6.80 and 7.01–7.35 (17H, m), 7.72 (1H, d) MS (m/z): 608 (M+1)$^+$

Example 113

N-Ethyl-N-(n-propyl)-2-[2-[N-(N-methyl-N-phenylcarbamoylmethyl)-N-[2-[3-(3-methylphenyl)ureido]acetyl]amino]phenoxy]acetamide (1–113)

mp 113–120° C. $^1$H-NMR (CDCl$_3$)δ: 0.85 (3H, t), 1.08 (3H, t), 1.47–1.51 (2H, m), 2.24 (3H, s), 3.21 (3H, s), 3.10–3.61 (5H, m), 3.92 (2H, d), 4.70–4.73 (3H, 6.20 (1H, brs), 6.75–6.82, 6.98–7.33, 7.65–7.70 (14H, m) MS (m/z): 574 (M+1)$^+$

Example 114

N-(n-Butyl)-N-ethyl-2-[2-[N-(N-methyl-N-phenylcarbamoylmethyl)-N-[2-[3-(3-methylphenyl)ureido]acetyl]amino]phenoxy]acetamide (1–114)

mp 107–115° C. $^1$H-NMR (CDCl$_3$)δ:
0.90 (3H, t), 1.11 (3H, t), 1.24–1.31 (2H, m), 1.45–1.54 (2H, 2.25 (3H, s), 3.22 (3H, s), 3.13–3.59 (5H, m), 3.92 (2H, d), 4.71 (3H, brs), 6.17 (1H, brs), 6.75–6.82, 6.98–7.33, 7.67–7.70 (14H, m) MS (m/z): 588 (M+1)$^+$

Example 115

N-Methyl-N-(3,5-dimethylphenyl)-2-[2-[N-(N-methyl-N-phenylcarbamoylmethyl)-N-[2-[3-(3-methylphenyl)ureido]acetyl]amino]phenoxy]acetamide (1–115)

mp 143–147° C. $^1$H-NMR (CDCl$_3$)δ: 2.26 (6H, s), 2.34 (3H, s), 3.22 (6H, brs), 3.56 (1H, d), 3.90 (2H, m), 4.59 (2H, s), 4.75 (1H, d), 5.98 (1H, brs), 6.75–6.83, 6.96–7.38 (16H, m), 7.71 (1H, d) MS (m/z): 622 (M+1)$^+$

Example 116

N-Methyl-N-(3,4-dimethylphenyl)-2-[2-[N-(N-methyl-N-phenylcarbamoylmethyl)-N-[2-[3-(3-methylphenyl)ureido]acetyl]amino]phenoxy]acetamide (1–116)

mp 106–112° C. $^1$H-NMR (CDCl$_3$)δ: 2.27 (3H, s), 2.28 (6H, s), 3.22 (3H, s), 3.23 (3H, s), 3.54 (1H, d), 3.89 (2H, m), 4.59 (2H, S), 4.75 (1H, d), 5.94 (1H, brs), 6.75–6.82, 6.93–7.36 (16H, m), 7.71 (1H, d) MS (m/z): 622 (M+1)$^+$

Example 117

N-Methyl-N-(4-methylphenyl)-2-[3-[N-(N-methyl-N-phenylcarbamoylmethyl)-N-[2-[3-(3-methylphenyl)ureido]acetyl]amino]phenoxy]acetamide (1–117)

mp 148–150° C. $^1$H-NMR (CDCl$_3$)δ: 2.25 (3H, s), 2.37 (3H,sS), 3.22 (3H, s), 3.29 (3H, s), 3.86 (2H, d), 4.08 (2H, s), 4.41 (2H, s), 6.09 (1H, brs), 6.75–7.35 (17H, m), 7.77 (1H, s) MS (m/z): 608 (M+1)$^+$ Elementary Analysis (for $C_{35}H_{37}N_5O_5$) Calculated: C, 69.18; H, 6.14 N, 11.52 Found C, 68.89; H, 6.30; N, 11.50

Example 118

N-(3-Chlorophenyl)-N-methyl-2-[3-[N-(N-methyl-N-phenylcarbamoylmethyl)-N-[2-[3-(3-methylphenyl)ureido]acetyl]amino]phenoxy]acetamide (1–118)

mp 140–143° C. $^1$H-NMR (CDCl$_3$)δ: 2.26 (3H, s), 3.23 (3H, s), 3.31 (3H, s), 3.86 (2H, d), 4.08 (2H, s), 4.45 (2H, s), 5.97 (1H, brs), 6.77–7.36 (17H, 7.51 (1H, s)

Example 119

N-(4-Chlorophenyl)-N-methyl-2-[3-[N-(N-methyl-N-phenylcarbamoylmethyl)-N-[2-[3-(3-methylphenyl)ureido]acetyl]amino]phenoxy] acetamide (1–119)

mp 108–110° C. $^1$H-NMR (CDCl$_3$)δ: 2.24 (3H, s), 3.22 (3H, s), 3.28 (3H, s), 3.86 (2H, d), 4.09 (2H, s), 4.43 (2H, s), 6.14 (1H, brs), 6.74–7.42 (17H, 7.94 (1H, s)

Elementary Analysis (for C$_{34}$H$_{34}$ClN$_5$O$_5$) Calculated: C, 65.01; H, 5.46; N, 11.15 Found: C, 64.55; H; 5.78; N, 10.76

Example 120

N-($^4$-Trifluoromethylphenyl)-N-methyl-2-[3-[N-(N-methyl-N-phenylcarbamoylmethyl)-N-[2-[3-( 3-methylphenyl)ureido]acetyl]amino]phenoxy] acetamide (1–120)

mp 128–131° C. $^1$H-NMR (CDCl$_3$)δ: 2.25 (3H, s), 3.23 (3H, s), 3.34 (3H, s), 3.84 (2H, d), 4.08 (2H, s), 4.45 (2H, s), 6.00 (1H, brs). 6.73–7.36 (17H, m), 7.61 (1H, s) MS (m/z): 662 (M+1)$^+$ Elementary Analysis (for C$_{65}$H$_{34}$F$_3$N$_5$O$_5$) Calculated: C, 63.53; H, 5.18; N, 10.58 Found: C, 63.50; H, 5.33; N, 10.59

Example 121

N-Ethyl-N-(3-methylphenyl)-2-[3-[N-(N-methyl-N-phenylcarbamoylmethyl)-N-[2-[3-(3-methylphenyl)ureido]acetyl]amino]phenoxy]acetamide (1–121)

mp 126–128° C. $^1$H-NMR (CDCl$_3$)δ: 1.14 (3H, t), 2.24 (3H, s), 2.38 (3H, s), 3.21 (3H, s), 3.77 (2H, q), 3.86 (2H, d), 4.07 (2H, S), 4.37 (2H, S), 6.10 (1H, brs), 6.74–6.80 (2H, m), 6.91 (1H, s), 7.00–7.32 (14H, m) 7.81 (1H, S) MS (m/z): 622 (M+1)$^+$ Elementary Analysis (for C$_{36}$H$_{39}$N$_5$O$_5$) Calculated: C, 69.55; H, 6.32; N, 11.26 Found: C, 69.23; H, 6.37; N, 11.18

Example 122

N-(3-Ethylphenyl)-N-methyl-2-[3-[N-(N-methyl-N-phenylcarbamoylmethyl)-N-[2-[3-(3-methylphenyl)ureido]acetyl]amino]phenoxy]acetamide (1–122)

mp 172–174° C. $^1$H-NMR (CDCl$_3$)δ: 1.23 (3H, t), 2.25 (3H, s), 2.67 (2H, q), 3.21 (3H, s), 3.32 (3H, s), 3.86 (2H, d), 4.07 (2H, s), 4.42 (2H, s), 6.08 (1H, brs). 6.74–6.80 (2H, m), 6.92 (1H, s), 7.00–7.38 (14H, m), 7.76 (1H, s) MS (m/z): 622 (M+1)$^+$ Elementary Analysis (for C$_{36}$H$_{39}$N$_5$O$_5$) Calculated: C, 69.55; H, 6.32; N, 11.26 Found: C, 69.85; H, 6.35; N, 11.33

Example 123

N-(3-Trifluoromethylphenyl)-N-methyl-2-[3-[N-(N-methyl-N-phenylcarbamoylmethyl)-N-[2-[3-(3-methylphenyl)ureido]acetyl]amino]phenoxy] acetamide (1–123)

mp 147–150° C. $^1$H-NMR (CDCl$_3$)δ: 2.25 (3H, s), 3.23 (3H, s), 3.34 (3H, s), 3.84 (2H, s), 4.07 (2H, s), 4.44 (2H, s), 5.98 (1H, brs), 6.79 (2H, d), 6.89 (1H, s), 7.00–7.61 (15H, m) MS (m/z): 662 (M+1)$^+$ Elementary Analysis (for C$_{35}$H$_{34}$F$_3$N$_5$O$_5$) Calculated: C, 63.53; H, 5.18; N, 10.58 Found: C, 63.27; H, 5.05; N, 10.54

Example 124

N-Methyl-N-(3,4-dimethylphenyl)-2-[3-[N-(N-methyl-N-phenylcarbamoylmethyl)-N-[2-[3-(3-methylphenyl)ureido]acetyl]amino]phenoxy] acetamide (1–124)

mp 193–195° C. $^1$H-NMR (CDCl$_3$)δ: 2.25 (3H, s), 2.27 (6H, s), 3.22 (3H, s), 3.29 (3H, s), 3.86 (2H, d), 4.08 (2H, s), 4.42 (2H, s), 6.03 (1H, brs), 6.76 (1H, d), 6.80 (1H, d), 6.99 (1H, s), 7.01–7.35 (13H), 7.62 (1H, brs) MS (m/z): 622 (M+1)$^+$ Elementary Analysis (for C$_{36}$H$_{39}$N$_5$O$_5$) Calculated: C, 69.55 H, 6.32; N, 11.26 Found: C, 69.14; H, 6.37 N, 11.16

Example 125

N-(3,5-Dimethylphenyl)-N-methyl-2-[3-[N-(N-methyl-N-phenylcarbamoylmethyl)-N-[2-[3-(3-methylphenyl) ureido]acetyl]amino]phenoxy] acetamide (1–125)

mp 192–194° C. $^1$H-NMR (CDCl$_3$)δ: 2.26 (3H, s), 2.33 (6H, S), 3.22 (3H, S), 3.29 (3H, s), 3. 86 (2H, d), 4.07 (2H, s), 4.42 (2H, s), 5.91 (1H, brs), 6.78–7.36 (17H, m) MS (m/z): 622 (M+1)$^+$

Example 126

N-Methyl-N-(2-thiazolyl)-2-[3-[N-(N-methyl-N-phenylcarbamoylmethyl)-N-[2-[3-(3-methylphenyl) ureido]acetyl]amino]phenoxy]acetamide (1–126)

$^1$H-NMR (CDCl$_3$)δ: 2.24 (3H, s), 3.19 (3H, s), 3.68 (3H, s), 3.88 (2H, d), 4.08 (2H, s), 4.84 (2H, s), 6.08 (1H, brs), 6.63 (1H, d), 6.74 (1H, d), 6.93 (1H, d), 6.95–7.34 (12H, m), 7.78 (1H, s) MS (m/z): 601 (M+1)$^+$

Example 127

N-(3-Benzyloxyphenyl)-N-methyl-2-[3-[N-(N-methyl-N-phenylcarbamoylmethyl )-N-[2-[3-(3-methylphenyl) ureido]acetyl]amino]phenoxy] acetamide (1–127):

mp 133–134° C. $^1$H-NMR (CDCl$_3$)δ: 2.28 (3H, s), 3.24 (3H, s), 3.31 (3H, s), 3.83 (2H, d), 4.07 (2H, s), 4.41 (2H, s), 5.08 (2H, s), 5.65 (1H, brs), 6.80–7.44 (23H, m) MS (m/z): 700 (M+1)$^+$ Elementary Analysis (for C$_{41}$H$_{41}$N$_5$O$_6$) Calculated: C, 70.37; H, 5.91;N; 10.01 Found: C, 70.16;H, 6.03 N, 10.23

Example 128

2-[3-[N-(N-Methyl-N-phenylcarbamoylmethyl)-N-[2-[3-(3-methylphenyl)ureido]acetyl]amino] phenoxy]acetamide (1–128)

mp 115–117° C. $^1$H-NMR (DMSO-d$_5$)δ: 2.22 (3H, s), 3.18 (3H, s), 3.36(2H, brs), 3.65 (2H, s), 4.06 (2H, s), 4.45 (2H, s), 6.30 (1H, brs), 6.70 (1H, d), 6.99–7.17 and 7.35–7.60 (12H, m), 8.72 (1H, s) MS (m/z): 504 (M+1)$^+$

Example 129

N-Methyl-2-[3-[N-(N-methyl-N-phenylcarbamoylmethyl)-N-[2-[3-(3-methylphenyl)ureido]acetyl]amino]phenoxy]acetamide (1–129)

mp 177–179° C. $^1$H-NMR (DMSO-d$_6$)δ: 2.22 (3H, s), 2. 66 (3H, d), 3.19 (3H, s), 3. 66 (2H, s), 4.06 (2H, s), 4.49 (2H, s), 6.29 (1H, brs), 6.70 (1H, d), 7.00–7.17 and 7.34–7.46 (12H, m), 8.08 (1H, d), 8.71 (1H, s) MS (m/z): 518 (M+1)$^+$

Example 130

N-Ethyl-2-[3-[N-(N-methyl-N-phenylcarbamoylmethyl)-N-[2-[3-(3-methylphenyl)ureido]acetyl]amino]phenoxy]acetamide (1–130)

mp 150–152° C. $^1$H-NMR (DMSO-d$_6$)δ: 1.04 (3H, t), 2.22 (3H, s), 3.15 (2H, m), 3.18 (3H, s), 3.65 (2H, d), 4.06 (2H, s), 4.48 (2H, s), 6.29 (1H, brs), 6.70 (1H, d), 7.00–7.17 and 7.34–7.48 (12H, m), 8.14 (1H, brs), 8.71 (1H, s) MS (m/z): 532 (M+1)$^+$ Elementary Analysis (for. C$_{29}$H$_{33}$N$_5$O$_5$) Calculated: C, 65.52; H, 6.26; N, 13.17 Found: C, 65.08; H, 6.30; N, 12.85

Example 131

N-Methyl-N-phenyl-2-[2-[N-(N-methyl-N-phenylcarbamoylmethyl)-N-[2-[3-(2-methylphenyl)ureido]acetyl]amino]phenoxy]acetamide (1–131)

mp 211–212° C. $^1$H-NMR (CDCl$_3$)δ: 2.20 (3H, s), 3.22 (3H, s), 3.23 (3H, s), 3.54 (1H d), 3.78 (1H, dd), 3.92 (1H, dd), 4.36 (2H, s), 4.67 (1H, d), 5.99 (1H, brs), 6.59 (1H s), 6.63 (1H, d), 6.96–7.03 and 7.12–7.43 (15H, m), 7.54 (1H, d), 7.68 (1H, d) MS (m/z): 594 (M+1)$^+$ Elementary Analysis (for C$_{24}$H$_{35}$N$_5$O$_5$) Calculated: C, 68.79; H, 5.94; N, 11.80 Found: C, 68.46; H 6.06; N, 11.68

Example 132

N-Methyl-N-phenyl-2-[2-[N-(N-methyl-N-phenylcarbamoylmethyl)-N-[2-[3-(4-methylphenyl)ureido]acetyl]amino]phenoxy]acetamide (1–132)

mp 176–177° C. $^1$H-NMR (CDCl$_3$)δ: 2.26 (3H. s), 3.22 (3H, s), 3.25 (3H, s), 3.54 (1H, d), 3.90 (2H, m), 4.38 (2H. s), 4.68 (1H, d), 6.00 (1H, brs), 6.62 (1H, d), 6.96–7.03 and 7.17–7.44 (17H, m), 7.69 (1H, d) MS (m/z): 594 (M+1)$^+$ Elementary Analysis (for C34H$_{35}$N$_5$O$_5$) Calculated: C, 68.79; H, 5.94 N, 11.80 Found: C, 68.38; H, 6.04; N 11.73

Example 133

N-Methyl-N-phenyl-2-[2-[N-[2-[3-(3-trifluoromethylphenyl)ureido]acetyl]-N-(N-methyl-N-phenylcarbamoylmethyl)amino]phenoxy]acetamide (1–133)

mp 148–150° C. $^1$H-NMR (CDCl$_3$)δ: 3.20 (3H, s), 3.26 (3H, s), 3.60 (1H, d), 3. 95 (2H, s), 4.43 (2H, s), 4.66 (1H, d), 6.65 (1H, d), 6.99 (1H, t), 7.12–7.70 (17H, m), 8.14 (1H, brs) MS (m/z): 648 (M+1)$^+$ Elementary Analysis (for C$_{34}$H$_{32}$F$_3$N$_5$O$_5$) Calculated: C, 63.05; H, 4.98; N, 10.81 Found: C, 62.77; H, 4.93; N, 10.68

Example 134

N-Methyl-N-phenyl-2-[2-[N-[2-[3-(3-ethylphenyl)ureido]acetyl]-N-(N-methyl-N-phenylcarbamoylmethyl) amino]phenoxy]acetamide (1–134)

mp 186–188° C. $^1$H-NMR (CDCl$_3$)δ: 1.18 (3H, t), 2.56 (2H, q), 3.20 (3H, s), 3.25 (3H, s), 3.56 (1H, d), 3.90 (2H; q), 4.39 (2H, s), 4.69 (1H, d), 6.63 (1H, d), 6.79 (1H, d), 6.96–7.43 (17H, m), 7.69 (1H, d) MS (m/z):608 (M+1)$^+$

Elementary Analysis (for C$_{35}$H$_{37}$N$_5$O$_5$) Calculated: C, 69.18; H, 6.14; N. 11.52 Found: C, 68.63; H, 6.11; N, 11.36

Example 135

N-Methyl-N-phenyl-2-[2-[N-[2-[3-(3-acetylphenyl)ureido]acetyl]-N-(N-methyl-N-phenylcarbamoylmethyl) amino]phenoxy]acetamide (1–135)

$^1$H-NMR (CDCl3)δ: 2.51 (3H, s), 3.20 (3H, s), 3.28 (3H, s), 3.58 (1H, d), 3.98 (2H, d), 4.43 (2H, s), 4.68 (1H, d), 6.32 (1H, brs), 6.64 (1H, d), 6.99 (1H, t), 7.15–7.57 (14H, m), 7.70 (1H, d), 7.89 (1H, s), 8.12 (1H, s) MS (m/z): 622 (M+1)$^+$

Example 136

N-Methyl-N-phenyl-2-[2-[N-[2-[3-[3-(1-hydroxyethyl)phenyl]ureido]acetyl]-N-(N-methyl-N-phenylcarbamoylmethyl) amino]phenoxy]acetamide (1–136)

$^1$H-NMR (CDCl$_3$)δ: 1.38 (3H, d), 3. 17 (3H, s), 3.25 (3H, s), 3.57 (1H, d), 3.89 (2H, brs), 4.39 (2H, s), 4.67–4.71 (2H, m), 6.26 (1H, brs), 6.63 (1H, d). 6.85 (1H, d), 6.97–7.44 (15H, m), 7.71 (1H, d), 7.87 (1H, brs) MS (m/z): 624 (M+1)$^+$

Example 137

N-Methyl-N-phenyl-2-[2-[N-[2-[3-[3-(1-hydroxyliminoethyl)phenyl]ureido]acetyl]-N-(N-methyl-N-phenylcarbamoylmethyl)amino]phenoxy]acetamide (1–137)

mp 175–182° C. $^1$H-NMR (DMSO-d$_6$)δ: 2.10 (3H, s), 3.34 (6H, brs), 3.50–3.54 (2H, m), 3.76 (1H, dd), 4.47–4.54 (3H, m), 6.24 (1H, brs), 6.85 (1H, brs), 7.04 (1H, t), 7.15–7.44 (14H, m), 7.59 (1H, d), 7.68 (IH, s), 8.86 (1H, s), 11.14 (1H, S) MS (m/z): 637 (Mt+1)$^+$

Example 138

N-Methyl-N-phenyl-2-[2-[N-[2-[3-[3-[1-(N-hydroxyamino)ethyl]phenyl]ureido]acetyl]-N-(N-methyl-N-phenylcarbamoylmethyl)amino]phenoxy]acetamide (1–138)

mp 117–125° C. $^1$H-NMR (CDCl$_3$)δ: 1.28 (3H, brs), 3.18 (3H, s), 3.26 (3H, s), 3.56 (1H, d), 3.84–4.06 (3H, m), 4.41 (2H, s), 4.68 (1H, d), 6.27 (1H, brs), 6.65 (1H, d), 6.83 (1H, d), 7.00–7.45 and 7.72–7.75 (17H, m) MS (m/z): 639 (M+1)$^+$

Example 139

N-Methyl-N-(3,5-dimethylphenyl)-2-[3-[N-[2-[3-(3-cyanophenyl)ureido]acetyl]-N-(N-methyl-N-phenylcarbamoylmethyl)amino]phenoxy]acetamide (1–139)

mp 118–120° C. $^1$H-NMR (CDCl$_3$)δ: 2.35 (6H, s), 3.23 (3H, s), 3.30 (3H, s), 3.88 (2H, d), 4.10 (2H, s), 4.46 (2Hz s), 6.23 (1H, brs), 6.79–7.45 (15H, m), 7.80 (1H, d), 8.48 (1H, s) MS (m/z): 633 (M+1)$^+$

Example 140

N-Methyl-N-(3,5-dimethylphenyl)-2-[3-[N-(N-methyl-N-phenylcarbamoylmethyl)-N-[2-[3-[3-(5-tetrazolyl) phenyl]ureido]acetyl]amino]phenoxy] acetamide (1–140)

mp 152–155° C. $^1$H-NMR (DMSO-d$_6$)δ: 2.27 (6H, s), 3.19 (6H, brs), 3.63 (2H, s), 4.03 (2H, s), 4.48 (2H. s), 6.40

(1H, brs), 6.83–7.07 and 7.34–7.55 (16H, m), 8.11 (1H, s), 9.08 (1H S) MS (m/z): 676 (M+1)⁺

Example 141

N-Methyl-N-(3,5-dimethylphenyl)-2-[2-[N-[2-[3-(3-acetylphenyl)ureido]acetyl]-N-(N-methyl-N-phenylcarbamoylmethyl)amino]phenoxy]acetamide (1–141)

mp 190–191° C. ¹H-NMR (CDCl₃)δ: 2.36 (6H, s), 2.55 (3H, s), 3.23 (3H, s), 3.30 (3H, s), 3.45 (1H, d), 3.99 (1H, dd), 4.10 (1H, dd), 4.46 (2H, s), 4.67 (1H, d), 6.15 (1H, brs), 6.60 (1H, d), 6.88 (2H, s), 6.97 (1H, t), 7.05 (1H, s), 7.19–7.37 (9H, m), 7.50 (1H, d), 7.69 (1H, t), 7.83 (1H, s)

Example 142

N-Methyl-N-(3,5-dimethylphenyl)-2-[2-[N-[2-[3-(3-hydroxymethylpheny)ureido]acetyl]-N-(N-methyl-N-phenylcarbamoylmethyl)amino]phenoxy]acetamide (1–142)

mp 186–188° C. ¹H-NMR (CDCl₃)δ: 2.10 (1H, brs), 2.34 (6H, s), 3.17 (3H, s), 3.22 (3H, s), 3.59 (1H, d), 3.92 (2H, d), 4.40 (2H, s), 4.47 (2H, s), 4.72 (1H, d), 6.27 (1H, brs), 6.63 (1H, d), 6.82–6.85 (3H, m), 6.97–7.31 (11H, m), 7.72 (1H, d), 7.85 (1H, brs)

Example 143

N-Methyl-N-(3,5-dimethylphenyl)-2-[2-[N-[2-[3-[3-(2-hydroxyethyl)pheny]ureido]acetyl]-N-(N-methyl-N-phenylcarbamoylmethyl)amino]phenoxy]acetamide (1–143)

mp 222–224° C. ¹H-NMR (CDCl₃)δ: 2.35 (6H, S), 2.78 (2H, t), 3.23 (3H, s), 3.24 (3H, s), 3.51 (1H, d), 3.81 (2H, t), 3.93 (2H, s), 4.43 (2H, s), 4.68 (1H, d), 6.07 (1H, brs), 6.61 (1H, d), 6.81–6.84 (3H, brs), 6.99 (1H, t), 7.04 (1H, s), 7.13–7.14 (2H, m), 7.21–7.37 (8H, m), 7.71 (1H, d)

Example 144

N-Methyl-N-(3,5-dimethylphenyl)-2-[2-[N-[2-[3-[3-(1-hydroxyethyl)pheny]ureido]acetyl]-N-(N-methyl-N-phenylcarbamoylmethyl)amino]phenoxy]acetamide (1–144)

mp 248–249° C. ¹H-NMR (CDCl₃+DMSO-d₆)δ: 1.40 (3H, d), 2.35 (6H, s), 3.22 (3H, s), 3.25 (3H, s), 3.54 (1H, d), 3.67 (1H, d), 3.89 (1H, d), 4.40 (2H, s), 4.72–4.77 (2H, m), 6.20 (1H, brs), 6.66 (1H, d), 6.85 (2H, s), 6.93–6.99 (2H, m), 7.03 (1H, s), 7.14 (1H, t), 7.24–7.42 (7H, m, 7.52 (1H, s), 7.66 (1H, d), 8.36 (1H, brs) MS (m/z): 652 (M+1)⁺

Example 145

N-Methyl-N-(3,5-dimethylphenyl)-2-[2-[N-[2-[3-[3-(N-hydroxyiminomethyl) pheny]ureido]acetyl]-N-(N-methyl-N-phenylcarbamoylmethyl)amino]phenoxy]acetamide (1–145)

mp 227–229° C. ¹H-NMR (ODCl₃+DMSO-d₆)δ: 2.35 (6H, s), 3.23 (3H, s), 3.25 (3H, S), 3.55 (1H, d), 3.77 (1H, dd), 3.91 (1H, dd), 4.40 (2H, s), 4.74 (1H, d), 6.22 (1H, brs), 6.64 (1H, d), 6.84 (2H, s), 6.97 (1H, t), 7.03 (1H, s), 7.17–7.41 (9H, m), 7.57 (1H, s), 7.68 (1H, d), 8.01 (1H, s), 8.21 (1H, brs), 10.41 (1H, s)

Example 146

N-Methyl-N-(3,5-dimethylphenyl)-2-[2-[N-(N-methyl-N-phenylcarbamoylmethyl)-N-[2-[3-[3-(N,N-dimethylamino) phenyl]ureido]acetyl]amino]phenoxy]acetamide (1–146)

mP 225–226° C. ¹H-NMR (CDCl₃)δ: 2.34 (6H, s), 2.90 (6H, s), 3.22 (3H, s), 3.23 (3H, s), 3.53 (1H, d), 3.85 (1H, dd), 3.95 (1H, dd), 4.40 (2H, s), 4.71 (1H, d), 6.05 (1H, brs), 6.38 (1H, dd), 6.49 (1H, d), 6.61 (1H, d), 6.82 (2H, s), 6.92–7.35 (11H, m), 7.70 (1H, d) MS (m/z): 651 (M+1)⁺

Example 147

N-Methyl-N-(3,5-dimethylphenyl)-2-[2-[N-(N-methyl-N-phenylcarbamoylmethyl)-N-[2-[3-[3-[1-(N,N-dimethylamino) ethyl]phenyl]ureido]acetyl] amino]phenoxy]acetamide (1–147)

¹H-NMR (CDCl₃)δ: 1.79 (3H, d), 2.36 (6H, s), 2.58 (3/2H, s), 2.64 (3/2H, s), 2.71 (3/2H. s). 2.76 (3/2H, S), 3.19 (3H. s), 3.25 (3H, s), 3.54 (1H, d), 3.88 (1H, d), 4.03 (1H, m), 4.22 (1H brs), 4.45 (2H s), 4.68 (1H, d), 6.65–7.46 (15H, m), 7.66 (1H, d), 8.44 (1H, brs), 11.94 (1H, brs) MS (m/z): 679 (M+1)⁺

Example 148

N-Methyl-N-(3,5-dimethylphenyl)-2-[2-[N-(N-methyl-N-phenylcarbamoylmethyl)-N-[2-[3-[3-[2-(N,N-dimethylamino) ethyl]phenyl]ureido]acetyl] amino]phenoxy]acetamide (1–148)

¹H-NMR (CDCl₃)δ: 2.35 (6H, s), 2.37 (6H, s), 2.63 (2H, brs), 2.76–2.79 (2H, brs), 3.22 (3H, s), 3.24 (3H, s), 3.56 (1H, d), 3.96 (2H, q), 4.43 (2H, s), 4.64 (1H, d), 6.19 (1H, brs), 6.61 (1H, d), 6.80 (1H, d), 6.85 (2H, s), 6.98 (1H, t), 7.00 (1H, s), 7.04–7.35 (9H, m), 7.65 (2H, brs) MS (m/z): 679 (M+1)⁺

Example 149

N-Methyl-N-phenyl-2-[3-[N-(N-methyl-N-phenylcarbamoylmethyl)-N-[2-[3-[3-(N,N-dimethylamino) phenyl]ureido]acetyl]amino] phenoxy]acetamide (1–149)

mp 184–185° C. ¹H-NMR (CDCl₃)δ: 2.91 (6H, s), 3.23 (3H, s), 3.24 (3H, s), 3.84 (2H, d), 4.06 (2H, s), 4.41 (2H, s). 5.92 (1H, brs), 6.42 (1H, brs), 6.56 (1H, d), 6.80 (1H, d), 6.84–6.87 (2H, m), 6.96 (1H, d), 7.04–7.24 and 7.32–7.48 (13H, m)

Example 150

N-Methyl-N-phenyl-2-[2-[N-(N-methyl-N-phenylcarbamoylmethyl)-N-[2-[3-[3-(1-pyrrolidinyl) phenyl]ureido]acetyl]amino]phenoxy]acetamide (1–150)

mp 227–228° C. ¹H-NMR (CDCl₃)δ: 1.94–1.98 (4H, m), 3.23–3.26 (10H, m), 3.51 (1H, d), 3.82 (1H, dd), 3.93 (1H, dd), 4.37 (2H, s), 4.71 (1H, d), 5.98 (1H, brs), 6.22 (1H, d), 6.42 (1H, d), 6.62 (1H, d), 6.71 (1H, s), 6.87 (1H, s), 6.98 (1H, t), 7.06 (1H, t), 7.20–7.44 (11H, m), 7.69 (1H, d) MS (m/z): 648 (M⁺)

Example 151

N-(3-Benzyloxyphenyl)-N-methyl-2-[2-[N-(N-methyl-N-phenylcarbamoylmethyl)-N-[2-[3-[3-(N,N-dimethylamino) phenyl]ureido]acetyl]amino] phenoxy]acetamide (1–151)

mp 157–158° C. ¹H-NMR (CDCl₃)δ: 2.91 (6H, s), 3.24 (6H, S), 3.50 (1H, d), 3.85 (1H, dd), 3.95 (1H, dd), 4.35 (2H, s), 4.70 (1H, d), 5.08 (2H, s), 5.94 (1H, brs), 6.39 (1H, dd), 6.49 (1H, d), 6.56 (1H, d), 6.79 (1H, s), 6.80 (1H, d), 6.85

(1H, s), 6.89 (1H, s), 6.96–7.01 (2H, m), 7.08 (1H, t), 7.20–7.43 (12H, m), 7.69 (1H, d) MS (m/z): 729 (M+1)⁺

Example 152

N-(3-Benzyloxyphenyl)-N-methyl-2-[3-[N-(N-methyl-N-phenylcarbamoylmethyl)-N-[2-[3-[3-(N,N-dimethylamino) phenyl]ureido]acetyl]amino] phenoxy]acetamide (1–152)

mp 128–129° C. ¹H-NMR (CDCl₃)δ: 2.91 (6H, s), 3.23 (3H, s), 3.31 (3H, s), 3.83 (2H, d), 4.06 (2H, s), 4.40 (2H, s), 5.08 (2H, s), 5.71 (1H, brs), 6.43 (1H, d), 6.53 (1H, d), 6.80 (2H, brs), 6.89–7.45 (19H, m) MS (m/z): 729 (M+1)⁺

Elementary Analysis (for C₄₂H₄₄N₆O₅) Calculated: C, 69.21; H, 6.08; N, 11.53 Found: C, 69.01; H, 6.17; N, 11.48

Example 153

N-(3-Hydroxyphenyl)-N-methyl-2-[2-[N-(N-methyl-N-phenylcarbamoylmethyl)-N-[2-[3-[3-(N,N-dimethylamino)phenyl]ureido]acetyl]amino] phenoxy]acetamide (1–153)

mp 252–254° C. ¹H-NMR (DMSO-d6)δ: 2.82 (6H, s), 3.11–3.15 (7H, m), 3.49 (1H, d), 3.76 (1H, dd), 4.49 (3H, m), 6.18 (1H, brs), 6.27 (1H, d), 6.56 (1H, d), 6.79–6.84 (5H, m), 6.98 (1H, t), 7.03 (1H, t), 7.23–7.43 (7H, m) 7.58 (1H, d), 8.61 (1H, s), 9.80 (1H, brs) MS (m/z): 639 (M+1)⁺

Elementary Analysis (for C₃₅H₃₈N₆O₆) Calculated: C, 65.82; H, 6.00; N, 13.16 Found: C, 65.56; H, 5.99; N, 12.97

Example 154

N-(3-Hydroxyphenyl)-N-methyl-2-[3-[N-(N-methyl-N-phenylcarbamoylmethyl)-N-[2-[3-[3-(N,N-dimethylamino) phenyl]ureido]acetyl]amino] phenoxy]acetamide (1–154)

mp 199–200° C. ¹H-NMR (DMSO-d₆)δ: 2.82 (6H, s), 3.18 (6H, brs), 3.60 (2H, s), 4.03 (2H, s), 4.50 (2H, s), 6.22 (1H, brs), 6.27 (1H, dd), 6.57 (1H, d), 6.81–7.01 and 7.22–7.46 (15H, m), 8.63 (1H, S), 9.78 (1H, brs) MS (m/z): 639 (M+1)⁺

Elementary Analysis (for C₃₅H₃₈N₆O₆) Calculated: C, 65.82; H, 6.00; N, 13.16 Found: C, 65.66; H, 6.02; N, 13.12

Example 155

Methyl 2-[2-methoxy-3-[3-[N-(N-methyl-N-phenylcarbamoylmethyl)-N-[2-(N-methyl-N-phenylcarbamoylmethyloxy)phenyl] carbamoylmethyl]-ureido]phenyl]acetate (1–154)

¹H-NMR (CDCl₃)δ: 3.26 (3H, s), 3.27 (3H, s), 3.52 (1H, d), 3.63 (2H, s), 3.68 (3H, s), 3.69 (3H, s), 3.84 (1H, dd), 3.96 (1H, dd), 4.39 (2H, s), 4.70 (1H, d), 6.22 (1H, brs), 6.62 (1H, d), 6.85 (1H, d), 6.97–7.01 (2H, m), 7.12 (1H, s), 7.22–7.45 (11H, m), 7.70 (1H, d), 7.90 (1H, d)

Example 156

Methyl 2-[4-methoxy-3-[3-[N-(N-methyl-N-phenylcarbamoylmethyl)-N-[2-(N-methyl-N-phenylcarbamoylmethyloxy)phenyl] carbamoylmethyl]ureido]phenyl]acetate (1–156)

mp 168–169° C. ¹H-NMR (CDCl₃)δ: 3.26 (6H, s), 3.52 (2H, s), 3.56 (1H, d), 3.64 (3H, s), 3.74 (1H, dd), 3.80 (3H, s), 3.93 (1H, dd), 4.37 (2H, s), 4.72 (1H, d), 5.93 (1H, brs), 6.63 (1H, d), 6.75 (1H, d), 6.82 (1H, dd), 6.97–7.01 (2H, m), 7.21–7.44 (11H, m), 7.71 (1H, d), 7.97 (1H, s) MS (m/z): 682 (M+1)⁺

Elementary Analysis (for C₃₇H₃₉N₅O₈) Calculated: C, 65.19; H, 5.77 N, 10.27 Found: C, 64.79 H, 5.80; N, 10.26

Example 157

2-[2-Methoxy-3-[3-[N-(N-methyl-N-phenylcarbamoylmethyl) -N-[2-(N-methyl-N-phenylcarbamoylmethyloxy)phenyl] carbamoylmethyl]ureido]phenyl]acetic acid (1–157)

¹H-NMR (CDCl₃)δ: 3.24 (3H, s), 3.25 (3H, s), 3.51 (3H, s), 3.56 (1H, d), 3.62 (2H, s), 3.71 (1H, dd), 3.92 (1H, dd), 4.38 (2H, s), 4.71 (1H, d), 6.61–6.63 (2H, m), 6.83 (1H, d), 6.97–6.99 (2H, m), 7.20–7.43 (12H, m), 7.69 (1H, d), 7.89 (1H, d)

Example 158

2-[4-Methoxy-3-[3-[N-(N-methyl-N-phenylcarbamoylmethyl)-N-[2-(N-methyl-N-phenylcarbamoylmethyloxy)phenyl] carbamoylmethyl]ureido]phenyl]acetic acid (1–158)

¹H-NMR (CDCl₃)δ: 3.24 (3H, s), 3.25 (3H, s), 3.51 (2H, s), 3.56 (1H, d), 3.73 (4H, brs), 3.88 (1H, dd), 4.36 (2H, s), 4.70 (1H, d), 6.13 (1H, brs), 6.63 (1H, d), 6.69 (1H, d), 6.81 (1H, dd), 6.97 (1H, t), 7.15–7.41 (12H, m), 7.67 (1H, d), 7.90 (1H, s) MS (m/z): 668 (M+1)⁺

Example 159

Methyl 2-[3-[3-[N-[2-[N-methyl-N-(2,5-dimethylphenyl)carbamoylmethyloxy]phenyl]-N-(N-methyl-N-phenylcarbamoylmethyl) carbamoylmethyl]ureido]phenyl]acetate (1–159)

mp 179–180° C. ¹H-NMR (CDCl₃)δ: 2.22 (3/2H, s), 2.24 (3/2H, s), 2.35 (3H, s), 3.20 (3H, s), 3.24 (3H, s), 3.53 (1H, d), 3.55 (2H, s), 3.65 (3H, s), 3.95 (2H, s), 4.14–4.21 (1H, m), 4.44 (1H, d), 4.68 (1H, d), 6.07 (1H, brs), 6.63 (1H, brs), 6.85 (1H, d), 6.96–7.00 (2H, m), 7.12–7.34 (11H, m), 7.53 (11H, brs), 7.70 (1H, d)

Example 160 tert-Butyl 2-[3-[3-[N-[2-[N-methyl-N-( 2,5-dimethylphenyl)carbamoylmethyloxy]phenyl]-N-(N-methyl-N-phenylcarbamoylmethyl) carbamoylmethyl]ureido]phenyl]acetate (1–160)

¹H-NMR (CDCl₃)δ: 1.42 (9H, s), 2.20 (3/2H, S), 2.26 (3/2H, s), 2.34 (3/2H, s), 2.35 (3/2H, s), 3.23 (3H, s), 3.24 (3H, s), 3.45 (2H, s), 3.46 (1H, d), 3.96 (2H, s), 4.18–4.20 (1H, in), 4.42 (1H, m), 4.67 (1H, d), 5.91 (1H, brs), 6.60 (1H, d), 6.88 (1H, d), 6.95–7.02 and 7.13–7.39 (14H, m), 7.69 (1H, d)

Example 161

Methyl (∓)-2-[3-[3-[N-[2-[N-methyl-N-(2,5-dimethylphenyl)carbamoylmethyloxy]phenyl]-N-(N-methyl-N-phenylcarbamoylmethyl) carbamoylmethyl]ureido]phenyl]propionate (1–161)

mp 196–197° C. ¹H-NMR (CDCl₃)δ: 1.43 (3H, d), 2.22 (3/2H, s), 2.23 (3/2H, s), 2.34 (3H, s), 3.20 (3H, s), 3.21 (3H, s), 3.54 (1H, d), 3.61 (3H, s), 3.62 (1H, q), 3.94 (2H, s), 4.15–4.21 (1H, m), 4.44 (1H, d), 4.68 (1H, d), 6.11 (1H, brs), 6.63 (1H, t), 6.87 (1H, d), 6.96–7.02 and 7.12–7.33 (13H, m), 7.59 (1H, brs), 7.69 (1H, d)

Example 162 tert-Butyl (±)-2-[3-[3-[N-[2-[N-methyl-N-( 2,5-dimethylphenyl)carbamoylmethyloxy]phenyl]-N-(N-methyl-N-phenylcarbamoylmethyl) carbamoylmethyl]ureido]phenyl]propionate (1–162)

$^1$H-NMR (CDCl$_3$)δ: 1.38 (9H, s), 1.39 (3H, d), 2.21 (3/2H, s), 2.27 (3/2H, s), 2.34 (3/2H, s), 2.36 (3/2H, s), 3.22 (3H, s), 3.24 (3H, s), 3.46 (1H, d), 3.53 (1H, q), 3.95 (2H, d), 4.14–4.21 (1H, m), 4.43 (1H, d), 4.67 (1H, d), 5.94 (1H, brs), 6.61 (1H, d), 6.90 (1H, d), 6.95–7.02 and 7.13–7.39 (14H, m), 7.70 (1H, d)

Example 163

Methyl 2-[3-[3-[N-[3-[N-methyl-N-(2,5-dimethylphenyl)carbamoylmethyloxy]phenyl]-N-(N-methyl-N-phenylcarbamoylmethyl) carbamoylmethyl]ureido]phenyl]acetate (1–163)

mp 160–161° C. $^1$H-NMR (CDCl$_3$)δ: 2.24 (3H, s), 2.33 (3H, s), 3.22 (3H, s), 3.23 (3H, s), 3.54 (2H, s), 3.64 (3H, s), 3.85 (2H, d), 4.08 (2H, s), 4.20 (1H, d), 4.40 (1H, d), 6.03 (1H, brs), 6.78 (1H, d), 6.86 (1H, d), 6.92 (1H, s), 7.02–7.36 (13H, m), 7.78 (1H, brs)

Example 164 tert-Butyl 2-[3-[3-[N-[3-[N-methyl-N-(2,5-dimethylphenyl)carbamoylmethyloxy]phenyl]-N-(N-methyl-N-phenylcarbamoylmethyl) carbamoylmethyl]ureido]phenyl]acetate (1–164)

$^1$H-NMR (CDCl$_3$)δ: 1.41 (9H, s), 2.24 (3H, s), 2.33 (3H, s), 3.21 (3H, s), 3.23 (3H, s), 3.43 (2H, s), 3.85 (2H, d), 4.08 (2H, s), 4.21 (1H, d), 4.40 (1H, d), 6.02 (1H, brs), 6.77 (1H, dd), 6.86 (1H, d), 6.91 (1H, s), 7.03 (1H, d), 7.06 (1H, s), 7.10–7.35 (11H, m), 7.78 (1H, brs)

Example 165

Methyl (±)-2-[3-[3-[N-[3-[N-methyl-N-(2,5-dimethylphenyl)carbamoylmethyloxy]phenyl]-N-(N-methyl-N-phenylcarbamoylmethyl) carbamoylmethyl]ureido]phenyl]propionate (1–165)

mp 169–170° C. $^1$H-NMR (CDCl$_3$)δ: 1.44 (3H, d), 2.24 (3H, s), 2.34 (3H, s), 3.22 (3H, s), 3.23 (3H, s), 3.61 (3H, s), 3.64 (1H, q), 3.86 (2H, d), 4.08 (2H, s), 4.21 (1H, d), 4.40 (1H, d), 5. 98 (1H, brs), 6.78 (1H, d), 6. 88–6.91 (2H, m), 7.02 (1H, d), 7.06 (1H, s), 7.10–7.37 (11H, m), 7.63 (1H, brs)

Example 166 tert-Butyl (±)-2-[3-[3-[N-[3-[N-methyl-N-(2,5-dimethylphenyl)carbamoylmethyloxy]phenyl]-N-(N-methyl-N-phenylcarbamoylmethyl) carbamoylmethyl]ureido]phenyl]propionate (1–166)

$^1$H-NMR (CDCl$_3$)δ: 1.37 (9H, s), 1.38 (3H, d), 2.24 (3H, s), 2.33 (3H, s), 3.22 (3H, s), 3.23 (3H, s), 3.53 (1H, q), 3.85 (2H, d), 4.08 (2H, s), 4.21 (1H, d), 4.40 (1H, d), 5.95 (1H, brs), 6.78 (1H, dd), 6.90 (2H, brs), 7.02 (1H, d) 7.07 (1H, s), 7.10–7.36 (11H, m), 7.60 (1H, brs)

Example 167

Methyl 2-[3-[3-[N-[2-[N-methyl-N-(2,6-dimethylphenyl)carbamoylmethyloxy]phenyl]-N-(N-methyl-N-phenylcarbamoylmethyl) carbamoylmethyl]ureido]phenyl]acetate (1–167)

mp 113–115° C. $^1$H-NMR (CDCl$_3$)δ: 2.23 (3H, s), 2.26 (3H, S), 3.17 (3H, s), 3.21 (3H, s), 3.53–3.55 (1H, m), 3.55 (2H, s), 3.65 (3H, s), 3.93 (2H, s), 4.21 (2H, s), 4.67 (1H, d), 6.07 (1H, brs), 6.65 (1H, d), 6.86 (1H, d), 6.98 (1H, t), 7.12–7.35 (12H, m), 7.50 (1H, s), 7.69 (1H, d)

Example 168

Methyl (±)-2-[3-[3-[N-[2-[N-methyl-N-(2,6-dimethylphenyl)carbamoylmethyloxy]phenyl]-N-(N-methyl-N-phenylcarbamoylmethyl) carbamoylmethyl]ureido]phenyl]propionate (1–168)

mp 120–122° C. $^1$H-NMR (CDCl$_3$)δ: 1.45 (3H, d), 2.25 (3H, s), 2.29 (3H, s), 3.19 (3H, s), 3.23 (3H, s), 3.50 (1H, d), 3.62 (3H, s), 3.65 (1H, q), 3.94 (2H, s), 4.21 (2H, s), 4.67 (1H, d), 6.03 (1H, brs), 6.64 (1H, d), 6.88 (1H, d), 6.98 (1H, t), 7.14–7.36 (13H, m), 7.69 (1H, d)

Example 169

Methyl 2-[3-[3-[N-[3-[N-methyl-N-(2,6-dimethylphenyl)carbamoylmethyloxy]phenyl]-N-(N-methyl-N-phenylcarbamoylmethyl) carbamoylmethyl]ureido]phenyl]acetate (1–169)

$^1$H-NMR (CDCl$_3$)δ: 2.28 (6H, s), 3.20 (6H, s), 3.53 (2H, s), 3.64 (3H, s), 3.85 (2H, d), 4.07 (2H, s), 4.21 (2H, s), 6.04 (1H, brs), 6.76 (1H, d), 6.85 (1H, d), 6.91 (1H, s), 7.03–7.36 (13H, m) 7.88 (1H, brs)

Example 170

Methyl (±)-2-[3-[3-[N-[3-[N-methyl-N-(2,6-dimethylphenyl)carbamoylmethyloxy]phenyl]-N-(N-methyl-N-phenylcarbamoylmethyl) carbamoylmethyl]ureido]phenyl]propionate (1–170)

$^1$H-NMR (CDCl$_3$)δ: 1.43 (3H, d), 2.28 (6H, s), 3.20 (3H, s), 3.21 (3H, s), 3.61 (3H, s), 3.64 (1H, q), 3.85 (2H, d), 4.08 (2H, s), 4.21 (2H, s), 6.02 (1H, brs), 6.76 (1H, d), 6.87–6.90 (2H, m), 7.03–7.38 (13H, m), 7.76 (1H, brs)

Example 171

Methyl 2-[3-[3-[N-(N-methyl-N-phenylcarbamoylmethyl)-N-[3-(N-methyl-N-phenylcarbamoylmethylthio)phenyl] carbamoylmethyl]ureido]phenyl]acetate (1–171)

mp 98–99° C. $^1$H-NMR (CDCl$_3$)δ: 3.23 (3H, s), 3.29 (3H, s), 3.52 (2H, s), 3.54 (2H, s), 3.65 (3H, s), 3.85 (2H, d), 4.08 (2H, s), 5.90 (1H, brs), 6.88 (1H, d), 7.14–7.52 (18H, m) MS (m/z): 668 (M+1)$^+$ Elementary Analysis (for C$_{36}$H$_{37}$N$_5$O$_6$S) Calculated: C, 64.75 H, 5.58; N, 10.49 Found: C, 64.46; H, 5.55; N, 10.50

Example 172

2-[3-[3-[N-(N-Methyl-N-phenylcarbamoylmethyl)-N-[3-(N-methyl-N-phenylcarbamoylmethylthio) phenyl]carbamoylmethyl]ureido]phenyl]acetic acid (1–172)

$^1$H-NMR (CDCl$_3$)δ: 3.24 (3H, s), 3.29 (3H, s), 3.53 (4H, m), 3.81 (2H, d), 4.06 (2H, s), 6.24 (1H, brs), 6.85 (1H, d), 7. 05 (1H, s), 7.11–7.44 (16H, m), 7.78 (1H, s) MS (m/z): 654 (M+1)$^+$

Example 173

2-[3-[3-[N-[2-[N-Methyl-N-(2,5-dimethylphenyl) carbamoylmethyloxy]phenyl]-N-(N-methyl-N-phenylcarbamoylmethyl)carbamoylmethyl]ureido] phenyl]acetic acid (1–173)

$^1$H-NMR (CDCl$_3$)δ: 2.15 (3/2H, s), 2.23 (3/2H, s), 2.30 (3/2H, s), 2.34 (3/2H, s), 3.15 (3H, s), 3.23 (3H, s), 3.50 (2H, s), 3.58 (1H, dd), 3.82–3.90 (2H, m), 4.15 (1H, dd), 4.40 (1H, dd), 4.71 (1H, dd), 6.35 (1H, brs), 6.64 (1H, m), 6.82 (1H, d), 6.93–6.99 (2H, m), 7.09–7.35 (10H, m), 7.46 (1H, d), 7.69 (1H, d), 7.77 (1H, s)

Example 174

(±)-2-[3-[3-[N-[2-[N-Methyl-N-(2,5-dimethylphenyl) carbamoylmethyloxy]phenyl]-N-(N-methyl-N-phenylcarbamoylmethyl) carbamoylmethyl]ureido]phenyl]propionic acid (1–174)

$^1$H-NMR (CDCl$_3$)δ: 1.48 (3H, m), 2.14 (1H, s), 2.16 (1H, s), 2.23 (1H, s), 2.31 (1H, s), 2.33 (1H, s), 2.35 (1H, s), 3.14 (3H, s), 3.22 (3/2H, s), 3.23 (3/2H, s), 3.55–3.68 (2H, m), 3.80–3.89 (2H, m), 4.13 (1H, d), 4.38 (1H, d), 4.68 (1H, m), 6.39 (1H, brs), 6.63 (1H, m), 6.89 (1H, d), 6.94–7.37 (12H, m), 7.49 (1H, d), 7.67 (1H, d), 7.81 (1H, s)

Example 175

2-[3-[3-[N-[3-[N-Methyl-N-(2,5-dimethylphenyl) carbamoylmethyloxy]phenyl]-N-(N-methyl-N-phenylcarbamoylmethyl)carbamoylmethyl]ureido] phenyl]acetic acid (1–175)

$^1$H-NMR (CDCl$_3$)δ: 2.23 (3H, s), 2.32 (3H, s), 3.22 (3H, s), 3.22 (3H, s), 3.50 (2H, s), 3.79 (2H, s), 4.05 (2H, s), 4.20 (1H, d), 4.39 (1H, d), 6.25 (1H, brs), 6.72 (1H, d), 6.81 (1H, d), 6.89 (1H, s), 6.97 (1H, d), 7.05–7.40 (12H, m), 7.98 (1H, s)

Example 176

(±) -2-[3-[3-[N-[3-[N-Methyl-N-(2,5-dimethylphenyl) carbamoylmethyloxy]phenyl]-N-(N-methyl-N-phenylcarbamoylmethyl )carbamoylmethyl]ureido]phenyl]propionic acid (1–176)

$^1$H-NMR (CDCl$_3$)δ: 1.43 (3H, d), 2.23 (3H, s), 2.32 (3H, s), 3.23 (6H, s), 3.62 (1H, q), 3.78 (2H, s), 4.04 (2H, s), 4.20 (1H, d), 4.39 (1H, d), 6.28 (1H, brs), 6.72 (1H, d), 6.86–6.88 (2H, m), 6.95 (1H, d), 7.05–7.43 (12H, m), 8.01 (1H, s)

Example 177

2-[3-[3-[N-[2-[N-Methyl-N-(2,6-dimethylphenyl) carbamoylmethyloxy]phenyl]-N-(N-methyl-N-phenylcarbamoylmethyl)carbamoylmethyl]ureido] phenyl]acetic acid (1–177)

mp 172–173° C. $^1$H-NMR (CDCl$_3$)δ: 2.19 (3H, s), 2.26 (3H, s), 3.13 (3H, s), 3.24 (3H, s), 3.55 (2H, s), 3.57 (1H, d), 3.83 (1H, dd), 3.89 (1H, dd), 4.17 (2H, s), 4.68 (1H, d), 6.32 (1H, brs), 6.66 (1H, d), 6.86 (1H, d), 6.97 (2H, brs), 7.10–7.38 (10H, m), 7.50 (1H, d), 7.60 (1H, s), 7.68 (1H, d)

Example 178

(±)-2-[3-[3-[N-[2-[N-Methyl-N-(2,6-dimethylphenyl) carbamoylmethyloxy]phenyl]-N-(N-methyl-N-phenylcarbamoylmethyl) carbamoylmethyl]ureido]phenyl]propionic acid (1–178)

$^1$H-NMR (CDCl$_3$)δ: 1.48 (3H, m), 2.16 (3/2H, s), 2.19 (3/2H, s), 2.25 (3H, s), 3.11 (3/2H, s), 3.12 (3/2H, s), 3.21 (3/2H, s), 3.23 (3/2H, s), 3.58 (1H, d), 3.65–3.75 (2H, m), 3.87 (1H, dd), 4.16 (2H, s), 4.66 (1H, d), 6.36 (1H, brs), 6.66 (1H, d), 6.90 (1H, d), 6.96 (1H, t), 7.03–7.36 (11H, m), 7.51 (1H, m), 7.66 (1H, d), 7.79 (1H, s)

Example 179

2-[3-[3-[N-[3-[N-Methyl-N-(2,6-dimethylphenyl) carbamoylmethyloxy]phenyl]-N-(N-methyl-N-phenylcarbamoylmethyl)carbamoylmethyl]ureido] phenyl]acetic acid (1–179)

$^1$H-NMR (CDCl$_3$)δ: 2.27 (6H, s), 3.20 (6H, s), 3.47 (2H s), 3.75 (2H, s), 4.03 (2H, s), 4.20 (2H, s), 6.25 (1H, brs), 6.71 (1H, d), 6.79 (1H, d), 6.87 (1H, s), 6.97 (1H, d), 7.03–7.35 (12H, m), 8.06 (1H, s)

Example 180

(±)-2-[3-[3-[N-[3-[N-Methyl-N-(2,6-dimethylphenyl) carbamoylmethyloxy]phenyl]-N-(N-methyl-N-phenylcarbamoylmethyl) carbamoylmethyl]ureido]phenyl]propionic acid (1–180)

$^1$H-NMR (CDCl$_3$)δ: 1.41 (3H, d), 2.27 (6H, s), 3.20 (6H, s), 3.61 (1H, q), 3.75 (2H, s), 4.03 (2H, d), 4.20 (2H, s), 6.27 (1H, brs), 6.71 (1H, d), 6.87 (2H, brs), 6.97 (1H, d), 7.06–7.39 (12H, m) 8.08 (1H, s)

Example 181

2-[3-[3-[N-[2-[N-Methyl-N-(3,5-dimethylphenyl) carbamoylmethyloxy]phenyl]-N-(3-methylbutyl) carbamoylmethyl]ureido]phenyl]acetic acid (1–181)

mp 155–157° C. $^1$H-NMR (CDCl$_3$)δ: 0.83–0.86 (6H, m), 1.36–1.50 (2H, m), 1.52–1.55 (1H, m), 2.35 (6H, s), 3.26 (3H, s), 3.36 (1H, m), 3.60 (2H, s), 3.67 (1H, m), 3.87 (1H, dd), 4.02 (1H, m), 4.47 (2H, q), 6.54 (1H, brs), 6.68 (1H, d), 6.87 (3H, brs), 6.95 (1H, s), 6.97 (1H, t), 7.04 (1H, s), 7.11 (1H, d), 7.18 (1H, t), 7.28 (1H t), 7.63 (2H, brs)

Example 182

(±)-2-[3-[3-[N-[2-[N-Methyl-N-(3,5-dimethylphenyl) carbamoylmethyloxy]phenyl]-N-(3-methylbutyl) carbamoylmethyl]ureido]phenyl] propionic acid (1–182)

mp 119–121° C. $^1$H-NMR (CDCl$_3$)δ: 0.82–0.85 (6H, m), 1.32–1.43 (2H, m), 1.48–1.54 (1H, m), 1.52 (3H, d), 2.36 (6H, s), 3.26 (3H, s), 3.32–3.39 (1H, m), 3.65 (1H, d), 3.72 (1H, q), 3.85 (1H, dd), 3.96–4.03 (1H, m), 4.47 (2H, q), 6.51 (1H, brs), 6.67 (1H, d), 6.87 (2H, s), 6.92 (1H, d), 6.96 (1H, t), 7.04 (1H, s), 7.11 (1H, d), 7.18 (1H, t), 7.25–7.29 (2H, m), 7.60 (1H, d), 7.76 (1H, s)

Example 183

2-[3-[3-[N-[2-(N-Methyl-N-phenylcarbamoylmethyl) phenyl]-N-(3-methylbutyl) carbamoylmethyl]ureido]phenyl]acetic acid (1–183)

mp 147–149° C. $^1$H-NMR (CDCl$_3$)δ: 0.83–0.86 (6H, m), 1.32–1.41 (2H, m), 1.50–1.55 (1H, m), 3.29 (3H, s), 3.32–3.39 (1H, m), 3.59 (2H, s), 3.62 (1H, d), 3.84 (1H, dd), 3. 96–4.03 (1H, m), 4.45 (2H, d), 6.50 (1H, brs), 6.67 (1H, d), 6.86 (1H, d), 6.95–6.99 (2H, m), 7.12 (1H, d), 7.17 (1H, t), 7.25–7.29 and 7.38–7.49 (6H, m), 7.58 (1H, d), 7.63(1H, s)

Example 184

2-[3-[3-[N-[2-[N-Methyl-N-(2-methylphenyl) carbamoylmethyloxy]phenyl]-N-(3-methylbutyl) carbamoylmethyl]ureido]phenyl]acetic acid (1–184)

$^1$H-NMR (CDCl$_3$)δ: 0.83–0.86 (6H, m), 1.32–1.43 (2H, m), 1.56–1.57 (1H, m), 2.30 (3/2H, s), 2.32 (3/2H. s), 3.22 (3H, s), 3.33–3.39 (1H, m), 3.58 (2H, s), 3.65 (1H, dd), 3.86 (1H, dd), 3.98–4.01 (1H, m), 4.22 (1H, t), 4.45 (1H, dd), 6.47 (1H, brs), 6.68 (1H, t), 6.86 (1H, d), 6.95–6.99 (2H, m), 7.11–7.36 (7H, m), 7.54 (1H, t), 7.62 (1H, s)

Example 185

2-[3-[3-[N-[2-[N-Methyl-N-(3-methylphenyl) carbamoylmethyloxy]phenyl]-N-(3-methylbutyl) carbamoylmethyl]ureido]phenyl]acetic acid (1–185)

mp 173–174° C. $^1$H-NMR (CDCl$_3$)δ: 0.83–0.86 (6H, m), 1.33–1.43 (2H, m), 1.50–1.57 (1H, m), 2.40 (3H, s), 3.27 (3H, s), 3.33–3.40 (1H, m), 3.60 (2H, s), 3.65 (1H, dd), 3.85 (1H, dd), 3.96–4.04 (1H, m), 4.46 (2H, q), 6.49 (1H, brs), 6.68 (1H, d), 6.87 (1H, d), 6. 95–6.99 (2H, m), 7.05–7.29 (6H, m), 7.35 (1H, t), 7.60 (2H, brs)

Elementary Analysis (for C$_{32}$H$_{38}$N$_4$O$_6$) Calculated: C, 66.88; H, 6.66; N, 9.75 Found: C, 66.68; H, 6.48 N, 9.63

Example 186

2-[3-[3-[N-[2-[N-Methyl-N-(2,6-dimethylphenyl) carbamoylmethyloxy]phenyl]-N-(3-methylbutyl) carbamoylmethyl]ureido]phenyl]acetic acid (1–186)

$^1$H-NMR (CDCl$_3$)δ: 0.81–0.86 (6H, m), 1.33–1.43 (2H, m), 1.51–1.57 (1H, m), 2.28 (3H, s), 2.30 (3H, s), 3.18 (3H, s), 3.33–3.40 (1H, m), 3.58 (2H, s), 3.62 (1H, dd), 3.86 (1H, dd), 3.96–4.04 (1H, m), 4.24 (2H, s), 6.47 (1H, brs), 6.70 (1H, d), 6.87 (1H, d), 6.95–6.99 and 7.08–7.28 (8H, m), 7.56 (1H, d), 7.60 (1H, s)

Example 187

2-[3-[3-[N-[2-[N-(3-Chlorophenyl)-N-methyl carbamoylmethyloxy]phenyl]-N-(3-methylbutyl) carbamoylmethyl]ureido]phenyl]acetic acid (1–187)

mp 165–167° C. $^1$H-NMR (CDCl$_3$)δ: 0.83–0.86 (6H, m), 1.37 (2H, m), 1.52–1.54 (1H, m), 3.26 (3H, S), 3.35 (1H, m), 3.58 (2H, s), 3.63 (1H, d), 3.83 (1H, d), 3.98 (1H, m), 4.47 (2H, s), 6.51 (1H, s), 6.68 (1H, brs), 6.86 (1H, d), 6.95–6.99 (2H, m), 7.12–7.17, 7.26–7.29 and 7.38–7.55 (8H, m), 7.65 (1H, s)

Elementary Analysis (for C$_{31}$H$_{35}$ClN$_4$O$_6$) Calculated: C, 62.57; H, 5.93; N, 9.41 Found: C, 62.22; H, 5.72; N, 9.24

Example 188

(±)-2-[3-[3-[N-[2-[N-(3-Chlorophenyl)-N-methylcarbamoylmethyloxy]phenyl]-N-(3-methylbutyl) carbamoylmethyl]ureido]phenyl] propionic acid (1–188)

mp 121–122° C. $^1$H-NMR (CDCl$_3$)δ: 0.83–0.86 (6H, m), 1.36 (2H, m), 1.53 (3H, d), 1.52–1.55 (1H, m), 3.26 (3H, s), 3.31–3.34 (1H, m), 3.63 (1H, d), 3.74 (1H, q), 3.81 (1H, d), 3.95–4.02 (1H, m), 4.47 (2H, s), 6.54 (1H, brs), 6.70 (1H, brs), 6.93 (1H, d), 6.97–7.01 (2H, m), 7.10–7.39 (7H, m), 7.65 (1H, brs), 7.74 (1H, s)

Elementary Analysis (for C$_{32}$H$_{37}$ClN$_4$O$_6$) Calculated: C, 63.10; H, 6.12; N, 9.20 Found: C, 62.67; H, 6.10; N, 9.12

Example 189

2-[3-[3-[N-[2-[N-(3-Bromophenyl)-N-methyl carbamoylmethyloxy]phenyl]-N-(3-methylbutyl) carbamoylmethyl]ureido]phenyl]acetic acid (1–189)

mp 172–173° C. $^1$H-NMR (DMSO-d$_6$)δ: 0.82–0.85 (6H, m), 1.25–1.33 (2H, m), 1.51–1.58 (1H, m), 3.21 (3H, s), 3.36–3.39 (1H, m), 3.45 (2H, s), 3.47 (1H, m), 3.66 (1H, dd), 3.83–3.91 (1H, m), 4.63 (2H, brs), 6.26 (1H, brs), 6.76 (1H, d), 6.97–7.58 (10H, m), 7.82 (1H, brs), 8.79 (1H, s), 12.27 (1H, brs)

Elementary Analysis (for C$_{31}$H$_{35}$BrN$_4$O$_6$) Calculated: C, 58.22; H, 5.52; N, 8.76 Found: C, 58.14; H, 5.63; N, 8.57

Example 190

(±)-2-[3-[3-[N-[2-[N-(3-Bromophenyl)-N-methylcarbamoylmethyloxy]phenyl]-N-(3-methylbutyl) carbamoylmethyl]ureido]phenyl] propionic acid (1–190)

mp 123–124° C. $^1$H-NMR (DMSO-d$_6$)δ: 0.82–0.84 (6H, m), 1.27–1.34 (2H, m), 1.30 (3H, d), 1.50–1.58 (1H, m), 3.29 (3H, s), 3.33 (1H, m), 3.46 (1H, dd), 3.55 (1H, q), 3.66 (1H, dd), 3.84–3.91 (1H, m), 4.63 (2H, brs), 6.24 (1H, brs), 6.79 (1H, d), 6.98–7.57 (10H, m), 7.82 (1H, brs), 8.83 (1H, s), 12.23 (1H, brs)

Elementary Analysis (for C$_{32}$H$_{37}$BrN$_4$O$_6$) Calculated: C, 58.81; H, 5.71; N, 8.57 Found: C, 58.59; H, 5.73; N, 8.58

Example 191

2-[3-[3-[N-[2-[N-(3-Trifluoromethylphenyl)-N-methylcarbamoylmethyloxy]phenyl]-N-(3-methylbutyl)carbamoylmethyl]ureido]phenyl]acetic acid (1–191)

$^1$H-NMR (CDCl$_3$)δ: 0.82–0.85 (6H, m), 1.36–1.43 (2H, m), 1.52–1.55 (1H, m), 3.29 (3H, s), 3.30–3.35 (1H, m), 3.56 (2H, s), 3.66 (1H, d), 3.82 (1H. d). 3.98 (1H, m). 4.45 (2H, s), 6.47 (1H, brs), 6.69 (1H, brs), 6.85 (1H, d), 6.98–7.01 (2H, m), 7.13–7.15, 7.27–7.29 and 7.47–7.66 (8H, m), 7.71 (1H, s)

Example 192

(±)-2-[3-[3-[N-[2-[N-(3-Trifluoromethylphenyl)-N-methylcarbamoylmethyloxy]phenyl]-N-(3-methylbutyl) carbamoylmethyl]ureido]phenyl] propionic acid (1–192)

$^1$H-NMR (CDCl$_3$)δ: 0.82–0.84 (6H, m), 1.35–1.45 (2H, m), 1.49 (3H, d), 1.51–1.54 (1H, m), 3.28 (3H, S), 3.29–3.33 (1H, m), 3.62–3.82 (3H, m), 3.94–4.01 (1H, m), 4.45 (2H, s), 6.52 (1H, brs), 6.67 (1H, brs), 6.91 (1H, d), 6.98 (1H, d), 7.03 (1H, S), 7.11–7.19, 7.26–7.30 and 7.49–7.65 (8H, m), 7.81 (1H, s)

Example 193

2-[3-[3-[N-[2-[N-Methyl-N-[3-(N,N-dimethylamino) phenyl]carbamoylmethyloxy]phenyl]-N-(3-methylbutyl) carbamoylmethyl]ureido]phenyl]acetic acid (1–193)

mp 152–153° C. $^1$H-NMR (DMSO-d$_6$)δ: 0.82–0.84 (6H, m), 1.24–1.31 (2H, m), 1.51–1.57 (1H, m), 2.93 (6H, s), 3.17

(3H, s), 3.32–3.39 (1H, m), 3.44 (2H, S), 3.46 (1H, d), 3.66 (1H, dd), 3.81–3.89 (1H, m), 4.60 (2H, s), 6.27 (1H, brs), 6.72–6.77 (4H, m), 6.87 (1H, d), 7. 03 (1H, t), 7.12 (1H, t), 7.22–7.27 (4H, m), 7.36 (1H, t), 8.80 (1H, s)

Example 194

2-[3-[3-[N-[3-[N-Methyl-N-(2-methylphenyl) carbamoylmethyloxy]phenyl]-N-(3-methylbutyl) carbamoylmethyl]ureido]phenyl]acetic acid (1–194)

δ:

mp 154–155° C. $^1$H-NMR (CDCl$_3$)δ: 0.85 (6H, d), 1.32–1.38 (2H, m), 1.50–1.54 (1H, m), 2.28 (3H, 3.25 (3H, s), 3.60 (2H, s), 3.63–3.69 (4H, m), 4.18 (1H, d), 4.39 (1H, d), 6.53 (1H, brs), 6.62 (1H, s), 6.75 (2H, brs), 6.88 (1H, d), 6.93 (1H, s), 7.18–7.33 (6H, m), 7.63 (2H, brs)

Example 195

2-[3-[3-[N-[3-[N-Methyl-N-(3,5-dimethylphenyl) carbamoylmethyloxy]phenyl]-N-(3-methylbutyl) carbamoylmethyl]ureido]phenyl]acetic acid (1–195)

mp 99–100° C. $^1$H-NMR (CDCl$_3$)δ: 0.85 (6H, d), 1.33–1.38 (2H, m), 1.51–1.52 (1H, m), 2.34 (6H, s), 3.29 (3H, s), 3.58 (2H, s), 3.64–3.69 (4H, m), 4.43. (2H, s), 6.51 (1H, brs), 6.66 (1H, s), 6.73–6.75 (2H, m), 6.86 (2H, s), 6.87 (1H, d), 6.95 (1H, s), 7.02 (1H, s), 7.17 (1H, t), 7.26 (1H, m), 7.57 (1H, t), 7.71 (1H, s)

Example 196

2-[3-[3-[N-[3-[N-Methyl-N-(3,5-dimethylphenyl) carbamoylmethyloxy]phenyl]-N-[(1-methylcyclohexyl) methyl]carbamoylmethyl]ureido] phenyl]acetic acid (1–196)

$^1$H-NMR (CDCl$_3$)δ: 0.83 (3H, s), 1.17–1.43 (10H, m), 2.34 (6H, s), 3.28 (3H, s), 3.57 (2H, s), 3.64 (2H, s), 3.75 (2H, s), 4.42 (2H, s), 6.46 (1H, brs), 6.66 (1H, brs), 6.73 (1H, s), 6.85 (2H, s), 6.86 (1H, d), 6.95 (1H, s), 7.02 (1H, s), 7.16–7.26 (3H, m), 7.53 (1H, brs), 7.71 (1H, s)

Example 197

2-[3-[3-[N-[3-(N-Methyl-N-phenylcarbamoylmethyloxy) phenyl]-N-(2,2-dimethylpropyl)carbamoylmethyl]ureido]phenyl] acetic acid (1–197)

mp 122–123° C. $^1$H-NNIR (CDCl$_3$)δ: 0.82 (9H, s), 3.32 (3H, s), 3.58 (4H, brs), 3.76 (2H, brs), 4.43 (2H, s), 6.49 (1H, brs), 6.65–6.69 (2H, m), 6.83–6.87 (2H, m), 6.95 (1H, s), 7.15–7.26 (4H, m), 7.39–7.46 (3H, m), 7.56 (1H, d), 7.71 (1H, s)

Example 198

2-[3-[3-[N-(2-Ethylbutyl)-N-[3-(N-methyl-N-phenylcarbamoylmethyloxy)phenyl] carbamoylmethyl]ureido]phenyl]acetic acid (1–198)

mp 129–130° C. $^1$H-NMR (DMSO-d$_6$)δ: 0.76 (6H, t), 1.24–1.30 (5H, m), 3.20 (3H, s), 3.46 (2H, s), 3.58 (4H, brs), 4.51 (2H, brs), 6.32 (1H, brs), 6.76–6.78 (3H, m) 6.91 (1H, d), 7.13 (1H, t), 7.23–7.25 (2H, m), 7.34–7.45 (6H, m), 8.82 (1H, s), 12.30 (1H, brs)

Example 199

2-[3-[3-[N-[2-(1-Adamanthyl)ethyl]-N-[3-(N-methyl-N-phenylcarbamoylmethyloxy)phenyl] carbamoylmethyl]ureido]phenyl]acetic acid (1–199)

$^1$H-NMR (CDCl$_3$)δ: 1.26 (2H, t), 1.42 and 1.56–1.68 (12H, m), 1.90 (3H, brs), 3.33 (3H, s), 3.54–3.66 (6H, m), 4.43 (2H, s), 6.51 (1H, s), 6.61 (1H, s), 6.71–6.76 (2H, m), 6.87 (1H, d), 6.95 (1H, s), 7.18–7.26 and 7.40–7.46 (7H, m), 7.57 (1H, brs), 7.72 (1H, brs)

Example 200

2-[3-[3-[N-Cyclohexylmethyl-N-[3-(N-methyl-N-phenylcarbamoylmethyloxy)phenyl] carbamoylmethyl]ureido]phenyl]acetic acid (1–200)

mp 147–149° C. $^1$H-NMR (CDCl3)δ: 0.96, 1.13, 1.43 and 1. 62–1.66 (11H, m), 3.33 (3H, s), 3.52 (2H, s), 3.61 (2H, s), 3.72 (2H, d), 4.43 (2H, s), 6.46 (1H, S), 6.64 (1H, d), 6.74–6.79 (2H, m), 6.88–6.96 (2H, 7.18–7.47 (7H, m), 7.54 (1H, s), 7.61 (1H, d)

Example 201

2-[3-[3-[N-Cyclopropylmethyl-N-[3-(N-methyl-N-phenylcarbamoylmethyloxy)phenyl] carbamoylmethyl]ureido]phenyl]acetic acid (1–201)

mp 108–110° C. $^1$H-NMR (CDCl$_3$)δ: 0.09–0.10 (2H, m), 0.40–0.42 (2H, m), 0.91 (1h, m), 3.33 (3H, 3.51 (2H, d), 3.58 (2H, s), 3.72 (2H, s), 4.43 (2H, s), 6.50 (1H, brs), 6.67 (1H, s), 6.75 (1H, d), 6.82 (1H, d), 6.87 (1H, d), 6.95 (1H, s), 7.16–7.46 (7H, m), 7.57 (1H, d), 7.70 (1H, s)

Example 202

2-[3-[3-[N-[3-(N-Methyl-N-phenylcarbamoylmethyloxy) phenyl]-N-[(1-methylcyclopropyl)methyl]carbamoylmethyl]ureido] phenyl]acetic acid (1–202)

mp 122–124° C. $^1$H-NMR (CDCl$_3$)δ: 0.02 (2H, m), 0.12–0.15 (2H, m), 1.03 (3H, s), 3.32 (3H, s), 3.58 (4H, brs), 3.73 (2H, d), 4.43 (2H, s), 6.50 (1H, brs), 6.65 (1H, s), 6.73 (1H, d), 6.81 (1H, d), 6.87 (1H, d), 6.96 (1H, s), 7.15–7.47 (7H, m), 7.55 (1H, d), 7.71 (1H, s)

Example 203

2-[3-[3-[N-(1-Adamanthylmethyl)-N-[3-(N-methyl-N-phenylcarbamoylmethyloxy)phenyl] carbamoylmethyl]ureido]phenyl]acetic acid (1–203)

mp 140–142° C. $^1$H-NMR (CDCl$_3$)δ: 1.42–1.65 (12H, m), 1.88 (3H, brs), 3.33 (3H, s), 3.47 (2H, s), 3.59 (2H, s), 3.77 (2H, s), 4.43 (2H, s), 6.47 (1H, brs), 6.67–6.71 (2H, m), 6.84–6.89 (2H, m), 6.95 (1H, s), 7.16–7.47 (7H, m), 7.58 (1H, d), 7.64 (1H, s)

Example 204

2-[3-[3-[N-Methyl-N-[3-(N-methyl-N-phenylcarbamoylmethyloxy)phenyl] carbamoylmethyl]ureido]phenyl]acetic acid (1–204)

mp 110–112° C. $^1$H-NMR (CDCl$_3$)δ: 3.32 (3H, s), 3.32 (3H, s) 3.55 (2H, s), 3.72 (2H, d), 4.44 (2H, s), 6.42 (1H, brs), 6.66 (1H, s), 6.71 (1H, d), 6.78 (1H, d), 6.86 (1H, d). 6.98 (1H, s), 7.15 (1H, t), 7.22–7.48 (7H, m), 7.78 (1H, s)

Example 205

2-[3-[3-[N-[3-(N-Methyl-N-phenylcarbamoylmethyloxy) phenyl]-N-(2-methylpropyl)carbamoylmethyl]ureido]phenyl]acetic acid (1–205)

mp 116–117° C. $^1$H-NMR (CDCl$_3$)δ: 0.86 (6H, d), 1.73 (1H, m), 3.32 (3H, s), 3.50 (2H, d), 3.58 (2H, s), 3.72 (2H, d), 4.43 (2H, s), 6.50 (1H, brs), 6.64 (1H, S), 6.73 (1H, d), 6.77 (1H, d), 6.87 (1H, d), 6.95 (1H, s), 7.18 (1H, t), 7.20–7.48 (6H, m) 7.58 (1H, d), 7.66 (1H, s)

Example 206

2-[3-[3-[N-Benzyl-N-[3-(N-methyl-N-phenylcarbamoylmethyloxy)phenyl]carbamoylmethyl]ureido]phenyl]acetic acid (1–206)

mP 112–114° C. $^1$H-NMR (DMSO-d$_6$)δ: 3.18 (3H, s), 3.47 (2H, s), 3.68 (2H. s), 4.42 (2H, s), 4.85 (2H, s), 6.38 (1H, S), 6.65–6.79 and 7.14–7.44 (18H, m), 8.86 (1H, s), 12.28 (1H, S)

Example 207

2-[3-[3-[N-[3-(N-Methyl-N-phenylcarbamoylmethyloxy) phenyl]-N-(2-phenylethyl)carbamoylmethyl]ureido]phenyl]acetic acid (1–207)

mp 123–124° C. $^1$H-NMR (DMSO-d6)δ: 2.76 (2H, t), 3.21 (3H, s), 3.47 (2H, s), 3.57 (2H, s), 3.83 (2H, t), 4.51 (2H, s), 6.32 (1H, s), 6.70–6.87 and 7.12–7.46 (18H, m), 8.85 (1H, s), 12.28 (1H, s)

Example 208

2-[3-[3-[N-(2,2-Diethoxyethyl)-N-[3-(N-methyl-N-phenylcarbamoylmethyloxy)phenyl]carbamoylmethyl]ureido]phenyl]acetic acid (1–208)

mp 107–109° C. $^1$H-NMR (DMSO-d$_6$)δ: 1.11 (6H, t), 3.22 (3H, S), 3.46 (2H, m), 3.54 (2H, S), 3.56 (2H, m), 3.72–3.74 (4H, m), 4.42 (2H, s), 4.68 (1H, t), 6.35 (1H, brs), 6.69 (1H, s), 6.73 (1H, d), 6.84 (2H, t), 7.00 (1H, s), 7.15 (1H, t), 7.20–7.47 (7H, m), 7.79 (1H, s)

Example 209

(±)-2-[3-[3-[N-[3-(N-Methyl-N-phenylcarbamoylmethyloxy)phenyl]-N-(3-methylpentyl) carbamoylmethyl]ureido]phenyl] acetic acid (1–209)

mp 140–142° C. $^1$H-NMR (DMSO-d$_6$)δ: 0.79 (3H, t), 0.82 (3H, d), 1.21–1.40 (5H, m), 3.21 (3H, s), 3.34 (2H, d), 3.46 (2H, s), 3.68 (2H, m), 4.52 (2H, s), 6.30 (1H, brs), 6.76–6.78 (3H, m), 6.90 (1H, d), 7.13 (1H, t), 7.24–7.45 (8H, m), 8.83 (1H, S), 12.28 (1H, brs)

Example 210

(±)-2-[3-[3-[N-[3-(N-Methyl-N-phenylcarbamoylmethyloxy) phenyl]-N-(3-phenylbutyl)carbamoylmethyl]ureido]phenyl]acetic acid (1–210)

mp 128–129° C. $^1$H-NMR (CDCl$_3$)δ: 1.20 (3H, d), 1.78 (2H, m), 2.64 (1H, m), 3.31 (3H, s), 3.49 (2H, m), 3.58 (2H, s), 3.67 (2H, s), 4.42 (2H, s), 6.46 (1H, brs), 6.58 (1H, s), 6.72–6.74 (2H, m), 6.88 (1H, d), 6.94 (1H, s), 7.09 (2H, d), 7.13–7.26 (8H, m), 7.37–7.44 (3H, m), 7.56 (1H, d), 7.64 (1H, s)

Example 211

2-[3-[3-[N-[3-(N-Methyl-N-phenylcarbamoylmethyloxy) phenyl]-N-(4-methyl-3-pentenyl)carbamoylmethyl]ureido]phenyl]acetic acid (1–211)

mp 118–120° C. $^1$H-NMR (CDCl$_3$)δ: 1.53 (3H, s), 1.65 (3H, s), 2.17 (2H, m), 3.32 (3H, s), 3.59 (2H, s), 3.63 (2H, m), 3.69 (2H, s), 4.43 (2H, s), 4.98 (1H, m), 6.49 (1H, brs), 6. 61 (1H, s), 6.75 (2H, d), 6.88 (1H, d), 6.95 (1H, s), 7.19 (1H, t), 7.25–7.26 (3H, m), 7.39–7.48 (3H, m), 7.58 (1H, d), 7.68 (1H, s)

Example 212

2-[3-[3-[N-[3-(N-Methyl-N-phenylcarbamoylmethyloxy) phenyl]-N-(4-methylpentyl)carbamoylmethyl]ureido]phenyl]acetic acid (1–212)

mp 128–129° C. $^1$H-NMR (CDCl$_3$)δ: 0.82 (6H, d), 1.10–1. 14 (2H, m), 1.43–1.46 (3H, m), 3.32 (3H, 3.58 (2H, s), 3.61 (2H, d), 3.70 (2H, s), 4.43 (2H, s), 6.48 (1H, brs), 6. 62 (1H, s), 6.75 (2H, m), 6.87 (1H, d), 6.96 (1H, s), 7.17 (1H, t), 7.26 (3H, m), 7. 39–7.48 (3Hm m), 7.55 (1H, d), 7.68 (1H, s)

Example 213

2-[3-[3-[N-[2-(N-Methyl-N-phenylcarbamoylmethyloxy) phenyl]-N-(2-methylpropyl)carbamoylmethyl]ureido]phenyl]acetic acid (1–213)

$^1$H-NMR (CDCl$_3$)δ: 0.85–0.90 (6H, m), 1.72–1.77 (1H, m), 3.19–3.25 (1H, m), 3.28 (3H, s), 3.57 (2H, s), 3.63 (1H, d), 3.78–3.90 (2H, m), 4.45 (2H, s), 6.48 (1H, s), 6.67 (1H, d), 6.85 (1H, d), 6.95–6.98 (2H, m), 7.14–7.55 (9H, m), 7.66 (1H, s)

Example 214

2-[3-[3-[N-Cyclohexylmethyl-N-[2-(N-methyl-N-phenylcarbamoylmethyloxy)phenyl]carbamoylmethyl]ureido]phenyl]acetic acid (1–214)

$^1$H-NMR (CDCl$_3$)δ: 0.90–0.97, 1.11–1.13 and 1.43–1.71 (1H, m), 3.19 (1H, dd), 3.29 (3H, s), 3.59 (2H, s), 3.61 (1H, d), 3.84–3.90 (2H, m), 4.44 (2H. d). 6.50 (1H, s), 6.68 (1H, d), 6.87 (1H, d), 6.96–6.99 (2H, m), 7.12–7.20 (2H, m), 7.25–7.62 (8H, m)

Example 215

2-[3-[3-[N-Benzyl-N-[2-(N-methyl-N-phenylcarbamoylmethyloxy)phenyl]carbamoylmethyl]ureido]phenyl]acetic acid (1–215)

$^1$H-NMR (CDCl$_3$)δ: 3.30 (3H, S), 3.58 (2H, s), 3.68 (1H, dd), 3.92 (1H, dd), 4.30–4.41 (3H, m), 5.35 (1H, d), 6.51 (1H, brs), 6.65 (1H, d), 6.76–6.79 (2H, m), 6.86 (1H, d), 7.01 (1H, s), 7.14–7.26 and 7.41–7.52 (13H, m), 7.58 (1H, s)

Example 216

2-[3-[3-[N-[2-(N-Methyl-N-phenylcarbamoylmethyloxy) phenyl]-N-(2-phenylethyl)carbamoylmethyl]ureido]phenyl]acetic acid (1–216)

mp 152–154° C. $^1$H-NMR (CDCl$_3$)δ: 2.85–2.89 (2H, m), 3.28 (3H, s), 3.60 (2H, s), 3.64–3.68 (2H, m), 3.86 (1H, dd), 4.12 (1H, m), 4.44 (2H, s), 6.47 (1H, s), 6.67 (1H, d), 6.91–6.99 (4H, m), 7.13–7.26 and 7.39–7.48 (13H, m), 7.58 (1H, s)

Example 217

2-[3-[3-[N-(2,2-Diethoxyethyl)-N-[2-(N-methyl-N-phenylcarbamoylmethyloxy)phenyl]carbamoylmethyl]ureido]phenyl]acetic acid (1–217)

$^1$H-NMR (CDCl$_3$)δ: 1.09–1.13 (6H, m), 3.24–3.27 (1H, m), 3.28 (3H, s), 3.43–3.50 (2H, m), 3.51–3.60 (2H, m), 3.56

(2H, s), 3.66 (1H, d), 3.92 (1H, dd), 4.22 (1H, dd), 4.44 (2H, s), 4.72 (1H, t), 6.38 (1H, brs), 6.64 (1H, d), 6.86 (1H, d), 6.95 (1H, t), 7.01 (1H, S), 7.16 (1H, t), 7.22–7.29 and 7.38–7.49 (8H, m), 7.64 (1H, s)

Example 218

(±)-2-[3-[3-[N-[2-(N-Methyl-N-phenylcarbamoylmethyloxy) phenyl]-N-(3-methylpentyl)carbamoylmethyl]ureido]phenyl]acetic acid (1–218)

mp 140–142° C. $^1$H-NMR (CDCl$_3$)δ: 0.77–0.83 (6H, m), 1.06–1.48 (5H, m), 3.29 (3H, s), 3.29–3.33 (1H, m), 3.60 (2H, s), 3.64 (1H, d), 3.85 (1H, dd), 3.99–4.01 (1H, m), 4.45 (2H, q), 6.49 (1H, brs), 6.67 (1H, d), 6.87 (1H, d), 6.95–6.99 (2H, m), 7.12–7.27 and 7.41–7.49 (8H, m). 7.58–7.61 (2H, m)

Elementary Analysis (for C$_{32}$H$_{38}$N$_4$O$_6$) Calculated: C, 66.88; H, 6.66; N, 9.75 Found: C, 66.68; H, 6.58; N, 9.44

Example 219

(±)-2-[3-[3-[N-[2-(N-Methyl-N-phenylcarbamoylmethyloxy) phenyl]-N-(3-phenylbutyl)carbamoylmethyl]ureido]phenyl]acetic acid (1–219)

$^1$H-NMR (CDCl$_3$)δ: 1.18–1.20 (3H, m), 1.77–1.87 (2H, m), 2.63–2.69 (1H, m), 3.26 (3H, s), 3.30–3.38 (1H, m), 3.57 (2H, s), 3.65–3.88 (3H, m), 4.38 (2H, q), 6.45 (1H, brs), 6.65 (1H, t), 6.86 (1H, d), 6.93–6.97 (2H, m), 7.06–7.26 and 7.37–7.47 (13H, m), 7.53 (1H, d), 7.63 (1H, s)

Example 220

2-[3-[3-[N-[2-(N-Methyl-N-phenylcarbamoylmethyloxy)phenyl]-N-(4-methyl-3-pentenyl) carbamoylmethyl]ureido]phenyl]acetic acid (1–220)

mp 168–169° C. $^1$H-NMR (DMSO-d$_6$)δ: 1.51 (3H, s), 1.62 (3H, s), 2.12 (2H, m), 3.19 (3H, s), 3.25–3.30 (1H, m), 3.33 (2H, s), 3.46–3.47 (1H, m), 3.63–3.76 (2H, m), 4.55 (2H, s), 5.03 (1H, t), 6.28 (1H, brs), 6.76 (1H, d), 6.87 (1H, brs), 7.04 (1H, t), 7.12 (1H, t), 7.22–7.50 (9H, in), 8.80 (1H, s), 12.27 (1H, brs)

Elementary Analysis (for C$_{32}$H36N$_4$O$_6$) Calculated: C, 67.12; H, 6.34; N, 9.78 Found: C, 66.85; H, 6.21; N, 9.61

Example 221

2-[3-[3-[N-[2-(N-Methyl-N-phenylcarbamoylmethyloxy )phenyl]-N-(4-methylpentyl) carbamoylmethyl]ureido]phenyl] acetic acid (1–221)

mp 177–179° C. $^1$H-NMR (CDCl$_3$)δ: 0.81 (6H, d), 1.09–1.15 (2H, m), 1.44–1.51 (3H, n), 3.27–3.34 (1H, m), 3. 29 (3H, s), 3.60 (2H, s), 3.62 (1H, dd), 3.85 (1H, dd), 3.93–3.96 (1H, m), 4.45 (2H, d), 6.49 (1H, brs), 6.68 (1H, d), 6.87 (1H, d), 6.95–6.99 (2H, m), 7.12 (1H, dd), 7.18 (1H, t), 7.25–7.29 and 7.40–7.49 (6H, m), 7.57–7.61 (2H, m)

Elementary Analysis (for C$_{32}$H$_{38}$N$_4$O$_6$) Calculated: C, 66.88; H, 6.66; N, 9.75 Found: C, 66.70; H, 6.52; N, 9.72

Example 222

(±)-2-[3-[3-[N-[2-(N-Methyl-N-phenylcarbamoylmethyloxy)phenyl]-N-(3,4-dimethylpentyl) carbamoylmethyl]ureido]phenyl] acetic acid (1–222)

$^1$H-NMR (CDCl$_3$)δ: 0.71–0.90 (9H, m), 1.25–1.28 and 1.43–1.52 (4H, m), 3.29 (3H, s), 3.30–3.33 (1H, m), 3.58 (2H, s), 3.60 (1H, d), 3.85 (1H, d), 3.98–4.01 (1H, m), 4.45 (2H, s), 6.48 (1H, brs), 6.68 (1H, d), 6.86 (1H, d), 6.95–6.97 (2H, m), 7.11–7.55 (9H, m), 7.64 (1H, s)

Example 223

(±)-2-[3-[3-[N-(3-Cyclohexylbutyl)-N-[2-(N-methyl-N-phenylcarbamoylmethyloxy)phenyl] carbamoylmethyl]ureido]phenyl]acetic acid (1–223)

mp 192–194° C. $^1$H-NMR (CDCl$_3$)δ: 0.78 (3H, d), 0.86–1.26 and 1.52–1.66 (14H, m), 3.29 (3H, s), 3.30–3.34 (1H, m), 3.60 (2H, S), 3.63–3.67 (1H, m), 3.85 (1H, dd), 3.98–4.06 (1H, m), 4.45 (2H, s), 6.50 (1H, brs), 6.68 (1H, d), 6.87 (1H, d), 6.97–6.99 (2H, m), 7.12 (1H, t), 7.18 (1H, t), 7.25–7.29 and 7.38–7.49 (6H, m), 7.60 (2H, brs)

Elementary Analysis (for C$_{36}$H$_{44}$N$_4$O$_6$) Calculated: C, 68.77; H, 7.05; N, 8.91 Found: C, 68.70; H, 6.93; N, 8.80

Example 224

2-[3-[3-[N-(3-ethylpentyl)-N-[2-(N-methyl-N-phenylcarbamoylmethyloxy)phenyl] carbamoylmethyl]ureido]phenyl]acetic acid (1–224)

mp 182–183° C. $^1$H-NMR (CDCl$_3$)δ: 0.74–0.79 (6H, m), 1.14–1.29 (5H, m), 1.41–1.48 (2H, m), 3.29 (3H, s), 3.30–3.33 (1H, m), 3.60 (2H, s), 3.64 (1H, d), 3.85 (1H, dd), 3.96–4.00 (1H, m), 4.45 (2H, d), 6.51 (1H, brs), 6.68 (1H, d), 6.87 (1H, d), 6.96–6.99 (2H, m), 7.13 (1H, d), 7.18 (1H, t), 7.25–7.27 and 0.40–7.49 (6H, m), 7.59–7.62 (2H, m)

Elementary Analysis (for C$_{33}$H$_{40}$N$_4$O$_6$) Calculated: C, 67.33; H, 6.85; N, 9.52 Found: C, 67.36; H, 6.69; N, 9.47

Example 225

(±)-2-[3-[3-[N-[2-(N-Methyl-N-phenylcarbamoylmethyloxy) phenyl]-N-(3-methylhexyl)carbamoylmethyl]ureido]phenyl]acetic acid (1–225)

mp 169–171° C. $^1$H-NMR (CDCl3)δ: 0.81–0.85 (6H, m), 1.01–1.49 (7H, m), 3.29 (3H, s), 3.30–3.33 (1H, m), 3.59 (2H, s), 3.64 (1H, d), 3.85 (1H, dd), 3.98–4.02 (1H, m), 4.45 (2H, s), 6.48 (1H, brs), 6.67 (1H, d), 6.86 (1H, d), 6.95–6.97 (2H, m), 7.11–7.51 (8H, m), 7.57 (1H, d), 7.61 (1H, s)

Elementary Analysis (for C$_{36}$H$_{40}$N$_4$O$_6$) Calculated: C, 67.33; H, 6.85; N, 9.52 Found: C, 67.14; H, 6.83; N, 9.47

Example 226

2-[3-[3-[N-Cyclohexylmethyl-N-[2-[N-methyl-N-(3,5-dimethylphenyl)carbamoylmethyloxy]phenyl] carbamoylmethyl]ureido]phenyl]acetic acid (1–226)

mp 172–173° C. $^1$H-NMR (CDCl$_3$)δ: 0.90–1.13 and 1.47–1.72 (11H, m), 2.35 (6H, s), 3.20 (1H, dd), 3.26 (3H, s), 3.59 (2H, s), 3.63 (1H, dd), 3.84–3.91 (2H, m) 4.47 (2H, q), 6.50 (1H, brs), 6.69 (1H, d), 6.86–6.87 (3H, m) 6.95–6.99 (2H, m), 7.03 (1H, s), 7.12 (1H, d), 7.14 (1H, t), 7.28 (1H, t), 7.60–7.61 (2H, m)

Elementary Analysis (for C$_{35}$H$_{42}$N$_4$O$_6$) Calculated: C, 68.38; H, 6.89; N, 9.11 Found: C, 68.33; H, 6.75; N, 8.92

Example 227

(±)-2-[3-[3-[N-Cyclohexylmethyl-N-[2-[N-methyl-N-(3,5-dimethylphenyl)carbamoylmethyloxy] phenyl]carbamoylmethyl]ureido]phenyl]propionic acid (1–227)

mp 167–168° C. $^1$H-NMR (CDCl$_3$)δ: 0.93, 1.12 and 1.41–1.66 (11H, m), 1.53 (3H, d), 2.35 (6H, s), 3.19 (1H, dd), 3.25 (3H, s), 3.62 (1H, d), 3.73 (1H, q), 3.83–3.89 (2H, m), 4.46 (2H, s), 6.53 (1H, brs), 6.69 (1H, d), 6.86 (2H, s), 6.91–7.29 (7H, m), 7.66 (1H, d), 7.73 (1H, s)

Elementary Analysis (for $C_{36}H_{44}N_4O_6$) Calculated: C, 68.77; H, 7.05; N, 8.91 Found: C, 68.27; H, 7.06; N, 8.88

Example 228

2-[3-[3-[N-(2-Ethylbutyl)-N-[2-(N-methyl-N-phenylcarbamoylmethyloxy)phenyl]carbamoylmethyl]ureido]phenyl]acetic acid (1–228)

mp 140–142° C. $^1$H-NMR (CDCl$_3$)δ: 0.75 (3H, t), 0.81 (3H, t), 1.25–1.29 (5H, m), 3.29 (3H, s), 3.29–3.33 (1H, m), 3.59 (2H, s), 3.63 (1H, d), 3.85–3.95 (2H, m), 4.44 (2H, d), 6.51 (1H, brs), 6.68 (1H, d), 6.87 (1H, d), 6.96–6.99 (2H, m), 7.13 (1H, d), 7.17 (1H, t), 7.25–7.29 and 7.38–7.49 (6H, m), 7.59–7.60 (2H, m)

Elementary Analysis (for $C_{32}H_{38}N_4O_6$) Calculated: C, 66.88; H, 6.66; N, 9.75 Found: C, 66.59; H, 6.61; N, 9.63

Example 229

2-[3-[3-[N-Cyclopropylmethyl-N-[2-(N-methyl-N-phenylcarbamoylmethyloxy)phenyl]carbamoylmethyl]ureido]phenyl]acetic acid (1–229)

mp 184–185° C. $^1$H-NMR (CDCl$_3$)δ: 0.05–0.09 (2H, m), 0.35–0.37 (2H, m), 0.92 (1H, m) 3.18 (1H, dd), 3.28 (3H, s), 3.58 (2H, s), 3.63 (1H, d), 3.86–3.93 (2H, m), 4.44 (2H, q), 6.50 (1H, brs), 6.66 (1H, d), 6.86 (1H, d), 6.95–6.99 (2H, m), 7.16 (1H, t), 7.22–7.29 and 7.39–7.48 (7H, m), 7.56 (1H, d), 7.66 (1H, s)

Example 230

2-[3-[3-[N-Cyclohexylmethyl-N-[2-[N-methyl-N-(3-methylphenyl)carbamoylmethyloxy]phenyl]carbamoylmethyl]ureido]phenyl]acetic acid (1–230)

mp 181–182° C. $^1$H-NMR (CDCl$_3$)δ: 0.90–1.13, 1.41–1.45 and 1.62–1.72 (11H, m), 2.40 (3H, s), 3.19 (1H, dd), 3.27 (3H, s), 3.59 (2H, s), 3.62 (1H, d), 3.84–3.90 (2H, m), 4.46 (2H, q), 6.50 (1H, brs), 6.68 (1H, d), 6.86 (1H, d), 6.97 (1H, t), 7.05–7.29 (8H, m), 7.35 (1H, t), 7.59 (1H, d), 7.64 (1H, s)

Elementary Analysis (for $C_{34}H_{40}N_4O_6$) Calculated: C, 67.98;H, 6.71; N, 9.33 Found: C, 67.86 ; H, 6.70; N, 9.42

Example 231

(±)-2-[3-[3-[N-Cyclohexylmethyl-N-[2-[N-methyl-N-(3-methylphenyl)carbamoylmethyloxy]phenyl]carbamoylmethyl]ureido]phenyl]propionic acid (1–231)

mp 120–122° C. $^1$H-NMR (CDCl$_3$)δ: 0.92–1.12 and 1.45–1.66 (11H, m), 1.52 (3H, d), 2.40 (3H, s) 3.18 (1H, dd), 3.28 (3H, s), 3.61 (2H, d), 3.73 (1H, q), 3.83–3.89 (2H, m), 4.45 (2H, s), 6.55 (1H, brs), 6.68 (1H, d), 6.91–7.37 (11H, m), 7.66 (1H, d), 7.75 (1H, s)

Elementary Analysis (for $C_{35}H_{42}N_4O_6$) Calculated: C, 68.38; H, 6.89; N, 9.11 Found: C, 67.89; H, 6.84 N, 9.16

Example 232

2-[3-[3-[N-[2(N-methyl-N-phenylcarbamoylmethyloxy) phenyl]-N-[(1-methylcyclohexyl)methyl]carbamoylmethyl]ureido] phenyl]acetic acid (1–232)

mp 173–174° C. $^1$H-NMR (CDCl$_3$)δ: 0.87 (3H, s), 1.19–1.41 (10H, m), 3.29 (3H, s), 3.46 (1H, d), 3.58 (2H, s), 3.64 (1H, d), 3.81 (1H, d), 3.90 (1H, dd), 4.46 (2H, q), 6.44 (1H, brs), 6.64 (1H, d), 6.86 (1H, d), 6.93–6.98 (2H, m), 7.15–7.29 and 7.39–7.49 (8H, m), 7.56 (1H, d), 7.62 (1H, s)

Elementary Analysis (for $C_{34}H_{40}N_4O_6$) Calculated: C, 67.98; H, 6.71; N, 9.33 Found: C, 67.51; H, 6.79; N, 9.10

Example 233

2-[3-[3-[N-[2-(N-Methyl-N-phenylcarbamoylmethyloxy) phenyl]-N-(2,2-dimethylpropyl)carbamoylmethyl]ureido]phenyl] acetic acid (1–233)

mp 172–173° C. $^1$H-NMR (DMSO-d$_6$)δ: 0.82 (9H, s), 3.20 (3H, s), 3.33 (2H, s), 3.43 (1H, d), 3.49 (1H, d), 3.67–3.76 (2H, m), 4.56 (2H, s), 6.28 (1H, brs), 6.76 (1H, d), 6.83 (1H, brs), 7.02 (1H, t), 7.12 (1H, t), 7.22–7.51 (9H, m). 8.79 (1H, s), 12.26 (1H, brs)

Elementary Analysis (for $C_{31}H_{36}N_4O_6$) Calculated: C, 66.41; H, 6.47; N, 9.99 Found: C, 65.92; H, 6.51; N, 9.64

Example 234

2-[3-[3-[N-[2-(1-Adamanthyl )ethyl]-N-[2-(N-methyl-N-phenylcarbamoylmethyloxy )phenyl]carbamoylmethyl]ureido]phenyl]acetic acid (1–234)

mp 213–215° C. $^1$H-NMR (CDCl$_3$)δ: 1.21–1.36 (2H, m), 1.41 and 1.53–1.65 (12H, m), 1.86 (3H, brs), 3.26–3.34 (3H, m), 3.30 (3H, s), 3.59 (2H, s), 3.63 (2H, d), 3.83 (1H, dd), 3.99–4.06 (1H, m), 4.45 (2H, q), 6.51 (1H, brs), 6.67 (1H, d), 6.86 (1H, d), 6.95–6.99 (2H, d), 7.12–7.19 (2H, m), 7.25–7.28 and 7.38–7.49 (6H, m), 7.56 (1H, d), 7.70 (1H, s)

Elementary Analysis (for $C_{38}H_{44}N_4O_6$) Calculated: C, 69.92;H 6.79; N, 8.58 Found: 69,56 H, 6.72 N, 8.53

Example 235

2-[3-[3-[N-(1-Adamanthylmethyl)-N-[2-(N-methyl-N-phenylcarbamoylmethyloxy)phenyl]carbamoylmethyl]ureido]phenyl]acetic acid (1–235)

mp 188–189° C. $^1$H-NMR (CDCl$_3$)δ: 1.40–1.64 (12H, m), 1.87 (3H, brs), 3.23 (3H, d), 3.29 (3H, s), 3.58 (2H, s), 3.59 (1H, d), 3.66 (1H, d), 3.91 (1H, dd), 4.46 (2H, q), 6.44 (1H, brs) 6.65 (1H, d), 6.86 (2H, d), 6.94–6.98 (2H, m), 7.14–7.28 and 7.37–7.48 (8H, m), 7.54 (1H, d), 7.64 (1H, s)

Elementary Analysis (for $C_{37}H_{42}N_{43}O_6$) Calculated: C, 69.57; H, 6.63; N, 8.77 Found: C, 69,27; H, 6.67; N, 8.70

Example 236

N-Methyl-N-(3,5-dimethylphenyl)-2-[2-[N-cyclohexyl -methyl-N-[2-[3-[3-(N,N-dimethylamino)phenyl]ureido]acetyl]amino] phenoxy]acetamide (1–236)

mp 205–207° C. $^1$H-NMR (CDCl$_3$)δ: 0.94–0.98, 1.11–1.13, 1.42 and 1.60–1.73 (11H, m), 2.37 (6H, s), 2.91 (3H, s), 2.94 (3H, s), 3.17 (1H, dd), 3.28 (3H, s), 3.81 (1H, dd), 3.84–3.91 (2H, m), 4.47 (2H, s), 6.05 (1H, brs), 6.39 (1H, dd), 6.48 (1H, d), 6.62 (1H, d), 6.87 (2H, s), 6.89–7.27 (7H, m)

Example 237

(±)-2-[3-[3-[N-[2-[N-Methyl-N-(3,5-dimethylphenyl) carbamoylmethyloxy]phenyl]-N-(3-methylpentyl) carbamoylmethyl]ureido]phenyl] acetic acid (1–237)

mp 156–157° C. $^1$H-NMR (CDCl$_3$)δ: 0.78–0.82 (6H, m), 1.07–1.12, 1.30 and 1.52 (5H, m), 2.35 (6H, s), 3.25 (3H, s), 3.29–3.35 (1H, m), 3.58 (2H, s), 3.67 (1H, d), 3.86 (1H, d), 4.02 (1H, m), 4.47 (2H, q), 6.49 (1H, brs), 6.68 (1H, d), 6.85–6.87 (3H, m), 6.95–6.97 (2H, m), 7.03 (1H, s), 7.12–7.29 (3H, m), 7.55 (1H, d), 7.67 (1H, s)

Example 238

(±)-2-[3-[3-[N-[2-[N-(3-chlorophenyl)-N-methylcarbamoylmethyloxy]phenyl]-N-(3-methylpentyl) carbamoylmethyl]ureido]phenyl] acetic acid (1–238)

mp 148–149° C. $^1$H-NMR (CDCl$_3$)δ: 0.77–0.83 (6H, m), 1.06–1.15, 1.25–1.36 and 1.45–1.51 (5H, m) 3.26 (3H, s), 3.30–3.37 (1H, m), 3.58 (2H, s), 3.64 (1H, d), 3.84 (1H, dd), 3.95–4.03 (1H, m), 4.47 (2H, s), 6.51 (1H, s), 6.70 (1H, d), 6.86 (1H, d), 6.96–7.00 (2H, m), 7.12–7. 39 (7H, 7.56 (1H, d), 7.65 (1H, s)

Elementary Analysis (for C32H$_{37}$ClN$_4$O$_6$) Calculated: C, 63.10; H, 6.12; N, 9.20 Found: C, 62.93; H, 6.08; N, 8.86

Example 239

Methyl 2-[3-[3-[N-[2-[N-methyl-N-(3,5-dimethylphenyl) carbamoylmethyloxy]phenyl]-N-(3-methylbutyl) carbamoylmethyl]ureido]phenyl] acetate (1–239)

mp 156–157° C. $^1$H-NMR (CDCl$_3$)δ: 0.82–0.85 (6H, m), 1.30–1.40 (2H, m), 1.50–1.59 (1H, m), 2.38 (6H, s), 3.31 (4H, brs), 3.56 (2H, s), 3.67 (3H, s), 3.89–3.95 (3H, m), 4.52 (2H, s), 6.01 (1H, brs), 6.65 (1H, d) 6.88 (1H, d), 6.91 (2H, s), 6.97 (1H, t), 7.07 (1H, s), 7.14–7.29 (6H, m)

Example 240

Methyl 2-[3-[3-[N-[2-[N-methyl-N-(3,5-dimethylphenyl) carbamoylmethyloxy]phenyl]-N-(3-methyl-2-butyl) carbamoylmethyl]ureido]phenyl] acetate (1–240)

mp 151–152° C. $^1$H-NMR (CDCl$_3$)δ: 1.36 (3H, s), 1.60 (3H, s), 2.38 (6H, s), 3.31 (3H s), 3.56 (2H, S), 3.67 (3H, s), 3.85 (1H, dd), 3.91 (2H, d), 4.52 (2H, s), 4.61 (1H, dd), 5.20 (1H, t), 6.09 (1H, brs), 6.64 (1H, d), 6.87–6.95 (4H, m), 7.07 (1H, s), 7.10 (1H, d), 7.16–7.30 (4H, m), 7.35 (1H, brs)

Example 241

Methyl (±)-2-[3-[3-[N-[2-[N-methyl-N-(3,5-dimethylphenyl)carbamoylmethyloxy]phenyl]-N-(3-methylbutyl) carbamoylmethyl]ureido]phenyl] propionate (1–241)

mp 180–181° C. $^1$H-NMR (CDCl$_3$)δ: 0.81–0.85 (6H, m), 1.35–1.55 (3H, m), 1.45 (3H, d), 2.38 (6H, s) 3.30 (4H, brs), 3.63 (3H, s), 3.64 (1H, q), 3.88–3.94 (3H, m), 4.52 (2H, s), 6.13 (1H, brs), 6.66 (1H, d), 6.88–7.27 (10H, m), 7.50 (1H, s)

Elementary Analysis (for C$_{35}$H$_{44}$N$_4$O$_6$) Calculated: C, 68.16; H, 7.19; N, 9.08 Found: C, 67.83; H, 7.12; N, 9.11

Example 242

Methyl 2-[3-[3-[N-[2-(N-methyl-N-phenylcarbamoylmethyloxy)phenyl]-N-(3-methylbutyl) carbamoylmethyl]ureido]phenyl] acetate (1–242)

mp 121–122° C. $^1$H-NMR (CDCl$_3$)δ: 0.82–0.85 (6H, m), 1.31–1.40 (2H, m), 1.52–1.55 (1H, m), 3.33 (3H, s), 3.33–3.39 (1H, m), 3.56 (2H, s), 3.66 (3H, s), 3.84–3.96 (3H, m), 4.48 (2H, s), 6.09 (1H, brs), 6.66 (1H, d), 6.88 (1H, d), 6.98 (1H, t), 7.15–7.52 (11H, m)

Elementary Analysis (for C$_{32}$H$_{38}$N$_4$O$_6$ Calculated: C, 66.88; H, 6.66 N, 9.75 Found: C, 66. 64; H, 6.57; N, 9.60

Example 243

Methyl 2-[3-[3-[N-[2-[N-methyl-N-(2-methylphenyl) carbamoylmethyloxy]phenyl]-N-(3-methylbutyl) carbamoylmethyl]ureido]phenyl]acetate (1–243)

$^1$H-NMR (CDCl$_3$)δ: 0.81–0.86 (6H, m), 1.31–1.41 (2H, m), 1.50–1.51 (1H, m), 2.32 (3/2H, s), 2.37 (3/2H, s), 3.26 (3H, s), 3.35 (1H, m), 3.55 (2H, s), 3.66 (3H, s), 3.84–3.92 (3H, m), 4.24 (1H, t), 4.48 (1H, dd), 6.11 (1H, brs), 6.66 (1H, d), 6.88 (1H, d), 6.93–6.99 (2H, m), 7.14–7.37 (9H, m)

Example 244

Methyl 2-[3-[3-[N-[2-[N-methyl-N-(3-methylphenyl) carbamoylmethyloxy]phenyl]-N-(3-methylbutyl) carbamoylmethyl]ureido]phenyl] acetate (1–244)

mp 159–160° C. $^1$H-NMR (CDCl$_3$)δ: 0.82–0.86 (6H, m), 1.30–1.43 (2H, m), 1.51–1.57 (1H, m), 2.43 (3H, S). 3.32 (3H, s), 3.32–3.33 (1H, m), 3.56 (2H, S), 3.66 (3H, s), 3.89 (2H, brs), 3.92–3.94 (1H, m), 4.50 (2H, s), 5.98 (1H, brs), 6.65 (1H, d), 6.88 (1H, d), 6.97 (1H, t), 7.09–7.29 (9H, m), 7.38 (1H, t)

Elementary Analysis (for C$_{33}$H$_{40}$N$_4$O$_6$) Calculated: C, 67.33; H, 6.85; N, 9.52 Found: C, 67.19; H, 6.77; N, 9.35

Example 245

Methyl 2-[3-[3-[N-[2-[N-methyl-N-(2,6-dimethylphenyl) carbamoylmethyloxy]phenyl]-N-(3-methylbutyl) carbamoylmethyl]ureido]phenyl] acetate (1–245)

$^1$H-NMR (CDCl$_3$)δ: 0.81–0.85 (6H, m), 1.31–1.41 (2H, m), 1.50–1.56 (1H, R), 2.30 (3H, s), 2.34 (3H, s), 3.22 (3H, s), 3.33–3.38 (1H, m), 3.55 (2H, s), 3.66 (3H, s), 3.84–3.99 (3H, m), 4.28 (2H, q), 6.09 (1H, brs), 6.68 (1H, d), 6.88 (1H, d), 6.97 (1H, t), 7.11–7.30 (8H, m), 7.39 (1H, s)

Example 246

Methyl 2-[3-[3-[N-[2-[N-(3-chlorophenyl)-N-methylcarbamoylmethyloxy]phenyl]-N-(3-methylbutyl) carbamoylmethyl]ureido]phenyl]acetate (1–246)

mp 144–145° C. $^1$H-NMR (CDCl$_3$)δ: 0.81–0.84 (6H, m), 1.33–1.41 (2H, m), 1.50–1.55 (1H, m), 3.29 (3H, s), 3.33–3.37 (1H, m), 3.54 (2H, s), 3.66 (3H, s), 3.82 (1H, d), 3.87 (1H, d), 3.98 (1H, m), 4.50 (2H, s), 6.15 (1H, brs), 6.68 (1H, d), 6.87 (1H, d), 7.00 (1H, t), 7.13–7.42 (9H, m), 7.53 (1H, s)

Elementary Analysis (for C$_{32}$H$_{37}$ClN$_4$O$_6$) Calculated: C, 63.10; H, 6.12; N, 9.20 Found: C, 62.88; H, 6.13 N, 8.98

Example 247

Methyl (±)-2-[3-[3-[N-[2-[N-(3-chlorophenyl)-N-methylcarbamoylmethyloxy]phenyl]-N-(3-methylbutyl) carbamoylmethyl]ureido]phenyl] propionate (1–247)

mp 149–150° C. $^1$H-NMR (CDCl$_3$)δ: 0.82–0.85 (6H, m), 1.35–1.41 (2H, m), 1.45 (3H, d), 1.49–1.57 (1H, m), 3.32

(3H, s), 3.33–3.35 (1H, m), 3.63 (3H, s), 3.65 (1H, q), 3.85 (2H, d), 3.93–3.97 (1H, m), 4.51 (2H, S), 6.00 (1H, brs), 6.68 (1H, brs), 6.90 (1H, d), 6.98 (1H, m), 7.15–7.43 (10H, m)

Elementary Analysis (for $C_{33}H_{39}ClN_4O_6$) Calculated: C, 63.61; H, 6.31; N, 8.99 Found: C, 62.56; H, 6.24; N, 9.06

Example 248

Methyl 2-[3-[3-[N-[2-[N-(3-bromophenyl)-N-methylcarbamoylmethyloxy]phenyl]-N-(3-methylbutyl) carbamoylmethyl]ureido]phenyl] acetate (1–248)

mp 150–152° C. $^1$H-NMR (CDCl$_3$)δ: 0.82–0.84 (6H, m), 1.33–1.43 (2H, m), 1.50–1.57 (1H, m), 3.29 (3H, s), 3.33–3.41 (1H, m), 3.54 (2H, s), 3.66 (3H, s), 3.80 (1H, dd), 3.88 (1H, dd), 3.94–4.01 (1H, m), 4.49 (2H, s), 6.14 (1H, brs), 6.68 (1H, d), 6.87 (1H, d), 6.99 (1H, t), 7.13–7.29 and 7.35–7.58 (10H, m)

Example 249

Methyl (±)-2-[3-[3-[N-[2-[N-(3-bromophenyl)-N-methylcarbamoylmethyloxy]phenyl]-N-(3-methylbutyl) carbamoylmethyl]ureido]phenyl] propionate (1–249)

mp 155–157° C. $^1$H-NMR (CDCl$_3$)δ: 0.82–0.85 (6H, m), 1. 34–1.41 (2H, m), 1. 45 (3H, d), 1.50–1.57 (1H, m), 3.31 (3H, s), 3.31–3.35 (1H, m), 3.63 (3H, s), 3.65 (1H, q), 3.81–3.86 (2H, m), 3.95–3.98 (1H, m), 4.51 (2H, s), 6.05 (1H, brs), 6.68 (1H, brs), 6.90 (1H, d), 6.98 (1H, m), 7.15–7. 40 (8H, m), 7.51 (1H, d), 7.57 (1H, brs)

Example 250

Methyl 2-[3-[3-[N-[2-[N-(3-trifluoromethylphenyl)-N-methylcarbamoylmethyloxy]phenyl]-N-(3-methylbutyl) carbamoylmethyl]ureido]phenyl] acetate (1–250)

$^1$H-NMR (CDCl$_3$)δ: 080–0.83 (6H, m), 1.37–1.41 (2H, m), 1.51–1.56 (1H, m), 3.30 (3H, s), 3.35–3.38 (1H, m), 3.52 (2H, s), 3.64 (3H, s), 3.76–3.90 (2H, m), 3.95–4.03 (1H, m), 4.47 (2H, S), 6.27 (1H, brs), 6.69 (1H, brs), 6.85 (1H, d), 6.99 (1H, t), 7.10–7.19 and 7.26–7.31 (5H, m), 7.51 (1H, d), 7.58 (1H, s), 7.63–7.67 (2H, m), 7.77 (1H, s)

Example 251

Methyl (±)-2-[3-[3-[N-[2-[N-(3-trifluoromethylphenyl)-N-methylcarbamoylmethyloxy]phenyl]-N-(3-methylbutyl) carbamoylmethyl]ureido]phenyl] propionate (1–251)

$^1$H-NMR (CDCl$_3$)δ: 0.80–0.83 (6H, m), 1.33–1.47 (2H, m), 1.43 (3H, d), 1.49–1.56 (1H, m), 3.33 (3H, s), 3.33–3.36 (1H, m), 3.61 (3H, s), 3.62 (1H, q), 3.80–3.88 (2H, m) 3.95–4.02 (1H, m), 4. 49 (2H, s), 6.18 (1H, brs), 6.69 (1H, brs), 6.88 (1H, d), 7.00 (1H, m), 7.12–7.28 and 7.51–7.69 (10H, m)

Example 252

Methyl 2-[3-[3-[N-[2-[N-methyl-N-[3-(N,N-dimethylamino) phenyl]carbamoylmethyloxy] phenyl]-N-(3-methylbutyl) carbamoylmethyl]ureido] phenyl]acetate (1–252)

mp 95–97° C. $^1$H-NMR (CDCl$_3$)δ: 0.82–0.85 (6H, m), 1.30–1.39 (2H, m), 1.50–1.55 (1H, m), 3.01 (6H, s), 3.34 (3H, s), 3.34–3.38 (1H, m), 3.56 (2H, s), 3.66 (3H, s), 3.89–4.01 (3H, m), 4.58 (2H, s), 6.08 (1H, brs), 6.54 (1H, s), 6.60 (1H, d), 6.67 (1H, d), 6.74 (1H, dd), 6.88 (1H, d), 6.97 (1H, t), 7.14–7.34 (6H, m), 7.41 (1H. s)

Example 253

Methyl 2-[3-[3-[N-[2-[N-methyl-N-(3-nitrophenyl) carbamoylmethyloxy]phenyl]-N-3-methylbutyl) carbamoylmethyl]ureido]phenyl]acetate (1–253)

$^1$H-NMR (CDCl$_3$)δ: 0.81–0.84 (6H, m), 1.33–1.41 (2H, m), 1.51–1.55 (1H, m), 3.30–3.33 (1H, m), 3. 34 (3H, s), 3.53 (2H, s), 3.65 (3H, s), 3.78–3.82 (2H, m), 3.93–3.98 (1H, m), 4. 54 (2H, brs), 6.15 (1H, brs), 6.76 (1H, brs), 6.87 (1H, d), 7.01 (1H, t), 7.12–7.18 and 7.26–7.31 (5H, m), 7.57 (1H, d), 7.65 (2H, brs), 8.19 (1H, s), 8.23 (1H, brs)

Example 254

Methyl 2-[3-[3-[N-[2-[N-( 3-aminophenyl)-N-methylcarbamoylmethyloxy]phenyl]-N-(3-methylbutyl) carbamoylmethyl]ureido]phenyl] acetate (1–254)

$^1$H-NMR (CDCl$_3$)δ: 0.81–0.85 (6H, m), 1.33–1.39 (2H, m), 1.49–1.56 (1H, m), 3.28 (3H, s), 3.35 (1H, m), 3.55 (2H, S), 3.66 (3H, s), 3.83–3.96 (3H, m), 4.55 (2H, d), 6.13 (1H, brs), 6.61 (1H, s), 6.63 (1H, d), 6.71–6.76 (2H, m), 6.88 (1H, d), 6.98 (1H, t), 7.13–7.31 (6H, m), 7.52 (1H, brs)

Example 255

Methyl (±)-2-[3-[3-[N-cyclohexylmethyl-N-[2-[N-methyl-N-(3,5-dimethylphenyl) carbamoylmethyloxy]phenyl]carbamoylmethyl] ureido]phenyl]propionate (1–255)

mp 203–205° C. $^1$H-NMR (CDCl$_3$)δ: 0.91–0.97, 1.10–1.12, 1.40–1.48 and 1.60–1.79 (11H, m), 1.45 (3H, d), 2.37 (6H, s), 3.17 (1H, dd), 3.30 (3H, s), 3.63 (3H, s), 3.64 (1H, q), 3.82–3.94 (3H, m), 4.51 (2H, s), 6.10 (1H, brs), 6.67 (1H, d), 6.88–6.91 (3H, m), 6.96 (1H, m), 7.06 (1H, s), 7.15–7.26 (5H, m), 7.44 (1H, s)

Example 256

Methyl 2-[3-[3-[N-(2-ethylbutyl)-N-[2-(N-methyl-N-phenylcarbamoylmethyloxy)phenyl] carbamoylmethyl]ureido]phenyl]acetate (1–256)

mp 103–105° C. $^1$H-NMR (CDCl$_3$)δ: 0.73 (3H, t), 0.80 (3H, t), 1.25–1.36 (5H, m), 3.29–3.32 (1H, m), 3.32 (3H, s), 3.55 (2H, s), 3.66 (3H, s), 3.80 (1H, d), 3.83–3.94 (2H, m), 4.48 (2H, s), 6.14 (1H, brs), 6.66 (1H, d), 6.87 (1H, d), 6.98 (1H, t), 7.13–7.31 and 7.41–7.52 (11H, m)

Elementary Analysis (for $C_{33}H_4N_{40}O_6$) Calculated: C, 67.33; H. 6.85; N, 9.52 Found: C, 67.28; H, 6.82; N, 9.51

Example 257

Methyl 2-[3-[3-[N-cyclopropylmethyl-N-[2-(N-methyl-N-phenylcarbamoylmethyloxy)phenyl] carbamoylmethyl]ureido]phenyl]acetate (1–257)

$^1$H-NMR (CDCl$_3$)δ: 0.01–0.07 (2H, m), 0.32–0.36 (2H, m), 0.90–0.93 (1H, m), 3.18 (1H, dd), 3.33 (3H, s), 3.56 (2H, s), 3.66 (3H, s), 3.81–3.96 (3H, m), 4.47 (2H, s), 6.12 (1H, brs), 6.65 (1H, d), 6.88 (1H, d), 6.98 (1H, t), 7.15–7.31 and 7.44–7.52 (11H, m)

Example 258

Methyl 2-[3-[3-[N-cyclohexylmethyl-N-[2-[N-methyl-N-(3-methylphenyl)carbamoylmethyloxy]phenyl]carbamoylmethyl]ureido]phenyl]acetate (1–258)

mp 174–175° C. $^1$H-NMR (CDCl$_3$)δ: 0.91–0.97, 1.10–1.19, 1.38–1.44 and 1.59–1.76 (11H, m), 2.42 (3H, s), 3.18 (1H, dd), 3.31 (3H, s), 3.55 (2H, s), 3.66 (3H, s), 3.79–3.93 (3H, m), 4.49 (2H, S), 6.10 (1H, brs), 6.67 (1H, d), 6.87 (1H, d), 6.98 (1H, t), 7.08–7.30 (8H, m), 7.38 (1H, t), 7.43 (1H, s)

Example 259

Methyl (±)-2-[3-[3-[N-cyclohexylmethyl-N-[2-[N-methyl-N-(3-methylphenyl)carbamoylmethyloxy)phenyl]carbamoyl methyl]ureido]phenyl]propionate (1–259)

mp 148–149° C. $^1$H-NMR (CDCl$_3$)δ: 0.91–0.97, 1.01–1.21, 1.38–1.46 and 1.62–1.71 (11H, m), 1.45 (3H, d), 2.42 (3H, s), 3.16 (1H, dd), 3.32 (3H, s), 3.63 (3H, s), 3.65 (1H, q), 3.81–3.94 (3H, m), 4.50 (2H, s), 6.06 (1H, brs), 6.66 (1H, d), 6.89 (1H, d), 6.97 (1H, t), 7.09–7.40 (10H, m)

Example 260

Methyl 2-[3-[3-[N-[2-(N-methyl-N-phenylcarbamoylmethyloxy)phenyl]-N-[(1-methylcyclohexyl) methyl]carbamoylmethyl]ureido]phenyl]acetate (1–260)

$^1$H-NMR (CDCl$_3$)δ: 0.86 (3H, s), 1.21–1.39 (10H, m), 3.32 (3H, s), 3.53 (1H, d), 3.55 (2H, s), 3. 66 (3H, s), 3.75 (1H, d), 3. 88 (2H, s), 4.50 (2H, s), 5.99 (1H, brs), 6.63 (1H, d), 6.88 (1H, d), 6.97 (1H, t), 7.15–7.53 (11H, m)

Example 261

Methyl 2-[3-[3-[N-[2-(N-methyl-N-phenylcarbamoylmethyloxy)phenyl]-N-(2,2-dimethylpropyl) carbamoylmethyl]ureido]phenyl]acetate (1–261)

mp 132–133° C. $^1$H-NMR (CDCl$_3$)δ: 0.85 (9H, s), 3.32 (3H, s), 3.53–3.55 (1H, m), 3.55 (2H, S), 3.66 (3H, s), 3.67 (1H, m), 3.90 (2H, S), 4.50 (2H, S), 5.98 (1H, brs), 6.62 (1H, d), 6.88 (1H, d), 6.97 (1H, t), 7.17–7.28 and 7.31–7.51 (11H, m)

Example 262

Methyl 2-[3-[3-[N-[2-(1-adamanthyl)ethyl]-N-[2-(N-methyl-N-phenylcarbamoylmethyloxy)phenyl] carbamoylmethyl]ureido]phenyl]acetate (1–262)

mp 135–136° C. $^1$H-NMR (CDCl$_3$) 1.19–1.32 (2H, m), 1.41 and 1.52–1.65 (12H, m), 1.86 (3H, brs), 3.28–3.33 (1H, m), 3.33 (3H, s), 3.55 (2H, s), 3.66 (3H, s), 3.84–3.97 (3H, s), 4.48 (2H, s), 6.13 (1H, brs), 6.66 (1H, d), 6.87 (1H, d), 6.97 (1H, t), 7.15–7.31 and 7.41–7.50 (11H, m)

Example 263

Methyl 2-[3-[3-[N-(1-adamanthylmethyl)-N-[2-(N-methyl-N-phenylcarbamoylmethyloxy)phenyl] carbamoylmethyl]ureido]phenyl]acetate (1–263)

mp 166–168° C. $^1$H-NMR (CDCl$_3$)δ: 1.41–1.63 (12H, m), 1.88 (3H, brs), 3.29 (1H, d), 3.32 (3H, s), 3.54 (2H, s), 3. 61 (1H. d), 3.65 (3H, s), 3.81 (1H, d), 3.92 (1H, dd), 4.50 (2H. s), 6.09 (1H, brs), 6.64 (1H, d), 6.88 (1H, d), 6.97 (1H, t), 7.13–7.31 and 7.41–7.50 (11H, m)

Example 264

Methyl (±)-2-[3-[3-[N-[2-[N-methyl-N-(3,5-dimethylphenyl)carbamoylmethyloxy]phenyl]-N-(3-methylpentyl) carbamoylmethyl]ureido]phenyl] acetate (1–264)

mp 149–151° C. $^1$H-NMR (CDCl$_3$)δ: 0.77–0.82 (6H, m), 1.06–1.11, 1.26–1.31 and 1.56–1.60 (5H, m), 2.37 (6H, s), 3.29 (3H, s), 3.30–3.33 (1H, m), 3.55 (2H, s), 3.66 (3H, s), 3.88–4.01 (3H, m), 4.51 (2H, s), 6.13 (1H, brs), 6.66 (1H, d), 6.87 (1H, d), 6.90 (2H, s), 6.97 (1 H, t), 7.06 (1H, s), 7.16–7.30 (5H, m), 7.51 (1H, s)

Example 265

Methyl (±)-2-[3-[3-[N-[2-[N-(3-chlorophenyl)-N-methylcarbamoylmethyloxy]phenyl]-N-(3-methylpentyl) carbamoylmethyl]ureido]phenyl] acetate (1–265)

mp 97–98° C. $^1$H-NMR (CDCl$_3$)δ: 0.78–0.83 (6H, m), 1.05–1.12, 1.25–1.31 and 1.48–1.51 (5H, m), 3.31 (3H, s), 3.31–3.33 (1H, m), 3.56 (2H, s), 3.67 (3H, s), 3.84 (2H, s), 3.95–3.97 (1H, m), 4.50 (2H, s), 5.99 (1H, brs), 6.67 (1H, d), 6.89 (1H, d), 6.99 (1H, t), 7.15–7.34 (8H, m), 7.43 (2H, brs)

Example 266 tert-Butyl 2-[3-[3-[N-[3-[N-(3,5-difluorophenyl)-N-methylcarbamoylmethyloxy]phenyl]-N-(3-methylbutyl) carbamoylmethyl]ureido]phenyl] acetate (1–266)

mp 176–177° C. $^1$H-NMR (CDCl$_3$)δ: 0.85 (6H, d), 1.38 (2H, m), 1.42 (9H, s), 1.53 (1H, m), 3.32 (3H, s), 3.45 (2H, s), 3.63–3.73 (4H, m), 4.57 (2H, s), 5.93 (1H, s), 6.69 (7H, m), 7.07 (1H, s), 7.17–7.21 (3H, m), 7.31 (1H, m)

Example 267 tert-Butyl (±)-2-[3-[3-[N-[3-[N-(3,5-difluorophenyl)-N-methylcarbamoylmethyloxy]phenyl]-N-( 3-methylbutyl)carbamoylmethyl]ureido] phenyl]propionate (1-267)

mp 182–184° C. $^1$H-NMR (CDCl$_3$)δ: 0.86 (6H, m), 1.24 (3H, m), 1.38 (9H, s), 1.40 (2H, m), 1.54 (1H, m), 3.32 (3H, s), 3.56 (1H, m), 3.63–3.83 (3H, m), 4.57 (1H, m), 4.75 (2H, s), 5.82 (1H, s), 6.68–6.97 (8H, m), 7.19–7.35 (4H, m)

Example 268

2-[3-[3-[N-[3-[N-(3,5-Difluorophenyl)-N-methylcarbamoylmethyloxy]phenyl]-N-(3-methylbutyl)carbamoylmethyl]ureido]phenyl]acetic acid (1–268)

mp 165–166° C. $^1$H-NMR (DMSO-d$_6$)δ: 0.84 (6H, d), 1.28 (2H, m), 1.53 (1H, m), 3.33 (2H, s), 3.46 (3H, s), 3.55–3.67 (4H, m), 4.77 (2H, brs), 6.30 (1H, m), 6.75–6.93 (4H, m), 7.13 (1H, m), 7.23–7.39 (6H, m), 8.83 (1H, s), 12.26 (1H, brs)

Example 269

(±)-2-[3-[3-[N-[3-[N-(3,5-Difluorophenyl)-N-methylcarbamoylmethyloxy]phenyl]-N-(3-methylbutyl) carbamoylmethyl]ureido]phenyl] propionic acid (1–269)

mp 172–174° C. $^1$H-NMR (DMSO-d$_6$)δ:

0.84 (6H, d), 1.27 (2H, m), 1.30 (3H, d), 1.54 (1H,m), 3.33 (3H, s), 3.52–3.67 (5H, m), 4.77 (2H, brs), 6.28 (1H, m), 6.78–6.93 (4H, m), 7.14 (1H, m), 7.22–7.39 (6H, m), 8.86 (1H, s), 12.21 (1H, brs)

Example 270 tert-Butyl 2-[3-[3-[N-[2-[N-(3,5-difluorophenyl)-N-methylcarbamoylmethyloxy]phenyl]-N-(3-methylbutyl) carbamoylmethyl]ureido]phenyl] acetate (1–270)

mp 51–55° C. $^1$H-NMR (CDCl$_3$)δ: 0.83 (3H, d), 0.85 (3H, d), 1.38 (2H, m), 1.42 (9H, s), 1.55 (1H, m), 3.30 (3H, s), 3.36 (1H, m), 3.45 (2H, s), 3.81 (2H, m), 3.95 (1H, m), 4.57 (2H, brs), 5.97 (1H, s), 6.89 (1H, m), 6.88–6.90 (4H, m), 7.00 (1H, dd), 7.15–7.29 (6H, m)

Example 271 tert-Butyl (±)-2-[3-[3-[N-[2-[N-(3,5-difluorophenyl)-N-methylcarbamoylmethyloxy]phenyl]-N-(3-methylbutyl)carbamoylmethyl]ureido]phenyl]propionate (1–271)

mp 57–60° C. $^1$H-NMR (CDCl$_3$)δ: 0.83 (3H, d), 0.85 (3H, d), 1.36 (2H, m), 1.38 (9H, s), 1.39 (3H, d), 1.54 (1H, m), 3.31 (3H, d), 3.34 (1H, m), 3.53 (3H, q), 3.82 (2H, m), 3.97 (2H, m), 4.58 (2H, brs), 5.94 (3H, s), 6.69 (1H, m), 6.88–6.92 (4H, m), 6.99 (1H, m), 7.14–7.29 (6H, m)

Example 272

2-[3-[3-[N-[2-[N-(3,5-Difluorophenyl)-N-methylcarbamoylmethyloxy]phenyl]-N-(3-methylbutyl) carbamoylmethyl]ureido]phenyl]acetic acid (1–272)

mp 135–137° C. $^1$H-NMR (DMSO-d$_6$)δ: 0.83 (3H, d), 0.84 (3H, d), 1.30 (2H, d), 1.55 (1H, m), 3.32 (3H, s), 3.33 (4H, m), 3.45 (2H, s), 3.46 (1H, q), 3.66 (1H, m), 3.88 (1H, m), 4.81 (2H, brs), 6.26 (1H, m), 6.76 (1H, d), 7.02–706 (2H, m), 7.12 (1H, m), 7.22–7.38 (7H, m), 8.80 (1H, s), 12.27 (1H, brs)

Example 273

(±)-2-[3-[3-[N-[2-[N-(3,5-Difluorophenyl)-N-methylcarbamoylmethyloxy]phenyl]-N-(3-methylbutyl) carbamoylmethyl]ureido]phenyl] propionic acid (1–273)

mp 168–170° C. $^1$H-NMR (DMSO-d$_6$)δ: 0.83 (3H, d), 0.85 (3H, d), 1.30 (3H, d), 1.22–1.38 (2H, m), 1.55 (1H, m), 3.32 (4H, m), 3.46 (1H, m), 3.55 (1H, q), 3.65 (1H, m), 3.86 (1H, m), 4.82 (2H, brs), 6.25 (1H, m), 6.79 (1H, d), 7.04 (2H, m), 7.13 (1H, t), 7.20–7.39 (7H, m), 8.83 (1H, s), 12.22 (1H, brs)

Example 274

Potassium [3-[3-[N-[2-[N-(3,5-difluorophenyl)-N-methylcarbamoylmethyloxy]phenyl]-N-(3-methylbutyl) carbamoylmethyl]ureido]phenyl] methanesulfonate (1–274)

mp 165–170° C. $^1$-NMR (DMSO-d$_6$)δ: 0.83 (3H, d), 0.85 (3H, d), 1.30 (2H, m), 1.55 (1H, n), 3.33 (4H, m), 3.46 (1H. m), 3.63 (2H, s), 3.66 (1H, m), 3.88 (1H, m),4.82 (2H, brs), 6.25 (1H, m), 6.81 (1H, d), 7.02–7.08 (3H, m), 7.13 (1H, s), 7.26–7.39 (6H, m), 8.76 (1H, s)

Example 275

Potassium (±)-1-[3-[3-[N-[2-[N-(3,5-difluorophenyl)-N-methylcarbamoylmethyloxy] phenyl]-N-(3-methylbutyl) carbamoylmethyl]ureido] phenyl]ethanesulfonate (1–275)

mp 156–160° C. $^1$H-NMR (DMSO-d$_6$)δ: 0.83 (3H, d), 0.84 (3H, d), 1.30 (2H, m), 1.40 (3H, d), 1.55 (1H, m), 3.32 (4H, m), 3.45 (1H, m), 3.55 (1H, q), 3.66 (1H, m), 3.88 (1H, m), 4.82 (2H, brs), 6.21 (1H, m), 6.83 (1H, d), 7.00–7.06 (3H, m), 7.13 (1H, s), 7.27–7.38 (6H, m), 8.75 (1H, s)

Example 276 tert-Butyl 2-[3-[3-[N-[2-[N-(2,5-difluorophenyl)-N-methylcarbamoylmethyloxy]phenyl]-N-(3-methylbutyl) carbamoylmethyl]ureido]phenyl] acetate (1–276)

$^1$H-NMR (CDCl$_3$)δ: 0.82 (3H, d), 0.84 (3H, d), 1.40 (2H, m), 1.42 (9H, s), 1.53 (1H, m), 3.27 (3H, s), 3.37 (1H, m), 3.44 (2H, s), 3.60–3.90 (2H, m), 3.97 (1H, m), 4.51 (2H, brs), 6.08 (1H, s), 6.72 (1H, d), 6.88 (1H, d), 6.99 (1H, t), 7.10–7.29 (8H, m), 7.36 (1H, brs)

Example 277

2-[3-[3-[N-[2-[N-(2,5-Difluorophenyl)-N-methylcarbamoylmethyloxy]phenyl]-N-(3-methylbutyl) carbamoylmethyl]ureido]phenyl]acetic acid (1–277)

mp 81–85° C. $^1$H-NMR (DMSO-d$_6$)δ: 0.83 (3H, d), 0.84 (3H, d), 1.30 (2H, m), 1.55 (1H, m), 3.33 (1H, m), 3.34 (3H, s), 3.41 (1H, m), 3.46 (2H, s), 3.66 (1H, dd), 3.87 (1H, m), 4.54 (1H, brs), 4.73 (1H, brs), 6.27 (1H, m), 6.76 (1H, d), 6.90 (1H, m), 7.05 (1H, t), 7.12 (1H, m), 7.21–7.69 (7H, m), 8.80(1H, s), 12.27 (1H, brs)

Example 278 tert-Butyl (±)-2-[3-[3-[N-[3-[N-(3,5-difluorophenyl)-N-methylcarbamoylmethyloxy] phenyl]-N-(N-methyl-N-phenylcarbamoylmethyl) carbamoylmethyl]ureido]phenyl]propionate (1–278)

mp 82–88° C. $^1$H-NMR (CDCl$_3$)δ: 1.37 (9H, s), 1.38 (3H, d), 3.24 (3H, s), 3.31 (3H, s), 3.53 (1H, q), 3.86 (2H, d), 4.08 (2H, s), 4.55 (2H, S), 5.87 (1H, s), 6.83–7.07 (7H, m), 7.13–7.41 (10H, m)

Example 279

(±)-2-[3-[3-[N-[3-[N-(3,5-Difluorophenyl)-Nmethylcarbamoylmethyloxy]phenyl]-N-(N-methyl-N-phenylcarbamoylmethyl)carbamoylmethyl]ureido]phenyl]propionic acid (1–279)

mp 102–110° C. $^1$H-NMR (DMSO-d$_6$)δ: 1.30 (3H, d), 3.19 (3H, S), 3.24 (3H,. s), 3.55 (1H, q), 3.62 (2H, s), 4.04 (2H, s), 4.72 (2H, s), 6.27 (1H, s), 6.79–7.03 (4H, m), 7.11–7.47 (12H, m), 8.31 (1H, s), 8.83 (1H, s)

Example 280

2-[3-[3-[N-[3-[N-Methyl-N-(3,5-dimethylphenyl) carbamoylmethyloxy]phenyl]-N-(3-methyl-2-butenyl) carbamoylmethyl]ureido]phenyl]acetic acid (1–280)

mp 115–117° C. $^1$H-NMR (DMSO-d$_6$)δ: 1.44 (3H, s), 1.64 (3H, s), 2.34 (6H, S), 3.28 (3H, s), 3.59 (2H, s), 3.71

(2H, d), 4.23 (2H, d), 4.41 (2H, s), 5.17 (1H, t), 6.48 (1H, brs), 6.66–7.60 (12H, m) MS (m/z): 587 (M+1)$^+$ Elementary Analysis (for $C_{33}H_{38}N_4O_6$) Calculated: C, 67.56; H, 6.53; N, 9.55 Found: C, 67.52; H, 6.48; N, 9.21

Example 281

(±)-2-[3-[3-[N-[3-[N-Methyl-N-(2-methylphenyl) carbamoylmethyloxy]phenyl]-N-(2-phenylpropyl) carbamoylmethyl]ureido]phenyl]acetic acid (1–281)

mp 154–156° C. $^1$H-NMR (DMSO-d$_6$)δ: 1.22 (3H, d), 2.28 (3H, s), 3.56–3.72 (5H, m), 3.98–4.03 (1H, m), 4.14–4.35 (2H, m), 6.38–7.59 (19H, m) MS (m/z): 623 (M+1)$^+$

Example 282

2-[3-[3-[N-(2-Cyclopentylethyl)-N-[3-(N-methyl-N-phenylcarbamoylmethyloxy]phenyl] carbamoylmethyl]ureido]phenyllacetic acid (1–282)

$^1$H-NMR (DMSO-d$_6$)δ: 0.84–1.70 (11H, m), 3.19–3.82 (9H, m), 4.55 (2H, s), 6.30 (1H, brs), 6.75–7.50 (13H, m), 8.80(1H, s) MS (m/z): 587 (Ni+)$^+$ Example 283

2-[3-[3-[N-(2-Cyclohexylethyl)-N-[3-(N-methyl-N-phenylcarbamoylmethyloxy)phenyl] carbamoylmethyl]ureido]phenyl]acetic acid (1–283)

mp 143–145° C. $^1$H-NMR (DMSO-d$_6$)δ: 0.81–0.87, 1.07–1.29 and 1.60–1.63 (13H, m), 3.21 (3H, s), 3.46–3.66 (6H, m), 4.51 (2H, s), 6.30–6.32, 6.76–7.45 and 8.82 (15H, m), 12.26 (1H, brs) MS (m/z): 601 (M+1)$^+$ Elementary Analysis (for $C_{34}H_{40}N_4O_6$) Calculated: C, 67.98; H, 6.71; N, 9.33 Found: C, 67.67; H, 6.68; N, 9.16

Example 284

2-[3-[3-[N-(2-Cyclopentylethyl)-N-[2-[N-methyl-N-(3,5-dimethylphenyl)carbamoylmethyloxy]phenyl] carbamoylmethyl]ureido]phenyl]acetic acid (1–284)

$^1$H-NMR (DMSO-d$_6$)δ:

0.86–1.71 (11H, m), 2.30 (6H, s), 3.15–3.87 (9H, m), 4.57 (2H, s), 6.27 (1H, s), 6.75–8.81 (12H, m), 12.29 (1H, brs) MS (m/z): 615 (M+1)$^+$ Example 285

2-[3-[3-[N-(2-Cyclohexylethyl)-N-[2-(N-methyl-N-phenylcarbamoylmethyloxy)phenyl] carbamoylmethyl]ureido]phenyl]acetic acid (1–285)

mp 185–186° C. $^1$H-NMR (DMSO-d$_6$)δ: 0.78–0.86 and 1.06–1.64 (13H, m), 3.19–3.85 (9H, m), 4.55 (2H, s), 6.28 (1H, brs), 6.76–7.50 (13H, m), 8.80 (1H, brs) MS (m/z): 601 (M+1)$^+$ Elementary Analysis (for $C_{34}H_{40}N_4O_6$) Calculated: C, 67.98; H, 6.71; N, 9.33 Found: C, 67.68, H, 6.69; N, 9.01

Example 286

2-[3-[3-[N-(3-Cyclohexylpropyl)-N-[2-(N-methyl-N-phenylcarbamoylmethyloxy)phenyl] carbamoylmethyl]ureido]phenyl]acetic acid (1–286)

$^1$H-NMR (DMSO-d$_6$)δ: 0.80–1.62 (15H, m), 3.19–3.76 (9H, m), 4.55 (2H, s), 6.28 (1H, brs), 6.76–7.50 (13H, m), 8.81 (1H, brs) MS (m/z): 615 (M+1)$^+$ Example 287

2-[3-[3-[N-Cyclopentylmethyl-N-[2-[N-methyl-N-(3,5-dimethyl)phenylcarbamoylmethyloxy]phenyl] carbamoylmethyl]ureido]phenyl]acetic acid (1–287)

$^1$H-NMR (DMSO-d$_6$)δ: 1.12–1.64 and 1.91–1.97 (9H, m), 2.30 (6H, s), 3.15 (3H, s), 3.24–3.48 (4H, m), 3.65–3.71, and 3.79–3.85 (2H, m), 4.57 (2H, s), 6.28 (1H, s), 6.75–7.38 (11H, m), 8.81 (1H, S) MS (m/z) 601 (M+1)$^+$ Example 288

2-[3-[3-[N-Cyclopentylmethyl-N-[2-(N-methyl-N-phenylcarbamoylmethyloxy)phenyl] carbamoylmethyl]ureido]phenyl]acetic acid (1–288)

$^1$H-NMR (DMSO-d$_6$)δ: 1.11–1.94 (9H, m), 3.19–3.45 (7H, m), 3.65–3.85 (2H, m), 4.55 (2H, s), 6.28 (1H, s), 6.75–7.51 (13H, m), 8.81 (1H, s) MS (m/z): 573 (M+1)$^+$

Example 289

2-[3-[3-[N-[2-[N-(3-Chlorophenyl)-N-methylcarbamoylmethyloxy)phenyl]-N-cyclopentylmethyl]carbamoylmethyl]ureido]phenyl] acetic acid (1–289)

mp 190–192° C. $^1$H-NMR (DMSO-d$_6$)δ: 0.84–1.63 and 1.92–1.99 (9H, m), 3.19–3.45 (7H, m), 3.65–3.85 (2H, m), 4.55 (2H, s), 6.28 (1H, s) 6.75–7.51 (12H, m), 8.81 (1H, s)

Elementary Analysis (for $C_{32}H_{35}ClN_4O_6$) Calculated: C, 63.31; H, 5.81; N, 9.23 Found: C, 63.05; H, 5.92; N, 8.90

Example 290

2-[3-[3-[N-Cyclobutylmethyl)-N-[2-(N-methyl-N-phenylcarbamoylmethyloxy)phenyl] carbamoylmethyl]ureido]phenyl]acetic acid (1–290)

mp 167–168° C. $^1$H-NMR (DMSO-d$_6$)δ: 1.51–1.89 (6H, m), 2.32–2.40 (1H, m), 3.20–3.92 (9H, m), 4.55 (2H, s), 6.28 (1H, s), 6.76–7.51 (13H, m), 8.81 (1H, s), 12.3 (1H, brs) MS (m/z): 559 (M+1)$^+$ Example 291

2-[3-[3-[N-Cyclobutylmethyl)-N-[2-[N-methyl-N-(3,5-dimethylphenyl)carbamoylmethyloxy]phenyl] carbamoylmethyl]ureido]phenyl]acetic acid (1–291)

mp 155–157° C. $^1$H-NMR (DMSO-d6)δ: 0.84–1.91 (6H, m), 2.31–2.41 (7H, m), 3.16–3.92 (9H, m), 4.57 (2H, s), 6.27 (1H, t), 6.76–7.38 (11H, m), 8.81 (1H, s) MS (m/z): 587 (M+1)$^+$

Example 292

2-[3-[3-[N-[2-[N-(3-Chlorophenyl)-N-methylcarbamoylmethyloxy]phenyl]-N-cyclobutylmethylcarbamoylmethyl]ureido]phenyl] acetic acid (1–292)

mp 194–195° C. $^1$H-NMR (DMSO-d$_6$)δ: 1.51–1.91 (6H, m), 2.33–2.41 (1H, m), 3.22–3.93 (9H, m), 4.64 (2H, brs), 6.27 (1H, s), 6.76–7.70 (12H, m), 8.81 (1H, s)

Example 293

2-[3-[3-[N-Cycloheptylmethyl]-N-[2-(N-methyl-N-phenylcarbamoylmethyloxy)phenyl] carbamoylmethyl]ureido]phenyl]acetic acid (1–293)

mp 179–181° C. $^1$H-NMR (DMSO-d$_6$)δ: 0.84–1.69 (13H, m), 3.19 (3H, s), 3.36–3.78 (6H, m), 4.56 (2H, s), 6.27 (1H, s), 6.76–7.50 (13H, m), 8.81 (1H, s) MS (m/z): 601 (M+1)$^+$

Example 294

2-[3-[3-[N-[2-[N-(3-Chlorophenyl)-N-methylcarbamoylmethyloxy]phenyl]-N-cycloheptylmethylcarbamoylmethyl]ureido]phenyl]acetic acid (1–294)

mp 189–191° C. $^1$H-NMR (DMSO-d$_6$)δ: 1.09–1.70 (13H, m), 3.21–3.80 (9H, m), 4.64 (2H, brs), 6.28 (1H, s), 6.76–7.69 (12H, m), 8.81 (1H, s), 12.30 (1H, brs)

Elementary Analysis (for C$_{34}$H$_{39}$ClN$_4$O$_6$) Calculated: C, 64.30; H, 6.19; N, 8.82 Found: C, 64.17; H, 6.27; N, 8.48

Example 295

2-[3-[3-[N-(n-Butyl)-N-[2-(N-methyl-N-phenylcarbamoylmethyloxy)phenyl]carbamoylmethyl]ureido]phenyl]acetic acid (1–295)

mp 139–141° C. $^1$H-NMR (DMSO-d$_6$)δ: 0.83 (3H, t), 1.22–1.39 (4H, m), 3.19–3.48 (7H, m), 3.64–3.69 and 3.79–3.86 (2H, m), 4.56 (2H, s), 6.28 (1H, t), 6.75–7.51 (13H, m) 8.82 (1H, s) MS (m/z): 547 (M+1)$^+$ Elementary Analysis (for C$_{30}$H$_{34}$N$_4$O$_6$) Calculated: C, 65.92; H, 6.27; N, 10.25 Found C, 65.57; H, 6.24; N, 10.17

Example 296

2-[3-[3-[N-(n-Butyl)-N-[2-[N-methyl-N-(3,5-dimethylphenyl)carbamoylmethyloxy)phenyl]carbamoylmethyl]-ureido]phenyl]acetic acid (1–296)

mp 111–115° C. $^1$H-NMR (DMSO-d$_6$)δ: 0.84 (3H, t), 1.23–1.37 (4H, m), 2.30 (6H, s), 3.15–3.86 (9H, m), 4.58 (2H, s), 6.28 (1H, t), 6.76–7.39 (1H, m), 8.82 (1H, s) MS (m/z):575 (M+1)$^+$

Example 297

2-[3-[3-[N-(n-Butyl)-N-[2-[N-(3-chlorophenyl)-N-methylcarbamoylmethyloxy]phenyl]carbamoylmethyl]ureido]phenyl]acetic acid (1–297)

mp 160–163° C. $^1$H-NMR (DMSO-d$_6$)δ: 0.84 (3H, t), 1.16–1.40 (4H, m), 3.21–3.88 (9H, m), 4.63 (2H, brs), 6.28 (1H, s), 6.76–7.71 (12H, m), 8.83 (1H, Elementary Analysis (for C$_{30}$H$_{33}$ClN$_4$O$_6$) Calculated: C, 62.01; H, 5.72; N, 9.64 Found: C, 61.81; H, 5.86; N, 9.35

Example 298

2-[3-[3-[N-[2-[N-(3-Chlorophenyl)-N-methylcarbamoylmethyloxy]phenyl]-N-[2-(1,3-dioxane-2-yl) ethyl]carbamoylmethyl]ureido]phenyl]acetic acid (1–298)

mp 153–154° C. $^1$H-NMR (DMSO-d$_6$)δ: 1.16–1.86 (4H, m), 3.15–4.06 (13H, ), 4.52–4.56 (3H, m), 6.27 (1H, brs), 6.46–7.39 (12H, m), 8.81 (1H, s), 12.29 (1H, brs)

Example 299

2-[3-[3-[N-[2-(1,3-Dioxane-2-yl)ethyl]-N-[2-[N-methyl-N-(3,5-dimethylphenyl)carbamoylmethyloxy]phenyl]carbamoylmethyl]ureido]phenyl]acetic acid (1–299)

mp 176–178° C. $^1$H-NMR (DMSO-d$_6$)δ: 1.24–1.85 (4H, m), 2.51 (6H, s), 3.21–3.94 (13H, m), 4.53–4.63 (3H, m), 6.28 (1H, brs), 6.76–7.48 (11H, m), 8.83 (1H, s), 12.27 (1H, brs) MS (m/z): 633 (M+1)$^+$

Example 300

2-[3-[3-[N-[2-(1,3-Dioxane-2-yl)ethyl]-N-[2-[N-methyl -N-phenylcarbamoylmethyloxy]phenyl] carbamoylmethyl]ureido]phenyl]acetic acid (1–300)

mp 183–185° C. $^1$H-NMR (DMSO-d$_6$)δ: 1.16–1.86 (4H, m), 3.20–4.06 (13H, m), 4.52–4.54 (3H, m), 6.28 (1H, brs), 6.76–7.51 (13H, m), 8.82 (1H, s), 12.27 (1H, brs) MS (m/z): 605 (M+1)$^+$ Elementary Analysis (for C$_{32}$H$_{36}$N$_4$O$_8$) Calculated: C, 63.57; H, 6.00; N, 9.27 Found: C, 63.59; H, 6.25; N, 8.77

Example 301

Methyl 2-[3-[3-[N-[2-[N-(2-methoxyphenyl)-N-methylcarbamoylmethyloxy]phenyl]-N-(3-methylbutyl) carbamoylmethyl]ureido]phenyl] acetate (1–301)

$^1$H-NMR (CDCl$_3$)δ: 0.82–0.88 (6H, m), 1.19–1.40 (3H, m), 3.27 (3H, s), 3.57 (2H, s), 3.67 (3H, s), 3.88–4.13 (7H, m), 4.37–4.53 (2H, m), 6.01 (1H, brs), 6.68–7.45 (13H, m) MS (m/z): 605 (M+1)$^+$

Example 302

Methyl 2-[3-[3-[N-[2-[N-(3-methoxyphenyl)-N-methylcarbamoylmethyloxy]phenyl]-N-(3-methylbutyl) carbamoylmethyl]ureido]phenyl] acetate (1–302)

mp 104–106° C. $^1$H-NMR (CDCl$_3$)δ: 0.82–0.85 (6H, m), 1.29–1.42 (2H, m), 1.49–1.57 (1H, m), 3.32 (3H, s), 3.35–3.39 (1H, m), 3.56 (2H, s), 3.67 (3H, s), 3.85 (3H, s), 3.85–3.98 (3H, m), 4.53 (2H, s), 6.04 (1H, brs), 6.65–7.43 (13H, m) MS (m/z): 605 (M+1)$^+$ Elementary Analysis (for C$_{33}$H$_{40}$ N$_4$O$_7$) Calculated: C, 65.55; H, 6.67; N, 9.27 Found: C, 65.17; H, 6.55; N, 9.26

Example 303

Methyl 2-[3-[3-[N-[2-[2-(2-methoxyphenyl)-2-oxoethyloxy]phenyl]-N-(3-methylbutyl) carbamoylmethyl]-ureido]phenyl]acetate (1–303)

mp 153–155° C. $^1$H-NMR (CDCl$_3$)δ: 0.86–0.89 (6H, m), 1.24–1.39 (2H, m), 1.49–1.54 (1H, m), 3.46–3.53 (1H, m), 3.55 (2H, s), 3.66 (3H, s), 3.68–3.97 (2H, m), 3.98 (3H, s), 4.00–4.02 (1H, m), 5.32 (2H, s), 5.98 (1H, brs), 6.70–7.90 (13H, m) MS (m/z): 576 (M+1)$^+$

Example 304

Methyl 2-[3-[3-[N-[2-[N-(3,5-dichlorophenyl)-N-methylcarbamoylmethyloxy]phenyl]-N-(3-methylbutyl) carbamoylmethyl]ureido]phenyl]acetate (1–304)

mp 160–162° C. $^1$H-NMR (CDCl$_3$)δ: 0.83–0.86 (6H, m), 1.25–1.44 (2H, m), 1.45–1.58 (1H, m), 3.29 (3H, s), 3.33–3.40 (1H, m), 3.56 (2H, s), 3.67 (3H, s), 3.83 (2H, d), 3.85–4.01 (1H, m), 4.55 (2H, brs), 5.95 (1H, brs), 6.71 (1H, m), 6.89–6.90 (1H, m), 6.99–7.03 (1H, m), 7.16–7.30 (8H, m), 7.43 (1H, s)

Elementary Analysis (for C$_{32}$H$_{36}$Cl$_2$N$_4$O$_6$) Calculated: C, 59.72; H, 5.64; N, 8.74 Found C: 59.44; H, 5.64; N, 8.67

Example 305

Methyl 2-[3-[3-[N-[2-N-(3,5-dimethoxyphenyl)-N-methylcarbamoylmethyloxy]phenyl]-N-(3-methylbutyl) carbamoylmethyl]ureido]phenyl] acetate (1–305)

mp 152–154° C. $^1$H-NMR (CDCl$_3$)δ: 0.83–0.86 (6H, m), 1.26–1.38 (2H, m), 1.40–1.58 (1H, m), 3.31 (3H, s), 3.35–3.38 (1H, m), 3.56 (2H, s), 3.67 (3H, s), 3.83 (6H, s), 3.88 (2H, d), 3.92–3.93 (1H, m), 4.59 (2H, brs), 5.98 (1H, brs), 6.43 (2H, m), 6.50 (1H, m), 6.66–6.68 (1H, m), 6.88–6.90 (1H, m), 6.96–7.00 (1H, m), 7.14–7.28 (6H, m) MS (m/z): 635 (M+1)$^+$ Elementary Analysis (for $C_{34}H_{42}N_4O_8$) Calculated: C, 64.34; H, 6.67; N, 8.83 Found: C, 64.14; H, 6.62; N, 8.74

Example 306

Methyl 2-[3-[3-[N-[2-[N-(3,5-trifluoromethyl)-N-methylcarbamoylmethyloxy]phenyl]-N-(3-methylbutyl) carbamoylmethyl]ureido]phenyl] acetate (1–306)

mp 145–147° C. $^1$H-NMR (CDCl$_3$)δ: 0.85 (6H, m), 1.36–1.43 (3H, ,) 3.67 (4H, m), 3.56 (2H, s), 3.67 (3H, s), 3.76–3.86 (2H, m), 3.94–4.02 (1H, m), 4.58 (2H, brs), 5.83 (1H, brs), 6.90–7.31 (9H, m), 7.78–7.93 (3H, m) MS (m/z): 711 (M+1)$^+$ Elementary Analysis (for $C_{34}H_{36}F_6N_4O_6$) Calculated: C, 57.46; H, 5.11; N, 7.88 Found: C, 67.36; H, 5.20; N, 7.71

Example 307

Methyl 2-[3-[3-[N-[2-[N-(3-fluorophenyl)-N-methylcarbamoylmethyloxy]phenyl]-N-(3-methylbutyl) carbamoylmethyl]ureido]phenyl] acetate (1–307)

mp 112–114° C. $^1$H-NMR (CDCl$_3$)δ: 0.83–0.86 (6H, m), 1.25–1.42 (2H, m), 1.44–1.60 (1H, m), 3.32 (3H, s), 3.36–3.39 (3H, m), 3.56 (2H, s), 3.67 (3H, s), 3.84 (2H, d), 3.89–3.99 (2H, m), 4.51 (2H, m), 5.96 (1H, brs), 6.65–6.67 (1H, m), 6.88–7.32 (11H, m), 7.45–7.51 (1H, m) MS (m/z): 593 (M+1)$^+$ Elementary Analysis (for $C_{32}H_{37}FN_4O_6$) Calculated: C, 64.85; H, 6.29;N, 9.45 Found: C, 64.18; H, 6.19; N, 9.27

Example 308

Methyl (±)-2-[3-[3-[N-[2-[N-(3-methoxyphenyl)-N-methylcarbamoylmethyloxy]phenyl]-N-(3-methylbutyl) carbamoylmethyl]ureido]phenyl]propionate (1–308)

mp 138–141° C. $^1$H-NMR (CDCl$_3$)δ: 0.84–0.86 (6H, m), 1.46 (3H, m), 1.26–1.58 (3H, m), 3.34–3.35 (4H, m), 3.64–3.65 (4H, m), 3.86–3.98 (6H, m), 4.54 (2H, brs), 5.95 (1H, brs), 6.64–7.43 (13H, m)

Example 309

Methyl 2-[3-[3-[N-[2-[N-methyl-N-phenylcarbamoylmethyloxy]phenyl]-N-(3-methylbutyl) carbamoylmethyl]ureido]phenyl] acetate (1–309)

$^1$H-NMR (CDCl$_3$)δ: 0.83–0.86 (6H, m), 1.33–1.38 (2H, m), 1.49–1.57 (1H, m), 3.28–3.31 (4H, m), 3.61–4.09 (8H, m), 4.46(2H, brs), 6.69–7.85 (15H, m)

Example 310

2-[3-[3-[N-[2-[N-(2-Methoxyphenyl)-N-methylcarbamoylmethyloxy]phenyl]-N-(3-methylbutyl) carbamoylmethyl]ureido]phenyl]acetic acid (1–310)

$^1$H-NMR (CDCl$_3$)δ: 0.82–0.88 (6H, m), 1.34–1.56 (3H, m), 3.22 (3H, s), 3.59 (2H, 3.36–3.88 (4H, m), 3.95 (3H, s), 4.37–4.49 (2H, m), 6.40–7.59 (14H, m) MS (m/z): 591 (M+1)$^+$

Example 311

2-[3-[3-[N-[2-[N-(3-Methoxyphenyl)-N-methylcarbamoylmethyloxy]phenyl]-N-(3-methylbutyl) carbamoylmethyl]ureido]phenyl]acetic acid (1–311)

mp 149–151° C. $^1$H-NMR (CDCl$_3$)δ: 0.84–0.86 (6H, m), 1.24–1.56 (3H, m), 3.28 (3H, S), 3.33–3.40 (1H, m), 3.61 (2H, s), 3.67 (1H, m), 3.83 (3H, s), 3.84–4.01 (2H, m), 4.50 (2H, s), 6.46–7.60 (14H, m) MS (m/z): 591 (M+1)$^+$

Example 312

2-[3-[3-[N-[2-[2-(2-Methoxyphenyl)-2-ooxcethyloxy]phenyl]-N-(3-methylbutyl) carbamoylmethyl]-ureido]phenyl]acetic acid (1–312)

mp 163–165° C. $^1$H-NMR (CDCl$_3$)δ: 0.87–0.90 (6H, m), 1.19–1. 49 (3H, m), 3.44–3. 51 (1H, m), 3.64 (2H, s), 3.67–3. 92 (2H, m), 3.95 (3H, s), 3.98 (1H, m), 5.29 (2H, s), 6.50–7.86 (14H, m) MS (m/z) 562 (M+1)$^+$

Elementary Analysis (for $C_{31}H_{35}N_3O_7$) Calculated: C, 66.30; H, 6.28; N, 7.48 Found: C, 65.65; H, 6.24; N, 7.38

Example 313

2-[3-[3-[N-[2-[N-(3,5-Dichlorophenyl)-N-methylcarbamoylmethyloxy]phenyl]-N-(3-methylbutyl) carbamoylmethyl]ureido]phenyl]acetic acid (1–313)

mp 118–120° C. $^1$H-NMR (CDCl$_3$)δ: 0.84–0.87 (6H, m), 1.32–1.42 (2H, m), 1.52–1.58 (1H, m), 3.26 (3H, s), 3.26–3.39 (1H, m) 3.60 (2H, s), 3.65–3.69 (1H, 3.81–3.84 (1H, m), 3.95–3.99 (1H, m), 4.53 (2H, brs), 6.47–7.63 (13H, m)

Example 314

2-[3-[3-[N-[2-[N-(3,5-Dimethoxyphenyl)-N-methylcarbamoylmethyloxy]phenyl]-N-(3-methylbutyl) carbamoylmethyl]ureido]phenyl]acetic acid (1–314)

mp 162–164° C. $^1$H-NMR (CDCl$_3$)δ: 0.84–0.86 (6H, m), 1.30–1.43 (2H, m), 1.44–1.59 (1H, m), 3.27 (3H, s), 3.31–3.40 (1H, m), 3.60 (2H, s), 3.81 (6H, s), 3.84–3.90 (1H, m), 3.96–4.03 (1H, m), 4.55 (2H, brs), 6.40–6.48 (4H, m), 6.68–6.70 (1H, m), 6.87–6.88 (1H, m), 6.96–7.00 (2H, m), 7.12–7.29 (4H, m), 7.55–7.58 (2H, m) MS (m/z): 621 (M+1)$^+$

Example 315

2-[3-[3-[N-[2-[N-[3,5-Bis(trifluoromethyl)phenyl]-N-methylcarbamoylmethyloxy]phenyl]-N-(3-methylbutyl) carbamoylmethyl]ureido]phenyl]acetic acid (1–315)

mp 139–141° C. $^1$H-NMR (DMSO-d$_6$)δ: 0.83–0.85 (6H, m), 1.25–1.36 (2H, m), 1.53–1.60 (1H, m), 3.32–3.43 (5H, m), 3.46 (2H, s), 3.64–3.69 (1H, m), 3.83–3.91 (1H, m), 4.79 (2H, m), 6.32 (1H, brs), 6.75–6.77 (1H, m), 7.04–7.41 (1OH, m), 8.82 (1H, s), 12.55 (1H, br) MS (m/z): 697 (M+1)$^+$

Example 316

2-[3-[3-[N-[2-[N-(3-Fluorophenyl)-N-methylcarbamoylmethyloxy]phenyl]-N-(3-methylbutyl) carbamoylmethyl]ureido]phenyl]acetic acid (1–316)

mp 154–156° C. $^1$H-NMR (CDCl$_3$)δ: 0.83–0.86 (6H, m), 1.33–1.43 (2H, m), 1.44–1.57 (1H, m), 3.27 (3H, s), 3.32–3.40 (1H, m), 3.58 (2H, s), 3.61–3.66 (1H, m), 3.80–3.85 (1H, m), 3.95–4.01 (1H, m), 4.49 (2H, m), 6.50–7.64 (14H, m) MS (m/z): 579 (M+1)$^+$

Elementary Analysis (for $C_{31}H_{35}FN_4O_6$) Calculated: C, 64.35; H, 6.10; N, 9.68 Found: C, 64.22; H, 6.12; N, 9.52

Example 317

(±)-2-[3-[3-[N-[2-[N-(3-Methoxyphenyl)-N-methylcarbamoylmethyloxy]phenyl]-N-(3-methylbutyl) carbamoylmethyl]ureido]phenyl] propionic acid (1–317)

mp 123–125° C. $^1$H-NMR (CDCl$_3$)δ: 0.82–0.86 (6H, m), 1.54 (3H, m), 1.22–1.61 (3H, m), 3.27–3.38 (4H, m), 3.62–4.03 (7H, m), 4.49 (2H, brs), 6.51–7.70 (14H, m) MS (m/z): 605 (M+1)$^+$ Elementary Analysis (for $C_{33}H_{40}N_4O_7$) Calculated: C, 65.55; H, 6.67; N, 9.27 Found: C, 65.23; H, 6.63; N, 9.18

Example 318

2-[3-[3-[N-[2-(N-Methyl-N-phenylcarbamoylmethyloxy) phenyl]-N-(3-methylbutyl)carbamoylmethyl]thioureido]phenyl] acetic acid (1–318)

$^1$H-NMR (CDCl$_3$)δ: 0.82–0.86 (6H, m), 1.30–1.41 (2H, m), 1.50–1.78 (1H, m), 3.30–3.34 (4H, m), 3.65 (2H, s), 3.81–3.95 (2H, m), 4.20–4.24 (1H, m), 4.44 (2H, brs), 6.67 (1H, m), 6.69–7.85 (13H, m), 8.49 (1H, brs) MS (m/z): 577 (M+1)$^+$

Example 319

Methyl (±)-2-[3-[3-[N-[2-[N-(3,5-dimethoxyphenyl)-N-methylcarbamoylmethyloxy]phenyl]-N-(N-methyl-N-phenylcarbamolylmethyl)carbamoylmethyl]ureido]phenyl]propionate (1–319)

mp 188–189° C. $^1$H-NMR (CDCl$_3$)δ: 1.45 (3H, m), 3.28 (6H, m), 3.48 (1H, d), 3.62–3.68 (4H, m) 3.81 (6H, s), 3.96 (2H, m), 4.51 (2H, brs), 4.68 (1H, d), 5.95 (1H, brs), 6.40–6.62 (4H, m), 6.88–7.00 (2H, m), 7.15–7.40 (10H, m), 7.70 (1H, d) MS (m/z): 726 (M+1)$^+$ Elementary Analysis (for $C_{39}H_{43}N_5O_9$) Calculated: C, 64.54; H, 5.97; N, 9.65 Found: C, 64.08; H, 5.97 N, 9.62

Example 320

Methyl (±)-2-[3-[3-[N-[2-[N-(2,5-dimethoxyphenyl)-N-methylcarbamoylmethyloxy]phenyl]-N-(N-methyl-N-phenylcarbamolylmethyl)carbamoylmethyl]ureido]phenyl]propionate (1–320):

mp 171–173° C. $^1$H-NMR (CDCl$_3$)δ: 1.45 (3H, d), 3.24 (6H, m), 3.34–3.49 (1H, m), 3.63–3.68 (4H, m), 3.79–4.13 (8H, m), 4.33–4.46 (2H, m), 4.70 (1H, m), 5.93 (1H, m), 6.63–7.72 (17H, m) MS (m/z): 726 (M+1)$^+$

Elementary Analysis (for $C_{39}H_{43}N_5O_9$) Calculated: C, 64.54; H, 5.97; N, 9.65 Found: C, 64.17; H, 6.00; N, 9.49

Example 321

Methyl 2-[3-[3-[N-[2-[N-(2,5-dimethoxyphenyl)-N-methylcarbamoylmethyloxy]phenyl]-N-(N-methyl-N-phenylcarbamolylmethyl)carbamoylmethyl]ureido]phenyl]acetate (1–321)

mp 103–105° C. $^1$H-NMR (CDCl$_3$)δ: 3.20 (3H, s), 3.23 (3H, s), 3.38 (1H, d) 3.55 (2H, s), 3.65 (3H, s), 3.79–4.07 (8H, m), 4.33–4.45 (2H, m), 4.66–4.73 (1H, m), 5.96 (1H, brs), 6.65–7.71 (17H, m) MS (m/z): 712 (M+1)$^+$

Example 322

Methyl (±)-2-[3-[3-[N-[3-[N-(2,5-dimethoxyphenyl)-N-methylcarbamoylmethyloxy]phenyl]-N-(N-methyl-N-phenylcarbamolylmethyl)carbamoylmethyl]ureido]phenyl] propionate (1–322)

mp 129–131° C. $^1$H-NMR (CDCl$_3$) δ: 1.45 (3H, d), 3.23 (6H, m), 3.62 (3H, s), 3.65 (1H, m), 3.77 (3H, s), 3.83 (3H, s), 3.85–3.86 (2H, m), 4.05 (1H, d), 4.14 (1H, d), 4.37 (1H, d), 4.44 (1H, d). 5.91 (1H, m), 6.82–7.52 (17H, m) MS (m/z): 726 (M+1)$^+$

Elementary Analysis (for $C_{39}H_{43}N_5O_9$) Calculated: C, 64.54; H, 5.97; N, 9.65 Found: C, 64.12; H, 5.91; N, 9.52

Example 323

Methyl 2-[3-[3-[N-[2-[N-(2,5-dimethoxyphenyl)-N-methylcarbamoylmethyloxy]phenyl]-N-(N-methyl-N-phenylcarbamolylmethyl)carbamoylmethyl] ureido]phenyl] acetate (1–323):

mp 136–138° C. $^1$H-NMR (CDCl$_3$) δ: 3.22 (6H, s), 3.55 (2H, s), 3.65 (3H, s), 3.77 (3H, s), 3.83 (3H, s), 3.85–3.86 (2H, m), 4.05 (1H, d), 4.14 (1H, d), 4.37 (1H, d) 4.44 (1H, d) 5.92 (1H, brs); 6.82–7.54 (17H, m) MS (m/z): 712 (M+1)$^+$ Elementary Analysis (for $C_{38}H_{41}N_5O_9$) Calculated: C, 64.12; H, 5.81; N, 9.84 Found: C, 63.65; H, 5.76; N, 9.69

Example 324

Methyl (±)-2-[3-[3-[N-[3-[N-(3-methoxyphenyl)-N-methylcarbamoylmethyloxy]phenyl]-N-(N-methyl-N-phenylcarbamolylmethyl)carbamoylmethyl] ureido]phenyl] propionate (1–324)

mp 133–134° C. $^1$H-NMR (CDCl$_3$) δ: 1.44 (3H, d), 3.24 (3H, s), 3.32 (3H, s), 3.62 (3H, s), 3.65 (1H, m), 3.81 (3H, s), 3.85 (2H, d), 4.08 (2H, s), 4.46 (2H, s), 5.85 (1H, brs), 6.80–7.00 (7H, m), 7.15–7.37 (11H, m) MS (m/z) 696 (M+1)$^+$

Example 325

Methyl 2-[3-[3-[N-[3-[N-(3-methoxyphenyl)-N-methylcarbamoylmethyloxy]phenyl]-N-(N-methyl-N-phenylcarbamolylmethyl)carbamoylmethyl] ureido]phenyl] acetate (1–325)

mp 115–117° C. $^1$H-NMR (CDCl$_3$) δ: 3.24 (3H, s), 3.32 (3H, s), 3.54 (2H, m), 3.64 (3H, s), 3.81 (3H, s), 3.85 (2H, d), 4.08 (2H, s), 4.46 (2H, s), 5.90 (1H, brs), 6.80–7.00 (7H, m), 7.14–7.48 (1 H, m) MS (m/z): 682 (M+1)$^+$

Example 326

Methyl 2-[3-[3-[N-[3-[N-(2-methoxyphenyl)-N-methylcarbamoylmethyloxy]phenyl]-N-(N-methyl-N-phenylcarbamolylmethyl)carbamoylmethyl]-3-methylureido] phenyl]acetate (1–326)

$^1$H-NMR (CDCl$_3$) δ: 2.93 (3H, s), 3.21 (3H, s), 3.32 (3H, s), 3.58 (2H, s), 3.67 (3H, s), 3.87 (3H, s), 3.91–4.17 (4H, m), 4.33 (1H, d), 4.43 (1H, d), 6.80–7.45 (18H, m) MS (m/z) 696 (M+1)$^+$

Example 327

Methyl 2-[3-[3-[N-[3-[2-(2-methoxyphenyl)-2-oxoethyloxy]phenyl]-N-(N-methyl-N-phenylcarbamolylmethyl)carbamoylmethyl]ureido]phenyl]acetate (1–327)

mp 165–168° C. $^1$H-NMR (CDCl$_3$) δ: 3.22 (3H, s), 3.55 (2H, s), 3.66 (3H, s), 3.90 (2H, d), 3.99 (3H, s), 4.10 (2H, s), 5.27 (2H, s), 5.81 (1H, brs), 6.89–7.56 (17H, m), 7.93 (1H, m) MS (m/z): 653 (M+1)$^+$ Elementary Analysis (for C$_{36}$H$_{36}$N$_4$O$_8$) Calculated: C, 66.25; H, 5.56; N, 8.58 Found: C, 66.03; H, 5.52; N, 8.42

Example 328

Methyl 2-[3-[3-[N-[3-[2-(3-methoxyphenyl)-2-oxoethyloxy]phenyl]-N-(N-methyl-N-phenylcarbamolylmethyl)-carbamoylmethyl]ureido]phenyl]acetate (1–328)

mp 115–118° C. $^1$H-NMR (CDCl$_3$) δ: 3.21 (3H, s), 3.54 (2H, s), 3.65 (3H, s), 3.85 (3H, s), 3.90 (2H, d), 4.09 (2H, s), 5.31 (2H, s), 5.88 (1H, brs), 6.88–7.57 (18H, m) MS (m/z): 653 (M+1)$^+$ Elementary Analysis (for C$_{36}$H$_{36}$N$_4$O$_8$) Calculated: C, 66.25; H, 5.56; N, 8.58 Found: C, 65.92; H, 5.57; N, 8.43

Example 329

(±)-2-[3-[3-[N-[2-[N-(3,5-Dimethoxyphenyl)-N-methylcarbamoylmethyloxy]phenyl]-N-(N-methyl-N-phenylcarbamolylmethyl)carbamoylmethyl]ureido]phenyl] propionic acid (1–329)

mp 209–210° C. $^1$H-NMR (CDCl$_3$) δ: 1.48 (3H, m), 3.22 (6H, s), 3.58 (1H, d), 3.66 (1H, m), 3.76–3.86 (8H, m), 4.46 (2H, brs), 4.69 (1H, dd), 6.31–7.68 (5H, m), 6.89–7.02 (3H, m), 7.14–7.37 (7H, m), 7.51–7.76 (3H, m) MS (m/z): 712 (M+1)$^+$

Example 330

2-[3-[3-[N-[2-[N-(3,5-Dimethoxyphenyl)-N-methylcarbamoylmethyloxy]phenyl]-N-(N-methyl-N-phenylcarbamolylmethyl)carbamoylmethyl]ureido]phenyl] acetic acid (1–330)

mp 202–203° C. $^1$H-NMR (CDCl$_3$) δ: 3.22 (3H, s), 3.25 (3H, s), 3.54 (2H, s), 3.56 (1H, m), 3.79 (6H, s), 3.87 (2H, m), 4.48 (2H, brs), 4.71 (1H, d), 6.31–6.63 (5H, m), 6.84–7.00 (3H, m), 7.14–7.36 (7H, m), 7.48–7.71 (3H, m) MS (m/z): 698 (M+1)$^+$

Example 331

(±)-2-[3-[3-[N-[2-[N-(2,5-Dimethoxyphenyl)-N-methylcarbamoylmethyloxy]phenyl]-N-(N-methyl-N-phenylcarbamolylmethyl)carbamoylmethyl]ureido]phenyl] propionic acid (1–331)

$^1$H-NMR (CDCl$_3$) δ: 1.48 (3H, m), 3.15–3.25 (6H, m), 3.62–3.87 (10H, m), 4.37–4.44 (2H, m), 4.62–4.73 (1H, m), 6.37–7.84 (18H, m) MS (m/z): 712 (M+1)$^+$

Example 332

2-[3-[3-[N-[2-[N-(2,5-Dimethoxyphenyl)-N-methylcarbamoylmethyloxy]phenyl]-N-(N-methyl-N-phenylcarbamolylmethyl)carbamoylmethyl]ureido]phenyl] acetic acid (1–332)

mp 128–130° C. $^1$H-NMR (CDCl$_3$) δ: 3.17 (3H, s), 3.24 (3H, s), 3.49–3.61 (3H, m), 3.73–3.88 (8H, m), 4.39 (2H, m), 4.72 (1H, m), 6.30–7.69 (18H, m) MS (m/z): 698 (M+1)$^+$

Example 333

(±)-2-[3-[3-[N-[3-[N-(2,5-Dimethoxyphenyl)-N-methylcarbamoylmethyloxy]phenyl]-N-(N-methyl-N-phenylcarbamolylmethyl)carbamoylmethyl]ureido]phenyl] propionic acid (1–333)

$^1$H-NMR (CDCl$_3$) δ: 1.50 (3H, d), 3.22 (3H, s), 3.25 (3H, s), 3.67–3.82 (9H, m), 4.11 (2H, m), 4.35 (1H, d), 4.43 (1H, d) 6.27–7.72 (18H, m) MS (m/z): 712 (M+1)$^+$

Example 334

2-[3-[3-[N-[3-[N-(2,5-Dimethoxyphenyl)-N-methylcarbamoylmethyloxy]phenyl]-N-(N-methyl-N-phenylcarbamolylmethyl)carbamoylmethyl]ureido]phenyl] acetic acid (1–334)

$^1$H-NMR (CDCl$_3$) δ: 3.22 (3H, s), 3.24 (3H, s), 3.55 (2H, s), 3.75–3.81 (8H, m), 4.00 (1H, d), 4.11 (1H, d), 4.35 (1H, d), 4.43 (1H, d), 6.26–7.79 (18H, m) MS (m/z) 698 (M+1)$^+$

Example 335

(±)-2-[3-[3-[N-[3-[N-(3-Methoxyphenyl)-N-methylcarbamoylmethyloxy]phenyl]-N-(N-methyl-N-phenylcarbamolylmethyl)carbamoylmethyl]ureido]phenyl] propionic acid (1–335)

$^1$H-NMR (CDCl$_3$) δ: 1.47 (3H, d), 3.24 (3H, S), 3.31 (3H, s), 3.66 (1H, m), 3.79 (5H, m), 4. 01 (1H, d), 4.07 (1H, d), 4.45 (2H, s), 6.30–7.88 (19H, m) MS (m/z): 682 (M+1)$^+$

Example 336

2-[3-[3-[N-[3-[N-(3-Methoxyphenyl)-N-methylcarbamoylmethyloxy]phenyl]-N-(N-methyl-N-phenylcarbamolylmethyl)carbamoylmethyl]ureido]phenyl] acetic acid (1–336)

$^1$H-NMR (CDCl$^3$) δ: 3.24 (3H, s), 3.31 (3H, s), 3.54 (2H, m), 3.79 (5H, m), 4.05 (2H, s), 4.45 (2H, s), 6.26–7.83 (19H, m) MS (m/z): 668 (M+1)$^+$

Example 337

2-[3-[3-[N-[3-[N-(2-Methoxyphenyl)-N-methylcarbamoylmethyloxy]phenyl]-N-(N-methyl-N-phenylcarbamolylmethyl)carbamoylmethyl]-3-methylureido] phenyl]acetic acid (1–337)

$^1$H-NMR (CDCl$^3$) δ: 2.91 (3H, s), 3.22 (3H, s), 3.31 (3H, s), 3.62 (2H, s), 3.86 (3H, s), 3.88–4.40 (6H, m), 6.80–7.45 (18H, m) MS (m/z): 682 (M+1)$^+$

Example 338

2-[3-[3-[N-[3-[2-(2-Methoxyphenyl)-2-oxoethyloxy]-phenyl]-N-(N-methyl-N-phenylcarbamolylmethyl)-carbamoylmethyl]ureido] phenyl]acetic acid (1–338)

$^1$H-NMR (CDCl$_3$) δ: 3.22 (3H, s), 3.53 (2H, s), 3.88 (2H, d), 3.98 (3H, s), 4.07 (2H, s), 5.27 (2H, s), 6.29 (1H, brs), 6.83–7.71 (17H, m), 7.93 (1H, m) MS (m/z): 639 (M+1)$^+$

Example 339

2-[3-[3-[N-[3-[2-(3-Methoxyphenyl)-2-oxoethyloxy]phenyl]-N-(N-methyl-N-phenylcarbamolylmethyl)-carbamoylmethyl]ureido]phenyl]acetic acid (1–339)

$^1$H-NMR (CDCl$_3$) δ: 3.21 (3H, s), 3.53 (2H, s), 3.85 (3H, s), 3.87 (2H, d), 4.06 (2H, s), 5.32 (2H, s), 6.29 (1H, brs), 6.83–7.69 (18H, m) MS (m/z): 639 (M+1)$^+$

Example 340 tert-Butyl 2-[2-[N-(N-methyl-N-phenylcarbamoylmethyl)-N-[2-[3-(3-methylphenyl)ureido]acetyl]amino]phenylthio] acetate (1–340)

mp 192–194° C. $^1$H-NMR (CDCl$_3$) δ 1.40 (9H, s), 2.29 (3H, s), 3.24 (3H, s), 3.39 (1H, d), 3.54 (2H, q), 3.75 (1H, dd), 3.94 (1H, dd), 4.75 (1H, d), 5.86 (1H, brs), 6.84 (2H, brs), 7.07–7.39 (11H, m), 7.82 (1H, d) MS (m/z): 578 (M+1)$^+$

Example 341

2-[2-[N-(N-Methyl-N-phenylcarbamoylmethyl)-N-[2-[3-(3-methylphenyl)ureido]acetyl]amino]phenylthio]acetic acid (1–341)

$^1$H-NMR (CDCl$_3$) δ: 2.24 (3H, s), 3.21 (3H, s), 3.40 (1H, d), 3.59 (2H, q), 3.75–3.92 (2H, m), 4.76 (1H, d), 6.18 (1H, brs), 6.82 (1H, d), 7.03–7.13 and 7.24–7.46 (11H, m), 7.72 (1H, d), 8.05 (1H, s)

Example 342

N-Methyl-N-phenyl-2-[2-[N-(N-methyl-N-phenylcarbamoyl methyl)-N-[2-[3-(3-methylphenyl)ureido]acetyl]amino] phenylthio]acetamide (1–342)

mp 231–232° C. $^1$H-NMR (DMSO-d$_6$) δ: 2.21 (3H, s), 3.29 (3H, s), 3.31 (3H, s), 3.37–3.42 (2H, m), 3.63–3.67 (3H, m), 4.52 (1H, d), 6.29 (1H, brs), 6.69 (1H, d), 7.05–7.46 (16H, m), 7.66 (1H, d), 8.70 (1H, s) MS (m/z): 610 (M+1)$^+$ Elementary Analysis (for C$_{34}$H$_{35}$N$_5$O$_4$S) Calculated: C, 66.97; H, 5.79; N, 11.49 Found: C, 66.86; H, 5.84; N, 11.56

Example 343

1-[2-[2-[N-(N-Methyl-N-phenylcarbamoylmethyl)-N-[2-[3-(3-methylphenyl)ureido]acetyl]amino] phenylthio]acetyl]-3,3-dimethylpiperidine(1–343)

mp 219–220° C. $^1$H-NMR (DMSO-d$_6$) δ: 0.77 (3H, s), 0.85 (3H, s), 1.31 (2H, brs), 1.42 (2H, m), 2.21 (3H, s), 3.05–3.12 (2H, m), 3.17 (3H, s), 3.33–3.42 (4H, m), 3.67 (1H, d), 4.03 (2H, s), 4.57 (1H, d), 6.30 (1H, s), 6.69 (1H, d), 7.05–7.69 (12H, m), 8.72 (1H, s) MS (m/z): 616 (M+1)$^+$ Elementary Analysis (for C$_{34}$H$_{41}$N$_5$O$_4$S) Calculated: C, 66.32; H, 6.71; N, 11.37 Found: C, 66.07; H, 6.75; N, 11.38

Example 344

N-Cyclohexyl-N-methyl-2-[2-[N-(N-methyl-N-phenyl carbamoylmethyl)-N-[2-[3-(3-methylphenyl)ureido]acetyl] amino]phenylthio]acetamide(1–344)

mp 194–195° C. $^1$H-NMR (DMSO-d$_6$) δ: 1.02–1.72 (10H, m), 2.21 (3H, s), 2.64 and 2.84 (3H, s), 3.17 (3H, s), 3.35–3.40 (2H, m), 3.61 and 4.12 (1H, m), 3.68 (1H, dd), 4.02 (2H, s), 4.56 (1H, d), 6.30 (1H, brs), 6.69 (1H, d), 7.05–7.69 (12H, m), 8.72 (1H, s) MS (m/z): 616 (M+1)$^+$ Elementary Analysis (for C$_{34}$H$_{41}$N$_5$O$_4$S) Calculated: C, 66.32; H, 6.71; N, 11.37 Found: C, 66.30; H, 6.66; N, 11.40

Example 345 tert-Butyl 3-[3-[N-(N-methyl-N-phenylcarbamoylmethyl)-N-[3-(N-methyl-N-phenylcarbamoylmethyloxy)phenyl] carbamoylmethyl]ureido]benzoate(1–345)

$^1$H-NMR (CDCl$_3$) δ: 1.55 (9H, s), 3.24 (3H, s), 3.32 (3H, s), 3.87 (2H, d), 4.10 (2H, s), 4.43 (2H, s), 6.07 (1H, brs), 6.80 (1H, d), 6.89 (1H, s), 7.02 (1H, d), 7.15–7.46 (12H, m), 7.56 (1H, d), 7.68 (1H, d), 7.89 (1H, s), 7.96 (1H, s)

Example 346

3-[3-[N-(N-Methyl-N-phenylcarbamoylmethyl)-N-[3-(N-methyl-N-phenylcarbamoylmethyloxy)phenyl] carbamoylmethyl]ureido]benzoic acid(1–346)

$^1$H-NMR (CDCl$_3$) δ: 3.26 (3H, s), 3.34 (3H, s), 3.91 (2H, d), 4.10 (2H, s), 4.44 (2H, s), 6.79–6.84 (2H, m), 6.97 (1H, s), 7.06 (1H, d), 7.21–7.47 (12H, m), 7.55 (1H, d), 7.72 (1H, s), 8.22 (1H, d), 8.39 (1H, s) MS (m/z): 624 (M+1)$^+$

Example 347

N-Methyl-N-phenyl-2-[2-[N-(N-methyl-N-phenylcarbamoyl methyl)-N-[2-[3-(3-methylphenyl)ureido]acetyl]amino] phenoxy]acetamide (1–347)

mp 183–184° C. $^1$H-NMR (CDCl$_3$) δ: 2.26 (3H, s), 3.22 (3H, s), 3.26 (3H, s), 3.55 (1H, d), 3.90 (2H, m) 4.39 (2H, s), 4.68 (2H, d), 6.04 (1H, brs), 6.62 (1H, d), 6.76 (1H, d), 6.99–7.44 (15H, m), 7.69 (1H, d) MS (m/z): 594 (M+1)$^+$

Example 348

Pivaloyloxymethyl 2-[3-[3-[N-(N-methyl-N-phenyl carbamoylmethyl)-N-[2-(N-methyl-N-phenylcarbamoyl methyloxy)phenyl]carbamoylmethyl]ureidophenyl]acetate (1–348)

mp 122–130° C. $^1$H-NMR (CDCl$_3$) δ: 1.15 (9H, s), 3.22 (3H, s), 3.28 (3H, s), 3.53 (1H, d), 3.57 (2H, s), 3.92 (2H, d), 4.41 (2H, s), 4.67 (1H, d), 5.73 (2H, s), 6.06 (1H, brs), 6.62 (9H, d), 6.84 (1H, d), 6.98 (1H, t), 7.12–7.53 (15H, m), 7.69 (1H, d) MS (m/z): 752 (M+1)$^+$ Elementary Analysis (for C$_{41}$H$_{45}$N$_5$O$_9$) Calculated: C, 65.50; H, 6.03; N, 9.32 Found: C, 65.58; H, 5.87; N, 9.44

Example 349

Ethyl 2-[3-[3-[N-(N-methyl-N-phenylcarbamoylmethyl)-N-(2-(N-methyl-N-phenylcarbamoylmethyloxy)phenyl] carbamoylmethyl]ureido]phenyl]acetate (1–349)

mp 147–148° C. $^1$H-NMR (CDCl$_3$) δ: 1.22 (3H, t), 3.21 (3H, s), 3.27 (3H, s), 3.52 (2H, s), 3.55 (1H, d), 3.91 (2H, s), 4.10 (2H, q), 4.41 (2H, s), 4.68 (1H, d), 6.09 (1H, brs), 6.62 (1H, d), 6.86 (1H, d), 6.98 (1H, brs), 7.13–7.45 (14H, m), 7.56 (1H, brs), 7.68 (1H, d) MS (m/z): 666 (M+1)$^+$ Elementary Analysis (for C$_{37}$H$_{39}$N$_5$O$_7$) Calculated: C, 66.75; H, 5.90; N, 10.52 Found: C, 66.91; H, 5.95; N, 10.57

Example 350

Isopropyl 2-[3-[3-[N-(N-methyl-N-phenylcarbamoylmethyl)-N-[2-(N-methyl-N-phenylcarbamoylmethyloxy)phenyl]carbamoyl methyl]ureido]phenyl]acetate (1–350)

mp 158–160° C. $^1$H-NMR (CDCl$_3$) δ: 1.20 (6H, d), 3.22 (3H, s), 3.27 (3H, s), 3.50 (2H, s), 3.53 (1H, d), 3.92 (2H, d), 4.41 (2H, s), 4.68 (1H, d), 4.98 (1H, m), 6.05 (1H, brs), 6.62 (1H, d), 6.87 (1H, d), 6.98 (1H, t), 7.12–7.45 (15H, m), 7.69 (1H, d) MS (m/z): 680 (M+1)$^+$ Elementary Analysis (for C$_{38}$H$_{41}$N$_5$O$_7$) Calculated: C, 67.14; H, 6.08; N, 10.30 Found: C, 67.33; H, 6.14; N, 10.28

Example 351

N-Methyl-N-(3,5-dimethylphenyl)-2-[3-[N-[2-[3-(3-cyanophenyl)ureido]acetyl]-N-(N-methyl-N-phenylcarbamoyl methyl)amino]phenoxy]acetamide (1–351)

mp 118–120° C. $^1$H-NMR (CDCl$_3$) δ: 2.35 (6H, s), 3.23 (3H, s), 3.30 (3H, s), 3.88 (2H, d), 4.10 (2H, s), 4.46 (2H, s), 6.23 (1H, brs), 6.79–7.45 (15H, m), 7.80 (1H, s), 8.48 (1H, brs) MS (m/z): 633 (M+1)+

Example 352

N-Methyl-N-(3,5-dimethylphenyl)-2-[3-[N-[2-[3-[3-(5-tetrazolyl)phenyl]ureido]acetyl]-N-(N-methyl-N-phenyl carbamoylmethyl)amino]phenoxy]acetamide (1–352)

mp 152–155° C. $^1$H-NMR (DMSO-d$_6$) δ: 2.27 (6H, s), 3.19 (6H, brs), 3.63 (2H, s), 4.03 (2H, s), 4.48 (2H, s), 6.40 (1H, brs), 6.83–7.07 and 7.34–7.55 (16H, m), 8.11 (1H, s), 9.08 (1H, s) MS (m/z): 676 (M+1)+

Example 353

Methyl 2-[3-[N-(N-methyl-N-phenylcarbamoylmethyl)-N-[2-[3-(3-methylphenyl)ureido]acetyl]amino]phenoxy]acetate (1– 353)

$^1$H-NMR (CDCl$_3$) δ: 2.26 (3H, s), 3.22 (3H, s), 3.81 (3H, s), 3.89 (2H, d), 4.09 (2H, s), 4.63 (2H, s), 6.06 (1H, brs), 6.77–7.43 (13H, m), 7.69 (1H, brs) MS (m/z): 519 (M+1)+

Example 354

Ethyl 2-[3-[N-(N-methyl-N-phenylcarbamoylmethyl)-N-[2-[3-(3-methylphenyl)ureido]acetyl]amino]phenoxy]acetate (1-354)

mp 92–94° C. $^1$H-NMR (DMSO-d$_6$) δ: 1.21 (3H, t), 2.22 (3H, s), 3.18 (3H, s), 3.64 (2H, s), 4.04 (2H, s), 4.18 (2H, q), 4.80 (2H, s), 6.28 (1H, brs), 6.70 (1H, d), 6.95–7.17 and 7.34–7.48 (12H, m), 8.70 (1H, s) MS (m/z): 533 (M+1)+

Example 355

Isopropyl 2-[3-[N-(N-methyl-N-phenylcarbamoylmethyl)-N-[2-[3-(3-methylphenyl)ureido]acetyl]amino]phenoxy]acetate (1–355)

mp 108–110° C. $^1$H-NMR (DMSO-d$_6$) δ: 1.21 (6H, d), 2.22 (3H, s), 3.18 (3H, s), 3.64 (2H, s), 4.04 (2H, s), 4.77 (2H, s), 4.99 (1H, m), 6.28 (1H, brs), 6.70 (1H, d), 6.96–7.17 and 7.33–7.46 (12H, m), 8.70 (1H, s) MS (m/z): 547 (M+1)+

Elementary Analysis (for C$_{30}$H$_{34}$N$_4$O$_6$) Calculated: C, 65.92; H, 6.27; N, 10.25 Found: C, 65.95; H, 6.25; N, 10.13

Example 356

Cyclopentyl 2-[3-[N-(N-methyl-N-phenylcarbamoylmethyl)-N-[2-[3-(3-methylphenyl)ureido]acetyl]amino]phenoxy] acetate (1–356)

mp 98–100° C. $^1$H-NMR (CDCl$_3$) δ: 1.57–1.88 (8H, m), 2.25 (3H, s), 3.21 (3H, s), 3.90 (2H, d), 4.09 (2H, s), 4.58 (2H, s), 5.29 (1H, m), 6.17 (1H, brs), 6.75 (1H, d), 6.89–7.14 and 7.28–7.34 (12H, m), 7.93 (1H, s) MS (m/z): 573 (M+1)+

Example 357

Cyclohexyl 2-[3-[N-(N-methyl-N-phenylcarbamoylmethyl)-N-[2-[3-(3-methylphenyl)ureido]acetyl]amino]phenoxy] acetate (1–357)

$^1$H-NMR (CDCl$_3$) δ: 1.24–1.86 (10H, m), 2.25 (3H, s), 3.21 (3H, s), 3.90 (2H, d), 4.09 (2H, s), 4.60 (2H, s), 4.90 (1H, m), 6.13 (1H, brs), 6.76 (1H, d), 6.90–7.15 and 7.26–7.34 (12H, m), 7.85 (1H, s) MS (m/z): 589 (M+1)+

Example 358 tert-Butyl 2-[3-[N-(N-methyl-N-phenylcarbamoylmethyl)-N-[2-[3-(3-methylphenyl)ureido]acetyl]amino]phenoxy] acetate (1–358)

mp 114–115° C. $^1$H-NMR (DMSO-d$_6$) δ: 1.43 (9H, s), 2.22 (3H, s), 3.18 (3H, s), 3.64 (2H, s), 4.04 (2H, s), 4.68 (2H, s), 6.28 (1H, brs), 6.69 (1H, d), 6.95 (1H, d), 7.05–7.17 and 7.34–7.46 (11H, m), 8.71 (1H, s) MS (m/z): 561 (M+1)+

Example 359

Methyl 2-[3-[3-[N-[3-(N-methyl-N-phenylcarbamoyl methylthio)phenyl]-N-(3-methylbutyl)carbamoylmethyl]ureido] phenyl] acetate (1–359)

mp 95–97° C. $^1$H-NMR (CDCl$_3$) δ: 0.84 (6H, d), 1.35–1.40 (2H, m), 1.52–1.55 (1H, m), 3.30 (3H, s), 3.54 (2H, s), 3.55 (2H, s), 3.66 (3H, s), 3.69 (2H, t), 3.74 (2H, d), 6.09 (1H, brs), 6.89 (1H, s), 7.03 (1H, d), 7.16 (2H, brs), 7.26–7.45 (10H, m)

Example 360

2-[3-[3-[N-[3-(N-Methyl-N-phenylcarbamoylmethylthio) phenyl]-N-(3-methylbutyl)carbamoylmethyl]ureido] phenyl]acetic acid (1–360)

mp 77–79° C. $^1$H-NMR (CDCl$_3$) δ: 0.85 (6H, d), 1.33–1.39 (2H, m), 1.50–1.55 (1H, m), 3.29 (3H, s), 3.55 (2H, s), 3.58 (2H, s), 3.65–3.71 (4H, m), 6.48 (1H, brs), 6.87 (1H, d), 6.98 (2H, s), 7.15–7.45 (9H, m), 7.52 (1H, d), 7.69 (1H, s) MS (m/z): 577 (M+1)+

Elementary Analysis (for C$_{31}$H$_{36}$N$_4$O$_5$S) Calculated: C, 64.56; H, 6.29; N, 9.71 Found: C, 64.54; H, 6.26; N, 9.73

Example 361

Methyl 2-[3-[3-[N-[2-(N-methyl-N-phenylcarbamoyl methylthio)phenyl]-N-(3-methylbutyl)carbamoylmethyl] ureido]phenyl] acetate (1–361)

mp 134–135° C. $^1$H-NMR (CDCl$_3$) δ: 0.83–0.97 (6H, m), 1.34 (1H, m), 1.52–1.55 (2H, m), 3.09 (1H, m), 3.31 (3H, s), 3.56 (2H, s), 3.58 (2H, s), 3.60 (1H, d), 3.67 (3H, s), 3.84 (1H, dd), 4.13 (1H, m) 5.94 (1H, brs), 6.92 (1H, brs), 7.10–7.49 (13H, m)

Example 362

2-[3-[3-[N-[2-(N-Methyl-N-phenylcarbamoylmethylthio) phenyl]-N-(3-methylbutyl)carbamoylmethyl]ureido] phenyl]acetic acid (1–362)

$^1$H-NMR (CDCl$_3$) δ: 0.84–0.88 (6H, m), 1.30–1.36 (1H, m), 1.43–1.56 (2H, m), 3.04–3.11 (1H, m), 3.29 (3H, s), 3.48 (1H, dd), 3.56 (2H, s), 3.60 (2H, s), 3.83 (1H, dd), 4.09–4.17 (1H, m), 6.50 (1H, brs), 6.88 (1H, d), 6.96 (1H, s), 7.08 (1H, d), 7.16–7.46 (9H, m), 7.59 (1H, d), 7.63 (1H, s) MS (m/z): 577 (M+1)+

Example 363

Methyl 2-[3-[3-[N-[2-[N-methyl-N-(3,5-dimethylphenyl) carbamoylmethylthio]phenyl]-N-(3-methylbutyl)carbamoyl methyl]ureido]phenyl] acetate (1–363)

$^1$H-NMR (CDCl$_3$) δ: 0.82–0.86 (6H, m), 1.31–1.35 (1H, m), 1.43–1.54 (2H, m), 2.34 (6H, s), 3.08–3.13 (1H, m), 3.28 (3H, s), 3.54 (2H, s), 3.59 (2H, s), 3.61–3.63 (1H, m), 3.66 (3H, s), 3.85 (1H, dd), 4.10–4.17 (1H, m), 6.05 (1H, brs), 6.84–6.91 (3H, m), 7.01 (1H, s), 7.11–7.31 (7H, m), 7.37 (1H, s)

Example 364

2-[3-[3-[N-[2-[N-Methyl-N-(3,5-dimethylphenyl)
carbamoyl methylthio]phenyl]-N-(3-methylbutyl)
carbamoylmethyl] ureido]phenyl]acetic acid
(1–364)

mp 128–130° C. $^1$H-NMR (CDCl$_3$) δ: 0.83–0.87 (6H, m), 1.33 (1H, m), 1.44–1.55 (2H, m), 2.32 (6H, s), 3.09 (1H, m), 3.26 (3H, s), 3.49 (1H, d), 3.58 (4H, brs), 3.84 (1H, dd), 4.11–4.13 (1H, m), 6.48 (1H, brs), 6.84 (2H, s), 6.87 (1H, d), 6.96 (1H, s), 7.00 (1H, s), 7.09 (1H, d), 7.15–7.19 (2H, m), 7.26–7.31 (2H, m), 7.55 (1H, d), 7.66 (1H, s) MS (m/z): 605 (M+1)$^+$

Example 365

Methyl 2-[3-[3-[N-cyclohexyl-N-[2-(N-methyl-N-
phenyl carbamoylmethylthio)phenyl]
carbamoylmethyl]ureido]phenyl] acetate (1–365)

$^1$H-NMR (CDCl$_3$) δ: 0.92–1.26 and 1.46–1.78 (11H, m), 2.90 (1H, dd), 3.31 (3H, s), 3.56 (2H, s), 3.57 (2H, s), 3.67 (3H, s), 3.68 (1H, d), 3.85 (1H, dd), 4.05 (1H, dd), 5.88 (1H, brs), 6.91 (1H, d), 6.99 (1H, brs), 7.18–7.48 (12H, m)

Example 366

2-[3-[3-[N-Cyclohexylmethyl-N-[2-(N-methyl-N-
phenyl carbamoylmethylthio)phenyl]
carbamoylmethyl]ureido]phenyl] acetic acid
(1–366)

$^1$H-NMR (CDCl$_3$) δ: 0.92–1.14 and 1.43–1.76 (11H, m), 2.89 (1H, dd), 3.29 (3H, s), 3.45 (1H, dd), 3.56 (2H, s), 3.59 (2H, s), 3.86 (1H, dd), 4.05 (1H, dd), 6.50 (1H, brs), 6.88 (1H, d), 6.96 (1H, s), 7.06–7.46 (10H, m), 7.60 (1H, d), 7.64 (1H, s) MS (m/z): 603 (M+1)$^+$

Example 367

2-[3-[3-[N-[2-[N-(3-Aminophenyl)-N-
methylcarbamoyl methyloxy]phenyl]-N-(3-
methylbutyl)carbamoylmethyl] ureido]phenyl]acetic
acid (1–367)

mp 169–171° C. $^1$H-NMR (CDCl$_3$) δ: 0.85–0.87 (6H, m), 1.32–1.37 (2H, m), 1.53–1.60 (1H, m), 3.27 (3H, s), 3.33–3.40 (1H, m), 3.50 (2H, s), 3.62 (1H, d), 3.80 (1H, dd), 3.96–4.03 (1H, m), 4.53 (2H, q), 6.29 (1H, brs), 6.59 (2H, s), 6.68 (1H, d), 6.73 (1H, d), 6.84 (1H, d), 6.97 (1H, t), 7.12–7.28 (6H, m), 8.25 (1H, s) MS (m/z): 576 (M+1)$^+$ Elementary Analysis (for C$_{31}$H$_{37}$N$_5$O$_6$) Calculated: C, 64.68; H, 6.48; N, 12.17 Found: C, 64.27; H, 6.39; N, 12.36

Example 368

Methyl 2-[3-[3-[N-(4-ethylhexyl)-N-[2-(N-methyl-
N-phenylcarbamoylmethyloxy)phenyl]
carbamoylmethyl]ureido] phenyl]acetate (1–368)

$^1$H-NMR (CDCl$_3$) δ: 0.76 (6H, t), 1.06–1.26 (7H, m), 1.43–1.46 (2H, m), 3.28–3.33 (1H, m), 3.33 (3H, s), 3.55 (2H, s), 3.66 (3H, s), 3.87–3.91 (3H, m), 4.48 (2H, s), 6.06 (1H, brs), 6.65 (1H, d), 6.88 (1H, d), 6.97 (1H, t), 7.15–7.36 and 7.42–7.53 (11H, m)

Example 369

2-[3-[3-[N-(4-Ethylhexyl)-N-[2-(N-methyl-N-phenyl
carbamoylmethyloxy)phenyl]carbamoylmethyl]
ureido] phenyl]acetic acid (1–369)

mp 203–204° C. $^1$H-NMR (CDCl$_3$) δ: 0.78 (6H, t), 1.09–1.23 (7H, m), 1.46 (2H, m), 3.26–3.30 (1H, m), 3.29 (3H, s), 3.60 (2H, s), 3.62 (1H, d), 3.86 (1H, dd), 3.92–3.98 (1H, m), 4.45 (2H, s), 6.50 (1H, s), 6.68 (1H, d), 6.87 (1H, d), 6.97–6.99 (2H, m), 7.13 (1H, d), 7.18 (1H, t), 7.20–7.27 and 7.40–7.49 (6H, m), 7.60 (2H, brs) MS(m/z): 603 (M+1)$^+$ Elementary Analysis (for C$_{34}$H$_{42}$N$_4$O$_6$) Calculated: C, 67.75; H, 7.02; N, 9.30 Found: C, 67.40; H, 6.93; N, 9.30

Example 370

Methyl (±)-2-[3-[3-[N-[2-[N-methyl-N-(3,5-
dimethyl phenyl)carbamoylmethyloxy]phenyl]-N-
(3-methylpentyl) carbamoylmethyl]ureido]phenyl]
acetate (1–370)

mp 149–151° C. $^1$H-NMR (CDCl$_3$) δ: 0.77–0.82 (6H, m), 1.06–1.11, 1.26–1.31 and 1.56–1.60 (5H, m), 2.37 (6H, s), 3.29 (3H, s), 3.30–3.33 (1H, m), 3.55 (2H, s), 3.66 (3H, s), 3.88–4.01 (3H, m), 4.51 (2H, s), 6.13 (1H, brs), 6.66 (1H, d), 6.87 (1H, d), 6.90 (2H, s), 6.97 (1H, t), 7.06 (1H, s), 7.16–7.30 (5H, m), 7.51 (1H, s)

Example 371

(±)-2-[3-[3-[N-[2-[N-Methyl-N-(3,5-
dimethylphenyl) carbamoylmethyloxy]phenyl]-N-
(3-methylpentyl)carbamoyl methyl]ureido]phenyl]
acetic acid (1–371)

mp 156–157° C. $^1$H-NMR (CDCl$_3$) δ: 0.78–0.82 (6H, m), 1.07–1.12, 1.30 and 1.52 (5H, m), 2.35 (6H, s), 3.25 (3H, s), 3.29–3.35 (1H, m), 3.58 (2H, s), 3.67 (1H, d), 3.86 (1H, d), 4.02 (1H, m), 4.47 (2H, q), 6.49 (1H, brs), 6.68 (1H, d), 6.85–6.87 (3H, m), 6.95–6.97 (2H, m), 7.03 (1H, s), 7.12–7.29 (3H, m), 7.55 (1H, d), 7.67 (1H, s) MS (m/z): 603 (M+1)$^+$

Example 372

Methyl (±)-2-[3-[3-[N-[2-[N-(3-chlorophenyl)-N-
methylcarbamoylmethyloxy]phenyl]-N-(3-
methylpentyl) carbamoylmethyl]ureido]phenyl]
acetate (1–372)

mp 97–98° C. $^1$H-NMR (CDCl$_3$) δ: 0.78–0.83 (6H, m), 1.05–1.12, 1.25–1.31 and 1.48–1.51 (5H, m), 3.31 (3H, s), 3.31–3.33 (1H, m), 3.56 (2H, s), 3.67 (3H, s), 3.84 (2H, s), 3.95–3.97 (1H, m), 4.50 (2H, s), 5.99 (1H, brs), 6.67 (1H, d), 6.89 (1H, d), 6.99 (1H, t), 7.15–7.34 (8H, m), 7.43 (2H, brs)

Example 373

(±)-2-[3-[3-[N-[2-[N-(3-Chlorophenyl)-N-
methylcarbamoyl methyloxy]phenyl]-N-(3-
methylpentyl)carbamoylmethyl] ureido]phenyl]
acetic acid (1–373)

mp 148–149° C. $^1$H-NMR (CDCl$_3$) δ: 0.77–0.83 (6H, m), 1.06–1.15, 1.25–1.36 and 1.45–1.51 (5H, m), 3.26 (3H, s), 3.30–3.37 (1H, m), 3.58 (2H, s), 3.64 (1H, d), 3.84 (1H, dd), 3.95–4.03 (1H, m), 4.47 (2H, s), 6.51 (1H, s), 6.70 (1H, d), 6.86 (1H, d), 6.96–7.00 (2H, m), 7.12–7.39 (7H, m), 7.56 (1H, d), 7.65 (1H, s)

Elementary Analysis (for C$_{32}$H$_{37}$ClN$_4$O$_6$) Calculated: C, 63.10; H, 6.12; N, 9.20 Found: C, 62.93; H, 6.08; N, 8.86

Example 374

Methyl (±)-2-[3-[3-[N-(2-hydroxy-3,3-
dimethylbutyl)-N-[2-(N-methyl-N-
phenylcarbamoylmethyloxy)phenyl]
carbamoylmethyl]ureido]phenyl]acetate (1–374)

mp 104–106° C. $^1$H-NMR (CDCl$_3$) δ: 0.86 (9/2H, s), 0.88 (9/2H, s), 3.21 (3/2H, s), 3.32 (3/2H, s), 3.25–3.34 (1H, m), 3.53 (1H, s), 3.55 (1H, s), 3.58–3.68 (1H, m), 3.64 (3/2H, s), 3.66 (3/2H, s), 3.78–3.92 (3H, m), 4.41–4.51 (3H, m), 6.03 (1/2H, brs), 6.26 (1/2H, brs), 6.60 (1/2H, d), 6.64 (1/2H, d), 6.87 (1H, t), 6.97–7.04 (1H, m), 7.12–7.34 and 7.43–7.52 (11H, m)

Example 375

(±)-2-[3-[3-[N-(2-Hydroxy-3,3-dimethylbutyl)-N-[2-(N-methyl-N-phenylcarbamoylmethyloxy)phenyl] carbamoyl methyl]ureido]phenyl]acetic acid (1–375)

mp 188–189° C. $^1$H-NMR (DMSO-$d_6$) δ: 0.79 (9/2H, s), 0.83 (9/2H, s), 3.14–3.19 (1H, m), 3.19 (3H, s), 3.34 (2H, s), 3.40–3.46 (2H, m), 3.66 (1H, d), 3.93–4.02 (1H, m), 4.53–4.68 (3H, m), 6.29 (1H, brs), 6.76 (1H, d), 6.83 (1H, brs), 7.02–7.50 (11H, m), 8.80 (1/2H, s), 8.83 (½H, s), 12.26 (1H, brs) MS (m/z): 591 (M+1)$^+$ Example 376

Methyl 2-[3-[3-[N-(3,3-dimethyl-2-oxobutyl)-N-[2-(N-methyl-N-phenylcarbamoylmethyloxy)phenyl] carbamoyl methyl]ureido]phenyl]acetate (1–376)

$^1$H-NMR (CDCl$_3$) δ: 1.11 (9H, s), 3.32 (3H, s), 3.54 (2H, s), 3.65 (3H, s), 3.92 (2H, d), 4.03 (1H, d), 4.52 (2H, s), 5.20 (1H, d), 6.03 (1H, brs), 6.64 (1H, d), 6.86 (1H, d), 6.96 (1H, t), 7.15–7.53 (11H, m)

Example 377

2-[3-[3-[N-(3,3-Dimethyl-2-oxobutyl)-N-[2-(N-methyl-N-phenylcarbamoylmethyloxy)phenyl] carbamoylmethyl]ureido] phenyl]acetic acid (1–377)

mp 141–143° C. $^1$H-NMR (CDCl$_3$) δ: 1.13 (9H, s), 3.29 (3H, s), 3.56 (2H, s), 3.78 (1H, dd), 3.90 (1H, dd), 4.08 (1H, d), 4.49 (2H, s), 5.23 (1H, d), 6.43 (1H, brs), 6.64 (1H, d), 6.84 (1H, d), 6.93–6.97 (2H, m), 7.15 (1H, t), 7.23–7.28 (3H, m), 7.42–7.56 (5H, m), 7.65 (1H, s) MS (m/z): 589 (M+1)$^+$ Elementary Analysis (for C$_{32}$H$_{36}$N$_4$O$_7$) Calculated: C, 65.29; H, 6.16; N, 9.52 Found: C, 64.97; H, 6.09; N, 9.08

Example 378

Methyl 2-[3-[3-[N-[2-[N-(3-chlorophenyl)-N-methyl carbamoylmethyloxy]phenyl]-N-(4-methylpentyl) carbamoyl methyl]ureido]phenyl]acetate (1–378)

mp 100–102° C. $^1$H-NMR (CDCl$_3$) δ: 0.79 (6H, d), 1.12 (2H, m), 1.43–1.48 (3H, m), 3.29 (3H, s), 3.30–3.33 (1H, m), 3.54 (2H, s), 3.65 (3H, s), 3.78 (1H, d), 3.87 (1H, dd), 3.90–4.01 (1H, m), 4.49 (2H, s), 6.19 (1H, brs), 6.70 (1H, brs), 6.87 (1H, d), 7.00 (1H, t), 7.15–7.41 (9H, m), 7.59 (1H, s)

Example 379

2-[3-[3-[N-[2-[N-(3-Chlorophenyl)-N-methylcarbamoyl methyloxy]phenyl]-N-(4-methylpentyl)carbamoylmethyl] ureido]phenyl] acetic acid (1–379)

mp 140–142° C. $^1$H-NMR (CDCl$_3$) δ: 0.81 (6H, d), 1.09–1.15 (2H, m), 1.44–1.52 (3H, m), 3.26 (3H, s), 3.30–3.34 (1H, m), 3.58 (2H, s), 3.64 (1H, d), 3.84 (1H, dd), 3.90–3.98 (1H, m), 4.47 (2H, s), 6.48 (1H, brs), 6.70 (1H, d), 6.86 (1H, d), 6.97–7.00 (2H, m), 7.13–7.42 (7H, m), 7.55 (1H, d), 7.65 (1H, s)

Elementary Analysis (for C$_{32}$H$_{37}$ClN$_4$O$_6$) Calculated: C, 63.10; H, 6.12; N, 9.20 Found: C, 63.15; H, 6.10; N, 9.12

Example 380

Methyl (±)-2-[3-[3-[N-[2-(N-methyl-N-phenylcarbamoyl methyloxy)phenyl]-N-(3-methylbutyl)carbamoylmethyl] ureido]phenyl] propionate (1–380)

mp 127–129° C. $^1$H-NMR (CDCl$_3$) δ: 0.81–0.85 (6H, m), 1.31–1.41 (2H, m), 1.46 (3H, d), 1.48–1.57 (1H, m), 3.31–3.38 (1H, m), 3.34 (3H, s), 3.63 (3H, s), 3.65 (1H, q), 3.85–3.95 (3H, m), 4.49 (2H, s), 6.07 (1H, brs), 6.65 (1H, d), 6.90 (1H, d), 6.97 (1H, m), 7.14–7.53 (11H, m)

Example 381

(±)-2-[3-[3-[N-[2-(N-Methyl-N-phenylcarbamoylmethyloxy) phenyl]-N-(3-methylbutyl)carbamoylmethyl]ureido] phenyl] propionic acid (1–381)

mp 100–102° C. $^1$H-NMR (CDCl$_3$) δ: 0.82–0.85 (6H, m), 1.36–1.38 (2H, m), 1.52–1.53 (1H, m), 1.52 (3H, d), 3.28 (3H, s), 3.29–3.34 (1H, m), 3.61 (1H, d), 3.73 (1H, q), 3.83 (1H, dd), 3.96–4.01 (1H, m), 4.45 (2H, s), 6.56 (1H, brs), 6.67 (1H, d), 6.91–7.47 (11H, m), 7.65 (1H, d), 7.77 (1H, d) MS (m/z): 575 (M+1)$^+$ Elementary Analysis (for C$_{32}$H$_{38}$N$_4$O$_6$) Calculated: C, 66.88; H, 6.66; N, 9.75 Found: C, 66.43; H, 6.61; N, 9.67

Example 382

Methyl (±)-2-[3-[3-[N-[2-[N-(3-chlorophenyl)-N-methylcarbamoylmethyloxy]phenyl]-N-(4-methylpentyl)carbamoyl methyl]ureido]phenyl] propionate (1–382)

mp 159–160° C. $^1$H-NMR (CDCl$_3$) δ: 0.80 (6H, d,), 1.11–1.14 (2H, m), 1.44–1.48 (3H, m), 1.45 (3H, d), 3.30 (3H, s), 3.30–3.33 (1H, m), 3.63 (3H, s), 3,65 (1H, q), 3.82–3.91 (3H, m), 4.51 (2H, s), 6.06 (1H, brs), 6.68 (1H, brs), 6.90 (1H, d), 6.97–7.02 (1H, m), 7.16–7.43 (10H, m)

Example 383

(±)-2-[3-[3-[N-[2-[N-(3-Chlorophenyl)-N-methylcarbamoyl methyloxy]phenyl]-N-(4-methylpentyl)carbamoylmethyl] ureido]phenyl] propionic acid(1–383)

mp 117–118° C. $^1$H-NMR (CDCl$_3$) δ: 0.79–0.82 (6H, m), 1.07–1.14 (2H, m), 1.43–1.49 (3H, m), 1.52 (3H, d), 3.26 (3H, s), 3.27–3.32 (1H, m), 3.62 (1H, d), 3.72 (1H, q), 3.82 (1H, dd), 3.90–3.97 (1H, m), 4.47 (2H, s), 6.55 (1H, brs), 6.70 (1H, d), 6.91–7.41 (10H, m), 7.63 (1H, d), 7.77 (1H, s)

Elementary Analysis (for C$_{33}$H$_{39}$ClN$_4$O$_6$) Calculated: C, 63.61; H, 6.31; N, 8.99 Found: C, 63.41; H, 6.30; N, 8.88

Example 384

Methyl (±)-2-[3-[3-[N-[2-(N-ethyl-N-phenylcarbamoyl methyloxy)phenyl]-N-(3-methylpentyl)carbamoylmethyl] ureido]phenyl] acetate (1–384)

$^1$H-NMR (CDCl$_3$) δ: 0.76–0.82 (6H, m), 1.04–1.67 (5H, m), 1.17 (3H, t), 3.34 (1H, m), 3.56 (2H, s), 3.67 (3H, s), 3.75–3.95 (5H, m), 4.43 (2H, s), 6.04 (1H, brs), 6.64 (1H, d), 6.89 (1H, d), 6.97 (1H, t), 7.14–7.32 and 7.44–7.54 (11H, m)

Example 385

(±)-2-[3-[3-[N-[2-(N-Ethyl-N-phenylcarbamoylmethyloxy) phenyl]-N-(3-methylpentyl)carbamoylmethyl]ureido]phenyl] acetic acid (1–385)

mp 150–151° C. $^1$H-NMR (CDCl$_3$) δ: 0.78–0.82 (6H, m), 1.05–1.51 (5H, m), 1.12 (3H, t), 3.31–3.37 (1H, m), 3.59 (2H, s), 3.61 (1H, d), 3.76 (2H, q), 3.86 (1H, dd), 3.96–4.05 (1H, m), 4.39 (2H, q), 6.51 (1H, brs), 6.66 (1H, d), 6.86 (1H, d), 6.94–6.98 (2H, m), 7.11–7.29 and 7.39–7.49 (8H, m), 7.57 (1H, d), 7.65 (1H, s) MS (m/z): 589 (M+1)$^+$ Elementary Analysis (for C$_{33}$H$_{40}$N$_4$O$_6$) Calculated: C, 67.33; H, 6.85; N, 9.52 Found: C, 67.06; H, 6.91; N, 9.22

Example 386

Methyl (±)-2-[3-[3-[N-[2-[N-ethyl-N-(3,5-dimethyl phenyl)carbamoylmethyloxy]phenyl]-N-(3-methylpentyl) carbamoylmethyl]ureido]phenyl] acetate (1–386)

mp 127–129° C. $^1$H-NMR (CDCl$_3$) δ: 0.76–0.85 (6H, m), 1.04–1.53 (5H, m), 1.16 (3H, t), 2.38 (6H, s), 3.31–3.33 (1H, m), 3.56 (2H, s), 3.67 (3H, s), 3.69–3.86 (2H, m), 3.89–3.97 (3H, m), 4.46 (2H, s), 6.10 (1H, brs), 6.65 (1H, d), 6.87–6.88 (3H, m), 6.96 (1H, t), 7.08 (1H, s), 7.13–7.29 (5H, m), 7.43(1H, s)

Example 387

(±)-2-[3-[3-[N-[2-[N-Ethyl-N-(3,5-dimethylphenyl) carbamoylmethyloxy]phenyl]-N-(3-methylpentyl) carbamoyl methyl]ureido]phenyl]acetic acid (1–387)

mp 153–154° C. $^1$H-NMR (CDCl$_3$) δ: 0.78–0.82 (6H, m), 1.05–1.52 (5H, m), 1.12 (3H, t), 2.36 (6H, s), 3.32–3.38 (1H, m), 3.58 (2H, s), 3.63–3.76 (3H, m), 3.86 (1H, dd), 4.01–4.03 (1H, m), 4.42 (2H, q), 6.51 (1H, brs), 6.67 (1H, d), 6.84–6.87 (3H, m), 6.94–6.98 (2H, m), 7.05 (1H, s), 7.11–7.20 (2H, m), 7.27 (1H, t), 7.58 (1H, brs), 7.64 (1H, s) MS (m/z): 617 (M+1)$^+$ Elementary Analysis (for C$_{35}$H$_{44}$N$_4$O$_6$) Calculated: C, 68.16; H, 7.19; N, 9.08 Found: C, 68.05; H, 7.23; N, 9.19

Example 388

Methyl 2-[3-[3-[N-[2-(N-methyl-N-phenylcarbamoyl -methyloxy)phenyl]-N-(3,3-dimethylbutyl)carbamoylmethyl] ureido]phenyl] acetate (1–388)

mp 135–136° C. $^1$H-NMR (CDCl$_3$) δ: 0.82 (9H, s), 1.36–1.47 (2H, m), 3.31 (3H, s), 3.35–3.38 (1H, m), 3.54 (2H, s), 3.65 (3H, s), 3.85 (1H, d), 3.93 (1H, dd), 3.97–4.01 (1H, m), 4.48 (2H, s), 6.26 (1H, brs), 6.68 (1H, d), 6.86 (1H, d), 6.98 (1H, t), 7.11–7.51 (10H, m), 7.72 (1H, s)

Example 389

2-[3-[3-[N-[2-(N-Methyl-N-phenylcarbamoylmethyloxy) phenyl]-N-(3,3-dimethylbutyl)carbamoylmethyl]ureido] phenyl] acetic acid (1–389)

mp 193–194° C. $^1$H-NMR (CDCl$_3$) δ: 0.84 (9H, s), 1.38–1.47 (2H, m), 3.29 (3H, s), 3.30–3.33 (1H, m), 3.59 (2H, s), 3.62 (1H, d), 3.85 (1H, dd), 3.99–4.02 (1H, m), 4.46 (2H, d), 6.49 (1H, brs), 6.68 (1H, d), 6.87 (1H, d), 6.95–6.99 (2H, m), 7.13 (1H, d), 7.18 (1H, t), 7.26–7.28 (3H, m), 7.40–7.49 (3H, m), 7.58 (1H, d), 7.64 (1H, s) MS (m/z): 575 (M+1)$^+$ Elementary Analysis (for C$_{32}$H$_{38}$N$_4$O$_6$) Calculated: C, 66.88; H, 6.66; N, 9.75 Found: C, 66.43; H, 6.79; N, 9.25

Example 390 tert-Butyl (±)-2-[3-[3-[N-[2-[N-(3,5-difluorophenyl)-N-methylcarbamoylmethyloxy] phenyl]-N-(3-methylpentyl)carbamoyl methyl] ureido]phenyl]acetate (1–390)

$^1$H-NMR (CDCl$_3$) δ: 0.78–0.83 (6H, m), 1.09–1.54 (5H, m), 1.42 (9H, s), 3.30 (3H, s), 3.30–3.32 (1H, m), 3.46 (2H, s), 3.83 (2H, d), 3.98 (1H, m), 4.57 (2H, s), 5.93 (1H, brs), 6.70 (1H, brs), 6.89–6.90 (3H, m), 7.00 (1H, t), 7.15–7.26 (7H, m)

Example 391

(±)-2-[3-[3-[N-[2-[N-(3,5-Difluorophenyl)-N-methyl carbamoylmethyloxy]phenyl]-N-(3-methylpentyl) carbamoyl methyl]ureido]phenyl]acetic acid (1–391)

mp 135–136° C. $^1$H-NMR (CDCl$_3$) δ: 0.77–0.83 (6H, m), 1.06–1.52 (5H, m), 3.25 (3H, s), 3.32–3.37 (1H, m), 3.57 (2H, s), 3.66 (1H, d), 3.81 (1H, d), 3.95–4.00 (1H, m), 4.55 (2H, s), 6.51 (1H, brs), 6.74 (1H, brs), 6.85–6.86 (4H, m), 6.95 (1H, s), 7.00 (1H, t), 7.12–7.18 (2H, m), 7.29 (1H, t), 7.54 (1H, d), 7.66 (1H, s) MS (m/z): 611 (M+1)$^+$ Elementary Analysis (for C$_{32}$H$_{36}$F$_2$N$_4$O$_6$) Calculated: C, 62.94; H, 5.94; N, 9.17 Found: C, 62.65; H, 5.89; N, 8.93

Example 392

Calcium (±)-2-[3-[3-[N-[2-[N-(3-chlorophenyl)-N-methylcarbamoylmethyloxy]phenyl]-N-(3-methylbutyl) carbamoylmethyl]ureido]phenyl] propionate(1–392)

$^1$H-NMR (DMSO-d$_6$) δ: 0.81–0.84 (6H, m), 1.25 (3H, d), 1.25–1.30 (2H, m), 1.50–1.57 (1H, m), 3.21 (3H, s), 3.29–3.46 (3H, m), 3.65 (1H, d), 3.82–3.90 (1H, m), 4.63 (2H, brs), 6.45 (1H, brs), 6.82 (1H, d), 7.00–7.05 (3H, m), 7.23–7.70 (8H, m), 8.99 (1H, s)

Elementary Analysis (for C$_{64}$H$_{72}$N$_8$O$_{12}$Ca.2H$_2$O) Calculated: C, 59.48; H, 5.93; N, 8.67 Found: C, 59.51; H, 5.83; N, 8.61

Example 393

N-Methyl-N-phenyl-2-[2-[N-(3-methylbutyl)-N-[2-[3-(3-methylphenyl)ureido]acetyl]amino]phenoxy] acetamide (1–393)

mp 128–130° C. $^1$H-NMR (CDCl$_3$) δ: 0.82–0.85 (6H, m), 1.32–1.41 (2H, m), 1.51–1.57 (1H, m), 2.28 (3H, s), 3.32 (3H, s), 3.34–3.41 (1H, m), 3.78 (1H, d), 3.88 (1H, d), 3.92–3.97 (1H, m), 4.47 (2H, s), 6.05 (1H, brs), 6.66 (1H, d), 6.79 (1H, d), 6.98 (1H, t), 7.06–7.29 and 7.41–7.52 (11H, m) MS (m/z): 517 (M+1)$^+$ Elementary Analysis (for C$_{30}$H$_{36}$N$_4$O$_4$) Calculated: C, 69.75; H, 7.02; N, 10.84 Found: C, 69.56; H, 6.96; N, 10.85

Example 394

N-Methyl-N-phenyl-2-[2-[N-[2-[3-(3-hydroxymethylphenyl) ureido]acetyl]-N-(3-methylbutyl)amino]phenoxy]acetamide (1–394)

$^1$H-NMR (CDCl$_3$) δ: 0.81–0.84 (6H, m), 1.31–1.42 (2H, m), 1.51–1.58 (1H, m), 2.83 (1H, brs), 3.30 (3H, s), 3.34–3.41 (1H, m), 3.74 (1H, d), 3.90 (1H, dd), 3.96–4.04 (1H, m), 4.45 (2H, s), 4.53 (2H, s), 6.28 (1H, brs), 6.66 (1H, d), 6.88 (1H, d), 6.99 (1H, t), 7.11–7.29 and 7.41–7.51 (10H, m), 7.71 (1H, s) MS (m/z): 533 (M+1)$^+$

Example 395

N-Methyl-N-phenyl-2-[2-[N-[2-[3-[3-(N,N-dimethylamino) phenyl]ureido]acetyl]-N-(3-methylbutyl)amino]phenoxy] acetamide (1–395)

mp 124–126° C. $^1$H-NMR (CDCl$_3$) δ: 0.82–0.85 (6H, m), 1.31–1.36 (2H, m), 1.50–1.55 (1H, m), 2.91 (6H, s), 3.31 (3H, s), 3.32–3.37 (1H, m), 3.71 (1H, d), 3.87 (1H, dd), 3.94–3.98 (1H, m), 4.45 (2H, s), 6.10 (1H, brs), 6.39 (1H, d), 6.50 (1H, d), 6.66 (1H, d), 6.91 (1H, s), 6.96 (1H, t), 7.06–7.13, 7.23–7.28 and 7.41–7.50 (9H, m) MS (m/z): 546 (M+1)$^+$ Elementary Analysis (for C$_{31}$H$_{39}$N$_5$O$_4$) Calculated: C, 68.23; H, 7.20; N, 12.83 Found: C, 68.20; H, 7.16; N, 13.18

Example 396

N-Methyl-N-phenyl-2-[2-[N-[2-[3-(3-cyanophenyl) ureido] acetyl]-N-(3-methylbutyl)amino]phenoxy] acetamide (1–396)

mp 157–159° C. $^1$H-NMR (CDCl$_3$) δ: 0.81–0.84 (6H, m), 1.34–1.38 (2H, m), 1.51–1.56 (1H, m), 3.35 (3H, s), 3.37 (1H, m), 3.91 (3H, brs), 4.52 (2H, s), 6.31 (1H, brs), 6.67 (1H, d), 7.01 (1H, t), 7.15–7.34 and 7.46–7.55 (10H, m), 7.66 (1H, s), 8.08 (1H, brs) MS (m/z): 528 (M+1)$^+$ Elementary Analysis (for C$_{30}$H$_{33}$N$_5$O$_4$) Calculated: C, 68.29; H, 6.30; N, 13.27 Found: C, 68.18; H, 6.25; N, 13.10

Example 397

N-Methyl-N-phenyl-2-[2-[N-(3-methylbutyl)-N-[2-[3-[3-(5-tetrazolyl)phenyl]ureido]acetyl]amino]phenoxy] acetamide (1–397)

$^1$H-NMR (CDCl$_3$) δ: 0.85–0.87 (6H, m), 1.24–1.28 (2H, m), 1.43 (1H, m), 3.27 (3H, s), 3.39 (1H, m), 3.94–4.01 (3H, m), 4.45 (2H, s), 6.52 (1H, brs), 6.69 (1H, d), 6.93 (1H, brs), 7.03 (1H, t), 7.16–7.51 (11H, m), 8.73 (1H, brs) MS (m/z): 571 (M+1)$^+$

Example 398

N-Methyl-N-phenyl-2-[2-[N-(3-methylbutyl)-N-[2-[3-[3-(5-oxo-1,2,4-oxadiazol-3-yl)phenyl]ureido] acetyl]amino] phenoxy]acetamide (1–398)

mp 151–152° C. $^1$H-NMR (CDCl$_3$) δ: 0.70–0.73 (6H, m), 1.29–1.33 (2H, m), 1.44–1.50 (1H, m), 3.29 (3H, s), 3.39–3.44 (1H, m), 3.92–3.99 (3H, m), 4.51 (2H, s), 6.39 (1H, brs), 6.41 (1H, d), 6.86 (1H, s), 7.06 (1H, t), 7.12 (1H, t), 7.21 (1H, d), 7.27–7.54 (8H, m), 8.69 (1H, s), 11.43 (1H, brs)

Example 399

Benzyl 3-[3-[N-[2-(N-methyl-N-phenylcarbamoylmethyloxy) phenyl]-N-(3-methylbutyl)carbamoylmethyl]ureido]benzoate (1–399)

$^1$H-NMR (CDCl$_3$) δ: 0.80–0.83 (6H, m), 1.26–1.38 (2H, m), 1.48–1.53 (1H, m), 3.29 (3H, s), 3.30–3.33 (1H, m), 3.86–3.96 (3H, m), 4.49 (2H, s), 5.32 (2H, s), 6.09 (1H, brs), 6.62 (1H, d), 6.96 (1H, t), 7.14 (1H, d), 7.21 (1H, t), 7.26–7.53 (11H, m), 7.65 (2H, d), 7.78 (1H, s), 7.85 (1H, d)

Example 400

3-[3-[N-[2-(N-Methyl-N-phenylcarbamoylmethyloxy)phenyl] -N-(3-methylbutyl)carbamoylmethyl]ureido]benzoic acid (1–400)

$^1$H-NMR (CDCl$_3$) δ: 0.89–0.91 (6H, m), 1.36–1.48 (2H, m), 1.57–1.63 (1H, m), 3.30 (3H, s), 3.39–3.46 (1H, m), 3.65 (1H, d), 3.88 (1H, dd), 4.04–4.09 (1H, m), 4.46 (2H, s), 6.72 (1H, d), 6.99 (1H, t), 7.11–7.13 (2H, m), 7.26–7.49 (7H, m), 7.64 (1H, d), 7.75 (1H, s), 8.21 (1H, s), 8.31 (1H, d)

Example 401

N-Methyl-N-(2-methylphenyl)-2-[3-[N-(N-methyl-N-phenylcarbamoylmethyl)-N-[2-[3-[3-[(N,N-dimethylamino) methyl]phenyl]ureido]acetyl]amino] phenoxy]acetamide(1–401):

$^1$H-NMR (CDCl$_3$) δ: 2.30 (3H, s), 2.37 (6H, s), 3.22 (3H, s), 3.25 (3H, s), 3.59 (2H, s), 3.84 (2H, d), 4.07 (2H, s), 4.19–4.42 (2H, m), 6.15 (1H, brs), 6.76–7.37 (18H, m) MS (m/z): 651 (M+1)$^+$

Example 402

N-Methyl-N-(2-methylphenyl)-2-[3-[N-(N-methyl-N-phenylcarbamoylmethyl)-N-[2-[3-[3-(N,N-dimethylamino)phenyl] ureido]acetyl]amino] phenoxy]acetamide(1–402)

mp 195–197° C. $^1$H-NMR (CDCl$_3$) δ: 2.30 (3H, s), 2.93 (6H, s), 3.25 (3H, s), 3.26 (3H, s), 3.83–4.40 (6H, m), 5.70 (1H, brs), 6.42–7.42 (18H, m) MS (m/z): 637 (M+1)$^+$

Example 403

(±)-2-[3-[3-[N-[2-[N-(3-Chlorophenyl)-N-methylcarbamoyl methyloxy]phenyl]-N-(N-methyl-N-phenylcarbamoylmethyl) carbamoylmethyl] ureido]phenyl] propionic acid (1–403)

$^1$H-NMR (CDCl$_3$) δ: 1.46–1.51 (3H, m), 3.20–3.25 (6H, m), 3.46–3.87 (5H, m), 4.39 (2H, s), 6.35 (1H, brs), 6.63–7.67 (18H, m)

Example 404

Methyl 2-[3-[3-[N-[3-[N-(3-chlorophenyl)-N-methylcarbamoylmethyloxy]phenyl]-N-(N-methyl-N-phenylcarbamoylmethyl)carbamoylmethyl] ureido] phenyl] acetate (1–404)

mp 148–150° C. $^1$H-NMR (CDCl$_3$) δ: 3.25 (3H, s), 3.31 (3H, s), 3.55 (2H, s), 3.66 (3H, s), 3.85 (2H, d), 4.08 (2H, s), 4.46 (2H, s), 5.83 (1H, brs), 6.82–7.00, 7.16–7.52 (18H, m)

Elementary Analysis (for C$_{36}$H$_{36}$ClN$_5$O$_7$) Calculated: C, 63.02; H, 5.29; N, 10.21 Found: C, 62.96; H, 5.38; N, 9.96

Example 405

Isopropyl 2-[3-[3-[N-[3-[N-methyl-N-(3,5-dimethyl phenyl)carbamoylmethyloxy]phenyl]-N-(N-methyl-N-phenylcarbamoylmethyl)carbamoylmethyl]ureido] phenyl]acetate (1–405)

mp 185–187° C. $^1$H-NMR (CDCl$_3$) δ: 1.20 (3H, s), 1.22 (3H, s), 2.35 (6H, s), 3.27–3.29 (6H, m), 3.52–5.02 (9H, m), 5.62 (1H, brs), 6.80–7.41 (17H, m) MS (m/z): 708 (M+1)$^+$

Example 406

Methyl (±)-2-[3-[3-[N-[3-[N-methyl-N-(3,5-dimethoxy phenyl)carbamoylmethyloxy]phenyl]-N-(N-methyl-N-phenylcarbamoylmethyl)carbamoylmethyl]ureido]phenyl] propionate(1–406)

$^1$H-NMR (CDCl$_3$) δ: 1.44 (3H, d), 3.23 (3H, s), 3.31 (3H, s), 3.45–4.51 (16H, m), 5.89 (1H, brs), 6.46–7.43 (17H, m) MS (m/z): 726 (M+1)$^+$

Example 407

Methyl 2-[3-[3-[N-[3-[N-methyl-N-(3,5-dimethylphenyl) carbamoylmethyloxy]phenyl]-N-(3-methyl-2-butenyl)carbamoyl methyl]ureido] phenyl]acetate (1–407)

mp 94–95° C. $^1$H-NMR (CDCl$_3$) δ: 1.43 (3H, s), 1.64 (3H, s), 2.35 (6H, s), 3.29 (3H, s), 3.55 (2H, s), 3.67 (3H, s), 3.74 (2H, d), 4.25 (2H, d), 4.43 (2H, s), 5.17–5.21 (1H, m), 5.88 (1H, brs), 6.67–7.35 (12H, m) MS (m/z): 601 (M+1)$^+$

Example 408

Methyl (±)-2-hydroxy-2-[3-[3-[N-[3-[N-methyl-N-(2-methylphenyl)carbamoylmethyloxy]phenyl]-N-(N-methyl-N-phenyl carbamoylmethyl)carbamoylmethyl]ureido]phenyl]acetate (1–408)

$^1$H-NMR (CDCl$_3$) δ: 2.30 (3H, s), 3.25 (6H, s), 3.72 (3H, s), 3.84 (3H, brs), 4.08 (2H, s), 4.19–4.42 (2H, m), 5.10 (1H, d), 5.87 (1H, brs), 6.76–7.36 (18H, m) MS (m/z): 682 (M+1)$^+$

Example 409

(±)-N-Methyl-N-(2-methylphenyl)-2-[3-[N-[2-[3-[3-[1-(N,N-dimethylamino)ethyl]phenyl]ureido]acetyl]-N-(N-methyl-N-phenylcarbamoylmethyl)amino] phenoxy]acetamide(1–409)

$^1$H-NMR (CDCl$_3$) δ: 1.51 (3H, d), 2.31 (3H, s), 2.37 (6H, s), 3.22 (3H, s), 3.25 (3H, s), 3.62 (1H, brs), 3.85 (2H, d), 4.10–4.13 (2H, m), 4.19–4.42 (2H, m), 6.11 (1H, brs), 6.75–7.39 (17H, m), 7.83 (1H, brs) MS (m/z): 665 (M+1)$^+$

Example 410

Methyl (±)-2-[3-[3-[N-[3-[N-methyl-N-(2-methylphenyl) carbamoylmethyloxy]phenyl]-N-(2-phenylpropyl)carbamoyl methyl]ureido]phenyl] acetate (1–410)

mp 123–126° C. $^1$H-NMR (CDCl$_3$) δ: 1.24 (3H, d), 2.29 (3H, s), 2.99–3.00 (1H, m), 3.25 (3H, s), 3.58 (2H, s), 3.68 (3H, s), 3.61–3.74 (2H, m), 4.01–4.06 (2H, m), 4.14–4.35 (2H, m), 5.53 (1H, brs), 6.41–7.34 (18H, m) MS (m/z): 637 (M+1)$^+$

Example 411

Methyl 2-[3-[3-[N-(2-cyclohexylethyl)-N-[3-(N-methyl-N-phenylcarbamoylmethyloxy)phenyl] carbamoylmethyl]ureido] phenyl]acetate (1–411)

mp 146–147° C. $^1$H-NMR (CDCl$_3$) δ: 0.79–1.67 (13H, s), 3.33 (3H, s), 3.54 (2H, s), 3.57–3.72 (7H, m), 4.45 (2H, s), 5.96 (1H, brs), 6.65–7.49 (14H, m) MS (m/z): 615 (M+1)$^+$

Example 412

Methyl 2-[3-[3-[N-(2-cyclopentylethyl)-N-[2-(N-methyl-N-phenylcarbamoylmethyloxy)phenyl] carbamoylmethyl]ureido] phenyl]acetate (1–412)

mp 134–135° C. $^1$H-NMR (CDCl$_3$) δ: 1.01–1.70 (11H, m), 3.30–3.35 (4H, m), 3.57 (2H, s), 3.67 (3H, s), 3.86–3.88 (3H, m), 4.48 (2H, s), 5.96 (1H, brs), 6.63–7.53 (14H, m) MS (m/z): 601 (M+1)$^+$ Elementary Analysis (for C$_{34}$H$_{40}$N$_4$O$_6$) Calculated: C, 67.98; H, 6.71; N, 9.33 Found: C, 67.67; H, 6.77; N, 9.17

Example 413

Methyl 2-[3-[3-[N-(2-cyclohexylethyl)-N-[2-(N-methyl-N-phenylcarbamoylmethyloxy)phenyl] carbamoylmethyl]ureido] phenyl]acetate (1–413)

$^1$H-NMR (CDCl$_3$) δ: 0.80–1.78 (13H, m), 3.35 (3H, s), 3.57 (2H, s), 3.67 (3H, s), 3.71–3.94 (4H, m), 4.48 (2H, s), 6.00 (1H, brs), 6.63–7.54 (14H, m) MS (m/z): 615 (M+1)$^+$

Example 414

Methyl 2-[3-[3-[N-(2-cyclopentylethyl)-N-[2-[N-methyl-N-(3,5-dimethylphenyl) carbamoylmethyloxy]phenyl] carbamoylmethyl]ureido]phenyl]acetate (1–414)

$^1$H-NMR (CDCl$_3$) δ: 1.04–1.70 (11H, m), 2.38 (6H, s), 3.31 (4H, s), 3.56 (2H, s), 3.67 (3H, s), 3.88–3.89 (3H, m), 4.51 (2H, s), 5.98 (1H, brs), 6.64–7.28 (12H, m) MS (m/z): 629 (M+1)$^+$

Example 415

Methyl 2-[3-[3-[N-(3-cyclohexylpropyl)-N-[2-(N-methyl-N-phenylcarbamoylmethyloxy)phenyl] carbamoylmethyl]ureido] phenyl]acetate (1–415)

mp 138–139° C. $^1$H-NMR (CDCl$_3$) δ: 0.78–1.78 (15H, m), 3.34 (3H, s), 3.57 (2H, s), 3.67 (3H, s), 3.28–3.87 (4H, m), 4.48 (2H, s), 6.02 (1H, brs), 6.64–7.53 (14H, m) MS (m/z): 629 (M+1)$^+$ Elementary Analysis (for C$_{36}$H$_{44}$N$_4$O$_6$) Calculated: C, 68.77; H, 7.05; N, 8.91 Found: C, 68.72; H, 6.87; N, 8.77

Example 416

Methyl 2-[3-[3-[N-cyclopentylmethyl-N-[2-[N-methyl-N-(3,5-dimethylphenyl) carbamoylmethyloxy]phenyl]carbamoyl methyl] ureido]phenyl]acetate (1–416)

mp 150–151° C. $^1$H-NMR (CDCl$_3$) δ: 1.16–1.64 (9H, m), 2.38 (6H, s), 3.31 (4H, brs), 3.57 (2H, s), 3.67 (3H, s), 3.89 (3H, brs), 4.51 (2H, s), 6.01 (1H, brs), 6.64–7.29 (12H, m) MS (m/z): 615 (M+1)$^+$ Elementary Analysis (for C$_{35}$H$_{42}$N$_4$O$_6$) Calculated: C, 68.38; H, 6.89; N, 9.11 Found: C, 67.94; H, 6.78; N, 8.92

Example 417

Methyl 2-[3-[3-[N-cyclopentylmethyl-N-[2-(N-methyl-N-phenylcarbamoylmethyloxy)phenyl] carbamoylmethyl]ureido] phenyl]acetate (1–417)

$^1$H-NMR (CDCl$_3$) δ: 1.15–1.78 (9H, m), 3.29–3.34 (4H, m), 3.57 (2H, s), 3.67 (3H, s), 3.86–3.94 (3H, m), 4.48 (2H, s), 5.95 (1H, brs), 6.63–7.53 (14H, m) MS (m/z): 587 (M+1)$^+$

Example 418

Methyl 2-[3-[3-[N-cyclopentylmethyl-N-[2-[N-(3-chlorophenyl)-N-methylcarbamoylmethyloxy] phenyl] carbamoylmethyl]ureido]phenyl]acetate (1–418)

mp 155–157° C. $^1$H-NMR (CDCl$_3$) δ: 1.14–2.09 (9H, m), 3.32 (4H, m), 3.56 (2H, s), 3.67 (3H, s), 3.69–3.95 (3H, m), 4.50 (2H, s), 5.92 (1H, s), 6.65–7.43 (13H, m)

Example 419

Methyl 2-[3-[3-[N-cyclobutylmethyl-N-[2-(N-methyl-N-phenylcarbamoylmethyloxy)phenyl]carbamoylmethyl] ureido]phenyl]acetate (1–419)

mp 112–114° C. $^1$H-NMR (CDCl$_3$) δ: 1.55–1.90 (6H, m), 2.39–2.46 (1H, m), 3.34 (3H, s), 3.41–3.48 (1H, m) , 3.56 (2H, s) , 3.67 (3H, s), 3.79–4.02 (3H, m) , 4.48 (2H, s) , 6.01 (1H, s), 6.62–7.53 (14H, m) MS (m/z): 573 (M+1)$^+$
Elementary Analysis (for C$_{32}$H$_{36}$N$_4$O$_6$) Calculated: C, 67.12; H, 6.34; N, 9.78 Found: C, 66.82; H, 6.29; N, 9.78

Example 420

Methyl 2-[3-[3-[N-cyclobutylmethyl-N-[2-[N-methyl-N-(3,5-dimethylphenyl)carbamoylmethyloxy]phenyl]carbamoyl -methyl] ureido]phenyl]acetate (1–420)

mp 147–148° C. $^1$H-NMR (CDCl$_3$) δ: 1.25–1.88 (6H, m), 2.38 (7H, s), 3.31 (3H, s), 3.40–3.48 (1H, m), 3.57 (2H, s), 3.67 (3H, s), 3.88 (2H, s), 3.95–4.00 (1H, m), 4.51 (2H, s), 5.94 (1H, s), 6.61–7.28 (12H, m) MS (m/z): 601 (M+1)$^+$

Example 421

Methyl 2-[3-[3-[N-cyclobutylmethyl-N-[2-[N-(3-chlorophenyl)-N-methylcarbamoylmethyloxy]phenyl] carbamoylmethyl]ureido]phenyl]acetate (1–421)

mp 101–104° C. $^1$H-NMR (CDCl$_3$) δ: 1.55–1.91 (6H, m), 2.38–2.49 (1H, m), 3.31 (3H, s), 3.42–3.47 (1H, m), 3.56 (2H, s), 3.67 (3H, s), 3.78–3.89 (2H, m), 3.98–4.03 (1H, m), 4.49 (2H, s), 5.97.(1H, brs), 6.63–7.43 (13H, m)

Example 422

Methyl 2-[3-[3-[N-cycloheptylmethyl-N-[2-(N-methyl-N-phenylcarbamoylmethyloxy)phenyl]carbamoylmethyl] ureido]phenyl]acetate (1–422)

mp 123–125° C. $^1$H-NMR (CDCl$_3$) δ: 1.12–1.68 (13H, m), 3.17–3.22 (1H, m), 3.33 (3H, s), 3.56 (2H, s), 3.66 (3H, s), 3.85–3.93 (3H, m), 4.48 (2H, s), 6.04 (1H, s), 6.65–7.53 (14H, m) MS (m/z): 615 (M+1)$^+$

Example 423

Methyl 2-[3-[3-[N-cycloheptylmethyl-N-[2-[N-(3-chlorophenyl)-N-methylcarbamoylmethyloxy]phenyl] carbamoylmethyl]ureido]phenyl]acetate (1–423)

mp 174–177° C. $^1$H-NMR (CDCl$_3$) δ: 1.11–1.75 (13H, m), 3.17–3.22 (1H, m), 3.31 (3H, s), 3.56 (2H, s), 3.67 (3H, s), 3.79–3.90 (3H, m), 4.50 (2H, s), 5.95 (1H, brs), 6.66–7.52 (13H, m)

Example 424

Methyl (±)-2-methoxy-2-[3-[3-[N-[3-[N-methyl-N-(3,5-dimethylphenyl)carbamoylmethyloxy]phenyl]-N-(N-methyl-N-phenylcarbamoylmethyl)carbamoylmethyl]ureido]phenyl] acetate (1–424)

mp 97–101° C. $^1$H-NMR(CDCl$_3$) δ: 2.34 (6H, s), 3.25–3.35 (9H, m), 3.68 (3H, s), 3.86 (2H, d), 4.09 (2H, s), 4.43 (2H, s), 4.71 (1H, s), 5.78 (1H, brs), 9.79–7.52 (17H, m) MS (m/z): 710 (M+1)$^+$

Example 425

(±)-2-Methoxy-2-[3-[3-[N-[3-[N-methyl-N-(3,5-dimethylphenyl)carbamoylmethyloxy]phenyl]-N-(N-methyl-N-phenylcarbamoylmethyl) carbamoylmethyl]ureido]phenyl]acetic acid(1–425)

mp 204–206° C. $^1$H-NMR (DMSO-d$_6$) δ: 2.27 (6H, s), 3.10–3.33 (9H, m), 3.60 (2H, s), 4.04 (2H, s), 4.48 (2H, s), 4.65 (1H, s), 6.27 (1H, s), 6.82–7.46 (16H, m), 8.89 (1H, s) MS (m/z): 696 (M+1)$^+$

Example 426

Methyl (±)-2-hydroxy-2-[3-[3-[N-[3-[N-methyl-N-(2-methylphenyl)carbamoylmethyloxy]phenyl]-N-(N-methyl-N-phenylcarbamoylmethyl)carbamoylmethyl]ureido]phenyl] acetate (1–426)

$^1$H-NMR (CDCl$_3$) δ: 2.30 (3H, s), 3.25 (6H, s), 3.72 (3H, s), 3.84 (3H, brs), 4.08 (2H, s), 4.19–4.42 (2H, m), 5.10 (1H, d), 5.87 (1H, brs), 6.76–7.36 (18H, m) MS (m/z): 682 (M+1)$^+$

Example 427

(±)-2-Hydroxy-2-[3-[3-[N-[3-[N-methyl-N-(2-methylphenyl)carbamoylmethyloxy]phenyl]-N-(N-methyl-N-phenylcarbamoylmethyl) carbamoylmethyl]ureido]phenyl]acetic acid(1–427)

$^1$H-NMR (DMSO-d$_6$) δ: 2.24 (3H, s), 3.11–3.66 (10H, m), 4.00–4.05 (2H, m), 4.23–4.43 (2H, m), 4.92 (1H, s), 6.28 (1H, s), 6.77–7.46 (17H, m), 8.85 (1H, s) MS (m/z): 668 (M+1)$^+$

Example 428

Methyl 2-[3-[3-[N-(tert-butoxycarbonylmethyl)-N-[2-(N-methyl-N-phenylcarbamoylmethyloxy)phenyl]carbamoylmethyl] ureido]phenyl]acetate (1–428)

mp 142–144° C. $^1$H-NMR (CDCl$_3$) δ: 1.42 (9H, s), 3.34 (3H, s), 3.56 (2H, s), 3.62–3.66 (1H, d), 3.67 (3H, s), 3.90–4.01 (2H, m), 4.51 (2H, s), 4.81 (1H, d), 5.90 (1H, brs), 6.63–7.54 (14H, m)

Example 429

2-[3-[3-[N-(tert-Butoxycarbonylmethyl)-N-[2-(N-methyl-N-phenylcarbamoylmethyloxy)phenyl]carbamoylmethyl]ureido] phenyl]acetic acid (1–429)

mp 194–196° C. $^1$H-NMR (CDCl$_3$) δ: 1.42 (9H, s), 3.30 (3H, s), 3.59 (2H, s), 3.70 (1H, d), 3.77 ($^1$H, dd) , 3.91 (1H, dd) , 4.47 (2H, s) , 4.81 (1H, d) 6.39–7.58 (15H, m) MS (m/z): 605 (M+1)$^+$

Example 430

Methyl 2-[3-[3-[N-(tert-butoxycarbonylmethyl)-N-[2-[N-(3,5-difluorophenyl)-N-methylcarbamoylmethyloxy] phenyl] carbamoylmethyl]ureido]phenyl]acetate (1–430)

mp 150–152° C. $^1$H-NMR (CDCl$_3$) δ: 1.43 (9H, s), 3.32 (3H, s), 3.57 (2H, s), 3.67 (1H, d), 3.68 (3H, s), 3.91–3.93 (2H, m), 4.60 (2H, s), 4.81 (1H, d), 5.78 (1H, brs), 6.70–7.50 (12H, m)

Example 431

2-[3-[3-[N-(tert-Butoxycarbonylmethyl)-N-[2-[N-(3,5-difluorophenyl)-N-methylcarbamoylmethyloxy] phenyl] carbamoylmethyl]ureido]phenyl]acetic acid (1–431)

mp 155–157° C. $^1$H-NMR (CDCl$_3$) δ: 1.43 (9H, s), 3.27 (3H, s), 3.59 (2H, s), 3.78 (1H, d), 3.77 (1H, br d), 3.89 (1H, dd), 4.58 (2H, s), 4.79 (1H, d), 6.41–7.58 (13H, m) MS (m/z): 641 (M+1)⁺

Elementary Analysis (for $C_{32}H_{34}F_2N_4O_8$) Calculated: C, 59.99; H, 5.35; N, 8.75 Found: C, 59.56; H, 5.36; N, 8.56

Example 432 tert-Butyl 3-[3-[N-[2-[N-(3,5-difluorophenyl)-N-methyl carbamoylmethyloxy]phenyl]-N-(3-methylbutyl)carbamoylmethyl] ureido]benzoate (1–432)

¹H-NMR (CDCl₃) δ: 0.82 (3H, d), 0.83 (3H, d), 1.36 (2H, m), 1.54 (1H, m), 1.56 (9H, s), 3.32 (3H, s), 3.37 (1H, m), 3.80–3.99 (3H, m), 4.58 (2H, brs), 5.99 (1H, m), 6.69 (1H, m), 6.87–6.92 (2H, m), 7.00 (1H, m), 7.17 (1H, m), 7.24–7.28 (3H, m), 7.43 (1H, s), 7.57 (1H, d), 7.70–7.74 (2H, m)

Example 433

3-[3-[N-[2-[N-(3,5-Difluorophenyl)-N-methylcarbamoyl methyloxy]phenyl]-N-(3-methylbutyl)carbamoylmethyl] ureido]benzoic acid (1–433)

mp 115–119° C. ¹H-NMR (DMSO-d₆) δ: 0.83 (3H, d), 0.85 (3H, d), 1.30 (2H, m), 1.54 (1H, m), 3.10–3.47 (4H, m), 3.48 (1H, dd), 3.67 (1H, dd), 3.89 (1H, m), 4.81 (2H, brs), 6.35 (1H, m), 7.02–7.06 (2H, m), 7.26–7.40 (6H, m), 7.45 (1H, d), 7.52 (1H, d), 7.96 (1H, s), 9.04 (1H, s)

Example 434

Methyl (±)-2-[3-[3-[N-[2-(N-methyl-N-phenylcarbamoyl methyloxy)phenyl]-N-(3-methylpentyl)carbamoylmethyl] ureido]phenyl] acetate (1–434)

mp 106–108° C. ¹H-NMR (CDCl₃) δ: 0.75–0.81 (6H, m), 1.04–1.12, 1.26–1.30 and 1.48–1.51 (5H, m), 3.32 (3H, s), 3.32–3.36 (1H, m), 3.55 (2H, s), 3.66 (3H, s), 3.80 (1H, d), 3.89 (1H, dd), 3.96 (1H, m), 4.48 (2H, s), 6.15 (1H, brs), 6.66 (1H, d), 6.87 (1H, d), 6.98 (1H, t), 7.15–7.31 and 7.43–7.52 (11H, m) $[\alpha]_D$ +1.9° (c=1.04, CHCl₃, 24° C.

Example 435

(±)-2-[3-[3-[N-[2-(N-Methyl-N-phenylcarbamoylmethyloxy) phenyl]-N-(3-methylpentyl)carbamoylmethyl]ureido]phenyl] acetic acid(1–435)

mp 153–154° C. ¹H-NMR (CDCl₃) δ: 0.77–0.83 (6H, m), 1.05–1.51 (5H, m), 3.29 (3H, s), 3.34–3.36 (1H, m), 3.59 (2H, s), 3.62 (1H, d), 3.85 (1H, dd), 4.00–4.02 (1H, m), 4.45 (2H, q), 6.52 (1H, brs), 6.68 (1H, d), 6.86 (1H, d), 6.95–6.99 (2H, m), 7.11–7.20 (2H, m), 7.25–7.29 and 7.38–7.49 (6H, m), 7.59 (1H, d), 7.64 (1H, s) MS (m/z): 575 (M+1)⁺

Elementary Analysis (for $C_{32}H_{38}N_4O_6$) Calculated: C, 66.88; H, 6.66; N, 9.75 Found: C, 66.45; H, 6.65; N, 9.39 $[\alpha]_D$+0.9° (c=1.3, CHCl₃, 22° C.

Example 436

N-(n-Butyl)-N-phenyl-2-[3-[N-(N-methyl-N-phenylcarbamoylmethyl)-N-[2-[3-(3-methylphenyl) ureido] acetyl]amino]phenoxy]acetamide(1–436)

mp 152–154° C. ¹H-NMR (CDCl₃) δ: 0.88 (3H, t), 1.30 (2H, m), 1,51 (2H, m), 2.25 (3H, s), 3.21 (3H, s), 3.73 (2H, t), 3.86 (2H, d), 4.07 (2H, s), 4.36 (2H, s), 6.10 (1H, brs), 6.74–7.47 (18H, m), 7.85 (1H, s)

Likewise, the following compounds can be prepared

Methyl 3-[3-[N-[2-[N-methyl-N-phenylcarbamoylmethyloxy] phenyl]-N-(3-methylbutyl) carbamoylmethyl]ureido]benzoate Methyl 3-[3-[N-[2-[N-(3,5-difluorophenyl)-N-methylcarbamoyl methyloxy]phenyl]-N-(3-methylbutyl) carbamoylmethyl]ureido] benzoate Methyl 2-[3-[3-[N-[2-[N-(3,5-difluorophenyl)-N-methyl carbamoylmethyloxy]phenyl]-N-(3-methylbutyl) carbamoyl methyl]ureido]phenyl]acetate Methyl (±)-2-[3-[3-[N-[2-[N-(3,5-difluorophenyl)-N-methylcarbamoylmethyloxy]phenyl]-N-(3-methylbutyl) carbamoylmethyl]ureido]phenyl]propionate tert-Butyl (±)-2-[3-[3-[N-[2-[N-(3,5-difluorophenyl)-N-methylcarbamoylmethyloxy]phenyl]-N-(3-methylbutyl) carbamoylmethyl]ureido]phenyl]propionate 3-[3-[N-[2-[N-(2,5-Difluorophenyl)-N-methyl carbamoylmethyl oxy]phenyl]-N-(3-methylbutyl)carbamoylmethyl] ureido]benzoic acid Methyl 3-[3-[N-[2-[N-(2,5-difluorophenyl)-N-methylcarbamoyl methyloxy]phenyl]-N-(3-methylbutyl) carbamoylmethyl] ureido]benzoate tert-Butyl 3-[3-[N-[2-[N-(2,5-difluorophenyl)-N-methyl carbamoylmethyloxy]phenyl]-N-(3-methylbutyl) carbamoylmethyl] ureido]benzoate Methyl 2-[3-[3-[N-[2-[N-(2,5-difluorophenyl)-N-methyl carbamoylmethyloxy]phenyl]-N-(3-methylbutyl) carbamoylmethyl] ureido]phenyl]acetate (±)-2-[3-[3-[N-[2-[N-(2,5-Difluorophenyl)-N-methylcarbamoyl methyloxy]phenyl]-N-(3-methylbutyl) carbamoylmethyl] ureido]phenyl]propionic acid Methyl (±)-2-[3-[3-[N-[2-[N-(2,5-difluorophenyl)-N-methylcarbamoylmethyloxy]phenyl]-N-(3-methylbutyl) carbamoyl methyl]ureido]phenyl]propionate tert-Butyl (±)-2-[3-[3-[N-[2-[N-(2,5-difluorophenyl)-N-methylcarbamoylmethyloxy]phenyl]-N-(3-methylbutyl) carbamoyl methyl]ureido]phenyl]propionate 3-[3-[N-[2-[N-(2,6-Difluorophenyl)-N-methylcarbamoylmethyl oxy]phenyl]-N-(3-methylbutyl) carbamoylmethyl]ureido]benzoic acid Methyl 3-[3-[N-[2-[N-(2,6-difluorophenyl)-N-methylcarbamoyl methyloxy]phenyl]-N-(3-methylbutyl) carbamoylmethyl] ureido]benzoate tert-Butyl 3-[3-[N-[2-[N-(2,6-difluorophenyl)-N-methyl carbamoylmethyloxy]phenyl]-N-(3-methylbutyl) carbamoylmethyl] ureido]benzoate 2-[3-[3-[N-[2-[N-(2,6-Difluorophenyl)-N-methylcarbamoyl methyloxy]phenyl]-N-(3-methylbutyl)carbamoylmethyl] ureido] phenyl]acetic acid Methyl 2-[3-[3-[N-[2-[N-(2,6-difluorophenyl)-N-methyl carbamoylmethyloxy]phenyl]-N-(3-methylbutyl) carbamoyl methyl]ureido]phenyl]acetate tert-Butyl 2-[3-[3-[N-[2-[N-(2,6-difluorophenyl)-N-methylcarbamoylmethyloxy]phenyl]-N-(3-methylbutyl) carbamoyl methyl]ureido]phenyl]acetate (±)-2-[3-[3-[N-[2-[N-(2,6-Difluorophenyl)-N-methylcarbamoyl methyloxy]phenyl]-N-(3-methylbutyl) carbamoylmethyl] ureido]phenyl]propionic acid Methyl (±)-2-[3-[3-[N-[2-[N-(2,6-difluorophenyl)-N-methyl carbamoylmethyloxy]phenyl]-N-(3-methylbutyl) carbamoylmethyl] ureido]phenyl]propionate tert-Butyl (±)-2-[3-[3-[N-[2-[N-(2,6-difluorophenyl)-N-methylcarbamoylmethyloxy]phenyl]-N-(3-methylbutyl) carbamoylmethyl]ureido]phenyl]propionate (±)-3-[3-[N-[2-(N-Methyl-N-phenylcarbamoylmethyloxy) phenyl]-N-(3-methylpentyl)carbamoylmethyl]ureido] benzoic acid Methyl (±)-3-[3-[N-[2-(N-methyl-N-phenylcarbamoylmethyloxy) phenyl]-N-(3-methylpentyl) carbamoylmethyl]ureido]benzoate tert-Butyl (±)-3-[3-[N-[2-(N-methyl-N-phenylcarbamoyl methyloxy)phenyl]-N-(3-methylpentyl) carbamoylmethyl] ureido]benzoate tert-Butyl (±)-2-[3-[3-[N-[2-(N-methyl-N-phenylcarbamoyl methyloxy)phenyl]-N-(3-methylpentyl) carbamoylmethyl]ureido] phenyl]acetate (±)-2-[3-[3-[N-[2-(N-Methyl-N-phenylcarbamoylmethyloxy) phenyl]-N-(3-methylpentyl) carbamoylmethyl]ureido]phenyl] propionic acid Methyl (±)-2-[3-[3-[N-[2-(N-methyl-N-phenylcarbamoyl methyloxy)phenyl]-N-(3-methylpentyl) carbamoylmethyl] ureido]phenyl]propionate tert-Butyl (±)-2-[3-[3-[N-[2-(N-methyl-N-phenylcarbamoyl methyloxy)phenyl]-N-(3-methylpentyl) carbamoylmethyl]ureido] phenyl]propionate (±)-3-[3-[N-[2-[N-(3,5-Difluorophenyl)-N-methylcarbamoyl methyloxy]phenyl]-N-(3-methylpentyl)carbamoylmethyl]ureido] benzoic acid Methyl (±)-3-[3-[N-[2-[N-(3,5-difluorophenyl)-N-methyl carbamoylmethyloxy]phenyl]-N-(3-methylpentyl) carbamoyl methyl]ureido]benzoate tert-Butyl (±)-3-[3-[N-[2-[N-(3,5-difluorophenyl)-N-methylcarbamoylmethyloxy]phenyl]-N-(3-methylpentyl) carbamoyl methyl]ureido]benzoate Methyl (±)-2-[3-[3-[N-[2-[N-(3,5-difluorophenyl)-N-methyl carbamoylmethyloxy]phenyl]-N-(3-methylpentyl)carbamoyl methyl] ureido]phenyl] acetate (±)-2-[3-[3-[N-[2-[N-(3,5-Difluorophenyl)-N-methylcarbamoyl methyloxy]phenyl]-N-(3-methylpentyl)carbamoylmethyl]ureido] phenyl]propionic acid Methyl (±)-2-[3-[3-[N-[2-[N-(3,5-difluorophenyl)-N-methyl carbamoylmethyloxy]phenyl]-N-(3-methylpentyl)carbamoyl methyl]ureido]phenyl] propionate tert-Butyl (±)-2-[3-[3-[N-[2-[N-(3,5-difluorophenyl)-N-methylcarbamoylmethyloxy]phenyl]-N-(3-methylpentyl) carbamoylmethyl]ureido]phenyl]propionate (±)-3-[3-[N-[2-[N-(2,5-Difluorophenyl)-N-methylcarbamoyl methyloxy]phenyl]-N-(3-methylpentyl)carbamoylmethyl] ureido]benzoic acid Methyl (±)-3-[3-[N-[2-[N-(2,5-difluorophenyl)-N-methyl carbamoylmethyloxy]phenyl]-N-(3-methylpentyl) carbamoyl methyl]ureido]benzoate tert-Butyl (±)-3-[3-[N-[2-[N-(2,5-difluorophenyl)-N-methyl carbamoylmethyloxy]phenyl]-N-(3-methylpentyl) carbamoyl methyl]ureido]benzoate (±)-2-[3-[3-[N-[2-[N-(2,5-Difluorophenyl)-N-methylcarbamoyl methyloxy]phenyl]-N-(3-methylpentyl)carbamoylmethyl]ureido] phenyl]acetic acid Methyl (±)-2-[3-[3-[N-[2-[N-(2,5-difluorophenyl)-N-methyl carbamoylmethyloxy]phenyl]-N-(3-methylpentyl)carbamoyl methyl]ureido]phenyl]acetate tert-Butyl (±)-2-[3-[3-[N-[2-[N-(2,5-difluorophenyl)-N-methylcarbamoylmethyloxy]phenyl]-N-(3-methylpentyl) carbamoyl methyl]ureido]phenyl]acetate (±)-2-[3-[3-[N-[2-[N-(2,5-Difluorophenyl)-N-methylcarbamoyl methyloxy]phenyl]-N-(3-methylpentyl)carbamoylmethyl]ureido] phenyl]propionic acid Methyl (±)-2-[3-[3-[N-[2-[N-(2,5-difluorophenyl)-N-methyl carbamoylmethyloxy]phenyl]-N-(3-methylpentyl)carbamoyl methyl]ureido]phenyl] propionate tert-Butyl (±)-2-[3-[3-[N-[2-[N-(2,5-difluorophenyl)-N-methylcarbamoylmethyloxy]phenyl]-N-(3-methylpentyl) carbamoyl methyl]ureido]phenyl]propionate (±)-3-[3-[N-[2-[N-(2,6-Difluorophenyl)-N-methylcarbamoyl methyloxy]phenyl]-N-(3-methylpentyl)carbamoylmethyl] ureido]benzoic acid Methyl (±)-3-[3-[N-[2-[N-(2,6-difluorophenyl)-N-methyl carbamoylmethyloxy]phenyl]-N-(3-methylpentyl) carbamoyl methyl]ureido]benzoate tert-Butyl (±)-3-[3-[N-[2-[N-(2,6-difluorophenyl)-N-methyl carbamoylmethyloxy]phenyl]-N-(3-methylpentyl) carbamoyl methyl]ureido]benzoate (±)-2-[3-[3-[N-[2-[N-(2,6-Difluorophenyl)-N-methylcarbamoyl methyloxy]phenyl]-N-(3-methylpentyl)carbamoylmethyl]ureido] phenyl]acetic acid Methyl (±)-2-[3-[3-[N-[2-[N-(2,6-difluorophenyl)-N-methyl carbamoylmethyloxy]phenyl]-N-(3-methylpentyl)carbamoyl methyl] ureido] phenyl] acetate tert-Butyl (±)-2-[3-[3-[N-[2-[N-(2,6-difluorophenyl)-N-methylcarbamoylmethyloxy]phenyl]-N-(3-methylpentyl) carbamoyl methyl] ureido]phenyl] acetate (±)-2-[3-[3-[N-[2-[N-(2,6-Difluorophenyl)-N-methylcarbamoyl methyloxy]phenyl]-N-(3-methylpentyl)carbamoylmethyl]ureido] phenyl]propionic acid Methyl (±)-2-[3-[3-[N-[2-[N-(2,6-difluorophenyl)-N-methyl carbamoylmethyloxy]phenyl]-N-(3-methylpentyl)carbamoyl methyl]ureido]phenyl] propionate tert-Butyl (±)-2-[3-[3-[N-[2-[N-(2,6-difluorophenyl)-N-methylcarbamoylmethyloxy]phenyl]-N-(3-methylpentyl) carbamoyl methyl]ureido]phenyl]propionate 3-[3-[N-(tert-Butoxycarbonylmethyl)-N-[2-(N-methyl-N-phenyl carbamoylmethyloxy)phenyl]carbamoylmethyl] ureido]benzoic acid Methyl 3-[3-[N-(tert-butoxycarbonylmethyl)-N-[2-(N-methyl-N-phenylcarbamoylmethyloxy)phenyl] carbamoylmethyl]ureido] benzoate tert-Butyl 3-[3-[N-(tert-butoxycarbonylmethyl)-N-[2-(N-methyl-N-phenylcarbamoylmethyloxy)phenyl] carbamoylmethyl] ureido]benzoate 3-[3-[N-(tert-Butoxycarbonylmethyl)-N-[2-[N-(3,5-difluoro phenyl)-N-methylcarbamoylmethyloxy]phenyl] carbamoylmethyl] ureido]benzoic acid Methyl 3-[3-[N-(tert-butoxycarbonylmethyl)-N-[2-[N-(3,5-difluorophenyl)-N-methylcarbamoylmethyloxy]phenyl] carbamoyl methyl]ureido]benzoate tert-Butyl 3-[3-[N-(tert-butoxycarbonylmethyl)-N-[2-[N-(3,5-difluorophenyl)-N-methylcarbamoylmethyloxy] phenyl]carbamoyl methyl]ureido]benzoate (±)-2-[3-[3-[N-(tert-Butoxycarbonylmethyl)-N-[2-(N-methyl-N-phenylcarbamoylmethyloxy)phenyl] carbamoylmethyl]ureido] phenyl]propionic acid Methyl (±)-2-[3-[3-[N-(tert-butoxycarbonylmethyl)-N-[2-(N-methyl-N-phenylcarbamoylmethyloxy)phenyl] carbamoylmethyl] ureido]phenyl]propionate tert-Butyl (±)-2-[3-[3-[N-(tert-butoxycarbonylmethyl)-N-[2-(N-methyl-N-phenylcarbamoylmethyloxy)phenyl] carbamoyl methyl]ureido]phenyl]propionate (±)-2-[3-[3-[N-(tert-Butoxycarbonylmethyl)-N-[2-[N-(3,5-difluorophenyl)-N-methylcarbamoylmethyloxy]phenyl] carbamoyl methyl]ureido]phenyl]propionic acid Methyl (±)-2-[3-[3-[N-(tert-butoxycarbonylmethyl)-N-[2-[N-(3,5-difluorophenyl)-N-methylcarbamoylmethyloxy] phenyl] carbamoylmethyl]ureido]phenyl]propionate tert-Butyl (±)-2-[3-[3-[N-(tert-butoxycarbonylmethyl)-N-[2-[N-(3,5-difluorophenyl)-N- methylcarbamoylmethyloxy]phenyl] carbamoylmethyl] ureido]phenyl]propionate

3-[3-[N-(tert-Butoxycarbonylmethyl)-N-[3-(N-methyl-N-phenylcarbamoylmethyloxy)phenyl]carbamoylmethyl] ureido] benzoic acid Methyl 3-[3-[N-(tert-butoxycarbonylmethyl)-N-[3-(N-methyl-N-phenylcarbamoylmethyloxy)phenyl] carbamoylmethyl]ureido]benzo ate tert-Butyl 3-[3-[N-(tert-butoxycarbonylmethyl)-N-[3-(N-methyl-N-phenylcarbamoylmethyloxy)phenyl] carbamoylmethyl] ureido]benzoate 3-[3-[N-(tert-Butoxycarbonylmethyl)-N-[3-[N-(3,5-difluoro phenyl)-N-methylcarbamoylmethyloxy]phenyl] carbamoylmethyl] ureido]benzoic acid Methyl 3-[3-[N-(tert-butoxycarbonylmethyl)-N-[3-[N-(3,5-difluorophenyl)-N-methylcarbamoylmethyloxy]phenyl] carbamoyl methyl]ureido]benzoate tert-Butyl 3-[3-[N-(tert-butoxycarbonylmethyl)-N-[3-[N-(3,5-difluorophenyl)-N-methylcarbamoylmethyloxy] phenyl]carbamoyl methyl]ureido]benzoate 2-[3-[3-[N-(tert-Butoxycarbonylmethyl)-N-[3-(N-methyl-N-phenylcarbamoylmethyloxy)phenyl]carbamoylmethyl] ureido] phenyl]acetic acid Methyl 2-[3-[3-[N-(tert-butoxycarbonylmethyl)-N-[3-(N-methyl-N-phenylcarbamoylmethyloxy)phenyl]carbamoyl methyl]ureido]phenyl]acetate tert-Butyl 2-[3-[3-[N-(tert-butoxycarbonylmethyl)-N-[3-(N-methyl-N-phenylcarbamoylmethyloxy)phenyl]carbamoyl methyl]ureido]phenyl]acetate 2-[3-[3-[N-(tert-Butoxycarbonylmethyl)-N-[3-[N-(3,5-difluorophenyl)-N-methylcarbamoylmethyloxy]phenyl] carbamoyl methyl]ureido]phenyl]acetic acid Methyl 2-[3-[3-[N-(tert-butoxycarbonylmethyl)-N-[3-[N-(3,5-difluorophenyl)-N-methylcarbamoylmethyloxy] phenyl]carbamoyl methyl]ureido]phenyl]acetate tert-Butyl 2-[3-[3-[N-(tert-butoxycarbonylmethyl)-N-[3-[N-(3,5-difluorophenyl)-N-methylcarbamoylmethyloxy] phenyl] carbamoylmethyl]ureido]phenyl]acetate (±)-2-[3-[3-[N-(tert-Butoxycarbonylmethyl)-N-[3-(N-methyl-N-phenylcarbamoylmethyloxy)phenyl] carbamoylmethyl]ureido] phenyl]propionic acid Methyl (±)-2-[3-[3-[N-(tert-butoxycarbonylmethyl)-N-[3-(N-methyl-N-phenylcarbamoylmethyloxy)phenyl] carbamoyl methyl]ureido]phenyl]propionate tert-Butyl (±)-2-[3-[3-[N-(tert-butoxycarbonylmethyl)-N-[3-(N-methyl-N-phenylcarbamoylmethyloxy)phenyl] carbamoyl methyl]ureido]phenyl]propionate (±)-2-,[3-[3-[N-(tert-Butoxycarbonylmethyl)-N-[3-[N-(3,5-difluorophenyl)-N-methylcarbamoylmethyloxy]phenyl] carbamoyl methyl]ureido]phenyl]propionic acid Methyl (±)-2-[3-[3-[N-(tert-butoxycarbonylmethyl)-N-[3-[N-(3,5-difluorophenyl)-N-methylcarbamoylmethyloxy] phenyl] carbamoylmethyl]ureido]phenyl]propionate tert-Butyl (±)-2-[3-[3-[N-(tert-butoxycarbonylmethyl)-N-[3-[N-(3,5-difluorophenyl)-N-methylcarbamoylmethyloxy]phenyl] carbamoylmethyl] ureido]phenyl]propionate 2-[3-[3-[N-[2-[N-(3-Chlorophenyl)-N-methylcarbamoylmethyl oxy]phenyl]-N-(2-cyclopentylethyl)carbamoylmethyl]ureido] phenyl]acetic acid Methyl 2-[3-[3-[N-[2-[N-(3-chlorophenyl)-N-methylcarbamoyl methyloxy]phenyl]-N-(2-cyclopentylethyl)carbamoylmethyl] ureido]phenyl]acetate tert-Butyl 2-[3-[3-[N-[2-[N-(3-chlorophenyl)-N-methyl carbamoylmethyloxy]phenyl]-N-(2-cyclopentylethyl) carbamoyl methyl]ureido]phenyl]acetate 2-[3-[3-[N-(2-Cyclopentylethyl)-N-[2-[N-(3,5-difluoro phenyl)-N-methylcarbamoylmethyloxy]phenyl] carbamoylmethyl] ureido]phenyl]acetic acid Methyl 2-[3-[3-[N-(2-cyclopentylethyl)-N-[2-[N-(3,5-difluoro phenyl)-N-methylcarbamoylmethyloxy]phenyl] carbamoylmethyl] ureido]phenyl]acetate tert-Butyl 2-[3-[3-[N-(2-cyclopentylethyl)-N-[2-[N-(3,5-difluorophenyl)-N-methylcarbamoylmethyloxy]phenyl] carbamoyl methyl]ureido]phenyl]acetate 2-[3-[3-[N-(2-Cyclopentylethyl)-N-[2-[N-(2,6-difluoro phenyl)-N-methylcarbamoylmethyloxy]phenyl] carbamoylmethyl] ureido]phenyl]acetic acid Methyl 2-[3-[3-[N-(2-cyclopentylethyl)-N-[2-[N-(2,6-difluoro phenyl)-N-methylcarbamoylmethyloxy]phenyl] carbamoyl methyl]ureido]phenyl]acetate tert-Butyl 2-[3-[3-[N-(2-cyclopentylethyl)-N-[2-[N-(2,6-difluorophenyl)-N-methylcarbamoylmethyloxy]phenyl] carbamoyl methyl] ureido]phenyl] acetate (±)-2-[3-[3-[N-(2-Cyclopentylethyl)-N-[2-[N-methyl-N-phenylcarbamoylmethyloxy]phenyl]carbamoylmethyl] ureido] phenyl]propionic acid Methyl (±)-2-[3-[3-[N-(2-cyclopentylethyl)-N-[2-[N-methyl-N-phenylcarbamoylmethyloxy]phenyl] carbamoylmethyl]ureido] phenyl]propionate tert-Butyl (±)-2-[3-[3-[N-(2-cyclopentylethyl)-N-[2-[N-methyl-N-phenylcarbamoylmethyloxy]phenyl]carbamoyl methyl]ureido]phenyl]propionate (±)-2-[3-[3-[N-(2-Cyclopentylethyl)-N-[2-[N-methyl-N-(3,5-dimethylphenyl)carbamoylmethyloxy]phenyl] carbamoylmethyl] ureido]phenyl]propionic acid Methyl (±)-2-[3-[3-[N-(2-cyclopentylethyl)-N-[2-[N-methyl-N-(3,5-dimethylphenyl)carbamoylmethyloxy] phenyl]carbamoyl methyl]ureido]phenyl]propionate tert-Butyl (±)-2-[3-[3-[N-(2-cyclopentylethyl)-N-[2-[N-methyl-N-( 3,5-dimethylphenyl)carbamoylmethyloxy] phenyl] carbamoylmethyl]ureido]phenyl]propionate (±)-2-[3-[3-[N-[2-[N-(3-Chlorophenyl)-N-methylcarbamoyl methyloxy]phenyl]-N-(2-cyclopentylethyl)carbamoylmethyl] ureido]phenyl] propionic acid Methyl (±)-2-[3-[3-[N-[2-[N-(3-chlorophenyl)-N-methyl carbamoylmethyloxy]phenyl]-N-(2-cyclopentylethyl) carbamoyl methyl]ureido]phenyl]propionate tert-Butyl (±)-2-[3-[3-[N-[2-[N-(3-chlorophenyl)-N-methyl carbamoylmethyloxy]phenyl]-N-(2-cyclopentylethyl) carbamoyl methyl]ureido]phenyl]propionate (±)-2-[3-[3-[N-(2-Cyclopentylethyl)-N-[2-[N-(3,5-difluoro phenyl)-N-methylcarbamoylmethyloxy]phenyl] carbamoylmethyl] ureido]phenyl]propionic acid Methyl (±)-2-[3-[3-[N-(2-cyclopentylethyl)-N-[2-[N-(3,5-difluorophenyl)-N-methylcarbamoylmethyloxy]phenyl] carbamoyl methyl]ureido]phenyl]propionate tert-Butyl (±)-2-[3-[3-[N-(2-cyclopentylethyl)-N-[2-[N-(3,5-difluorophenyl)-N-methylcarbamoylmethyloxy] phenyl]carbamoyl methyl]ureido]phenyl]propionate (±)-2-[3-[3-[N-(2-Cyclopentylethyl)-N-[2-[N-(2,6-difluoro phenyl)-N-methylcarbamoylmethyloxy]phenyl] carbamoylmethyl] ureido]phenyl]propionic acid Methyl (±)-2-[3-[3-[N-(2-cyclopentylethyl)-N-[2-[N-(2,6-difluorophenyl)-N-methylcarbamoylmethyloxy]phenyl] carbamoyl methyl]ureido]phenyl] propionate tert-Butyl (±)-2-[3-[3-[N-(2-cyclopentylethyl)-N-[2-[N-(2,6-difluorophenyl)-N-methylcarbamoylmethyloxy] phenyl]carbamoyl methyl]ureido]phenyl]propionate 3-[3-[N-(2-Cyclopentylethyl)-N-[2-[N-methyl-N-phenyl carbamoylmethyloxy]phenyl]carbamoylmethyl]ureido] benzoic acid Methyl 3-[3-[N-(2-cyclopentylethyl)-N-[2-[N-methyl-N-phenyl carbamoylmethyloxy]phenyl]carbamoylmethyl] ureido]benzoate
tert-Butyl 3-[3-[N-(2-cyclopentylethyl)-N-[2-[N-methyl-N-phenylcarbamoylmethyloxy]phenyl]carbamoylmethyl] ureido] benzoate
3-[3-[N-(2-Cyclopentylethyl)-N-[2-[N-methyl-N-(3,5-dimethyl phenyl)carbamoylmethyloxy]phenyl] carbamoylmethyl]ureido] benzoic acid
Methyl 3-[3-[N-(2-cyclopentylethyl)-N-[2-[N-methyl-N-(3,5-dimethylphenyl)carbamoylmethyloxy]phenyl] carbamoylmethyl] ureido]benzoate tert-Butyl 3-[3-[N-(2-cyclopentylethyl)-N-[2-[N-methyl-N-(3,5-dimethylphenyl)carbamoylmethyloxy]phenyl]carbamoyl methyl]ureido]benzoate
3-[3-[N-[2-[N-(3-Chlorophenyl)-N-methylcarbamoylmethyloxy] phenyl]-N-(2-cyclopentylethyl)carbamoylmethyl]ureido]benzoic acid
Methyl 3-[3-[N-[2-[N-(3-chlorophenyl)-N-methylcarbamoyl methyloxy]phenyl]-N-(2-cyclopentylethyl)carbamoylmethyl] ureido]benzoate
tert-Butyl 3-[3-[N-[2-[N-(3-chlorophenyl)-N-methylcarbamoyl methyloxy]phenyl]-N-(2-cyclopentylethyl)carbamoylmethyl] ureido]benzoate
3-[3-[N-(2-Cyclopentylethyl)-N-[2-[N-(3,5-difluorophenyl)-N-methylcarbamoylmethyloxy]phenyl] carbamoylmethyl]ureido] benzoic acid
Methyl 3-[3-[N-(2-cyclopentylethyl)-N-[2-[N-(3,5-difluoro phenyl)-N-methylcarbamoylmethyloxy]phenyl] carbamoylmethyl] ureido]benzoate
tert-Butyl 3-[3-[N-(2-cyclopentylethyl)-N-[2-[N-(3,5-difluorophenyl)-N-methylcarbamoylmethyloxy]phenyl] carbamoyl methyl]ureido]benzoate
3-[3-[N-(2-Cyclopentylethyl)-N-[2-[N-(2,6-difluorophenyl)-N-methylcarbamoylmethyloxy]phenyl] carbamoylmethyl]ureido] benzoic acid
Methyl 3-[3-[N-(2-cyclopentylethyl)-N-[2-[N-(2,6-difluoro phenyl)-N-methylcarbamoylmethyloxy]phenyl] carbamoylmethyl] ureido]benzoate
tert-Butyl 3-[3-[N-(2-cyclopentylethyl)-N-[2-[N-(2,6-difluorophenyl)-N-methylcarbamoylmethyloxy]phenyl] carbamoyl methyl]ureido]benzoate
2-[3-[3-[N-Cyclopentylmethyl-N-[2-[N-(3,5-difluorophenyl)-N-methylcarbamoylmethyloxy]phenyl] carbamoylmethyl]ureido] phenyl]acetic acid
Methyl 2-[3-[3-[N-cyclopentylmethyl-N-[2-[N-(3,5-difluoro phenyl)-N-methylcarbamoylmethyloxy]phenyl] carbamoyl methyl]ureido]phenyl]acetate
tert-Butyl 2-[3-[3-[N-cyclopentylmethyl-N-[2-[N-(3,5-difluorophenyl)-N-methylcarbamoylmethyloxy]phenyl] carbamoyl methyl] ureido]phenyl] acetate
2-[3-[3-[N-Cyclopentylmethyl-N-[2-[N-(2,6-difluorophenyl)-N-methylcarbamoylmethyloxy]phenyl] carbamoylmethyl]ureido] phenyl]acetic acid
Methyl 2-[3-[3-[N-cyclopentylmethyl-N-[2-[N-(2,6-difluoro phenyl)-N-methylcarbamoylmethyloxy]phenyl] carbamoylmethyl] ureidolphenyl]acetate
tert-Butyl 2-[3-[3-[N-cyclopentylmethyl-N-[2-[N-(2,6-difluorophenyl)-N-methylcarbamoylmethyloxy]phenyl] carbamoyl methyl]ureido]phenyl]acetate
(±)-2-[3-[3-[N-Cyclopentylmethyl-N-[2-[N-methyl-N-phenyl carbamoylmethyloxy]phenyl]carbamoylmethyl] ureido]phenyl] propionic acid
Methyl (±)-2-[3-[3-[N-cyclopentylmethyl-N-[2-[N-methyl-N-phenylcarbamoylmethyloxy]phenyl]carbamoylmethyl] ureido] phenyl]propionate
tert-Butyl (±)-2-[3-[3-[N-cyclopentylmethyl-N-[2-[N-methyl-N-phenylcarbamoylmethyloxy]phenyl carbamoylmethyl]ureido] phenyl]propionate
(±)-2-[3-[3-[N-Cyclopentylmethyl-N-[2-[N-methyl-N-(3,5-dimethylphenyl)carbamoylmethyloxy]phenyl] carbamoylmethyl] ureido]phenyl]propionic acid
Methyl (±)-2-[3-[3-[N-cyclopentylmethyl-N-[2-[N-methyl-N-(3,5-dimethylphenyl)carbamoylmethyloxy]phenyl] carbamoyl methyl]ureido]phenyl]propionate
tert-Butyl (±)-2-[3-[3-[N-cyclopentylmethyl-N-[2-[N-methyl-N-(3,5-dimethylphenyl)carbamoylmethyloxy] phenyl]carbamoyl methyl]ureido]phenyl]propionate
(±)-2-[3-[3-[N-[2-[N-(3-Chlorophenyl)-N-methylcarbamoyl methyloxy]phenyl]-N-cyclopentylmethylcarbamoylmethyl]ureido] phenyl] propionic acid
Methyl (±)-2-[3-[3-[N-[2-[N-(3-chlorophenyl)-N-methyl carbamoylmethyloxy]phenyl]-N-cyclopentylmethylcarbamoyl methyl]ureido]phenyl] propionate
tert-Butyl (±)-2-[3-[3-[N-[2-[N-(3-chlorophenyl)-N-methyl carbamoylmethyloxy]phenyl]-N-cyclopentylmethylcarbamoyl methyl]ureido]phenyl] propionate
(±)-2-[3-[3-[N-Cyclopentylmethyl-N-[2-[N-(3,5-difluoro phenyl)-N-methylcarbamoylmethyloxy]phenyl] carbamoyl methyl]ureido]phenyl]propionic acid
Methyl (±)-2-[3-[3-[N-cyclopentylmethyl-N-[2-[N-(3,5-difluorophenyl)-N-methylcarbamoylmethyloxy]phenyl] carbamoyl methyl]ureido]phenyl]propionate
tert-Butyl (±)-2-[3-[3-[N-cyclopentylmethyl-N-[2-[N-(3,5-difluorophenyl)-N-methylcarbamoylmethyloxy]phenyl] carbamoyl methyl]ureido]phenyl]propionate
(±)-2-[3-[3-[N-Cyclopentylmethyl-N-[2-[N-(2,6-difluoro phenyl)-N-methylcarbamoylmethyloxy]phenyl] carbamoyl methyl]ureido]phenyl]propionic acid
Methyl,(±)-2-[3-[3-[N-cyclopentylmethyl-N-[2-[N-(2,6-difluorophenyl)-N-methylcarbamoylmethyloxy]phenyl] carbamoyl methyl]ureido]phenyl]propionate
tert-Butyl (±)-2-[3-[3-[N-cyclopentylmethyl-N-[2-[N-(2,6-difluorophenyl)-N-methylcarbamoylmethyloxy]phenyl] carbamoyl methyl]ureido]phenyl]propionate
3-[3-[N-Cyclopentylmethyl-N-[2-[N-methyl-N-phenylcarbamoyl methyloxy]phenyl]carbamoylmethyl] ureido]benzoic acid
Methyl 3-[3-[N-cyclopentylmethyl-N-[2-[N-methyl-N-phenyl carbamoylmethyloxy]phenyl]carbamoylmethyl] ureido]benzoate
tert-Butyl 3-[3-[N-cyclopentylmethyl-N-[2-[N-methyl-N-phenyl carbamoylmethyloxy]phenyl]carbamoylmethyl] ureido]benzoate
3-[3-[N-Cyclopentylmethyl-N-[2-[N-methyl-N-(3,5-dimethyl phenyl)carbamoylmethyloxy]phenyl] carbamoylmethyl]ureido] benzoic acid
Methyl 3-[3-[N-cyclopentylmethyl-N-[2-[N-methyl-N-(3,5-dimethylphenyl)carbamoylmethyloxy]phenyl] carbamoylmethyl] ureido]benzoate
tert-Butyl 3-[3-[N-cyclopentylmethyl-N-[2-[N-methyl-N-(3,5-dimethylphenyl)carbamoylmethyloxy]phenyl] carbamoylmethyl] ureido]benzoate
3-[3-[N-[2-[N-(3-Chlorophenyl)-N-methylcarbamoylmethyloxy] phenyl]-N-cyclopentylmethylcarbamoylmethyl]ureido]benzoic acid
Methyl 3-[3-[N-[2-[N-(3-chlorophenyl)-N-methylcarbamoyl methyloxy]phenyl]-N-cyclopentylmethylcarbamoylmethyl] ureido]benzoate
tert-Butyl 3-(3-[N-[2-[N-(3-chlorophenyl)-N-methyl carbamoylmethyloxy]phenyl]-N-cyclopentylmethylcarbamoyl methyl]ureido]benzoate
3-[3-[N-Cyclopentylmethyl-N-[2-[N-(3,5-difluorophenyl)-N-methylcarbamoylmethyloxy]phenyl] carbamoylmethyl]ureido] benzoic acid Methyl 3-[3-[N-cyclopentylmethyl-N-[2-[N-(3,5-difluoro phenyl)-N-methylcarbamoylmethoxy]phenyl]carbamoylmethyl] ureido] benzoate tert-Butyl 3-[3-[N-cyclopentylmethyl-N-[2-[N-(3,5-difluoro phenyl)-N-methylcarbamoylmethyloxy]phenyl] carbamoylmethyl] ureido]benzoate 3-[3-[N-Cyclopentylmethyl-N-[2-[N-(2,6-difluorophenyl)-N-methylcarbamoylmethyloxy]phenyl]carbamoylmethyl]ureido] benzoic acid Methyl 3-[3-[N-cyclopentylmethyl-N-[2-[N-(2,6-difluoro phenyl)-N-methylcarbamoylmethyloxy]phenyl]carbamoylmethyl] ureido]benzoate tert-Butyl 3-[3-[N-cyclopentylmethyl-N-[2-[N-(2,6-difluoro phenyl)-N-methylcarbamoylmethyloxy]phenyl] carbamoyl methyl]ureido]benzoate 2-[3-[3-[N-[2-[N-(3-Chlorophenyl)-N-methylcarbamoyl methyloxy]phenyl]-N-cyclohexylmethylcarbamoylmethyl] ureido]phenyl]acetic acid Methyl 2-[3-[3-[N-[2-[N-(3-chlorophenyl)-N-methylcarbamoyl methyloxy]phenyl]-N-cyclohexylmethylcarbamoylmethyl] ureido]phenyl] acetate tert-Butyl 2-[3-[3-[N-[2-[N-(3-chlorophenyl)-N-methyl carbamoylmethyloxy]phenyl]-N-cyclohexylmethylcarbamoyl methyl]ureido]phenyl] acetate 2-[3-[3-[N-Cyclohexylmethyl-N-[2-[N-(3,5-difluorophenyl)-N-methylcarbamoylmethyloxy]phenyl] carbamoylmethyl]ureido] phenyl]acetic acid Methyl 2-[3-[3-[N-cyclohexylmethyl-N-[2-[N-(3,5-difluoro phenyl)-N-methylcarbamoylmethyloxy]phenyl] carbamoyl methyl]ureido]phenyl]acetate tert-Butyl 2-[3-[3-[N-cyclohexylmethyl-N-[2-[N-(3,5-difluoro phenyl)-N-methylcarbamoylmethyloxy]phenyl] carbamoylmethyl] ureido]phenyl]acetate 2-[3-[3-[N-Cyclohexylmethyl-N-[2-[N-(2,6-difluorophenyl)-N-methylcarbamoylmethyloxy]phenyl] carbamoylmethyl]ureido] phenyl]acetic acid Methyl 2-[3-[3-[N-cyclohexylmethyl-N-[2-[N-(2,6-difluoro phenyl)-N-methylcarbamoylmethyloxy]phenyl] carbamoylmethyl]ureido]phenyl]acetate tert-Butyl 2-[3-[3-[N-cyclohexylmethyl-N-[2-[N-(2,6-difluorophenyl)-N-methylcarbamoylmethyloxy]phenyl] carbamoyl methyl]ureido]phenyl]acetate (±)-2-[3-[3-[N-Cyclohexylmethyl-N-[2-[N-methyl-N-phenyl carbamoylmethyloxy]phenyl]carbamoylmethyl] ureido]phenyl]prop ionic acid Methyl (±)-2-[3-[3-[N-cyclohexylmethyl-N-[2-[N-methyl-N-phenylcarbamoylmethyloxy]phenyl]carbamoylmethyl] ureido] phenyl]propionate tert-Butyl (±)-2-[3-[3-[N-cyclohexylmethyl-N-[2-[N-methyl-N-phenylcarbamoylmethyloxy]phenyl]carbamoylmethyl]ureido] phenyl]propionate (±)-2-[3-[3-[N-[2-[N-(3-Chlorophenyl)-N-methylcarbamoyl methyloxy]phenyl]-N-cyclohexylmethylcarbamoylmethyl]ureido] phenyl]propionic acid Methyl (±)-2-[3-[3-[N-[2-[N-(3-chlorophenyl)-N-methyl carbamoylmethyloxy]phenyl]-N-cyclohexylmethylcarbamoyl methyl]ureido]phenyl] propionate tert-Butyl (±)-2-(3-[3-[N-[2-[N-(3-chlorophenyl)-N-methyl carbamoylmethyloxy]phenyl]-N-cyclohexylmethylcarbamoyl methyl]ureidolphenyl] propionate (±)-2-[3-[3-[N-Cyclohexylmethyl-N-[2-[N-(3,5-difluoro phenyl)-N-methylcarbamoylmethyloxy]phenyl] carbamoyl methyl]ureido]phenyl]propionic acid Methyl (±)-2-[3-[3-[N-cyclohexylmethyl-N-[2-[N-(3,5-difluorophenyl)-N-methylcarbamoylmethyloxy]phenyl] carbamoyl methyl]ureido]phenyl]propionate tert-Butyl (±)-2-[3-[3-[N-cyclohexylmethyl-N-[2-[N-(3,5-difluorophenyl)-N-methylcarbamoylmethyloxy]phenyl] carbamoyl methyl]ureido]phenyl]propionate (±)-2-[3-[3-[N-Cyclohexylmethyl-N-[2-[N-(2,6-difluoro phenyl)-N-methylcarbamoylmethyloxy]phenyl] carbamoyl methyl]ureido]phenyl]propionic acid Methyl (±)-2-[3-[3-[N-cyclohexylmethyl-N-[2-[N-(2,6-difluorophenyl)-N-methylcarbamoylmethyloxy]phenyl] carbamoyl methyl]ureido]phenyl]propionate tert-Butyl (±)-2-[3-[3-[N-cyclohexylmethyl-N-[2-[N-(2,6-difluorophenyl)-N-methylcarbamoylmethyloxy]phenyl] carbamoyl methyl]ureido]phenyl]propionate 3-[3-[N-Cyclohexylmethyl-N-[2-[N-methyl-N-phenylcarbamoyl methyloxy]phenyl]carbamoylmethyl]ureido]benzoic acid Methyl 3-[3-[N-cyclohexylmethyl-N-[2-[N-methyl-N-phenyl carbamoylmethyloxy]phenyl]carbamoylmethyl] ureido]benzoate tert-Butyl 3-[3-[N-cyclohexylmethyl-N-[2-[N-methyl-N-phenyl carbamoylmethyloxy]phenyl]carbamoylmethyl] ureido]benzoate 3-[3-[N-Cyclohexylmethyl-N-[2-[N-methyl-N-(3,5-dimethyl phenyl)carbamoylmethyloxy]phenyl] carbamoylmethyl]ureido] benzoic acid Methyl 3-[3-[N-cyclohexylmethyl-N-[2-[N-methyl-N-(3,5-dimethylphenyl)carbamoylmethyloxy]phenyl] carbamoylmethyl] ureido]benzoate tert-Butyl 3-[3-[N-cyclohexylmethyl-N-[2-[N-methyl-N-(3,5-dimethylphenyl)carbamoylmethyloxy]phenyl] carbamoylmethyl] ureido]benzoate 3-[3-[N-[2-[N-(3-Chlorophenyl)-N-methylcarbamoylmethyloxy] phenyl]-N-cyclohexylmethylcarbamoylmethyl]ureido]benzoic acid Methyl 3-[3-[N-[2-[N-(3-chlorophenyl)-N-methyl carbamoylmethyloxy]phenyl]-N-cyclohexylmethylcarbamoyl methyl]ureido]benzoate tert-Butyl 3-[3-[N-[2-[N-(3-chlorophenyl)-N-methylcarbamoyl methyloxy]phenyl]-N-cyclohexylmethylcarbamoylmethyl] ureido]benzoate 3-[3-[N-Cyclohexylmethyl-N-[2-[N-(3,5-difluorophenyl)-N-methylcarbamoylmethyloxy]phenyl] carbamoylmethyl]ureido] benzoic acid Methyl 3-[3-[N-cyclohexylmethyl-N-[2-[N-(3,5-difluoro phenyl)-N-methylcarbamoylmethyloxy]phenyl] carbamoylmethyl] ureido]benzoate tert-Butyl 3-[3-[N-cyclohexylmethyl-N-[2-[N-(3,5-difluoro phenyl)-N-methylcarbamoylmethyloxy]phenyl] carbamoyl methyl]ureido]benzoate 3-[3-[N-Cyclohexylmethyl-N-[2-[N-(2,6-difluorophenyl)-N-methylcarbamoylmethyloxy]phenyl] carbamoylmethyl]ureido] benzoic acid Methyl 3-[3-[N-cyclohexylmethyl-N-[2-[N-(2,6-difluoro phenyl)-N-methylcarbamoylmethyloxy]phenyl] carbamoyl methyl]ureido]benzoate tert-Butyl 3-[3-[N-cyclohexylmethyl-N-[2-[N-(2,6-difluoro phenyl)-N-methylcarbamoylmethyloxy]phenyl] carbamoyl methyl]ureido]benzoate 2-[3-[3-[N-(2-Cyclohexylethyl)-N-[2-[N-methyl-N-(3,5-dimethylphenyl)carbamoylmethyloxy]phenyl] carbamoylmethyl] ureido]phenyl]acetic acid Methyl 2-[3-[3-[N-(2-cyclohexylethyl)-N-[2-[N-methyl-N-(3,5-dimethylphenyl)carbamoylmethyloxy]phenyl] carbamoylmethyl] ureido]phenyl]acetate tert-Butyl 2-[3-[3-[N-(2-cyclohexylethyl)-N-[2-[N-methyl-N-(3,5-dimethylphenyl)carbamoylmethyloxy]phenyl] carbamoyl methyl]ureido]phenyl]acetate 2-[3-[3-[N-[2-[N-(3-Chlorophenyl)-N-methylcarbamoyl methyloxy]phenyl]-N-(2-cyclohexylethyl) carbamoylmethyl] ureido]phenyl]acetic acid Methyl 2-[3-[3-[N-[2-[N-(3-chlorophenyl)-N-methylcarbamoyl methyloxy]phenyl]-N-(2-cyclohexylethyl)carbamoylmethyl] ureido]phenyl]acetate tert-Butyl 2-[3-[3-[N-[2-[N-(3-chlorophenyl)-N-methyl carbamoylmethyloxy]phenyl]-N-(2-cyclohexylethyl) carbamoyl methyl]ureido]phenyl]acetate 2-[3-[3-[N-(2-Cyclohexylethyl)-N-[2-[N-(3,5-difluorophenyl)-N-methylcarbamoylmethyloxy]phenyl] carbamoylmethyl]ureido] phenyl]acetic acid Methyl 2-[3-[3-[N-(2-cyclohexylethyl)-N-[2-[N-(3,5-difluoro phenyl)-N-methylcarbamoylmethyloxy]phenyl] carbamoyl methyl]ureido]phenyl]acetate tert-Butyl 2-[3-[3-[N-(2-cyclohexylethyl)-N-[2-[N-(3,5-difluorophenyl)-N-methylcarbamoylmethyloxy]phenyl] carbamoyl methyl]ureido]phenyl]acetate 2-[3-[3-[N-(2-Cyclohexylethyl)-N-[2-[N-(2,6-difluorophenyl)-N-methylcarbamoylmethyloxy]phenyl] carbamoylmethyl]ureido] phenyl]acetic acid Methyl 2-[3-[3-[N-(2-cyclohexylethyl)-N-[2-[N-(2,6-difluorophenyl)-N-methylcarbamoylmethyloxy]phenyl] carbamoyl methyl]ureido]phenyl]acetate tert-Butyl 2-[3-[3-[N-(2-cyclohexylethyl)-N-[2-[N-(2,6-difluorophenyl)-N-methylcarbamoylmethyloxy]phenyl] carbamoyl methyl]ureido]phenyl]acetate (±)-2-[3-[3-[N-(2-Cyclohexylethyl)-N-[2-[N-methyl-N-phenyl carbamoylmethyloxy]phenyl]carbamoylmethyl] ureido]phenyl] propionic acid Methyl (±)-2-[3-[3-[N-(2-cyclohexylethyl)-N-[2-[N-methyl-N-phenylcarbamoylmethyloxy]phenyl] carbamoylmethyl]ureido] phenyl]propionate tert-Butyl (±)-2-[3-[3-[N-(2-cyclohexylethyl)-N-[2-[N-methyl-N-phenylcarbamoylmethyloxy]phenyl] carbamoylmethyl] ureido]phenyl]propionate (±)-2-[3-[3-[N-(2-Cyclohexylethyl)-N-[2-[N-methyl-N-(3,5-dimethylphenyl)carbamoylmethyloxy]phenyl] carbamoylmethyl] ureido]phenyl]propionic acid Methyl (±)-2-[3-[3-[N-(2-cyclohexylethyl)-N-[2-[N-methyl-N-(3,5-dimethylphenyl)carbamoylmethyloxy] phenyl]carbamoyl methyl]ureido]phenyl]propionate tert-Butyl (±)-2-[3-[3-[N-(2-cyclohexylethyl)-N-[2-[N-methyl-N-(3,5-dimethylphenyl)carbamoylmethyloxy] phenyl] carbamoylmethyl]ureido]phenyl]propionate (±)-2-[3-[3-[N-[2-[N-(3-Chlorophenyl)-N-methylcarbamoyl methyloxy]phenyl]-N-(2-cyclohexylethyl)carbamoylmethyl] ureido]phenyl] propionic acid Methyl (±)-2-[3-[3-[N-[2-[N-(3-chlorophenyl)-N-methyl carbamoylmethyloxy]phenyl]-N-(2-cyclohexylethyl) carbamoyl methyl]ureido]phenyl]propionate tert-Butyl (±)-2-[3-[3-[N-[2-[N-(3-chlorophenyl)-N-methyl carbamoylmethyloxy]phenyl]-N-(2-cyclohexylethyl) carbamoyl methyl]ureido]phenyl]propionate (±)-2-[3-[3-[N-(2-Cyclohexylethyl)-N-[2-[N-(3,5-difluoro phenyl)-N-methylcarbamoylmethyloxy]phenyl] carbamoylmethyl] ureido]phenyl]propionic acid Methyl (±)-2-[3-[3-[N-(2-cyclohexylethyl)-N-[2-[N-(3,5-difluorophenyl)-N-methylcarbamoylmethyloxy]phenyl] carbamoyl methyl]ureido]phenyl]propionate tert-Butyl (±)-2-[3-[3-[N-(2-cyclohexylethyl)-N-[2-[N-(3,5-difluorophenyl)-N-methylcarbamoylmethyloxy]phenyl] carbamoyl methyl]ureido]phenyl]propionate (±)-2-[3-[3-[N-(2-Cyclohexylethyl)-N-[2-[N-(2,6-difluoro phenyl)-N-methylcarbamoylmethyloxy]phenyl] carbamoylmethyl] ureido]phenyl]propionic acid Methyl (±)-2-[3-[3-[N-(2-cyclohexylethyl)-N-[2-[N-(2,6-difluorophenyl)-N-methylcarbamoylmethyloxy]phenyl] carbamoyl methyl]ureido]phenyl]propionate tert-Butyl (±)-2-[3-[3-[N-(2-cyclohexylethyl)-N-[2-[N-(2,6-difluorophenyl)-N-methylcarbamoylmethyloxy]phenyl] carbamoyl methyl]ureido]phenyl]propionate 3-[3-[N-(2-Cyclohexylethyl)-N-[2-[N-methyl-N-phenyl carbamoylmethyloxy]phenyl]carbamoylmethyl]ureido] benzoic acid Methyl 3-[3-[N-(2-cyclohexylethyl)-N-[2-[N-methyl-N-phenyl carbamoylmethyloxy]phenyl]carbamoylmethyl] ureido]benzoate tert-Butyl 3-[3-[N-(2-cyclohexylethyl)-N-[2-[N-methyl-N-phenylcarbamoylmethyloxy]phenyl]carbamoylmethyl] ureido] benzoate 3-[3-[N-(2-Cyclohexylethyl)-N-[2-[N-methyl-N-(3,5-dimethyl phenyl)carbamoylmethyloxy]phenyl] carbamoylmethyl]ureido] benzoic acid Methyl 3-[3-[N-(2-cyclohexylethyl)-N-[2-[N-methyl-N-(3, 5-dimethylphenyl)carbamoylmethyloxy]phenyl] carbamoylmethyl] ureido]benzoate tert-Butyl 3-[3-[N-(2-cyclohexylethyl)-N-[2-[N-methyl-N-(3,5-dimethylphenyl)carbamoylmethyloxy]phenyl] carbamoyl methyl]ureido]benzoate 3-[3-[N-[2-[N-(3-Chlorophenyl)-N-methylcarbamoylmethyloxy] phenyl]-N-(2-cyclohexylethyl)carbamoylmethyl]ureido]benzoic acid Methyl 3-[3-[N-[2-[N-(3-chlorophenyl)-N-methylcarbamoyl methyloxy]phenyl]-N-(2-cyclohexylethyl)carbamoylmethyl] ureido]benzoate tert-Butyl 3-[3-[N-[2-[N-(3-chlorophenyl)-N-methylcarbamoyl methyloxy]phenyl]-N-(2-cyclohexylethyl)carbamoylmethyl] ureido]benzoate 3-[3-[N-(2-Cyclohexylethyl)-N-[2-[N-(3,5-difluorophenyl)-N-methylcarbamoylmethyloxy]phenyl] carbamoylmethyl]ureido] benzoic acid Methyl 3-[3-[N-(2-cyclohexylethyl)-N-[2-[N-(3,5-difluoro phenyl)-N-methylcarbamoylmethyloxy]phenyl] carbamoyl methyl]ureido]benzoate tert-Butyl 3-[3-[N-(2-cyclohexylethyl)-N-[2-[N-(3,5-difluorophenyl)-N-methylcarbamoylmethyloxy]phenyl] carbamoyl methyl]ureido]benzoate 3-[3-[N-(2-Cyclohexylethyl)-N-[2-[N-(2,6-difluorophenyl)-N-methylcarbamoylmethyloxy]phenyl] carbamoylmethyl]ureido] benzoic acid Methyl 3-[3-[N-(2-cyclohexylethyl)-N-[2-[N-(2,6-difluoro phenyl)-N-methylcarbamoylmethyloxy]phenyl] carbamoyl methyl]ureido]benzoate tert-Butyl 3-[3-[N-(2-cyclohexylethyl)-N-[2-[N-(2,6-difluoro phenyl)-N-methylcarbamoylmethyloxy]phenyl] carbamoyl methyl]ureido]benzoate Test Example 1

Inhibition of binding against receptors

The following receptor binding test was performed so as to investigate biological activities of the compounds of the present invention.

Test Method:

Separation of human CCK-B/gastrin receptor cDNA clone, separation of human CCK-A receptor cDNA clone, and expression of respective cloned receptors in heterologous cells.

cDNA of human CCK-B/gastrin receptor cDNA (Pisegna et al.: Biochem. Biophys. Res. Commun., 189, 296–303, 1992) and human CCK-A receptor cDNA (Ulrich et al.: Biochem. Biophys. Res. Commun., 193, 204–211, 1993) have already been isolated. The cDNAs having the reported nucleotide sequences were prepared using routine genetic engineering techniques. The isolated human CCK-B/gastrin receptor cDNA or human CCK-A receptor cDNA was integrated in an expression vector using routine genetic engineering techniques and transfected to CHO cells derived from the Chinese hamster ovary so as to induce expression of respective receptors.

1) Inhibition of binding against gastrin receptor

The compounds of the present invention were evaluated by the receptor-binding assay using $^{125}$I-gastrin and human CCK-B/gastrin receptor expressed in CHO cells. CHO cells expressing the human CCK-B/gastrin receptor were cultured using a Dulbecco's modified Eagle minimum essential medium: nutrient mixture F-12 (hereinafter abbreviated as DMEM/F-12) containing 10% fetal bovine serum at 37° C. in an aerobic phase of 5% $CO_2$ and 95% air. Using a culture dish having a diameter of 16 mm (base area: 2 $cm^2$), the cells were cultured so as to obtain $5\times10^5$ cells. The cells were washed with a binding buffer (Earle's balanced salt solution containing 10 mM 4-(2-hydroxyethyl)-1-piperazine ethanesulfonic acid (HEPES) (pH 7.4), 0.1% bovine serum albumin, 2 mM glutamine, and 0.22% sodium hydrogen carbonate) twice, after which a binding buffer (0.5 ml) was added to the dish. To this binding buffer, a test compound (5 $\mu$l) dissolved in dimethylsulfoxide (DMSO) was added. The reaction was then allowed to start by adding 0.01 ml (final concentration: 25 pM) of [$^{125}$I]gastrin. When a nonspecific binding amount was obtained, reaction was carried out in the presence of 1 $\mu$M of non-labelled gastrin. Reaction was allowed to proceed at 37° C. in an aerobic phase of 5% $CO_2$ and 95% air, after which the cells were washed with phosphate-buffered saline (PBS). [$^{125}$I]gastrin which had not been bound to the cells was removed, and the cells were lysed by adding 1% Triton X-100 (250 $\mu$l) to the dish. Radioactivity of this solution was measured by a gamma counter. A specific binding amount was obtained by subtracting a nonspecific binding amount from a total binding amount. Using the thus-obtained specific binding amount, the percentage of the value obtained from a test substance addition group with respect to that of the DMSO addition group was calculated. The percentage was subjected to Hill conversion and then a least squares method, obtaining a 50% inhibitory concentration ($IC_{50}$).

A specific example showing gastrin receptor antagonizing activities of typical compounds of the present invention and a comparative compound will next be described.

TABLE 1

|  | Gastrin receptor binding $IC_{50}$ (nM) |
|---|---|
| Control compound A | 6.5 |
| Compound of Example 73 | 1.9 |
| Compound of Example 79 | 1.6 |
| Compound of Example 86 | 1.0 |
| Compound of Example 87 | 0.87 |
| Compound of Example 92 | 0.5 |

2) Inhibition of binding against CCK-A receptor

Test method: The compounds of the present invention were evaluated by the receptor-binding assay using $^{125}$I-gastrin and human CCK-B/gastrin receptor expressed in CHO cells. CHO cells expressing a human CCK-A receptor were cultured using a DMEM/F-12 containing 10% fetal bovine serum at 37° C. in an aerobic phase of 5% $CO_2$ and 95% air. Using a culture dish having a diameter of 16 mm (base area: 2 $cm^2$), the cells were cultured so as to obtain $5\times10^5$ cells. The cells were washed with a binding buffer (Earle's balanced salt solution containing 10 mM HEPES (pH 7.4), 0.1% bovine serum albumin, 2 mM glutamine, and 0.22% sodium hydrogen carbonate) twice, after which a binding buffer (0.5 ml) was added to the dish. To this binding buffer, a test compound (5 $\mu$l) dissolved in DMSO was added. The reaction was then allowed to start by adding 0.01 ml (final concentration: 25 pM) of [$^{125}$I]CCK8. When a nonspecific binding amount was obtained, reaction was carried out in the presence of 1 $\mu$M of non-labelled CCK-8. Reaction was allowed to proceed at 37° C. in an aerobic phase of 5% $CO_2$ and 95% air, after which the cells were washed with PBS. [$^{125}$I]CCK8 which had not been bound to the cells was removed, and the cells were lysed by adding 1% Triton X-100 (250 $\mu$l) to the dish. Radioactivity of this solution was measured by a gamma counter. A specific binding amount was obtained by subtracting a nonspecific binding amount from a total binding amount. Using the thus-obtained specific binding amount, the percentage of the value obtained from a test substance addition group with respect to that of the DMSO addition group was calculated. The percentage was subjected to Hill conversion and then to a least squares method, obtaining a 50% inhibitory concentration ($IC_{50}$).

In this receptor binding test, the binding inhibition ($IC_{50}$) of the control compound (=compound A described in Example 1 of WO94/06825, i.e., potassium (±)-1-[3-[3-[N-(3-methoxyphenyl-N-(N-methyl-N-phenylcarbomoylmethyl)-carbamoylmethyl]ureido] phenylethane sulfonate) was 1476 nM, and its receptor selectivity ($IC_{50}$ ratio of CCK-A/gastrin) was factor 238. In contrast, the CCK-A binding inhibition of the compound of Example 92 of the present invention was 3640 nM and that of the compound of Example 87 was 3179 nM. Gastrin receptor selectivities of these compounds were factor 7280 and factor 3654, respectively, indicating remarkably high selectivities.

As described above, the compounds of the present invention have potent gastrin receptor binding inhibition or CCK-A receptor binding inhibition and thus are useful as therapeutic agents for the treatment of digestive diseases or central nervous system diseases. Of the compounds of the present invention, particularly preferred compounds have strong inhibition in binding assay with gastrin receptor and exhibit higher selectivity in inhibition of binding to gastrin receptors than to CCK-A receptors. Therefore, these compounds are particularly useful as preventive and therapeutic agents for digestive diseases such as peptic ulcers.

We claim:

1. A compound represented by the following formula

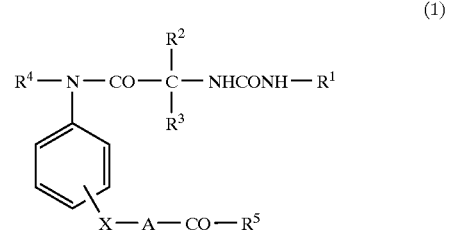

(1)

wherein X represents an oxygen atom or a sulfur atom,

A represents a linear or branched alkylene group, $R^1$ represents a phenyl group which may have a substituent, $R^2$ and $R^3$, which may be identical to or different from each other, each independently represent a hydrogen atom or an alkyl group, $R^4$ represents an alkyl or alkenyl group which may have a substituent, $R^5$ represents a hydroxyl group, an alkoxyl group, an aralkyl group, an aryl group, a cycloalkyl group which may have a substituent, or a group —N($R^6$)$R^7$ wherein $R^6$ and $R^7$ are identical to or different from each other, each independently representing a hydrogen atom, an alkyl group which may have a substituent, an alkoxyl group, a phenyl group which may have a substituent, and an aralkyl group which may have a substituent; a salt thereof; or an optical isomer the compound or the salt.

2. A compound as defined in claim 1, a salt thereof, or an optical isomer of the compound or the salt, wherein $R_1$ is a phenyl group which may be substituted by one or more members selected from the group consisting of an alkylamino group, a dialkylamino group, an alkoxyiminoalkyl group, an arylalkoxyiminoalkyl group, a halogen atom, an alkyl group, an alkoxyl group, an alkylthio group, a hydroxyl group, a carboxyl group, a hydroxyalkyl group, a nitro group, an acyl group, a cyano group, an amino group, a carbamoyl group, a sulfamoyl group, a trifluoromethane sulfonyl amino group, an alkoxycarbonyl group, an alkoxyaminocarbonyl group, a sulfo group, an alkylsulfonyl group, an acyloxyalkyl group, an alkoxyalkyl group, a carboxyalkyl group, an alkoxycarbonyl alkyl group, an carboxyalkyloxy group, an alkoxycarbonylalkyloxy group, a sulfoalkyl group, a N-alkyl-N-alkoxyamino group, and a hydroxyiminoalkyl group.

3. A compound as defined in claim 1, a salt thereof, or an optical isomer of the compound or the salt, wherein $R^4$ is an alkyl or alkenyl group which may be substituted by one or more groups selected from an aryl group, a carboxyl group, an alkoxylcarbonyl group, an aryloxycarbonyl group, an aralkyloxycarbonyl group, a hydroxyl group, an alkoxyl group, an amino group, an alkylamino group, a dialkylamino group, and a group —$CON(R^8)R^9$ wherein $R^8$ and $R^9$ are identical to or different from each other, each independently representing a hydrogen atom, an alkyl group which may have a substituent, an alkoxyl group, an aralkyl group, or a phenyl group which may have a substituent.

4. A compound as defined in claim 1, a salt thereof, or an optical isomer of the compound or the salt, wherein $R^6$ and $R^7$ are identical to or different from each other and each independently represent an alkyl group, alkoxy group, alkoxyalkyl group, or an aralkyl group, or a phenyl group which may be substituted by one ore more members selected from the group consisting of a hydroxyl group, a halogen atom, an alkyl group, an alkoxyl group, an acetyl group, a trifluoromethyl group, nitro group, cyano group, alkylthio group, and benzyloxy group.

5. A compound as defined in claim 1, a salt thereof, or an optical isomer of the compound or the salt, wherein X is an oxygen atom.

6. A compound as defined in claim 1, a salt thereof, or an optical isomer of the compound or the salt, wherein $R^1$ is a 3-alkoxycarbonylmethylphenyl group, a 3-(1-alkoxycarbonylethylphenyl) group, a 3-carboxymethylphenyl group or a 3-(1-carboxyethylphenyl) group.

7. A compound as defined in claim 1, a salt thereof, or an optical isomer of the compound or the salt, wherein $R^2$ and $R^3$ are hydrogen atoms.

8. A compound as defined in claim 1, a salt thereof, or an optical isomer of the compound or the salt, wherein R4 is n-butyl, 3-methylbutyl, 4-methylpentyl, 3-methylpentyl, 3-ethylpentyl, 4-ethylhexyl, cyclopentylmethyl, cyclopentylethyl, cyclohexylmethyl, cyclohexylethyl, tert-butoxycarbonylmethyl, or N-methyl-N-phenylcarbamoylmethyl.

9. A compound as defined in claim 1, a salt thereof, or an optical isomer of the compound or the salt, wherein X is bound to the ortho- or meta-position and is an oxygen atom.

10. A compound as defined in claim 1, a salt thereof, or an optical isomer of the compound or the salt, wherein $R^5$ is a group —$N(R^6)(R^7)$ wherein either one of $R^6$ or $R^7$ is a methyl or ethyl group, and the other is a phenyl group substituted by one or more members selected from a methyl group, a methoxy group, a fluorine atom, a bromine atom, and a chlorine atom.

11. 2-[3-[3-[N-[2-[N-Methyl-N-(3-methylphenyl)-carbamoylmethyloxy]phenyl]-N-(N-methyl-N-phenylcarbamoylmethyl)carbamoylmethyl]ureido]phenyl] acetic acid.

12. (±)-2-[3-[3-[N-[3-[N-Methyl-N-(2-methylphenyl)-carbamoylmethyloxy]phenyl]-N-(N-methyl-N-phenylcarbamoylmethyl)carbamoylmethyl]ureido]phenyl]-propionic acid.

13. (±)-2-[3-[3-[N-[2-[N-(3-Methoxyphenyl)-N-methylcarbamoylmethyloxy]phenyl]-N-(N-methyl-N-phenylcarbamoylmethyl)carbamoylmethyl]ureido]phenyl]-propionic acid.

14. 2-[3-[3-[N-[2-[N-(3-Methoxyphenyl)-N-methylcarbamoylmethyloxy]phenyl]-N-(N-methyl-N-phenylcarbamoylmethyl)carbamoylmethyl]ureido]phenyl] acetic acid.

15. Sodium (±)-2-[3-[3-[N-[2-[N-methyl-N-(3,5-dimethylphenyl)carbamoylmethyloxy]phenyl]-N-(N-methyl-N-phenylcarbamoylmethyl)carbamoylmethyl] ureido]phenyl]-propionate.

16. An medicine comprising as an active component a compound as defined in claim 1, a salt thereof, or an optical isomer of the compound or the salt.

17. An anti-cholecystokinin agent and an anti-gastrin agent comprising, as an active component, a compound as defined in claim 1, a salt thereof, or an optical isomer of the compound or the salt.

18. A therapeutic agent for peptic ulcers comprising, as an active component, a compound as defined in claim 1, a salt thereof, or an optical isomer of the compound or the salt.

19. A therapeutic agent for gastritis comprising, as an active component, a compound as defined in claim 1, a salt thereof, or an optical isomer of the compound or the salt.

20. A therapeutic agent for rectal/colonic cancer comprising, as an active component, a compound as defined in claim 1, a salt thereof, or an optical isomer of the compound or the salt.

21. A therapeutic agent for Zollinger-Ellison syndrome comprising, as an active component, a compound as defined in claim 1, a salt thereof, or an optical isomer of the compound or the salt.

22. A therapeutic agent for anxiety syndrome comprising, as an active component, a compound as defined in claim 1, a salt thereof, or an optical isomer of the compound or the salt.

23. A pharmaceutical composition comprising a compound as defined in claim 1, a salt thereof, or an optical isomer of the compound or the salt and a pharmaceutically acceptable carrier therefor.

24. A method of treating peptic ulcers, comprising administering an effective amount of the compound as claimed in claim 1 to a patient in need thereof.

25. A method of treating gastritis, comprising administering an effective amount of the compound as claimed in claim 1 to a patient in need thereof.

26. A method of treating rectal/colonic cancer, comprising administering an effective amount of the compound as claimed in claim 1 to a patient in need thereof.

27. A method of treating Zollinger-Ellison syndrome, comprising administering an effective amount of the compound as claimed in claim 1 to a patient in need thereof.

28. A method of treating anxiety syndrome, comprising administering an effective amount of the compound as claimed in claim 1 to a patient in need thereof.

* * * * *

UNITED STATES PATENT AND TRADEMARK OFFICE
CERTIFICATE OF CORRECTION

PATENT NO. : 5,919,824
DATED : JULY 6, 1999
INVENTOR(S) : Shuichi YOKOHAMA, et al.

It is certified that error appears in the above-identified patent and that said Letters Patent is hereby corrected as shown below:

Column 147, line 6, "isomer" should read --isomer of--.

Signed and Sealed this

Twenty-eighth Day of December, 1999

Attest:

Q. TODD DICKINSON

Attesting Officer     Acting Commissioner of Patents and Trademarks